US012767729B2

(12) United States Patent
Dedi et al.

(10) Patent No.: US 12,767,729 B2
(45) Date of Patent: Oct. 20, 2026

(54) ANTIBODIES AGAINST KLK5

(71) Applicant: UCB BIOPHARMA SRL, Brussels (BE)

(72) Inventors: Neesha Dedi, Slough (GB); Peter Charles Elliott, Slough (GB); Seppe Frans Roman Leysen, Slough (GB); Sean Mason, Slough (GB); David James Mcmillan, Slough (GB); Gillian Claire Ness, Slough (GB); Niccolo Pengo, Slough (GB); Martin Anthony Redhead, Slough (GB); Alison Turner, Slough (GB); Kerry Louise Tyson, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 998 days.

(21) Appl. No.: 17/759,988

(22) PCT Filed: Feb. 1, 2021

(86) PCT No.: PCT/EP2021/052249
§ 371 (c)(1),
(2) Date: Aug. 2, 2022

(87) PCT Pub. No.: WO2021/156171
PCT Pub. Date: Aug. 12, 2021

(65) Prior Publication Data

US 2023/0070261 A1 Mar. 9, 2023

(30) Foreign Application Priority Data

Feb. 3, 2020 (GB) .................................... 2001447
May 28, 2020 (GB) .................................... 2008022

(51) Int. Cl.
*C07K 16/40* (2006.01)
*A61P 17/00* (2006.01)
*C12N 15/63* (2006.01)

(52) U.S. Cl.
CPC .............. *C07K 16/40* (2013.01); *A61P 17/00* (2018.01); *C12N 15/63* (2013.01); *C07K 2317/24* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2317/94* (2013.01)

(58) Field of Classification Search
CPC ................ C07K 16/40; C07K 2317/24; C07K 2317/565; C07K 2317/76; C07K 2317/34; A61P 17/00; A61P 35/00; A61K 2039/505
See application file for complete search history.

(56) References Cited

U.S. PATENT DOCUMENTS

| | | | |
|---|---|---|---|
| 5,834,290 A | 11/1998 | Egelrud et al. | |
| 5,981,256 A | 11/1999 | Egelrud et al. | |
| 8,309,596 B2 | 11/2012 | Flohr et al. | |
| 9,642,898 B2 | 5/2017 | Fontana et al. | |
| 9,695,194 B2 | 7/2017 | Wagberg et al. | |
| 2015/0368665 A1 | 12/2015 | Bancel et al. | |
| 2019/0078160 A1* | 3/2019 | Dressen ................ | C07K 16/40 |

FOREIGN PATENT DOCUMENTS

| | | | |
|---|---|---|---|
| EP | 0703985 | A1 | 4/1996 |
| EP | 1398326 | A2 | 3/2004 |
| EP | 1716248 | A1 | 11/2006 |
| EP | 1721003 | A1 | 11/2006 |
| EP | 2244728 | A2 | 11/2010 |
| EP | 2245150 | A1 | 11/2010 |
| EP | 2266612 | A2 | 12/2010 |
| EP | 2405925 | A1 | 1/2012 |
| EP | 2731604 | A1 | 5/2014 |
| EP | 2764140 | A1 | 8/2014 |
| KR | 100931997 | B1 | 12/2009 |
| KR | 101409610 | B1 | 6/2014 |
| WO | 9500651 | A1 | 1/1995 |
| WO | 0164747 | A1 | 9/2001 |
| WO | 0244736 | A2 | 6/2002 |
| WO | 2004075723 | A2 | 9/2004 |
| WO | 2005078123 | A1 | 8/2005 |
| WO | 2007/079096 | A2 | 7/2007 |
| WO | 2013151668 | A2 | 10/2013 |
| WO | 2016/033464 | A1 | 3/2016 |
| WO | 2017123401 | A1 | 7/2017 |
| WO | 2018195472 | A1 | 10/2018 |
| WO | 2018232300 | A1 | 12/2018 |
| WO | 2019178316 | A1 | 9/2019 |
| WO | 2021055577 | A2 | 3/2021 |

(Continued)

OTHER PUBLICATIONS

Paul, WE, "Fundamental Immunology: Third Edition", 1993, Raven Press, 292-295. (Year: 1993).*
Bendig, MM, "Humanization of Rodent Monoclonal Antibodies by CDR Grafting", 1995, Methods: A Companion to Methods in Enzymology, 8, 83-93. (Year: 1995).*
Rudikoff, S et. al. "Single amino acid substitution altering antigen-binding specificity", 1982, Proceedings of the National Academy of Sciences USA, 79, 1979-1983. (Year: 1982).*
Evans, TRJ and Kaye, SB, "Vaccine therapy for cancer—fact or fiction?", 1999, Q. J. Med., 92, 299-307. (Year: 1999).*
Komenaka, I et. a. "Immunotherapy for Melanoma", 2004, Clinics in Dermatology, 22, 251-265. (Year: 2004).*

(Continued)

*Primary Examiner* — Laura B Goddard
*Assistant Examiner* — Alyssa Rae Stonebraker
(74) *Attorney, Agent, or Firm* — MEDLER FERRO WOODHOUSE & MILLS PLLC

(57) ABSTRACT

The present invention relates to antibodies which bind and inhibit KLK5 and methods of using the same to treat diseases caused by KLK5 imbalance. In particular, the present invention relates to inhibitory anti-KLK5 antibodies and their use in the treatment of Netherton disease, atopic dermatitis and cancer.

15 Claims, 12 Drawing Sheets

Specification includes a Sequence Listing.

(56) References Cited

FOREIGN PATENT DOCUMENTS

WO 2021/156170 A1 8/2021
WO 2022/192647 A1 9/2022

OTHER PUBLICATIONS

Hernandez-Ledesma, B et. al. "Lunasin, a novel seed peptide for cancer prevention", 2009, Peptides, 30, 426-430. (Year: 2009).*

Schiffman, M and Castle, PE, "The Promise of Global Cervical-Cancer Prevention", 2005, N. Engl. J. Med., 335(20), 2101-2104. (Year: 2005).*

Cuzick, J et. al. "Overview of the main outcomes in breast-cancer prevention trials", 2003, Lancet, 361, 296-300. (Year: 2003).*

Bonsignori, et. al. "Maturation Pathway from Germline to Broad HIV-1 Neutralizer of a CD4-Mimic Antibody", 2016, Cell, 165, 449- 463. (Year: 2016).*

Panka, et. al. "Variable region framework differences result in decreased or increased affinity of variant anti-digoxin antibodies", 1988, Proc. Natl. Acad. Sci. USA, 85, 3080-3084. (Year: 1988).*

Azouz et al., "Functional role of kallikrein 5 and proteinase-activated receptor 2 in eosinophilic esophagitis," Sci Transl Med 12(545):1-34 (2020).

Barry-Hamilton et al., "Allosteric inhibition of lysyl oxidase-like-2 impedes the development of a pathologic microenvironment," Nature Medicine 16(9):1009-1018 (2010).

Dragatin et al., "Secukinumab distributes into dermal interstitial fluid of psoriasis patients as demonstrated by open flow microperfusion," Experimental Dermatology 25;151-164 (2016).

Fortugno et al., "Proteolytic Activation Cascade of the Netherton Syndrome-Defective Protein, LEKTI, in the Epidermis: Implications for Skin Homeostasis," Journal of Investigative Dermatology 131:2223-2232 (2011).

Zhao, et al., "Characterization of a novel modification of aCHO-produced mAb: Evidence for the presence of tyrosine sulfation," mAbs. 9(6):85-995 (2017).

Zhu, et al., "Persistent kallikrein 5 activation induces atopic dermatitis-like skin architecture independent of PAR2 activity," J Allergy Clin Immunol. 140(5):1310-1322 (2017).

Bitoun, et al., "Netherton Syndrome: Disease Expression and Spectrum of SPINK5 Mutations in 21 Families," Society for Investigative Dermatology Inc. 118(2):352-361 (2002).

Brattsand, et al., "A Proteolytic Cascade of Kallikreins in the Stratum Corneum," J Invest Dermatol. 124:198-203 (2005).

Briot, et al., "Kallikrein 5 induces atopic dermatitis-like lesions through PAR2-mediated thymic stromal lymphopoietin expression in Netherton syndrome," Journal of Experimental Medicine. 206(5):1135-1147 (2009).

Caubet, et al., "Degradation of Corneodesmosome Proteins by Two Serine Proteases of the Kallikrein Family, SCTE/KLK5/hK5 and SCCE/KLK7/hK7," The Journal of Investigative Dermatology. 122:1235-1244 (2004).

Corren, et al., "TSLP: from allergy to cancer," Nature Immunology. 20:1603-1609 (2019).

Debela, et al., "Structural basis of the zinc inhibition of human tissue kallikrein 5," J Mol Biol. 373:1017-1031 (2007).

Debela, et al., "Structures and specificity of the human kallikrein-related peptidases KLK 4, 5, 6, and 7," Biol. Chem. 389:623-632 (2008).

Deraison, et al., "LEKTI Fragments specifically inhibit KLK5, KLK7, and KLK14 and control desquamation through a pH-dependent interaction," Molecular Biology of the Cell. 18:3607-3619 (2007).

Di Paolo, et al., "The role of kallikreins in inflammatory skin disorders and their potential as therapeutic targets," Critical Reviews in Clinical Laboratory Sciences (2020).

Dorn, et al., "Assessment of kallikrein-related peptidase 5 (KLK5) protein expression in tumor tissue of advanced ovarian cancer patients by immunohistochemistry and ELISA: correlation with clinical outcome," Am J Cancer Res. 6 (1):61-70 (2016).

Egawa, et al., "Multifactorial skin barrier deficiency and atopic dermatitis: Essential topics to prevent the atopic march," J Allergy Clin Immunol. 138(2):350-358 (2016).

Egawa, et al., "Barrier dysfunction in the skin allergy," Allergology International. 67:3-11 (2018).

Eissa, et al., "Human tissue kallikreins as promiscuous modulators of homeostatic skin barrier functions," Biol. Chem. 389:669-680 (2008).

Farady, et al., "Structure of an Fab-protease complex reveals a highly specific non-canonical mechanism of inhibition," J Mol Biol. 380(2):351-360 (2008).

Filippou, et al., "Kallikrein-related peptidases (KLKs) and the hallmarks of cancer," Crit Rev Clin Lab Sci. 53(4):277-291 (2016).

Furio, et al., "Netherton Syndrome: defective kallikrein inhibition in the skin leads to skin inflammation and allergy," Biol Chem. 395(9):945-958 (2014).

Furio, et al., "Transgenic kallikrein 5 mice reproduce major cutaneous and systemic hallmarks of Netherton Syndrome," J Exp Med. 211(3):499-513 (2014).

Furio, et al., "KLK5 inactivation reverses cutaneous hallmarks of Netherton Syndrome," PLOS Genetics. pp. 1-20 (2015).

Gong, et al., "Quantitative assessment and clinical relevance of kallikrein-related peptidase 5mRNA expression in advanced high-grade serous ovarian cancer," BMC Cancer. 19:696 (2019).

Goettig, et al., "Natural and synthetic inhibitors of kallikrein-related peptidases (KLKs)," Biochimie. 92:1546-1567 (2010).

Hachem, et al., "Serine Protease Activity and Residual LEKTI Expression Determine Phenotype in Netherton Syndrome," Journal of Investigative Dermatology. 126:1609-1621 (2006).

Hovnanian, A., "Netherton syndrome: skin inflammation and allergy by loss of protease inhibition," Cell tissue Res. 351:289-300 (2013).

Kapadia, et al., "Human kallikrein 13: Production and purification of recombinant protein and monoclonal and polyclonal antibodies, and development of a sensitive and specific immunofluorometric assay," Clinical Chemistry. 49(1):77-86 (2003).

Kasparek, et al., "KLK5 and KLK7 ablation fully rescues lethality of Netherton Syndrome-like phenotype," PLOS Genetics. pp. 1-21 (2017).

Kim, et al., "Significance of Skin Barrier Dysfunction in Atopic Dermatitis," Allergy Asthma Immunol Res. 10(3):207-215 (2018).

Komatsu, et al., "Human tissue kallikrein expression in the stratum corneum and serum of atopic dermatitis patients," Experimental Dermatology. 16:513-519 (2007).

Limon, et al., "Multifunctional Serine Protease Inhibitor-Coated Water-Soluble Gold Nanoparticles as a Novel Targeted Approach for the Treatment of inflammatory skin diseases," Bioconjugate Chemistry. 29:1060-1072 (2018).

Loessner, et al., "Kallikrein-related peptidases represent attractive therapeutic targets for ovarian cancer," Expert opinion on therapeutic targets. 22(9):745-763 (2018).

Michael, et al., "Biochemical and Enzymatic characterization of human kallikrein 5 (hK5), a novel serine protease potentially involved in cancer progression," Journal of Biological Chemistry. 280(15):14628-14635 (2005).

Nauroy, et al., "Kallikreins: Essential epidermal messengers for regulation of the skin microenvironment during homeostasis, repair and disease," Matrix Biology Plus. pp. 1-12 (2019).

Obiezu, et al., "Human Kallikrein 4: enzymatic activity, inhibition, and degradation of extracellular matrix proteins," Biol Chem. 387:749-759 (2006).

Oikonomopoulou, et al., "Kallikrein-mediated cell signalling: targeting proteinase-activated receptors (PARs)," Biol. Chem. 387:817-824 (2006).

Oiso, et al., "LEKTI: Netherton syndrome and Atopic Dermatitis," Current Genetics in Dermatology. Chapter 5, pp. 67-72.

Ovaere, et al., "The emerging roles of serine protease cascades in the epidermis," Trends in Biochemical Sciences. 34(9):453-463 (2009).

Prassas, et al., "Unleashing the therapeutic potential of human kallikrein-related serine proteases," Nature Reviews—Drug Discovery. 14:183-202 (2015).

Sarri, et al., "Netherton Syndrome: A Genotype-Phenotype Review," Mol Diagn Ther. 21:137-152 (2017).

(56) References Cited

OTHER PUBLICATIONS

Sexton, et al., "Specific inhibition of tissue kallikrein 1 with a human monoclonal antibody reveals a potential role in airway diseases," Biochem J. 422:383-392 (2009).
Shinoda, et al., "Association of KLK5 overexpression with invasiveness of urinary bladder carcinoma cells," Cancer Sci. 98(7):1078-1086 (2007).
Silverberg, et al., "Inside Out or Outside In: Does Atopic Dermatitis Disrupt Barrier Function or Does Disruption of Barrier Function Trigger Atopic Dermatitis?," Cutis. 96:359-361 (2015).
Sotiropoulou, et al., "Functional Roles of human Kallikrein-related Peptidases," Journal of Biological Chemistry. 284(48):32989-32994 (2009).
Takeichi, et al., "Inherited ichthyosis: Non-syndromic forms," Journal of Dermatology. 43:242-251 (2016).
Two, et al., "Kallikrein 5-Mediated Inflammation in Rosacea : Clinically Relevant Correlations with Acute and Chronic Manifestations in Rosacea and How Individual Treatments May Provide Therapeutic Benefit," Journal of clinical aesthetic dermatology. 7(11):20-25 (2014).
Vahlquist, et al., "Inherited Nonsyndromic Ichthyoses: An Update on Pathophysiology, Diagnosis and Treatment," Am J Clin Dermatol. 19:51-66 (2018).
Voegeli, et al., "Increased mass levels of certain serine proteases in the stratum corneum in acute eczematous atopic skin," International Journal of Cosmetic Science. 33:560-565 (2011).
Weidinger, et al., "Atopic dermatitis," Nature Reviews. Disease Primers. 4:1 (2018).
Wu, et al., "Structural insight into distinct mechanisms of protease inhibition by antibodies," PNAS. 104(50):19784-19789 (2007).
Yamamoto, et al., "Clinical and molecular implications of structural changes to desmosomes and corneodesmosomes," Journal of Dermatology. 45:385-389 (2018).
Yamasaki, et al., "Kallikrein-mediated proteolysis regulates the antimicrobial effects of cathelicidins in skin," The FASEB Journal. 20:2068-2080 (2006).
Yamasaki, et al., "Increased serine protease activity and cathelicidin promotes skin inflammation in rosacea," Nature Medicine. 13(8) : 975-980 (2007).
Yang, et al., "Skin Barrier Abnormalities and Immune Dysfunction in Atopic Dermatitis," Int. J. Mol. Sci. 21:2867 (2020).

* cited by examiner

A

B

A

B

A

B

A

B

SEQUENCE LISTING

<160> NUMBER OF SEQ ID NOS: 186

<210> SEQ ID NO 1

<211> LENGTH: 13
<212> TYPE: PRT
<213> ORGANISM: Artificial Sequence
<220> FEATURE:
<223> OTHER INFORMATION: CDR-L1

<400> SEQUENCE: 1

Gln Ser Ser Gln Ser Val Tyr Asn Asn Asn Asp Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2

Arg Ala Ser Thr Leu Ala Ser
1               5

<210> SEQ ID NO 3
<211> LENGTH: 12
<212> TYPE: PRT
<213> ORGANISM: Artificial Sequence
<220> FEATURE:
<223> OTHER INFORMATION: CDR-L3

<400> SEQUENCE: 3

Leu Gly Gly Tyr Asp Asp Asp Val Asp Thr Tyr Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR-H1

<400> SEQUENCE: 4

Gly Phe Ser Leu Ser Ser Tyr Gly Met Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CDR-H2

<400> SEQUENCE: 5

Ile Ile Ser Ser Ser Gly Ser Thr Tyr Tyr Ala Ser Trp Ala Lys Gly
1               5                   10                  15

<210> SEQ ID NO 6
<211> LENGTH: 20
<212> TYPE: PRT
<213> ORGANISM: Artificial Sequence
<220> FEATURE:
<223> OTHER INFORMATION: CDR-H3

<400> SEQUENCE: 6

Asp His Ile Tyr Arg Tyr Asp Asp Tyr Gly Asp Tyr Pro Thr Tyr Tyr
1               5                   10                  15

Gly Met Asp Pro
            20

-continued

<210> SEQ ID NO 7
<211> LENGTH: 13
<212> TYPE: PRT
<213> ORGANISM: Artificial Sequence
<220> FEATURE:
<223> OTHER INFORMATION: CDR-L1 Q1R

<400> SEQUENCE: 7

Arg Ser Ser Gln Ser Val Tyr Asn Asn Asn Asp Leu Ala
1 5 10

<210> SEQ ID NO 8
<211> LENGTH: 13
<212> TYPE: PRT
<213> ORGANISM: Artificial Sequence
<220> FEATURE:
<223> OTHER INFORMATION: CDR-L1 Q1K

<400> SEQUENCE: 8

Lys Ser Ser Gln Ser Val Tyr Asn Asn Asn Asp Leu Ala
1 5 10

<210> SEQ ID NO 9
<211> LENGTH: 13
<212> TYPE: PRT
<213> ORGANISM: Artificial Sequence
<220> FEATURE:
<223> OTHER INFORMATION: CDR-L1 Q1H

<400> SEQUENCE: 9

His Ser Ser Gln Ser Val Tyr Asn Asn Asn Asp Leu Ala
1 5 10

<210> SEQ ID NO 10
<211> LENGTH: 20
<212> TYPE: PRT
<213> ORGANISM: Artificial Sequence
<220> FEATURE:
<223> OTHER INFORMATION: CDR-H3 D19N

<400> SEQUENCE: 10

Asp His Ile Tyr Arg Tyr Asp Asp Tyr Gly Asp Tyr Pro Thr Tyr Tyr
1 5 10 15

Gly Met Asn Pro
20

<210> SEQ ID NO 11
<211> LENGTH: 20
<212> TYPE: PRT
<213> ORGANISM: Artificial Sequence
<220> FEATURE:
<223> OTHER INFORMATION: CDR-H3 D19E

<400> SEQUENCE: 11

Asp His Ile Tyr Arg Tyr Asp Asp Tyr Gly Asp Tyr Pro Thr Tyr Tyr
1 5 10 15

Gly Met Glu Pro
20

<210> SEQ ID NO 12
<211> LENGTH: 20
<212> TYPE: PRT
<213> ORGANISM: Artificial Sequence
<220> FEATURE:
<223> OTHER INFORMATION: CDR-H3 Y4F -continued

<400> SEQUENCE: 12

Asp His Ile Phe Arg Tyr Asp Asp Tyr Gly Asp Tyr Pro Thr Tyr Tyr
1 5 10 15

Gly Met Asp Pro
20

<210> SEQ ID NO 13
<211> LENGTH: 20
<212> TYPE: PRT
<213> ORGANISM: Artificial Sequence
<220> FEATURE:
<223> OTHER INFORMATION: CDR-H3 Y6F

<400> SEQUENCE: 13

Asp His Ile Tyr Arg Phe Asp Asp Tyr Gly Asp Tyr Pro Thr Tyr Tyr
1 5 10 15

Gly Met Asp Pro
20

<210> SEQ ID NO 14
<211> LENGTH: 20
<212> TYPE: PRT
<213> ORGANISM: Artificial Sequence
<220> FEATURE:
<223> OTHER INFORMATION: CDR-H3 Y9F

<400> SEQUENCE: 14

Asp His Ile Tyr Arg Tyr Asp Asp Phe Gly Asp Tyr Pro Thr Tyr Tyr
1 5 10 15

Gly Met Asp Pro
20

<210> SEQ ID NO 15
<211> LENGTH: 20
<212> TYPE: PRT
<213> ORGANISM: Artificial Sequence
<220> FEATURE:
<223> OTHER INFORMATION: CDR-H3 Y12F

<400> SEQUENCE: 15

Asp His Ile Tyr Arg Tyr Asp Asp Tyr Gly Asp Phe Pro Thr Tyr Tyr
1 5 10 15

Gly Met Asp Pro
20

<210> SEQ ID NO 16
<211> LENGTH: 20
<212> TYPE: PRT
<213> ORGANISM: Artificial Sequence
<220> FEATURE:
<223> OTHER INFORMATION: CDR-H3 Y15F

<400> SEQUENCE: 16

Asp His Ile Tyr Arg Tyr Asp Asp Tyr Gly Asp Tyr Pro Thr Phe Tyr
1 5 10 15

Gly Met Asp Pro
20

<210> SEQ ID NO 17
<211> LENGTH: 20
<212> TYPE: PRT
<213> ORGANISM: Artificial Sequence
<220> FEATURE:
<223> OTHER INFORMATION: CDR-H3 Y16F

<400> SEQUENCE: 17

```
Asp His Ile Tyr Arg Tyr Asp Asp Tyr Gly Asp Tyr Pro Thr Tyr Phe
1               5                   10                  15

Gly Met Asp Pro
            20
```

<210> SEQ ID NO 18
<211> LENGTH: 20
<212> TYPE: PRT
<213> ORGANISM: Artificial Sequence
<220> FEATURE:
<223> OTHER INFORMATION: CDR-H3 T14N

<400> SEQUENCE: 18

```
Asp His Ile Tyr Arg Tyr Asp Asp Tyr Gly Asp Tyr Pro Asn Tyr Tyr
1               5                   10                  15

Gly Met Asp Pro
            20
```

<210> SEQ ID NO 19
<211> LENGTH: 20
<212> TYPE: PRT
<213> ORGANISM: Artificial Sequence
<220> FEATURE:
<223> OTHER INFORMATION: CDR-H3 T14V

<400> SEQUENCE: 19

```
Asp His Ile Tyr Arg Tyr Asp Asp Tyr Gly Asp Tyr Pro Val Tyr Tyr
1               5                   10                  15

Gly Met Asp Pro
            20
```

<210> SEQ ID NO 20
<211> LENGTH: 20
<212> TYPE: PRT
<213> ORGANISM: Artificial Sequence
<220> FEATURE:
<223> OTHER INFORMATION: CDR-H3 T14S

<400> SEQUENCE: 20

```
Asp His Ile Tyr Arg Tyr Asp Asp Tyr Gly Asp Tyr Pro Ser Tyr Tyr
1               5                   10                  15

Gly Met Asp Pro
            20
```

<210> SEQ ID NO 21
<211> LENGTH: 20
<212> TYPE: PRT
<213> ORGANISM: Artificial Sequence
<220> FEATURE:
<223> OTHER INFORMATION: CDR-H3 Y4F/D19N

<400> SEQUENCE: 21

```
Asp His Ile Phe Arg Tyr Asp Asp Tyr Gly Asp Tyr Pro Thr Tyr Tyr
1               5                   10                  15

Gly Met Asn Pro
            20
```

<210> SEQ ID NO 22
<211> LENGTH: 20
<212> TYPE: PRT
<213> ORGANISM: Artificial Sequence
<220> FEATURE:

-continued

<223> OTHER INFORMATION: CDR-H3 Y6F/D19N

<400> SEQUENCE: 22

Asp His Ile Tyr Arg Phe Asp Asp Tyr Gly Asp Tyr Pro Thr Tyr Tyr
1 5 10 15

Gly Met Asn Pro
20

<210> SEQ ID NO 23
<211> LENGTH: 20
<212> TYPE: PRT
<213> ORGANISM: Artificial Sequence
<220> FEATURE:
<223> OTHER INFORMATION: CDR-H3 Y9F/D19N

<400> SEQUENCE: 23

Asp His Ile Tyr Arg Tyr Asp Asp Phe Gly Asp Tyr Pro Thr Tyr Tyr
1 5 10 15

Gly Met Asn Pro
20

<210> SEQ ID NO 24
<211> LENGTH: 20
<212> TYPE: PRT
<213> ORGANISM: Artificial Sequence
<220> FEATURE:
<223> OTHER INFORMATION: CDR-H3 Y12F/D19N

<400> SEQUENCE: 24

Asp His Ile Tyr Arg Tyr Asp Asp Tyr Gly Asp Phe Pro Thr Tyr Tyr
1 5 10 15

Gly Met Asn Pro
20

<210> SEQ ID NO 25
<211> LENGTH: 20
<212> TYPE: PRT
<213> ORGANISM: Artificial Sequence
<220> FEATURE:
<223> OTHER INFORMATION: CDR-H3 Y15F/D19N

<400> SEQUENCE: 25

Asp His Ile Tyr Arg Tyr Asp Asp Tyr Gly Asp Tyr Pro Thr Phe Tyr
1 5 10 15

Gly Met Asn Pro
20

<210> SEQ ID NO 26
<211> LENGTH: 20
<212> TYPE: PRT
<213> ORGANISM: Artificial Sequence
<220> FEATURE:
<223> OTHER INFORMATION: CDR-H3 Y16F/D19N

<400> SEQUENCE: 26

Asp His Ile Tyr Arg Tyr Asp Asp Tyr Gly Asp Tyr Pro Thr Tyr Phe
1 5 10 15

Gly Met Asn Pro
20

<210> SEQ ID NO 27
<211> LENGTH: 20
<212> TYPE: PRT
<213> ORGANISM: Artificial Sequence

<220> FEATURE:
<223> OTHER INFORMATION: CDR-H3 T14N/D19N

<400> SEQUENCE: 27

Asp His Ile Tyr Arg Tyr Asp Asp Tyr Gly Asp Tyr Pro Asn Tyr Tyr
1               5                   10                  15

Gly Met Asn Pro
            20

<210> SEQ ID NO 28
<211> LENGTH: 20
<212> TYPE: PRT
<213> ORGANISM: Artificial Sequence
<220> FEATURE:
<223> OTHER INFORMATION: CDR-H3 T14V/D19N

<400> SEQUENCE: 28

Asp His Ile Tyr Arg Tyr Asp Asp Tyr Gly Asp Tyr Pro Val Tyr Tyr
1               5                   10                  15

Gly Met Asn Pro
            20

<210> SEQ ID NO 29
<211> LENGTH: 20
<212> TYPE: PRT
<213> ORGANISM: Artificial Sequence
<220> FEATURE:
<223> OTHER INFORMATION: CDR-H3 T14S/D19N

<400> SEQUENCE: 29

Asp His Ile Tyr Arg Tyr Asp Asp Tyr Gly Asp Tyr Pro Ser Tyr Tyr
1               5                   10                  15

Gly Met Asn Pro
            20

<210> SEQ ID NO 30
<211> LENGTH: 112
<212> TYPE: PRT
<213> ORGANISM: Artificial Sequence
<220> FEATURE:
<223> OTHER INFORMATION: Rabbit VL

<400> SEQUENCE: 30

Ala Val Val Leu Thr Gln Thr Pro Ser Pro Met Ser Ala Ala Val Gly
1               5                   10                  15

Gly Thr Val Thr Ile Ser Cys Gln Ser Ser Gln Ser Val Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Asp
                85                  90                  95

Asp Val Asp Thr Tyr Thr Phe Gly Gly Gly Thr Glu Val Val Val Lys
            100                 105                 110

<210> SEQ ID NO 31
<211> LENGTH: 336
<212> TYPE: DNA
<213> ORGANISM: Artificial Sequence
<220> FEATURE:
<223> OTHER INFORMATION: Rabbit VL nucl.

<400> SEQUENCE: 31
gcagtcgtgc tgactcagac accatcaccc atgtctgcag ctgtgggagg cacagtcacc 60
atcagttgcc agtccagtca gagtgtttat aataataacg acttagcctg gtatcagcag 120
aaaccagggc agcctcctaa gctcctgatc tacagggcat ccactctggc atctggggtc 180
ccgtcgcggt tcagcggcag tggatctggg acacagttca ctctcaccat cagcggcgtg 240
cagtgtgacg atgctgccac ttactactgt ctaggcggtt atgatgatga tgttgatacg 300
tatactttcg gcggagggac cgaggtggtg gtcaaa 336

<210> SEQ ID NO 32
<211> LENGTH: 125
<212> TYPE: PRT
<213> ORGANISM: Artificial Sequence
<220> FEATURE:
<223> OTHER INFORMATION: Rabbit VH

<400> SEQUENCE: 32

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Gly
20 25 30

Met Ser Trp Val Arg Gln Ala Pro Gly Lys Gly Leu Glu Trp Ile Gly
35 40 45

Ile Ile Ser Ser Ser Gly Ser Thr Tyr Tyr Ala Ser Trp Ala Lys Gly
50 55 60

Arg Phe Thr Ile Ser Lys Thr Ser Thr Thr Val Asp Leu Lys Ile Ala
65 70 75 80

Ser Pro Thr Thr Glu Asp Thr Ala Thr Tyr Phe Cys Ala Arg Asp His
85 90 95

Ile Tyr Arg Tyr Asp Asp Tyr Gly Asp Tyr Pro Thr Tyr Tyr Gly Met
100 105 110

Asp Pro Trp Gly Pro Gly Thr Leu Val Thr Val Ser Ser
115 120 125

<210> SEQ ID NO 33
<211> LENGTH: 375
<212> TYPE: DNA
<213> ORGANISM: Artificial Sequence
<220> FEATURE:
<223> OTHER INFORMATION: Rabbit VH nucl.

<400> SEQUENCE: 33
cagtcggtgg aggagtccgg gggtcgcctg gtcacgcctg ggacacccct gacactcacc 60
tgcacagtct ctggattctc cctcagtagc tatggaatga gctgggtccg ccaggctcca 120
gggaaggggc tggaatggat cggaattatt agtagtagtg gtagcacata ctacgcgagc 180
tgggcgaaag gccgattcac catctccaag acctcgacca cggtggatct gaaaatcgcc 240
agtccgacaa ccgaggacac ggccacctat ttctgtgcca gagatcacat ttataggtac 300
gatgactatg gtgattaccc tacctactac ggcatggacc cctggggccc aggcaccctg 360
gtcaccgtct cgagc 375

<210> SEQ ID NO 34
<211> LENGTH: 112
<212> TYPE: PRT

<213> ORGANISM: Artificial Sequence
<220> FEATURE:
<223> OTHER INFORMATION: 10273 gL2 VL

<400> SEQUENCE: 34

```
Ala Ile Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110
```

<210> SEQ ID NO 35
<211> LENGTH: 336
<212> TYPE: DNA
<213> ORGANISM: Artificial Sequence
<220> FEATURE:
<223> OTHER INFORMATION: 10273 gL2 VL nucl.

<400> SEQUENCE: 35

```
gccattcaac tgactcagtc cccatcctcc ctgtccgcat ccgtgggga tagagtcacc      60

atcacctgtc agtcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaag                              336
```

<210> SEQ ID NO 36
<211> LENGTH: 219
<212> TYPE: PRT
<213> ORGANISM: Artificial Sequence
<220> FEATURE:
<223> OTHER INFORMATION: 10273 gL2 Light Chain

<400> SEQUENCE: 36

```
Ala Ile Gln Leu Thr Gln Ser Pro Ser Ser Leu Ser Ala Ser Val Gly
1               5                   10                  15

Asp Arg Val Thr Ile Thr Cys Gln Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110
```

```
Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 37
<211> LENGTH: 657
<212> TYPE: DNA
<213> ORGANISM: Artificial Sequence
<220> FEATURE:
<223> OTHER INFORMATION: 10273 gL2 Ligh Chain nucl.

<400> SEQUENCE: 37

gccattcaac tgactcagtc cccatcctcc ctgtccgcat ccgtggggga tagagtcacc      60

atcacctgtc agtcgagcca gtcagtgtac aacaacaacg acctggcctg gtatcagcag     120

aagccgggaa aggctcccaa gttgctgatc taccgggcct caacgctcgc gtcgggagtg     180

cctagccgct tttccggttc cggatctggc accgacttca ctctcaccat ttcgagcctt     240

caaccggagg acttcgccac ttactactgc ctgggcggtt acgatgacga tgtggacacc     300

tacaccttcg gcggagggac caaagtggaa atcaagcgta cggtggccgc tccctccgtg     360

ttcatcttcc caccctccga cgagcagctg aagtccggca ccgcctccgt cgtgtgcctg     420

ctgaacaact tctacccccg cgaggccaag gtgcagtgga aggtggacaa cgccctgcag     480

tccggcaact cccaggaatc cgtcaccgag caggactcca aggacagcac ctactccctg     540

tcctccaccc tgaccctgtc caaggccgac tacgagaagc acaaggtgta cgcctgcgaa     600

gtgacccacc agggcctgtc cagccccgtg accaagtcct tcaaccgggg cgagtgc       657


<210> SEQ ID NO 38
<211> LENGTH: 112
<212> TYPE: PRT
<213> ORGANISM: Artificial Sequence
<220> FEATURE:
<223> OTHER INFORMATION: 10273 gL2 VL Q1R

<400> SEQUENCE: 38

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80
```

-continued

```
Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110


<210> SEQ ID NO 39
<211> LENGTH: 336
<212> TYPE: DNA
<213> ORGANISM: Artificial Sequence
<220> FEATURE:
<223> OTHER INFORMATION: 10273 gL2 VL Q1R nucl.

<400> SEQUENCE: 39

gccattcaac tgactcagtc cccatcctcc ctgtccgcat ccgtgggga tagagtcacc      60

atcacctgtc ggtcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaag                              336


<210> SEQ ID NO 40
<211> LENGTH: 219
<212> TYPE: PRT
<213> ORGANISM: Artificial Sequence
<220> FEATURE:
<223> OTHER INFORMATION: 10273 gL2 Light Chain Q1R

<400> SEQUENCE: 40

Ala Ile Gln Leu Thr Gln Ser Pro Ser Ser Leu Ser Ala Ser Val Gly
1               5                   10                  15

Asp Arg Val Thr Ile Thr Cys Arg Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

-continued

<210> SEQ ID NO 41
<211> LENGTH: 657
<212> TYPE: DNA
<213> ORGANISM: Artificial Sequence
<220> FEATURE:
<223> OTHER INFORMATION: 10273 gL2 Light Chain Q1R nucl.

<400> SEQUENCE: 41

```
gccattcaac tgactcagtc cccatcctcc ctgtccgcat ccgtggggga tagagtcacc     60

atcacctgtc ggtcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaagcgta cggtggccgc tccctccgtg    360

ttcatcttcc caccctccga cgagcagctg aagtccggca ccgcctccgt cgtgtgcctg    420

ctgaacaact tctacccccg cgaggccaag gtgcagtgga aggtggacaa cgccctgcag    480

tccggcaact cccaggaatc cgtcaccgag caggactcca aggacagcac ctactccctg    540

tcctccaccc tgaccctgtc caaggccgac tacgagaagc acaaggtgta cgcctgcgaa    600

gtgacccacc agggcctgtc cagccccgtg accaagtcct tcaaccgggg cgagtgc       657
```

<210> SEQ ID NO 42
<211> LENGTH: 112
<212> TYPE: PRT
<213> ORGANISM: Artificial Sequence
<220> FEATURE:
<223> OTHER INFORMATION: 10273 gL2 VLQ1K

<400> SEQUENCE: 42

```
Ala Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110
```

<210> SEQ ID NO 43
<211> LENGTH: 336
<212> TYPE: DNA
<213> ORGANISM: Artificial Sequence
<220> FEATURE:
<223> OTHER INFORMATION: 10273 gL2 L Q1K nucl.

<400> SEQUENCE: 43

```
gccattcaac tgactcagtc cccatcctcc ctgtccgcat ccgtggggga tagagtcacc     60

atcacctgta aatcgagcca gtcagtgtac aacaacaacg acctggcctg gtatcagcag    120

aagccgggaa aggctcccaa gttgctgatc taccgggcct caacgctcgc gtcgggagtg    180
```

```
cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaag                              336


<210> SEQ ID NO 44
<211> LENGTH: 219
<212> TYPE: PRT
<213> ORGANISM: Artificial Sequence
<220> FEATURE:
<223> OTHER INFORMATION: 10273 gL2 Light Chain Q1K

<400> SEQUENCE: 44

Ala Ile Gln Leu Thr Gln Ser Pro Ser Ser Leu Ser Ala Ser Val Gly
1               5                   10                  15

Asp Arg Val Thr Ile Thr Cys Lys Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 45
<211> LENGTH: 657
<212> TYPE: DNA
<213> ORGANISM: Artificial Sequence
<220> FEATURE:
<223> OTHER INFORMATION: 10273 gL2 Light Chain Q1K nucl.

<400> SEQUENCE: 45

gccattcaac tgactcagtc cccatcctcc ctgtccgcat ccgtggggga tagagtcacc     60

atcacctgta aatcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300
```

```
tacaccttcg gcggagggac caaagtggaa atcaagcgta cggtggccgc tccctccgtg    360

ttcatcttcc caccctccga cgagcagctg aagtccggca ccgcctccgt cgtgtgcctg    420

ctgaacaact tctacccccg cgaggccaag gtgcagtgga aggtggacaa cgccctgcag    480

tccggcaact cccaggaatc cgtcaccgag caggactcca aggacagcac ctactccctg    540

tcctccaccc tgaccctgtc caaggccgac tacgagaagc acaaggtgta cgcctgcgaa    600

gtgacccacc agggcctgtc cagccccgtg accaagtcct tcaaccgggg cgagtgc       657
```

```
<210> SEQ ID NO 46
<211> LENGTH: 112
<212> TYPE: PRT
<213> ORGANISM: Artificial Sequence
<220> FEATURE:
<223> OTHER INFORMATION: 10273 gL2 VL Q1H

<400> SEQUENCE: 46

Ala Ile Gln Leu Thr Gln Ser Pro Ser Ser Leu Ser Ala Ser Val Gly
1               5                   10                  15

Asp Arg Val Thr Ile Thr Cys His Ser Ser Gln Ser Val Tyr Asn Asn
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110
```

```
<210> SEQ ID NO 47
<211> LENGTH: 336
<212> TYPE: DNA
<213> ORGANISM: Artificial Sequence
<220> FEATURE:
<223> OTHER INFORMATION: 10273 gL2 VL Q1H nucl.

<400> SEQUENCE: 47

gccattcaac tgactcagtc cccatcctcc ctgtccgcat ccgtggggga tagagtcacc     60

atcacctgtc actcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaag                              336
```

```
<210> SEQ ID NO 48
<211> LENGTH: 219
<212> TYPE: PRT
<213> ORGANISM: Artificial Sequence
<220> FEATURE:
<223> OTHER INFORMATION: 1027 gL2 Light Chain Q1H

<400> SEQUENCE: 48

Ala Ile Gln Leu Thr Gln Ser Pro Ser Ser Leu Ser Ala Ser Val Gly
1               5                   10                  15

Asp Arg Val Thr Ile Thr Cys His Ser Ser Gln Ser Val Tyr Asn Asn
```

```
            20                  25                  30

Asn Asp Leu Ala Trp Tyr Gln Gln Lys Pro Gly Lys Ala Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Val Asp Thr Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 49
<211> LENGTH: 657
<212> TYPE: DNA
<213> ORGANISM: Artificial Sequence
<220> FEATURE:
<223> OTHER INFORMATION: 10273 gL2 Light Chain Q1H nucl.

<400> SEQUENCE: 49

gccattcaac tgactcagtc cccatcctcc ctgtccgcat ccgtgggga tagagtcacc      60

atcacctgtc actcgagcca gtcagtgtac aacaacaacg acctggcctg gtatcagcag    120

aagccgggaa aggctcccaa gttgctgatc taccgggcct caacgctcgc gtcgggagtg    180

cctagccgct tttccggttc cggatctggc accgacttca ctctcaccat ttcgagcctt    240

caaccggagg acttcgccac ttactactgc ctgggcggtt acgatgacga tgtggacacc    300

tacaccttcg gcggagggac caaagtggaa atcaagcgta cggtggccgc tccctccgtg    360

ttcatcttcc caccctccga cgagcagctg aagtccggca ccgcctccgt cgtgtgcctg    420

ctgaacaact tctacccccg cgaggccaag gtgcagtgga aggtggacaa cgccctgcag    480

tccggcaact cccaggaatc cgtcaccgag caggactcca aggacagcac ctactccctg    540

tcctccaccc tgaccctgtc caaggccgac tacgagaagc acaaggtgta cgcctgcgaa    600

gtgacccacc agggcctgtc cagccccgtg accaagtcct tcaaccgggg cgagtgc       657


<210> SEQ ID NO 50
<211> LENGTH: 128
<212> TYPE: PRT
<213> ORGANISM: Artificial Sequence
<220> FEATURE:
<223> OTHER INFORMATION: 10273 gH1 VH

<400> SEQUENCE: 50
```

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125
```

<210> SEQ ID NO 51
<211> LENGTH: 384
<212> TYPE: DNA
<213> ORGANISM: Artificial Sequence
<220> FEATURE:
<223> OTHER INFORMATION: 10273 gH1 VH nucl.

<400> SEQUENCE: 51

```
gaagtgcagc tcgtcgaatc cggaggtgga ctggtgcagc caggcggaag cctcaggttg     60

tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatggaccc ctggggtcaa    360

ggcaccactg tgactgtctc gagc                                           384
```

<210> SEQ ID NO 52
<211> LENGTH: 455
<212> TYPE: PRT
<213> ORGANISM: Artificial Sequence
<220> FEATURE:
<223> OTHER INFORMATION: 10273 gH1 Heavy Chain

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110
```

```
Tyr Gly Met Asp Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 53
<211> LENGTH: 1365
<212> TYPE: DNA
<213> ORGANISM: Artificial Sequence
<220> FEATURE:
<223> OTHER INFORMATION: 10273 gH1 Heavy chain nucl.

<400> SEQUENCE: 53
gaagtgcagc tcgtcgaatc cggaggtgga ctggtgcagc caggcggaag cctcaggttg 60

```
tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatggaccc ctggggtcaa    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag   1200

accaccccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

<210> SEQ ID NO 54
<211> LENGTH: 128
<212> TYPE: PRT
<213> ORGANISM: Artificial Sequence
<220> FEATURE:
<223> OTHER INFORMATION: 10273 gH1 VH D19N

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125
```

<210> SEQ ID NO 55
<211> LENGTH: 384
<212> TYPE: DNA
<213> ORGANISM: Artificial Sequence
<220> FEATURE:
<223> OTHER INFORMATION: 10273 gH1 VH D19N nucl.

<400> SEQUENCE: 55
gaagtgcagc tcgtcgaatc cggaggtgga ctggtgcagc caggcggaag cctcaggttg 60
tcctgcgcgg tgtcagggtt cagcctgtcg tcatacggaa tgtcctgggt cagacaggcc 120
cctggcaaag gccttgagtg gattgggatc atctcctcct ccgggtccac ctactacgcc 180
tcttgggcca agggacggtt caccatttcg aaggacagct cgaagaacac cgtgtatctg 240
cagatgaaca gcctgcgggc agaggacacc gctgtgtact actgtgcccg cgatcacatc 300
taccgctatg acgactacgg cgattacccg acttactacg gaatgaaccc ctggggtcaa 360
ggcaccactg tgactgtctc gagc 384

<210> SEQ ID NO 56
<211> LENGTH: 455
<212> TYPE: PRT
<213> ORGANISM: Artificial Sequence
<220> FEATURE:
<223> OTHER INFORMATION: 10273 gH1 Heavy Chain D19N

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys

```
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 57
<211> LENGTH: 1365
<212> TYPE: DNA
<213> ORGANISM: Artificial Sequence
<220> FEATURE:
<223> OTHER INFORMATION: 10273 gH1 Heavy Chain D19N nucl.

<400> SEQUENCE: 57

```
gaagtgcagc tcgtcgaatc cggaggtgga ctggtgcagc caggcggaag cctcaggttg     60

tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatgaaccc ctggggtcaa    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840
```

```
gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

tacccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

```
<210> SEQ ID NO 58
<211> LENGTH: 128
<212> TYPE: PRT
<213> ORGANISM: Artificial Sequence
<220> FEATURE:
<223> OTHER INFORMATION: 10273 gH1 VH D19E

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Glu Pro Trp Gly Gln Gly Thr Thr Val Thr Val Ser Ser
        115                 120                 125
```

```
<210> SEQ ID NO 59
<211> LENGTH: 384
<212> TYPE: DNA
<213> ORGANISM: Artificial Sequence
<220> FEATURE:
<223> OTHER INFORMATION: 10273 gH1 VH D19E nucl.

<400> SEQUENCE: 59

gaagtgcagc tcgtcgaatc cggaggtgga ctggtgcagc caggcggaag cctcaggttg     60

tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatggagcc ctggggtcaa    360

ggcaccactg tgactgtctc gagc                                           384
```

```
<210> SEQ ID NO 60
<211> LENGTH: 455
```

<212> TYPE: PRT
<213> ORGANISM: Artificial Sequence
<220> FEATURE:
<223> OTHER INFORMATION: 10273 gH1 Heavy Chain D19E

<400> SEQUENCE: 60

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Glu Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380
```

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 61
<211> LENGTH: 1365
<212> TYPE: DNA
<213> ORGANISM: Artificial Sequence
<220> FEATURE:
<223> OTHER INFORMATION: 10273 gH1 Heavy Chain D19E nucl.

<400> SEQUENCE: 61

```
gaagtgcagc tcgtcgaatc cggaggtgga ctggtgcagc caggcggaag cctcaggttg     60

tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatggagcc ctggggtcaa    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

tacccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                  1365
```

<210> SEQ ID NO 62
<211> LENGTH: 128
<212> TYPE: PRT
<213> ORGANISM: Artificial Sequence
<220> FEATURE:
<223> OTHER INFORMATION: 10273 gH4 VH

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125
```

<210> SEQ ID NO 63
<211> LENGTH: 384
<212> TYPE: DNA
<213> ORGANISM: Artificial Sequence
<220> FEATURE:
<223> OTHER INFORMATION: 10273 gH4 VH nucl.

<400> SEQUENCE: 63

```
gaagtgcagc tcgtcgaatc cggtggcgga ctggtgcagc ccggaggatc cctgaggctt      60

tcttgtgccg cctccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggactacccg acctactacg gaatggaccc ttggggacag     360

ggcaccactg tgactgtctc gagc                                            384
```

<210> SEQ ID NO 64
<211> LENGTH: 455
<212> TYPE: PRT
<213> ORGANISM: Artificial Sequence
<220> FEATURE:
<223> OTHER INFORMATION: 10273 gH4 Heavy Chain

<400> SEQUENCE: 64

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
```

```
            100                 105                 110

Tyr Gly Met Asp Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 65
<211> LENGTH: 1365
<212> TYPE: DNA
<213> ORGANISM: Artificial Sequence
<220> FEATURE:
<223> OTHER INFORMATION: 10273 gH4 Heavy Chain nucl.

<400> SEQUENCE: 65
gaagtgcagc tcgtcgaatc cggtggcgga ctggtgcagc ccggaggatc cctgaggctt     60

```
tcttgtgccg cctccgggtt ctccctgagc tcctacggga tgtcgtgggt cagacaagca    120
ccaggaaagg gtctggagtg gatcggaatt atctcctcct cgggctcaac ctactacgcg    180
tcatgggcca agggccggtt caccattagc aaggacagct ccaagaacac tgtgtacctc    240
caaatgaact cgctgcgggc tgaggacacc gccgtgtact actgcgcccg cgatcacatc    300
taccgctatg atgactacgg ggactacccg acctactacg gaatggaccc ttggggacag    360
ggcaccactg tgactgtctc gagcgcttct acaaagggcc cctccgtgtt ccctctggcc    420
ccttgctccc ggtccacctc cgagtctacc gccgctctgg gctgcctggt caaggactac    480
ttccccgagc ccgtgacagt gtcctggaac tctggcgccc tgacctccgg cgtgcacacc    540
ttccctgccg tgctgcagtc ctccggcctg tactccctgt cctccgtcgt gaccgtgccc    600
tcctccagcc tgggcaccaa gacctacacc tgtaacgtgg accacaagcc ctccaacacc    660
aaggtggaca agcgggtgga atctaagtac ggccctccct gccccccctg ccctgcccct    720
gaatttctgg gcggaccttc cgtgttcctg ttccccccaa agcccaagga caccctgatg    780
atctcccgga cccccgaagt gacctgcgtg gtggtggacg tgtcccagga agatcccgag    840
gtccagttca attggtacgt ggacggcgtg gaagtgcaca atgccaagac caagcccaga    900
gaggaacagt tcaactccac ctaccgggtg gtgtccgtgc tgaccgtgct gcaccaggac    960
tggctgaacg gcaaagagta caagtgcaag gtgtccaaca agggcctgcc ctccagcatc   1020
gaaaagacca tctccaaggc caagggccag ccccgcgagc cccaggtgta caccctgccc   1080
cctagccagg aagagatgac caagaaccag gtgtccctga cctgtctggt caagggcttc   1140
tacccctccg acattgccgt ggaatgggag tccaacggcc agcccgagaa caactacaag   1200
accacccccc ctgtgctgga cagcgacggc tccttcttcc tgtactctcg gctgaccgtg   1260
gacaagtccc ggtggcagga aggcaacgtc ttctcctgct ccgtgatgca cgaggccctg   1320
cacaaccact acacccagaa gtccctgtcc ctgagcctgg gcaag                   1365
```

<210> SEQ ID NO 66
<211> LENGTH: 128
<212> TYPE: PRT
<213> ORGANISM: Artificial Sequence
<220> FEATURE:
<223> OTHER INFORMATION: 10273 gH4 VH D19N

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125
```

<210> SEQ ID NO 67
<211> LENGTH: 384
<212> TYPE: DNA
<213> ORGANISM: Artificial Sequence
<220> FEATURE:
<223> OTHER INFORMATION: 10273 gH4 VH D19N nucl.

<400> SEQUENCE: 67
gaagtgcagc tcgtcgaatc cggaggtgga ctggtgcagc caggcggaag cctcaggttg 60
tcctgcgcgg cttcagggtt cagcctgtcg tcatacggaa tgtcctgggt cagacaggcc 120
cctggcaaag gccttgagtg gattgggatc atctcctcct ccgggtccac ctactacgcc 180
tcttgggcca agggacggtt caccatttcg aaggacagct cgaagaacac cgtgtatctg 240
cagatgaaca gcctgcgggc agaggacacc gctgtgtact actgtgcccg cgatcacatc 300
taccgctatg acgactacgg cgattacccg acttactacg gaatgaaccc ctggggtcaa 360
ggcaccactg tgactgtctc gagc 384

<210> SEQ ID NO 68
<211> LENGTH: 455
<212> TYPE: PRT
<213> ORGANISM: Artificial Sequence
<220> FEATURE:
<223> OTHER INFORMATION: 10273 gH4 Heavy Chain D19N

<400> SEQUENCE: 68

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Thr Tyr
100 105 110

Tyr Gly Met Asn Pro Trp Gly Gln Gly Thr Thr Val Thr Val Ser Ser
115 120 125

Ala Ser Thr Lys Gly Pro Ser Val Phe Pro Leu Ala Pro Cys Ser Arg
130 135 140

Ser Thr Ser Glu Ser Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Lys Thr
195 200 205

Tyr Thr Cys Asn Val Asp His Lys Pro Ser Asn Thr Lys Val Asp Lys
210 215 220

Arg Val Glu Ser Lys Tyr Gly Pro Pro Cys Pro Pro Cys Pro Ala Pro
225 230 235 240

```
Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 69
<211> LENGTH: 1365
<212> TYPE: DNA
<213> ORGANISM: Artificial Sequence
<220> FEATURE:
<223> OTHER INFORMATION: 10273 gH4 Heavy Chain D19N nucl.

<400> SEQUENCE: 69

```
gaagtgcagc tcgtcgaatc cggaggtgga ctggtgcagc caggcggaag cctcaggttg     60

tcctgcgcgg cttcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg aaggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatgaaccc ctggggtcaa    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840
```

gtccagttca attggtacgt ggacggcgtg gaagtgcaca atgccaagac caagcccaga 900
gaggaacagt tcaactccac ctaccgggtg gtgtccgtgc tgaccgtgct gcaccaggac 960
tggctgaacg gcaaagagta caagtgcaag gtgtccaaca agggcctgcc ctccagcatc 1020
gaaaagacca tctccaaggc caagggccag ccccgcgagc cccaggtgta caccctgccc 1080
cctagccagg aagagatgac caagaaccag gtgtccctga cctgtctggt caagggcttc 1140
tacccctccg acattgccgt ggaatgggag tccaacggcc agcccgagaa caactacaag 1200
accacccccc ctgtgctgga cagcgacggc tccttcttcc tgtactctcg gctgaccgtg 1260
gacaagtccc ggtggcagga aggcaacgtc ttctcctgct ccgtgatgca cgaggccctg 1320
cacaaccact acacccagaa gtccctgtcc ctgagcctgg gcaag 1365

<210> SEQ ID NO 70
<211> LENGTH: 128
<212> TYPE: PRT
<213> ORGANISM: Artificial Sequence
<220> FEATURE:
<223> OTHER INFORMATION: 10273 gH5 VH

<400> SEQUENCE: 70

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Val
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Thr Tyr
100 105 110

Tyr Gly Met Asp Pro Trp Gly Gln Gly Thr Thr Val Thr Val Ser Ser
115 120 125

<210> SEQ ID NO 71
<211> LENGTH: 384
<212> TYPE: DNA
<213> ORGANISM: Artificial Sequence
<220> FEATURE:
<223> OTHER INFORMATION: 10273 gH5 VH nucl.

<400> SEQUENCE: 71
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg ggtcggaatt atctcctcct cgggctcaac ctactacgcg 180
tcatgggcca agggccggtt caccattagc aaggacagct ccaagaacac tgtgtacctc 240
caaatgaact cgctgcgggc tgaggacacc gccgtgtact actgcgcccg cgatcacatc 300
taccgctatg atgactacgg ggactacccg acctactacg gaatggaccc ttggggacag 360
ggcaccactg tgactgtctc gagc 384

<210> SEQ ID NO 72

```
<211> LENGTH: 455
<212> TYPE: PRT
<213> ORGANISM: Artificial Sequence
<220> FEATURE:
<223> OTHER INFORMATION: 10273 gH5 Heavy Chain

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Val
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380
```

```
Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 73
<211> LENGTH: 1365
<212> TYPE: DNA
<213> ORGANISM: Artificial Sequence
<220> FEATURE:
<223> OTHER INFORMATION: 10273 gH5 Heavy Chain nucl.

<400> SEQUENCE: 73

```
gaagtgcagc tcgtcgaatc cggtggcgga ctggtgcagc ccggaggatc cctgaggctt      60
tcttgtgccg tgtccgggtt ctccctgagc tcctacggga tgtcgtgggt cagacaagca     120
ccaggaaagg gtctggagtg ggtcggaatt atctcctcct cgggctcaac ctactacgcg     180
tcatgggcca agggccggtt caccattagc aaggacagct ccaagaacac tgtgtacctc     240
caaatgaact cgctgcgggc tgaggacacc gccgtgtact actgcgcccg cgatcacatc     300
taccgctatg atgactacgg ggactacccg acctactacg gaatggaccc ttggggacag     360
ggcaccactg tgactgtctc gagcgcttct acaaagggcc cctccgtgtt ccctctggcc     420
ccttgctccc ggtccacctc cgagtctacc gccgctctgg gctgcctggt caaggactac     480
ttccccgagc ccgtgacagt gtcctggaac tctggcgccc tgacctccgg cgtgcacacc     540
ttccctgccg tgctgcagtc ctccggcctg tactccctgt cctccgtcgt gaccgtgccc     600
tcctccagcc tgggcaccaa gacctacacc tgtaacgtgg accacaagcc ctccaacacc     660
aaggtggaca agcgggtgga atctaagtac ggccctccct gccccccctg ccctgcccct     720
gaatttctgg gcggaccttc cgtgttcctg ttccccccaa agcccaagga caccctgatg     780
atctcccgga cccccgaagt gacctgcgtg gtggtggacg tgtcccagga agatcccgag     840
gtccagttca attggtacgt ggacggcgtg gaagtgcaca atgccaagac caagcccaga     900
gaggaacagt tcaactccac ctaccgggtg gtgtccgtgc tgaccgtgct gcaccaggac     960
tggctgaacg gcaaagagta caagtgcaag gtgtccaaca agggcctgcc ctccagcatc    1020
gaaaagacca tctccaaggc caagggccag ccccgcgagc cccaggtgta caccctgccc    1080
cctagccagg aagagatgac caagaaccag gtgtccctga cctgtctggt caagggcttc    1140
tacccctccg acattgccgt ggaatgggag tccaacggcc agcccgagaa caactacaag    1200
accacccccc ctgtgctgga cagcgacggc tccttcttcc tgtactctcg gctgaccgtg    1260
gacaagtccc ggtggcagga aggcaacgtc ttctcctgct ccgtgatgca cgaggccctg    1320
cacaaccact acacccagaa gtccctgtcc ctgagcctgg gcaag                    1365
```

<210> SEQ ID NO 74
<211> LENGTH: 128
<212> TYPE: PRT
<213> ORGANISM: Artificial Sequence
<220> FEATURE:
<223> OTHER INFORMATION: 10273 gH5 VH D19N

<400> SEQUENCE: 74

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Val
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125
```

<210> SEQ ID NO 75
<211> LENGTH: 384
<212> TYPE: DNA
<213> ORGANISM: Artificial Sequence
<220> FEATURE:
<223> OTHER INFORMATION: 10273 gH5 VH D19N nucl.

<400> SEQUENCE: 75

```
gaagtgcagc tcgtcgaatc cggaggtgga ctggtgcagc caggcggaag cctcaggttg      60

tcctgcgcgg tgtcagggtt cagcctgtcg tcatacggaa tgtcctgggt cagacaggcc     120

cctggcaaag gccttgagtg ggtcgggatc atctcctcct ccgggtccac ctactacgcc     180

tcttgggcca agggacggtt caccatttcg aaggacagct cgaagaacac cgtgtatctg     240

cagatgaaca gcctgcgggc agaggacacc gctgtgtact actgtgcccg cgatcacatc     300

taccgctatg acgactacgg cgattacccg acttactacg gaatgaaccc ctggggtcaa     360

ggcaccactg tgactgtctc gagc                                            384
```

<210> SEQ ID NO 76
<211> LENGTH: 455
<212> TYPE: PRT
<213> ORGANISM: Artificial Sequence
<220> FEATURE:
<223> OTHER INFORMATION: 10273 gH5 Heavy Chain D19N

<400> SEQUENCE: 76

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Val
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95
```

```
Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 77
<211> LENGTH: 1365
<212> TYPE: DNA
<213> ORGANISM: Artificial Sequence
<220> FEATURE:
<223> OTHER INFORMATION: 10273 gH5 Heavy Chain D19N nucl.

<400> SEQUENCE: 77

```
gaagtgcagc tcgtcgaatc cggaggtgga ctggtgcagc caggcggaag cctcaggttg     60
tcctgcgcgg tgtcagggtt cagcctgtcg tcatacggaa tgtcctgggt cagacaggcc    120
cctggcaaag gccttgagtg ggtcgggatc atctcctcct ccgggtccac ctactacgcc    180
tcttgggcca agggacggtt caccatttcg aaggacagct cgaagaacac cgtgtatctg    240
cagatgaaca gcctgcgggc agaggacacc gctgtgtact actgtgcccg cgatcacatc    300
taccgctatg acgactacgg cgattacccg acttactacg gaatgaaccc ctggggtcaa    360
ggcaccactg tgactgtctc gagcgcttct acaaagggcc cctccgtgtt ccctctggcc    420
ccttgctccc ggtccacctc cgagtctacc gccgctctgg gctgcctggt caaggactac    480
ttccccgagc ccgtgacagt gtcctggaac tctggcgccc tgacctccgg cgtgcacacc    540
ttccctgccg tgctgcagtc ctccggcctg tactccctgt cctccgtcgt gaccgtgccc    600
tcctccagcc tgggcaccaa gacctacacc tgtaacgtgg accacaagcc ctccaacacc    660
aaggtggaca agcgggtgga atctaagtac ggccctccct gccccccctg ccctgcccct    720
gaatttctgg gcggaccttc cgtgttcctg ttccccccaa agcccaagga caccctgatg    780
atctcccgga cccccgaagt gacctgcgtg gtggtggacg tgtcccagga agatcccgag    840
gtccagttca attggtacgt ggacggcgtg gaagtgcaca atgccaagac caagcccaga    900
gaggaacagt tcaactccac ctaccgggtg gtgtccgtgc tgaccgtgct gcaccaggac    960
tggctgaacg gcaaagagta caagtgcaag gtgtccaaca agggcctgcc ctccagcatc   1020
gaaaagacca tctccaaggc caagggccag ccccgcgagc cccaggtgta caccctgccc   1080
cctagccagg aagagatgac caagaaccag gtgtccctga cctgtctggt caagggcttc   1140
tacccctccg acattgccgt ggaatgggag tccaacggcc agcccgagaa caactacaag   1200
accacccccc ctgtgctgga cagcgacggc tccttcttcc tgtactctcg gctgaccgtg   1260
gacaagtccc ggtggcagga aggcaacgtc ttctcctgct ccgtgatgca cgaggccctg   1320
cacaaccact acacccagaa gtccctgtcc ctgagcctgg gcaag                   1365
```

```
<210> SEQ ID NO 78
<211> LENGTH: 128
<212> TYPE: PRT
<213> ORGANISM: Artificial Sequence
<220> FEATURE:
<223> OTHER INFORMATION: 10273 gH8 VH

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125
```

<210> SEQ ID NO 79
<211> LENGTH: 384
<212> TYPE: DNA
<213> ORGANISM: Artificial Sequence
<220> FEATURE:
<223> OTHER INFORMATION: 10273 gH8 VH nucl.

<400> SEQUENCE: 79
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc cgggacagct ccaagaacac tgtgtacctc 240
caaatgaact cgctgcgggc tgaggacacc gccgtgtact actgcgcccg cgatcacatc 300
taccgctatg atgactacgg ggactacccg acctactacg gaatggaccc ttggggacag 360
ggcaccactg tgactgtctc gagc 384

<210> SEQ ID NO 80
<211> LENGTH: 455
<212> TYPE: PRT
<213> ORGANISM: Artificial Sequence
<220> FEATURE:
<223> OTHER INFORMATION: 10273 gH8 Heavy Chain

<400> SEQUENCE: 80

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Arg Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Thr Tyr
100 105 110

Tyr Gly Met Asp Pro Trp Gly Gln Gly Thr Thr Val Thr Val Ser Ser
115 120 125

Ala Ser Thr Lys Gly Pro Ser Val Phe Pro Leu Ala Pro Cys Ser Arg
130 135 140

Ser Thr Ser Glu Ser Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Lys Thr
195 200 205

Tyr Thr Cys Asn Val Asp His Lys Pro Ser Asn Thr Lys Val Asp Lys
210 215 220

Arg Val Glu Ser Lys Tyr Gly Pro Pro Cys Pro Pro Cys Pro Ala Pro
225 230 235 240

```
Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 81
<211> LENGTH: 1365
<212> TYPE: DNA
<213> ORGANISM: Artificial Sequence
<220> FEATURE:
<223> OTHER INFORMATION: 10273 gH8 Heavy Chain nucl.

<400> SEQUENCE: 81

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc cgggacagct ccaagaacac tgtgtacctc    240

caaatgaact cgctgcgggc tgaggacacc gccgtgtact actgcgcccg cgatcacatc    300

taccgctatg atgactacgg ggactacccg acctactacg gaatggaccc ttggggacag    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780
```

-continued

```
atctcccgga cccccgaagt gacctgcgtg gtggtggacg tgtcccagga agatcccgag     840

gtccagttca attggtacgt ggacggcgtg gaagtgcaca atgccaagac caagcccaga     900

gaggaacagt tcaactccac ctaccgggtg gtgtccgtgc tgaccgtgct gcaccaggac     960

tggctgaacg gcaaagagta caagtgcaag gtgtccaaca agggcctgcc ctccagcatc    1020

gaaaagacca tctccaaggc caagggccag ccccgcgagc cccaggtgta caccctgccc    1080

cctagccagg aagagatgac caagaaccag gtgtccctga cctgtctggt caagggcttc    1140

tacccctccg acattgccgt ggaatgggag tccaacggcc agcccgagaa caactacaag    1200

accacccccc ctgtgctgga cagcgacggc tccttcttcc tgtactctcg gctgaccgtg    1260

gacaagtccc ggtggcagga aggcaacgtc ttctcctgct ccgtgatgca cgaggccctg    1320

cacaaccact acacccagaa gtccctgtcc ctgagcctgg gcaag                    1365
```

<210> SEQ ID NO 82
<211> LENGTH: 128
<212> TYPE: PRT
<213> ORGANISM: Artificial Sequence
<220> FEATURE:
<223> OTHER INFORMATION: 10273 gH VH D19N

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125
```

<210> SEQ ID NO 83
<211> LENGTH: 384
<212> TYPE: DNA
<213> ORGANISM: Artificial Sequence
<220> FEATURE:
<223> OTHER INFORMATION: 10273 gH8 VH D19N nucl.

<400> SEQUENCE: 83

```
gaagtgcagc tcgtcgaatc cggaggtgga ctggtgcagc caggcggaag cctcaggttg      60

tcctgcgcgg tgtcagggtt cagcctgtcg tcatacggaa tgtcctgggt cagacaggcc     120

cctggcaaag gccttgagtg gattgggatc atctcctcct ccgggtccac ctactacgcc     180

tcttgggcca agggacggtt caccatttcg cgggacagct cgaagaacac cgtgtatctg     240

cagatgaaca gcctgcgggc agaggacacc gctgtgtact actgtgcccg cgatcacatc     300

taccgctatg acgactacgg cgattacccg acttactacg gaatgaaccc ctggggtcaa     360

ggcaccactg tgactgtctc gagc                                           384
```

```
<210> SEQ ID NO 84
<211> LENGTH: 455
<212> TYPE: PRT
<213> ORGANISM: Artificial Sequence
<220> FEATURE:
<223> OTHER INFORMATION: 10273 gH8 Heavy Chain D19N

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Arg Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
```

```
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 85
<211> LENGTH: 1365
<212> TYPE: DNA
<213> ORGANISM: Artificial Sequence
<220> FEATURE:
<223> OTHER INFORMATION: 10273 gH Heavy Chain D19N nucl.

<400> SEQUENCE: 85

```
gaagtgcagc tcgtcgaatc cggaggtgga ctggtgcagc caggcggaag cctcaggttg     60

tcctgcgcgg tgtcagggtt cagcctgtcg tcatacggaa tgtcctgggt cagacaggcc    120

cctggcaaag gccttgagtg gattgggatc atctcctcct ccgggtccac ctactacgcc    180

tcttgggcca agggacggtt caccatttcg cgggacagct cgaagaacac cgtgtatctg    240

cagatgaaca gcctgcgggc agaggacacc gctgtgtact actgtgcccg cgatcacatc    300

taccgctatg acgactacgg cgattacccg acttactacg gaatgaaccc ctggggtcaa    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

<210> SEQ ID NO 86
<211> LENGTH: 128
<212> TYPE: PRT
<213> ORGANISM: Artificial Sequence
<220> FEATURE:

<223> OTHER INFORMATION: 10273 gH10 VH nucl.

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125
```

<210> SEQ ID NO 87
<211> LENGTH: 384
<212> TYPE: DNA
<213> ORGANISM: Artificial Sequence
<220> FEATURE:
<223> OTHER INFORMATION: 10273 gH10 VH nucl.

<400> SEQUENCE: 87

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tttgtacctc    240

caaatgaact cgctgcgggc tgaggacacc gccgtgtact actgcgcccg cgatcacatc    300

taccgctatg atgactacgg ggactacccg acctactacg gaatggaccc ttggggacag    360

ggcaccactg tgactgtctc gagc                                           384
```

<210> SEQ ID NO 88
<211> LENGTH: 455
<212> TYPE: PRT
<213> ORGANISM: Artificial Sequence
<220> FEATURE:
<223> OTHER INFORMATION: 10273 gH10 Heavy Chain

<400> SEQUENCE: 88

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95
```

```
Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 89
<211> LENGTH: 1365
<212> TYPE: DNA
<213> ORGANISM: Artificial Sequence
<220> FEATURE:
<223> OTHER INFORMATION: 10273 gH10 Hevy Chain nucl.

<400> SEQUENCE: 89

-continued

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tttgtacctc    240

caaatgaact cgctgcgggc tgaggacacc gccgtgtact actgcgcccg cgatcacatc    300

taccgctatg atgactacgg ggactacccg acctactacg gaatggaccc ttggggacag    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                  1365
```

<210> SEQ ID NO 90
<211> LENGTH: 128
<212> TYPE: PRT
<213> ORGANISM: Artificial Sequence
<220> FEATURE:
<223> OTHER INFORMATION: 10273 gH10 VH D19N

<400> SEQUENCE: 90

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
```

115 120 125

<210> SEQ ID NO 91
<211> LENGTH: 384
<212> TYPE: DNA
<213> ORGANISM: Artificial Sequence
<220> FEATURE:
<223> OTHER INFORMATION: 10273 gH10 VH D19N nucl.

<400> SEQUENCE: 91
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc aaggacagct ccaagaacac tttgtacctc 240
caaatgaact cgctgcgggc tgaggacacc gccgtgtact actgcgcccg cgatcacatc 300
taccgctatg atgactacgg ggactacccg acctactacg gaatgaaccc ttggggacag 360
ggcaccactg tgactgtctc gagc 384

<210> SEQ ID NO 92
<211> LENGTH: 455
<212> TYPE: PRT
<213> ORGANISM: Artificial Sequence
<220> FEATURE:
<223> OTHER INFORMATION: 10273 gH10 Heavy Chain D19N

<400> SEQUENCE: 92

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Leu Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Thr Tyr
100 105 110

Tyr Gly Met Asn Pro Trp Gly Gln Gly Thr Thr Val Thr Val Ser Ser
115 120 125

Ala Ser Thr Lys Gly Pro Ser Val Phe Pro Leu Ala Pro Cys Ser Arg
130 135 140

Ser Thr Ser Glu Ser Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Lys Thr
195 200 205

Tyr Thr Cys Asn Val Asp His Lys Pro Ser Asn Thr Lys Val Asp Lys
210 215 220

Arg Val Glu Ser Lys Tyr Gly Pro Pro Cys Pro Pro Cys Pro Ala Pro

-continued

```
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 93
<211> LENGTH: 1365
<212> TYPE: DNA
<213> ORGANISM: Artificial Sequence
<220> FEATURE:
<223> OTHER INFORMATION: 10273 gH10 Heavy Chain D19N nucl.

<400> SEQUENCE: 93

```
gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tttgtacctc     240

caaatgaact cgctgcgggc tgaggacacc gccgtgtact actgcgcccg cgatcacatc     300

taccgctatg atgactacgg ggactacccg acctactacg gaatgaaccc ttggggacag     360

ggcaccactg tgactgtctc gagcgcttct acaaagggcc cctccgtgtt ccctctggcc     420

ccttgctccc ggtccacctc cgagtctacc gccgctctgg gctgcctggt caaggactac     480

ttccccgagc ccgtgacagt gtcctggaac tctggcgccc tgacctccgg cgtgcacacc     540

ttccctgccg tgctgcagtc ctccggcctg tactccctgt cctccgtcgt gaccgtgccc     600

tcctccagcc tgggcaccaa gacctacacc tgtaacgtgg accacaagcc ctccaacacc     660

aaggtggaca agcgggtgga atctaagtac ggccctccct gccccccctg ccctgcccct     720

gaatttctgg gcggaccttc cgtgttcctg ttccccccaa agcccaagga caccctgatg     780
```

```
atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag  1200

accaccccccc ctgtgctgga cagcgacggc tccttcttcc tgtactctcg gctgaccgtg  1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

<210> SEQ ID NO 94
<211> LENGTH: 128
<212> TYPE: PRT
<213> ORGANISM: Artificial Sequence
<220> FEATURE:
<223> OTHER INFORMATION: 10273 gH11 VH

<400> SEQUENCE: 94

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125
```

<210> SEQ ID NO 95
<211> LENGTH: 384
<212> TYPE: DNA
<213> ORGANISM: Artificial Sequence
<220> FEATURE:
<223> OTHER INFORMATION: 10273 gH11 VH nucl.

<400> SEQUENCE: 95

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc cgggacaact ccaagaacac tgtgtacctc    240

caaatgaact cgctgcgggc tgaggacacc gccgtgtact actgcgcccg cgatcacatc    300

taccgctatg atgactacgg ggactacccg acctactacg gaatggaccc ttggggacag    360

ggcaccactg tgactgtctc gagc                                           384
```

<210> SEQ ID NO 96
<211> LENGTH: 455
<212> TYPE: PRT
<213> ORGANISM: Artificial Sequence
<220> FEATURE:
<223> OTHER INFORMATION: 10273 gH11 Heavy Chain

<400> SEQUENCE: 96

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Tyr Gly Met Asp Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365
```

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455


<210> SEQ ID NO 97
<211> LENGTH: 1365
<212> TYPE: DNA
<213> ORGANISM: Artificial Sequence
<220> FEATURE:
<223> OTHER INFORMATION: 10273 gH11 Heavy Chain nucl.

<400> SEQUENCE: 97

gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc cgggacaact ccaagaacac tgtgtacctc     240

caaatgaact cgctgcgggc tgaggacacc gccgtgtact actgcgcccg cgatcacatc     300

taccgctatg atgactacgg ggactacccg acctactacg gaatggaccc ttggggacag     360

ggcaccactg tgactgtctc gagcgcttct acaaagggcc cctccgtgtt ccctctggcc     420

ccttgctccc ggtccacctc cgagtctacc gccgctctgg gctgcctggt caaggactac     480

ttccccgagc ccgtgacagt gtcctggaac tctggcgccc tgacctccgg cgtgcacacc     540

ttccctgccg tgctgcagtc ctccggcctg tactccctgt cctccgtcgt gaccgtgccc     600

tcctccagcc tgggcaccaa gacctacacc tgtaacgtgg accacaagcc ctccaacacc     660

aaggtggaca agcgggtgga atctaagtac ggccctccct gccccccctg ccctgcccct     720

gaatttctgg gcggaccttc cgtgttcctg ttccccccaa agcccaagga caccctgatg     780

atctcccgga cccccgaagt gacctgcgtg gtggtggacg tgtcccagga agatcccgag     840

gtccagttca attggtacgt ggacggcgtg gaagtgcaca atgccaagac caagcccaga     900

gaggaacagt tcaactccac ctaccgggtg gtgtccgtgc tgaccgtgct gcaccaggac     960

tggctgaacg gcaaagagta caagtgcaag gtgtccaaca agggcctgcc ctccagcatc    1020

gaaaagacca tctccaaggc caagggccag ccccgcgagc cccaggtgta caccctgccc    1080

cctagccagg aagagatgac caagaaccag gtgtccctga cctgtctggt caagggcttc    1140

taccccctccg acattgccgt ggaatgggag tccaacggcc agcccgagaa caactacaag    1200

accacccccc ctgtgctgga cagcgacggc tccttcttcc tgtactctcg gctgaccgtg    1260

gacaagtccc ggtggcagga aggcaacgtc ttctcctgct ccgtgatgca cgaggccctg    1320

cacaaccact acacccagaa gtccctgtcc ctgagcctgg gcaag                   1365


<210> SEQ ID NO 98
<211> LENGTH: 128
<212> TYPE: PRT
<213> ORGANISM: Artificial Sequence
```

<220> FEATURE:
<223> OTHER INFORMATION: 10273 gH11 VH D19N

<400> SEQUENCE: 98

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Arg Asp Asn Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Thr Tyr
100 105 110

Tyr Gly Met Asn Pro Trp Gly Gln Gly Thr Thr Val Thr Val Ser Ser
115 120 125

<210> SEQ ID NO 99
<211> LENGTH: 384
<212> TYPE: DNA
<213> ORGANISM: Artificial Sequence
<220> FEATURE:
<223> OTHER INFORMATION: 10273 gH11 VH D19N nucl.

<400> SEQUENCE: 99
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc cgggacaact ccaagaacac tgtgtacctc 240
caaatgaact cgctgcgggc tgaggacacc gccgtgtact actgcgcccg cgatcacatc 300
taccgctatg atgactacgg ggactacccg acctactacg gaatgaaccc ttggggacag 360
ggcaccactg tgactgtctc gagc 384

<210> SEQ ID NO 100
<211> LENGTH: 455
<212> TYPE: PRT
<213> ORGANISM: Artificial Sequence
<220> FEATURE:
<223> OTHER INFORMATION: 10273 gH 11 Heavy Chain D19N

<400> SEQUENCE: 100

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Arg Asp Asn Ser Lys Asn Thr Val Tyr Leu
65 70 75 80

Gln Met Asn Ser Leu Arg Ala Glu Asp Thr Ala Val Tyr Tyr Cys Ala

-continued

```
                85                  90                  95

Arg Asp His Ile Tyr Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 101
<211> LENGTH: 1365
<212> TYPE: DNA
<213> ORGANISM: Artificial Sequence
<220> FEATURE:
<223> OTHER INFORMATION: 10273 gH11 Heavy Chain D19N nucl.

<400> SEQUENCE: 101

```
gaagtgcagc tcgtcgaatc cggtggcgga ctggtgcagc ccggaggatc cctgaggctt      60
tcttgtgccg tgtccgggtt ctccctgagc tcctacggga tgtcgtgggt cagacaagca     120
ccaggaaagg gtctggagtg gatcggaatt atctcctcct cgggctcaac ctactacgcg     180
tcatgggcca agggccggtt caccattagc cgggacaact ccaagaacac tgtgtacctc     240
caaatgaact cgctgcgggc tgaggacacc gccgtgtact actgcgcccg cgatcacatc     300
taccgctatg atgactacgg ggactacccg acctactacg gaatgaaccc ttggggacag     360
ggcaccactg tgactgtctc gagcgcttct acaaagggcc cctccgtgtt ccctctggcc     420
ccttgctccc ggtccacctc cgagtctacc gccgctctgg gctgcctggt caaggactac     480
ttccccgagc ccgtgacagt gtcctggaac tctggcgccc tgacctccgg cgtgcacacc     540
ttccctgccg tgctgcagtc ctccggcctg tactccctgt cctccgtcgt gaccgtgccc     600
tcctccagcc tgggcaccaa gacctacacc tgtaacgtgg accacaagcc ctccaacacc     660
aaggtggaca agcgggtgga atctaagtac ggccctccct gccccccctg ccctgcccct     720
gaatttctgg gcggaccttc cgtgttcctg ttccccccaa agcccaagga caccctgatg     780
atctcccgga cccccgaagt gacctgcgtg gtggtggacg tgtcccagga agatcccgag     840
gtccagttca attggtacgt ggacggcgtg gaagtgcaca atgccaagac caagcccaga     900
gaggaacagt tcaactccac ctaccgggtg gtgtccgtgc tgaccgtgct gcaccaggac     960
tggctgaacg gcaaagagta caagtgcaag gtgtccaaca agggcctgcc ctccagcatc    1020
gaaaagacca tctccaaggc caagggccag ccccgcgagc cccaggtgta caccctgccc    1080
cctagccagg aagagatgac caagaaccag gtgtccctga cctgtctggt caagggcttc    1140
taccctccg acattgccgt ggaatgggag tccaacggcc agcccgagaa caactacaag    1200
accacccccc ctgtgctgga cagcgacggc tccttcttcc tgtactctcg gctgaccgtg    1260
gacaagtccc ggtggcagga aggcaacgtc ttctcctgct ccgtgatgca cgaggccctg    1320
cacaaccact acacccagaa gtccctgtcc ctgagcctgg gcaag                   1365
```

<210> SEQ ID NO 102
<211> LENGTH: 128
<212> TYPE: PRT
<213> ORGANISM: Artificial Sequence
<220> FEATURE:
<223> OTHER INFORMATION: 10273 gH1 VH Y4F D19N

<400> SEQUENCE: 102

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Phe Arg Tyr Asp Asp Tyr Gly Asp Tyr Pro Thr Tyr
            100                 105                 110
```

```
Tyr Gly Met Asn Pro Trp Gly Gln Gly Thr Thr Val Thr Val Ser Ser
        115                 120                 125
```

<210> SEQ ID NO 103
<211> LENGTH: 384
<212> TYPE: DNA
<213> ORGANISM: Artificial Sequence
<220> FEATURE:
<223> OTHER INFORMATION: 10273 gH1 VH Y4F D19N nucl.

<400> SEQUENCE: 103

```
gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

ttccgctatg atgactacgg ggactacccg acctactacg gaatgaaccc ttggggacag     360

ggcaccactg tgactgtctc gagc                                            384
```

<210> SEQ ID NO 104
<211> LENGTH: 455
<212> TYPE: PRT
<213> ORGANISM: Artificial Sequence
<220> FEATURE:
<223> OTHER INFORMATION: 10273 gH1 Heavy Chain Y4F D19N

<400> SEQUENCE: 104

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Phe Arg Tyr Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220
```

```
Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 105
<211> LENGTH: 1365
<212> TYPE: DNA
<213> ORGANISM: Artificial Sequence
<220> FEATURE:
<223> OTHER INFORMATION: 10273 gH1 Heavy Chain Y4F D19N nucl.

<400> SEQUENCE: 105

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tgtgtacctc    240

caaatgaact cgctgcgggc tgaggacacc gccgtgtact actgcgcccg cgatcacatc    300

ttccgctatg atgactacgg ggactacccg acctactacg gaatgaaccc ttggggacag    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720
```

gaatttctgg gcggaccttc cgtgttcctg ttccccccaa agcccaagga caccctgatg 780
atctcccgga cccccgaagt gacctgcgtg gtggtggacg tgtcccagga agatcccgag 840
gtccagttca attggtacgt ggacggcgtg gaagtgcaca atgccaagac caagcccaga 900
gaggaacagt tcaactccac ctaccgggtg gtgtccgtgc tgaccgtgct gcaccaggac 960
tggctgaacg gcaaagagta caagtgcaag gtgtccaaca agggcctgcc ctccagcatc 1020
gaaaagacca tctccaaggc caagggccag ccccgcgagc cccaggtgta caccctgccc 1080
cctagccagg aagagatgac caagaaccag gtgtccctga cctgtctggt caagggcttc 1140
tacccctccg acattgccgt ggaatgggag tccaacggcc agcccgagaa caactacaag 1200
accacccccc ctgtgctgga cagcgacggc tccttcttcc tgtactctcg gctgaccgtg 1260
gacaagtccc ggtggcagga aggcaacgtc ttctcctgct ccgtgatgca cgaggccctg 1320
cacaaccact acacccagaa gtccctgtcc ctgagcctgg gcaag 1365

<210> SEQ ID NO 106
<211> LENGTH: 128
<212> TYPE: PRT
<213> ORGANISM: Artificial Sequence
<220> FEATURE:
<223> OTHER INFORMATION: 10273 gH1 VH Y6F D19N

<400> SEQUENCE: 106

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Phe Asp Asp Tyr Gly Asp Tyr Pro Thr Tyr
100 105 110

Tyr Gly Met Asn Pro Trp Gly Gln Gly Thr Thr Val Thr Val Ser Ser
115 120 125

<210> SEQ ID NO 107
<211> LENGTH: 384
<212> TYPE: DNA
<213> ORGANISM: Artificial Sequence
<220> FEATURE:
<223> OTHER INFORMATION: 10273 gH1 VH Y6F D19N nucl.

<400> SEQUENCE: 107
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc aaggacagct ccaagaacac tgtgtacctc 240
caaatgaact cgctgcgggc tgaggacacc gccgtgtact actgcgcccg cgatcacatc 300
taccgctttg atgactacgg ggactacccg acctactacg gaatgaaccc ttggggacag 360
ggcaccactg tgactgtctc gagc 384

-continued

<210> SEQ ID NO 108
<211> LENGTH: 455
<212> TYPE: PRT
<213> ORGANISM: Artificial Sequence
<220> FEATURE:
<223> OTHER INFORMATION: 10273 gH1 Heavy Chain Y6F D19N

<400> SEQUENCE: 108

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Phe Asp Asp Tyr Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365
```

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 109
<211> LENGTH: 1365
<212> TYPE: DNA
<213> ORGANISM: Artificial Sequence
<220> FEATURE:
<223> OTHER INFORMATION: 10273 gH1 Heavy Chain  Y6F D19N nucl.

<400> SEQUENCE: 109

```
gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctttg atgactacgg ggactacccg acctactacg gaatgaaccc ttggggacag     360

ggcaccactg tgactgtctc gagcgcttct acaaagggcc cctccgtgtt ccctctggcc     420

ccttgctccc ggtccacctc cgagtctacc gccgctctgg gctgcctggt caaggactac     480

ttccccgagc ccgtgacagt gtcctggaac tctggcgccc tgacctccgg cgtgcacacc     540

ttccctgccg tgctgcagtc ctccggcctg tactccctgt cctccgtcgt gaccgtgccc     600

tcctccagcc tgggcaccaa gacctacacc tgtaacgtgg accacaagcc ctccaacacc     660

aaggtggaca agcgggtgga atctaagtac ggccctccct gccccccctg ccctgcccct     720

gaatttctgg gcggaccttc cgtgttcctg ttccccccaa agcccaagga caccctgatg     780

atctcccgga cccccgaagt gacctgcgtg gtggtggacg tgtcccagga agatcccgag     840

gtccagttca attggtacgt ggacggcgtg gaagtgcaca atgccaagac caagcccaga     900

gaggaacagt tcaactccac ctaccgggtg gtgtccgtgc tgaccgtgct gcaccaggac     960

tggctgaacg gcaaagagta caagtgcaag gtgtccaaca agggcctgcc ctccagcatc    1020

gaaaagacca tctccaaggc caagggccag ccccgcgagc cccaggtgta caccctgccc    1080

cctagccagg aagagatgac caagaaccag gtgtccctga cctgtctggt caagggcttc    1140

taccccctccg acattgccgt ggaatgggag tccaacggcc agcccgagaa caactacaag   1200

accacccccc ctgtgctgga cagcgacggc tccttcttcc tgtactctcg gctgaccgtg    1260

gacaagtccc ggtggcagga aggcaacgtc ttctcctgct ccgtgatgca cgaggccctg    1320

cacaaccact acacccagaa gtccctgtcc ctgagcctgg gcaag                   1365
```

<210> SEQ ID NO 110
<211> LENGTH: 128
<212> TYPE: PRT

<213> ORGANISM: Artificial Sequence
<220> FEATURE:
<223> OTHER INFORMATION: 10273 gH1 VH Y9F D19N

<400> SEQUENCE: 110

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Phe Gly Asp Tyr Pro Thr Tyr
100 105 110

Tyr Gly Met Asn Pro Trp Gly Gln Gly Thr Thr Val Thr Val Ser Ser
115 120 125

<210> SEQ ID NO 111
<211> LENGTH: 384
<212> TYPE: DNA
<213> ORGANISM: Artificial Sequence
<220> FEATURE:
<223> OTHER INFORMATION: 10273 gH1 VH Y9F D19N nucl.

<400> SEQUENCE: 111
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc aaggacagct ccaagaacac tgtgtacctc 240
caaatgaact cgctgcgggc tgaggacacc gccgtgtact actgcgcccg cgatcacatc 300
taccgctatg atgacttcgg ggactacccg acctactacg gaatgaaccc ttggggacag 360
ggcaccactg tgactgtctc gagc 384

<210> SEQ ID NO 112
<211> LENGTH: 455
<212> TYPE: PRT
<213> ORGANISM: Artificial Sequence
<220> FEATURE:
<223> OTHER INFORMATION: 10273 gH1 Heavy Chain Y9F D19N

<400> SEQUENCE: 112

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

```
Gln Met Asn Ser Leu Arg Ala Glu Asp Thr Ala Val Tyr Tyr Cys Ala
                85                  90                  95

Arg Asp His Ile Tyr Arg Tyr Asp Asp Phe Gly Asp Tyr Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 113
<211> LENGTH: 1365
<212> TYPE: DNA
<213> ORGANISM: Artificial Sequence
<220> FEATURE:
<223> OTHER INFORMATION: 10273 gH1 Heavy Chain Y9F D19N nucl.

<400> SEQUENCE: 113

```
gaagtgcagc tcgtcgaatc cggtggcgga ctggtgcagc ccggaggatc cctgaggctt     60
tcttgtgccg tgtccgggtt ctccctgagc tcctacggga tgtcgtgggt cagacaagca    120
ccaggaaagg gtctggagtg gatcggaatt atctcctcct cgggctcaac ctactacgcg    180
tcatgggcca agggccggtt caccattagc aaggacagct ccaagaacac tgtgtacctc    240
caaatgaact cgctgcgggc tgaggacacc gccgtgtact actgcgcccg cgatcacatc    300
taccgctatg atgacttcgg ggactacccg acctactacg gaatgaaccc ttggggacag    360
ggcaccactg tgactgtctc gagcgcttct acaaagggcc cctccgtgtt ccctctggcc    420
ccttgctccc ggtccacctc cgagtctacc gccgctctgg gctgcctggt caaggactac    480
ttccccgagc ccgtgacagt gtcctggaac tctggcgccc tgacctccgg cgtgcacacc    540
ttccctgccg tgctgcagtc ctccggcctg tactccctgt cctccgtcgt gaccgtgccc    600
tcctccagcc tgggcaccaa gacctacacc tgtaacgtgg accacaagcc ctccaacacc    660
aaggtggaca agcgggtgga atctaagtac ggccctccct gccccccctg ccctgcccct    720
gaatttctgg gcggaccttc cgtgttcctg ttccccccaa agcccaagga caccctgatg    780
atctcccgga cccccgaagt gacctgcgtg gtggtggacg tgtcccagga agatcccgag    840
gtccagttca attggtacgt ggacggcgtg gaagtgcaca atgccaagac caagcccaga    900
gaggaacagt tcaactccac ctaccgggtg gtgtccgtgc tgaccgtgct gcaccaggac    960
tggctgaacg gcaaagagta caagtgcaag gtgtccaaca agggcctgcc ctccagcatc   1020
gaaaagacca tctccaaggc caagggccag ccccgcgagc cccaggtgta caccctgccc   1080
cctagccagg aagagatgac caagaaccag gtgtccctga cctgtctggt caagggcttc   1140
tacccctccg acattgccgt ggaatgggag tccaacggcc agcccgagaa caactacaag   1200
accacccccc ctgtgctgga cagcgacggc tccttcttcc tgtactctcg gctgaccgtg   1260
gacaagtccc ggtggcagga aggcaacgtc ttctcctgct ccgtgatgca cgaggccctg   1320
cacaaccact acacccagaa gtccctgtcc ctgagcctgg gcaag                   1365
```

<210> SEQ ID NO 114
<211> LENGTH: 128
<212> TYPE: PRT
<213> ORGANISM: Artificial Sequence
<220> FEATURE:
<223> OTHER INFORMATION: 10273 gH1 VH Y12F D19N

<400> SEQUENCE: 114

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Phe Pro Thr Tyr
            100                 105                 110
```

```
Tyr Gly Met Asn Pro Trp Gly Gln Gly Thr Thr Val Thr Val Ser Ser
        115                 120                 125
```

<210> SEQ ID NO 115
<211> LENGTH: 384
<212> TYPE: DNA
<213> ORGANISM: Artificial Sequence
<220> FEATURE:
<223> OTHER INFORMATION: 10273 gH1 VH Y12F D19N nucl.

<400> SEQUENCE: 115

```
gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggacttcccg acctactacg gaatgaaccc ttggggacag     360

ggcaccactg tgactgtctc gagc                                            384
```

<210> SEQ ID NO 116
<211> LENGTH: 455
<212> TYPE: PRT
<213> ORGANISM: Artificial Sequence
<220> FEATURE:
<223> OTHER INFORMATION: 10273 gH1 Heavy Chain Y12F D19N

<400> SEQUENCE: 116

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Phe Pro Thr Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220
```

```
Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 117
<211> LENGTH: 1365
<212> TYPE: DNA
<213> ORGANISM: Artificial Sequence
<220> FEATURE:
<223> OTHER INFORMATION: 10273 gH1 Heavy Chain Y12F D19N nucl.

<400> SEQUENCE: 117

```
gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggacttcccg acctactacg gaatgaaccc ttggggacag     360

ggcaccactg tgactgtctc gagcgcttct acaaagggcc cctccgtgtt ccctctggcc     420

ccttgctccc ggtccacctc cgagtctacc gccgctctgg gctgcctggt caaggactac     480

ttccccgagc ccgtgacagt gtcctggaac tctggcgccc tgacctccgg cgtgcacacc     540

ttccctgccg tgctgcagtc ctccggcctg tactccctgt cctccgtcgt gaccgtgccc     600

tcctccagcc tgggcaccaa gacctacacc tgtaacgtgg accacaagcc ctccaacacc     660

aaggtggaca agcgggtgga atctaagtac ggccctccct gccccccctg ccctgcccct     720
```

```
gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

tacccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

<210> SEQ ID NO 118
<211> LENGTH: 128
<212> TYPE: PRT
<213> ORGANISM: Artificial Sequence
<220> FEATURE:
<223> OTHER INFORMATION: 10273 gH1 VH Y15F D19N

<400> SEQUENCE: 118

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Phe
            100                 105                 110

Tyr Gly Met Asn Pro Trp Gly Gln Gly Thr Thr Val Thr Val Ser Ser
        115                 120                 125
```

<210> SEQ ID NO 119
<211> LENGTH: 384
<212> TYPE: DNA
<213> ORGANISM: Artificial Sequence
<220> FEATURE:
<223> OTHER INFORMATION: 10273 gH1 VH Y15F D19N nucl.

<400> SEQUENCE: 119

```
gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tgtgtacctc    240

caaatgaact cgctgcgggc tgaggacacc gccgtgtact actgcgcccg cgatcacatc    300

taccgctatg atgactacgg ggactacccg accttctacg gaatgaaccc ttggggacag    360
```

-continued

```
ggcaccactg tgactgtctc gagc                                        384


<210> SEQ ID NO 120
<211> LENGTH: 455
<212> TYPE: PRT
<213> ORGANISM: Artificial Sequence
<220> FEATURE:
<223> OTHER INFORMATION: 10273 gH1 Heavy Chain Y15F D19N

<400> SEQUENCE: 120

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Phe
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
```

```
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455


<210> SEQ ID NO 121
<211> LENGTH: 1365
<212> TYPE: DNA
<213> ORGANISM: Artificial Sequence
<220> FEATURE:
<223> OTHER INFORMATION: 10273 gH1 Heavy Chain Y15F D19N nucl.

<400> SEQUENCE: 121

gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tgtgtacctc    240

caaatgaact cgctgcgggc tgaggacacc gccgtgtact actgcgcccg cgatcacatc    300

taccgctatg atgactacgg ggactacccg accttctacg gaatgaaccc ttggggacag    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660

aaggtggaca agcgggtgga atctaagtac ggccctccct gccccccctg ccctgcccct    720

gaatttctgg gcggaccttc cgtgttcctg ttccccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365


<210> SEQ ID NO 122
<211> LENGTH: 128
```

```
<212> TYPE: PRT
<213> ORGANISM: Artificial Sequence
<220> FEATURE:
<223> OTHER INFORMATION: 10273 gH1 VH Y16F D19N

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Phe Gly Met Asn Pro Trp Gly Gln Gly Thr Thr Val Thr Val Ser Ser
        115                 120                 125


<210> SEQ ID NO 123
<211> LENGTH: 384
<212> TYPE: DNA
<213> ORGANISM: Artificial Sequence
<220> FEATURE:
<223> OTHER INFORMATION: 10273 gH1 VH Y16F D19N nucl.

<400> SEQUENCE: 123

gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggactacccg acctacttcg gaatgaaccc ttggggacag     360

ggcaccactg tgactgtctc gagc                                             384


<210> SEQ ID NO 124
<211> LENGTH: 455
<212> TYPE: PRT
<213> ORGANISM: Artificial Sequence
<220> FEATURE:
<223> OTHER INFORMATION: 10273 gH1 Heavy Chain Y16F D19N

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80
```

```
Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Thr Tyr
            100                 105                 110

Phe Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 125
<211> LENGTH: 1365
<212> TYPE: DNA
<213> ORGANISM: Artificial Sequence
<220> FEATURE:

<223> OTHER INFORMATION: 10273 gH1 Heavy Chain Y16F D19N nucl.

<400> SEQUENCE: 125

```
gaagtgcagc tcgtcgaatc cggtggcgga ctggtgcagc ccggaggatc cctgaggctt      60
tcttgtgccg tgtccgggtt ctccctgagc tcctacggga tgtcgtgggt cagacaagca     120
ccaggaaagg gtctggagtg gatcggaatt atctcctcct cgggctcaac ctactacgcg     180
tcatgggcca agggccggtt caccattagc aaggacagct ccaagaacac tgtgtacctc     240
caaatgaact cgctgcgggc tgaggacacc gccgtgtact actgcgcccg cgatcacatc     300
taccgctatg atgactacgg ggactacccg acctacttcg gaatgaaccc ttggggacag     360
ggcaccactg tgactgtctc gagcgcttct acaaagggcc cctccgtgtt ccctctggcc     420
ccttgctccc ggtccacctc cgagtctacc gccgctctgg gctgcctggt caaggactac     480
ttccccgagc ccgtgacagt gtcctggaac tctggcgccc tgacctccgg cgtgcacacc     540
ttccctgccg tgctgcagtc ctccggcctg tactccctgt cctccgtcgt gaccgtgccc     600
tcctccagcc tgggcaccaa gacctacacc tgtaacgtgg accacaagcc ctccaacacc     660
aaggtggaca agcgggtgga atctaagtac ggccctccct gccccccctg ccctgcccct     720
gaatttctgg gcggaccttc cgtgttcctg ttccccccaa agcccaagga caccctgatg     780
atctcccgga cccccgaagt gacctgcgtg gtggtggacg tgtcccagga agatcccgag     840
gtccagttca attggtacgt ggacggcgtg gaagtgcaca atgccaagac caagcccaga     900
gaggaacagt tcaactccac ctaccgggtg gtgtccgtgc tgaccgtgct gcaccaggac     960
tggctgaacg gcaaagagta caagtgcaag gtgtccaaca agggcctgcc ctccagcatc    1020
gaaaagacca tctccaaggc caagggccag ccccgcgagc cccaggtgta caccctgccc    1080
cctagccagg aagagatgac caagaaccag gtgtccctga cctgtctggt caagggcttc    1140
tacccctccg acattgccgt ggaatgggag tccaacggcc agcccgagaa caactacaag    1200
accacccccc ctgtgctgga cagcgacggc tccttcttcc tgtactctcg gctgaccgtg    1260
gacaagtccc ggtggcagga aggcaacgtc ttctcctgct ccgtgatgca cgaggccctg    1320
cacaaccact acacccagaa gtccctgtcc ctgagcctgg gcaag                    1365
```

<210> SEQ ID NO 126
<211> LENGTH: 128
<212> TYPE: PRT
<213> ORGANISM: Artificial Sequence
<220> FEATURE:
<223> OTHER INFORMATION: 10273 gH1 VH T14N D19N nucl.

<400> SEQUENCE: 126

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Asn Tyr
```

-continued

```
            100                 105                 110

Tyr Gly Met Asn Pro Trp Gly Gln Gly Thr Thr Val Thr Val Ser Ser
        115                 120                 125


<210> SEQ ID NO 127
<211> LENGTH: 384
<212> TYPE: DNA
<213> ORGANISM: Artificial Sequence
<220> FEATURE:
<223> OTHER INFORMATION: 10273 gH1 VH T14N D19N nucl.

<400> SEQUENCE: 127

gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggactacccg aactactacg gaatgaaccc ttggggacag     360

ggcaccactg tgactgtctc gagc                                            384


<210> SEQ ID NO 128
<211> LENGTH: 455
<212> TYPE: PRT
<213> ORGANISM: Artificial Sequence
<220> FEATURE:
<223> OTHER INFORMATION: 10273 gH1 Heavy Chain T14N D19N

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Asn Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
```

```
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455


<210> SEQ ID NO 129
<211> LENGTH: 1365
<212> TYPE: DNA
<213> ORGANISM: Artificial Sequence
<220> FEATURE:
<223> OTHER INFORMATION: 10273 gH1 Heavy Chain T14N D19N nucl.

<400> SEQUENCE: 129

gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tgtgtacctc    240

caaatgaact cgctgcgggc tgaggacacc gccgtgtact actgcgcccg cgatcacatc    300

taccgctatg atgactacgg ggactacccg aactactacg gaatgaaccc ttggggacag    360

ggcaccactg tgactgtctc gagcgcttct acaaagggcc cctccgtgtt ccctctggcc    420

ccttgctccc ggtccacctc cgagtctacc gccgctctgg gctgcctggt caaggactac    480

ttccccgagc ccgtgacagt gtcctggaac tctggcgccc tgacctccgg cgtgcacacc    540

ttccctgccg tgctgcagtc ctccggcctg tactccctgt cctccgtcgt gaccgtgccc    600

tcctccagcc tgggcaccaa gacctacacc tgtaacgtgg accacaagcc ctccaacacc    660
```

```
aaggtggaca agcgggtgga atctaagtac ggccctccct gcccccctg ccctgcccct    720

gaatttctgg gcggaccttc cgtgttcctg ttcccccaa agcccaagga caccctgatg    780

atctcccgga cccccgaagt gacctgcgtg gtggtggacg tgtcccagga agatcccgag    840

gtccagttca attggtacgt ggacggcgtg gaagtgcaca atgccaagac caagcccaga    900

gaggaacagt tcaactccac ctaccgggtg gtgtccgtgc tgaccgtgct gcaccaggac    960

tggctgaacg gcaaagagta caagtgcaag gtgtccaaca agggcctgcc ctccagcatc   1020

gaaaagacca tctccaaggc caagggccag ccccgcgagc cccaggtgta caccctgccc   1080

cctagccagg aagagatgac caagaaccag gtgtccctga cctgtctggt caagggcttc   1140

taccccctccg acattgccgt ggaatgggag tccaacggcc agcccgagaa caactacaag   1200

accacccccc ctgtgctgga cagcgacggc tccttcttcc tgtactctcg gctgaccgtg   1260

gacaagtccc ggtggcagga aggcaacgtc ttctcctgct ccgtgatgca cgaggccctg   1320

cacaaccact acacccagaa gtccctgtcc ctgagcctgg gcaag                   1365
```

```
<210> SEQ ID NO 130
<211> LENGTH: 128
<212> TYPE: PRT
<213> ORGANISM: Artificial Sequence
<220> FEATURE:
<223> OTHER INFORMATION: 10273 gH1 VH T14V D19N

<400> SEQUENCE: 130

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Val Tyr
            100                 105                 110

Tyr Gly Met Asn Pro Trp Gly Gln Gly Thr Thr Val Thr Val Ser Ser
        115                 120                 125


<210> SEQ ID NO 131
<211> LENGTH: 384
<212> TYPE: DNA
<213> ORGANISM: Artificial Sequence
<220> FEATURE:
<223> OTHER INFORMATION: 10273 gH1 VH T14V D19N nucl.

<400> SEQUENCE: 131

gaagtgcagc tcgtcgaatc cggtggcgga ctggtgcagc ccggaggatc cctgaggctt     60

tcttgtgccg tgtccgggtt ctccctgagc tcctacggga tgtcgtgggt cagacaagca    120

ccaggaaagg gtctggagtg gatcggaatt atctcctcct cgggctcaac ctactacgcg    180

tcatgggcca agggccggtt caccattagc aaggacagct ccaagaacac tgtgtacctc    240

caaatgaact cgctgcgggc tgaggacacc gccgtgtact actgcgcccg cgatcacatc    300

taccgctatg atgactacgg ggactacccg gtgtactacg gaatgaaccc ttggggacag    360
```

ggcaccactg tgactgtctc gagc 384

<210> SEQ ID NO 132
<211> LENGTH: 455
<212> TYPE: PRT
<213> ORGANISM: Artificial Sequence
<220> FEATURE:
<223> OTHER INFORMATION: 10273 gH1 Heavy Chain T14V D19N

<400> SEQUENCE: 132

Glu Val Gln Leu Val Glu Ser Gly Gly Gly Leu Val Gln Pro Gly Gly
1 5 10 15

Ser Leu Arg Leu Ser Cys Ala Val Ser Gly Phe Ser Leu Ser Ser Tyr
20 25 30

Gly Met Ser Trp Val Arg Gln Ala Pro Gly Lys Gly Leu Glu Trp Ile
35 40 45

Gly Ile Ile Ser Ser Ser Gly Ser Thr Tyr Tyr Ala Ser Trp Ala Lys
50 55 60

Gly Arg Phe Thr Ile Ser Lys Asp Ser Ser Lys Asn Thr Val Tyr Leu
65 70 75 80

Gln Met Asn Ser Leu Arg Ala Glu Asp Thr Ala Val Tyr Tyr Cys Ala
85 90 95

Arg Asp His Ile Tyr Arg Tyr Asp Asp Tyr Gly Asp Tyr Pro Val Tyr
100 105 110

Tyr Gly Met Asn Pro Trp Gly Gln Gly Thr Thr Val Thr Val Ser Ser
115 120 125

Ala Ser Thr Lys Gly Pro Ser Val Phe Pro Leu Ala Pro Cys Ser Arg
130 135 140

Ser Thr Ser Glu Ser Thr Ala Ala Leu Gly Cys Leu Val Lys Asp Tyr
145 150 155 160

Phe Pro Glu Pro Val Thr Val Ser Trp Asn Ser Gly Ala Leu Thr Ser
165 170 175

Gly Val His Thr Phe Pro Ala Val Leu Gln Ser Ser Gly Leu Tyr Ser
180 185 190

Leu Ser Ser Val Val Thr Val Pro Ser Ser Ser Leu Gly Thr Lys Thr
195 200 205

Tyr Thr Cys Asn Val Asp His Lys Pro Ser Asn Thr Lys Val Asp Lys
210 215 220

Arg Val Glu Ser Lys Tyr Gly Pro Pro Cys Pro Pro Cys Pro Ala Pro
225 230 235 240

Glu Phe Leu Gly Gly Pro Ser Val Phe Leu Phe Pro Pro Lys Pro Lys
245 250 255

Asp Thr Leu Met Ile Ser Arg Thr Pro Glu Val Thr Cys Val Val Val
260 265 270

Asp Val Ser Gln Glu Asp Pro Glu Val Gln Phe Asn Trp Tyr Val Asp
275 280 285

Gly Val Glu Val His Asn Ala Lys Thr Lys Pro Arg Glu Glu Gln Phe
290 295 300

Asn Ser Thr Tyr Arg Val Val Ser Val Leu Thr Val Leu His Gln Asp
305 310 315 320

Trp Leu Asn Gly Lys Glu Tyr Lys Cys Lys Val Ser Asn Lys Gly Leu
325 330 335

Pro Ser Ser Ile Glu Lys Thr Ile Ser Lys Ala Lys Gly Gln Pro Arg
340 345 350

-continued

```
Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455


<210> SEQ ID NO 133
<211> LENGTH: 1365
<212> TYPE: DNA
<213> ORGANISM: Artificial Sequence
<220> FEATURE:
<223> OTHER INFORMATION: 10273 gH1 Heavy Chain T14V D19N nucl.

<400> SEQUENCE: 133

gaagtgcagc tcgtcgaatc cggtggcgga ctggtgcagc ccggaggatc cctgaggctt      60

tcttgtgccg tgtccgggtt ctccctgagc tcctacggga tgtcgtgggt cagacaagca     120

ccaggaaagg gtctggagtg gatcggaatt atctcctcct cgggctcaac ctactacgcg     180

tcatgggcca agggccggtt caccattagc aaggacagct ccaagaacac tgtgtacctc     240

caaatgaact cgctgcgggc tgaggacacc gccgtgtact actgcgcccg cgatcacatc     300

taccgctatg atgactacgg ggactacccg gtgtactacg gaatgaaccc ttggggacag     360

ggcaccactg tgactgtctc gagcgcttct acaaagggcc cctccgtgtt ccctctggcc     420

ccttgctccc ggtccacctc cgagtctacc gccgctctgg gctgcctggt caaggactac     480

ttccccgagc ccgtgacagt gtcctggaac tctggcgccc tgacctccgg cgtgcacacc     540

ttccctgccg tgctgcagtc ctccggcctg tactccctgt cctccgtcgt gaccgtgccc     600

tcctccagcc tgggcaccaa gacctacacc tgtaacgtgg accacaagcc ctccaacacc     660

aaggtggaca agcgggtgga atctaagtac ggccctccct gccccccctg ccctgcccct     720

gaatttctgg gcggaccttc cgtgttcctg ttccccccaa agcccaagga caccctgatg     780

atctcccgga cccccgaagt gacctgcgtg gtggtggacg tgtcccagga agatcccgag     840

gtccagttca attggtacgt ggacggcgtg gaagtgcaca atgccaagac caagcccaga     900

gaggaacagt tcaactccac ctaccgggtg gtgtccgtgc tgaccgtgct gcaccaggac     960

tggctgaacg gcaaagagta caagtgcaag gtgtccaaca agggcctgcc ctccagcatc    1020

gaaaagacca tctccaaggc caagggccag ccccgcgagc cccaggtgta caccctgccc    1080

cctagccagg aagagatgac caagaaccag gtgtccctga cctgtctggt caagggcttc    1140

taccccctccg acattgccgt ggaatgggag tccaacggcc agcccgagaa caactacaag    1200

accacccccc ctgtgctgga cagcgacggc tccttcttcc tgtactctcg gctgaccgtg    1260

gacaagtccc ggtggcagga aggcaacgtc ttctcctgct ccgtgatgca cgaggccctg    1320

cacaaccact acacccagaa gtccctgtcc ctgagcctgg gcaag                    1365


<210> SEQ ID NO 134
```

<211> LENGTH: 128
<212> TYPE: PRT
<213> ORGANISM: Artificial Sequence
<220> FEATURE:
<223> OTHER INFORMATION: 10273 gH1 VH T14S D19N

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Ser Tyr
            100                 105                 110

Tyr Gly Met Asn Pro Trp Gly Gln Gly Thr Thr Val Thr Val Ser Ser
        115                 120                 125

<210> SEQ ID NO 135
<211> LENGTH: 384
<212> TYPE: DNA
<213> ORGANISM: Artificial Sequence
<220> FEATURE:
<223> OTHER INFORMATION: 10273 gH1 VH T14S D19N nucl.

<400> SEQUENCE: 135
gaagtgcagc tcgtcgaatc cggtggcgga ctggtgcagc ccggaggatc cctgaggctt 60
tcttgtgccg tgtccgggtt ctccctgagc tcctacggga tgtcgtgggt cagacaagca 120
ccaggaaagg gtctggagtg gatcggaatt atctcctcct cgggctcaac ctactacgcg 180
tcatgggcca agggccggtt caccattagc aaggacagct ccaagaacac tgtgtacctc 240
caaatgaact cgctgcgggc tgaggacacc gccgtgtact actgcgcccg cgatcacatc 300
taccgctatg atgactacgg ggactacccg tcctactacg gaatgaaccc ttggggacag 360
ggcaccactg tgactgtctc gagc 384

<210> SEQ ID NO 136
<211> LENGTH: 455
<212> TYPE: PRT
<213> ORGANISM: Artificial Sequence
<220> FEATURE:
<223> OTHER INFORMATION: 10273 gH1 Heavy Chain T14S D19N

<400> SEQUENCE: 136

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Tyr
            20                  25                  30

Gly Met Ser Trp Val Arg Gln Ala Pro Gly Lys Gly Leu Glu Trp Ile
        35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Asp Ser Ser Lys Asn Thr Val Tyr Leu

-continued

```
65                  70                  75                  80

Gln Met Asn Ser Leu Arg Ala Glu Asp Thr Ala Val Tyr Tyr Cys Ala
                85                  90                  95

Arg Asp His Ile Tyr Arg Tyr Asp Asp Tyr Gly Asp Tyr Pro Ser Tyr
            100                 105                 110

Tyr Gly Met Asn Pro Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455
```

<210> SEQ ID NO 137
<211> LENGTH: 1365
<212> TYPE: DNA
<213> ORGANISM: Artificial Sequence
<220> FEATURE:
<223> OTHER INFORMATION: 10273 gH1 Heavy Chain T14S D19N nucl.

<400> SEQUENCE: 137

```
gaagtgcagc tcgtcgaatc cggtggcgga ctggtgcagc ccggaggatc cctgaggctt      60
tcttgtgccg tgtccgggtt ctccctgagc tcctacggga tgtcgtgggt cagacaagca     120
ccaggaaagg gtctggagtg gatcggaatt atctcctcct cgggctcaac ctactacgcg     180
tcatgggcca agggccggtt caccattagc aaggacagct ccaagaacac tgtgtacctc     240
caaatgaact cgctgcgggc tgaggacacc gccgtgtact actgcgcccg cgatcacatc     300
taccgctatg atgactacgg ggactacccg tcctactacg gaatgaaccc ttggggacag     360
ggcaccactg tgactgtctc gagcgcttct acaaagggcc cctccgtgtt ccctctggcc     420
ccttgctccc ggtccacctc cgagtctacc gccgctctgg gctgcctggt caaggactac     480
ttccccgagc ccgtgacagt gtcctggaac tctggcgccc tgacctccgg cgtgcacacc     540
ttccctgccg tgctgcagtc ctccggcctg tactccctgt cctccgtcgt gaccgtgccc     600
tcctccagcc tgggcaccaa gacctacacc tgtaacgtgg accacaagcc ctccaacacc     660
aaggtggaca agcgggtgga atctaagtac ggccctccct gccccccctg ccctgcccct     720
gaatttctgg gcggaccttc cgtgttcctg ttccccccaa agcccaagga caccctgatg     780
atctcccgga cccccgaagt gacctgcgtg gtggtggacg tgtcccagga agatcccgag     840
gtccagttca attggtacgt ggacggcgtg gaagtgcaca atgccaagac caagcccaga     900
gaggaacagt tcaactccac ctaccgggtg gtgtccgtgc tgaccgtgct gcaccaggac     960
tggctgaacg gcaaagagta caagtgcaag gtgtccaaca agggcctgcc ctccagcatc    1020
gaaaagacca tctccaaggc caagggccag ccccgcgagc cccaggtgta caccctgccc    1080
cctagccagg aagagatgac caagaaccag gtgtccctga cctgtctggt caagggcttc    1140
tacccctccg acattgccgt ggaatgggag tccaacggcc agcccgagaa caactacaag    1200
accacccccc ctgtgctgga cagcgacggc tccttcttcc tgtactctcg gctgaccgtg    1260
gacaagtccc ggtggcagga aggcaacgtc ttctcctgct ccgtgatgca cgaggccctg    1320
cacaaccact acacccagaa gtccctgtcc ctgagcctgg gcaag                    1365
```

<210> SEQ ID NO 138
<211> LENGTH: 107
<212> TYPE: PRT
<213> ORGANISM: Artificial Sequence
<220> FEATURE:
<223> OTHER INFORMATION: Human IGKV1D-13 JK4 acceptor framework

<400> SEQUENCE: 138

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Leu
                85                  90                  95
```

```
Thr Phe Gly Gly Gly Thr Lys Val Glu Ile Lys
            100                 105


<210> SEQ ID NO 139
<211> LENGTH: 321
<212> TYPE: DNA
<213> ORGANISM: Artificial Sequence
<220> FEATURE:
<223> OTHER INFORMATION: Human IGKV1D-13 JK4 acceptor framework nucl.

<400> SEQUENCE: 139

gccatccagt tgacccagtc tccatcctcc ctgtctgcat ctgtaggaga cagagtcacc     60

atcacttgcc gggcaagtca gggcattagc agtgctttag cctggtatca gcagaaacca    120

gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt accctctcac tttcggcgga    300

gggaccaagg tggagatcaa a                                              321


<210> SEQ ID NO 140
<211> LENGTH: 117
<212> TYPE: PRT
<213> ORGANISM: Artificial Sequence
<220> FEATURE:
<223> OTHER INFORMATION: Human IGHV3-66 JH6 acceptor framework

<400> SEQUENCE: 140

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Tyr Tyr Tyr Tyr Tyr Gly Met Asp Val Trp Gly Gln Gly Thr Thr
            100                 105                 110

Val Thr Val Ser Ser
        115


<210> SEQ ID NO 141
<211> LENGTH: 351
<212> TYPE: DNA
<213> ORGANISM: Artificial Sequence
<220> FEATURE:
<223> OTHER INFORMATION: Human IGHV3-66 JH6 acceptor framework nucl.

<400> SEQUENCE: 141

gaggtgcagc tggtggagtc tgggggaggc ttggtccagc ctggggggtc cctgagactc     60

tcctgtgcag cctctggatt caccgtcagt agcaactaca tgagctgggt ccgccaggct    120

ccagggaagg ggctggagtg ggtctcagtt atttatagcg gtggtagcac atactacgca    180

gactccgtga agggcagatt caccatctcc agagacaatt ccaagaacac gctgtatctt    240

caaatgaaca gcctgagagc cgaggacacg gctgtgtatt actgtgcgag atactactac    300
```

tactacggta tggacgtctg ggggcaaggg accacggtca ccgtctcctc a 351

<210> SEQ ID NO 142
<211> LENGTH: 293
<212> TYPE: PRT
<213> ORGANISM: Artificial Sequence
<220> FEATURE:
<223> OTHER INFORMATION: Human KLK5 (full length with signal sequence)

<400> SEQUENCE: 142

Met Ala Thr Ala Arg Pro Pro Trp Met Trp Val Leu Cys Ala Leu Ile
1 5 10 15

Thr Ala Leu Leu Leu Gly Val Thr Glu His Val Leu Ala Asn Asn Asp
20 25 30

Val Ser Cys Asp His Pro Ser Asn Thr Val Pro Ser Gly Ser Asn Gln
35 40 45

Asp Leu Gly Ala Gly Ala Gly Glu Asp Ala Arg Ser Asp Asp Ser Ser
50 55 60

Ser Arg Ile Ile Asn Gly Ser Asp Cys Asp Met His Thr Gln Pro Trp
65 70 75 80

Gln Ala Ala Leu Leu Leu Arg Pro Asn Gln Leu Tyr Cys Gly Ala Val
85 90 95

Leu Val His Pro Gln Trp Leu Leu Thr Ala Ala His Cys Arg Lys Lys
100 105 110

Val Phe Arg Val Arg Leu Gly His Tyr Ser Leu Ser Pro Val Tyr Glu
115 120 125

Ser Gly Gln Gln Met Phe Gln Gly Val Lys Ser Ile Pro His Pro Gly
130 135 140

Tyr Ser His Pro Gly His Ser Asn Asp Leu Met Leu Ile Lys Leu Asn
145 150 155 160

Arg Arg Ile Arg Pro Thr Lys Asp Val Arg Pro Ile Asn Val Ser Ser
165 170 175

His Cys Pro Ser Ala Gly Thr Lys Cys Leu Val Ser Gly Trp Gly Thr
180 185 190

Thr Lys Ser Pro Gln Val His Phe Pro Lys Val Leu Gln Cys Leu Asn
195 200 205

Ile Ser Val Leu Ser Gln Lys Arg Cys Glu Asp Ala Tyr Pro Arg Gln
210 215 220

Ile Asp Asp Thr Met Phe Cys Ala Gly Asp Lys Ala Gly Arg Asp Ser
225 230 235 240

Cys Gln Gly Asp Ser Gly Gly Pro Val Val Cys Asn Gly Ser Leu Gln
245 250 255

Gly Leu Val Ser Trp Gly Asp Tyr Pro Cys Ala Arg Pro Asn Arg Pro
260 265 270

Gly Val Tyr Thr Asn Leu Cys Lys Phe Thr Lys Trp Ile Gln Glu Thr
275 280 285

Ile Gln Ala Asn Ser
290

<210> SEQ ID NO 143
<211> LENGTH: 271
<212> TYPE: PRT
<213> ORGANISM: Artificial Sequence
<220> FEATURE:
<223> OTHER INFORMATION: Human KLK5 pro-form

<400> SEQUENCE: 143

-continued

```
Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
            20                  25                  30

Gly Glu Asp Ala Arg Ser Asp Asp Ser Ser Ser Arg Ile Ile Asn Gly
        35                  40                  45

Ser Asp Cys Asp Met His Thr Gln Pro Trp Gln Ala Ala Leu Leu Leu
    50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
        115                 120                 125

Ser Asn Asp Leu Met Leu Ile Lys Leu Asn Arg Arg Ile Arg Pro Thr
    130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
        195                 200                 205

Cys Ala Gly Asp Lys Ala Gly Arg Asp Ser Cys Gln Gly Asp Ser Gly
    210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255

Cys Lys Phe Thr Lys Trp Ile Gln Glu Thr Ile Gln Ala Asn Ser
            260                 265                 270


<210> SEQ ID NO 144
<211> LENGTH: 227
<212> TYPE: PRT
<213> ORGANISM: Artificial Sequence
<220> FEATURE:
<223> OTHER INFORMATION: Active human KLK5

<400> SEQUENCE: 144

Ile Ile Asn Gly Ser Asp Cys Asp Met His Thr Gln Pro Trp Gln Ala
1               5                   10                  15

Ala Leu Leu Leu Arg Pro Asn Gln Leu Tyr Cys Gly Ala Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
    50                  55                  60

Gln Gln Met Phe Gln Gly Val Lys Ser Ile Pro His Pro Gly Tyr Ser
65                  70                  75                  80

His Pro Gly His Ser Asn Asp Leu Met Leu Ile Lys Leu Asn Arg Arg
                85                  90                  95
```

```
Ile Arg Pro Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Lys
        115                 120                 125

Ser Pro Gln Val His Phe Pro Lys Val Leu Gln Cys Leu Asn Ile Ser
    130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Lys Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Arg Pro Asn Arg Pro Gly Val
        195                 200                 205

Tyr Thr Asn Leu Cys Lys Phe Thr Lys Trp Ile Gln Glu Thr Ile Gln
    210                 215                 220

Ala Asn Ser
225


<210> SEQ ID NO 145
<211> LENGTH: 295
<212> TYPE: PRT
<213> ORGANISM: Artificial Sequence
<220> FEATURE:
<223> OTHER INFORMATION: Human LEKTI D5 Rabbit Fc

<400> SEQUENCE: 145

Glu Ile Val Lys Leu Cys Ser Gln Tyr Gln Asn Gln Ala Lys Asn Gly
1               5                   10                  15

Ile Leu Phe Cys Thr Arg Glu Asn Asp Pro Ile Arg Gly Pro Asp Gly
            20                  25                  30

Lys Met His Gly Asn Leu Cys Ser Met Cys Gln Ala Tyr Phe Gln Ala
        35                  40                  45

Glu Asn Glu Glu Lys Lys Lys Ala Glu Ala Arg Ala Arg Asn Leu Glu
    50                  55                  60

Lys Thr Val Ala Pro Ser Thr Cys Ser Lys Pro Thr Cys Pro Pro Pro
65                  70                  75                  80

Glu Leu Leu Gly Gly Pro Ser Val Phe Ile Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Asp Asp Pro Glu Val Gln Phe Thr Trp Tyr Ile Asn
        115                 120                 125

Asn Glu Gln Val Arg Thr Ala Arg Pro Pro Leu Arg Glu Gln Gln Phe
    130                 135                 140

Asn Ser Thr Ile Arg Val Val Ser Thr Leu Pro Ile Ala His Gln Asp
145                 150                 155                 160

Trp Leu Arg Gly Lys Glu Phe Lys Cys Lys Val His Asn Lys Ala Leu
                165                 170                 175

Pro Ala Pro Ile Glu Lys Thr Ile Ser Lys Ala Arg Gly Gln Pro Leu
            180                 185                 190

Glu Pro Lys Val Tyr Thr Met Gly Pro Pro Arg Glu Glu Leu Ser Ser
        195                 200                 205

Arg Ser Val Ser Leu Thr Cys Met Ile Asn Gly Phe Tyr Pro Ser Asp
    210                 215                 220
```

```
Ile Ser Val Glu Trp Glu Lys Asn Gly Lys Ala Glu Asp Asn Tyr Lys
225                 230                 235                 240

Thr Thr Pro Ala Val Leu Asp Ser Asp Gly Ser Tyr Phe Leu Tyr Ser
                245                 250                 255

Lys Leu Ser Val Pro Thr Ser Glu Trp Gln Arg Gly Asp Val Phe Thr
            260                 265                 270

Cys Ser Val Met His Glu Ala Leu His Asn His Tyr Thr Gln Lys Ser
        275                 280                 285

Ile Ser Arg Ser Pro Gly Lys
    290                 295


<210> SEQ ID NO 146
<211> LENGTH: 231
<212> TYPE: PRT
<213> ORGANISM: Artificial Sequence
<220> FEATURE:
<223> OTHER INFORMATION: Human KLK7 pro-form

<400> SEQUENCE: 146

Glu Glu Ala Gln Gly Asp Lys Ile Ile Asp Gly Ala Pro Cys Ala Arg
1               5                   10                  15

Gly Ser His Pro Trp Gln Val Ala Leu Leu Ser Gly Asn Gln Leu His
            20                  25                  30

Cys Gly Gly Val Leu Val Asn Glu Arg Trp Val Leu Thr Ala Ala His
        35                  40                  45

Cys Lys Met Asn Glu Tyr Thr Val His Leu Gly Ser Asp Thr Leu Gly
    50                  55                  60

Asp Arg Arg Ala Gln Arg Ile Lys Ala Ser Lys Ser Phe Arg His Pro
65                  70                  75                  80

Gly Tyr Ser Thr Gln Thr His Val Asn Asp Leu Met Leu Val Lys Leu
                85                  90                  95

Asn Ser Gln Ala Arg Leu Ser Ser Met Val Lys Lys Val Arg Leu Pro
            100                 105                 110

Ser Arg Cys Glu Pro Pro Gly Thr Thr Cys Thr Val Ser Gly Trp Gly
        115                 120                 125

Thr Thr Thr Ser Pro Asp Val Thr Phe Pro Ser Asp Leu Met Cys Val
    130                 135                 140

Asp Val Lys Leu Ile Ser Pro Gln Asp Cys Thr Lys Val Tyr Lys Asp
145                 150                 155                 160

Leu Leu Glu Asn Ser Met Leu Cys Ala Gly Ile Pro Asp Ser Lys Lys
                165                 170                 175

Asn Ala Cys Asn Gly Asp Ser Gly Gly Pro Leu Val Cys Arg Gly Thr
            180                 185                 190

Leu Gln Gly Leu Val Ser Trp Gly Thr Phe Pro Cys Gly Gln Pro Asn
        195                 200                 205

Asp Pro Gly Val Tyr Thr Gln Val Cys Lys Phe Thr Lys Trp Ile Asn
    210                 215                 220

Asp Thr Met Lys Lys His Arg
225                 230


<210> SEQ ID NO 147
<211> LENGTH: 224
<212> TYPE: PRT
<213> ORGANISM: Artificial Sequence
<220> FEATURE:
<223> OTHER INFORMATION: Active himan KLK7

<400> SEQUENCE: 147
```

```
Ile Ile Asp Gly Ala Pro Cys Ala Arg Gly Ser His Pro Trp Gln Val
1               5                   10                  15

Ala Leu Leu Ser Gly Asn Gln Leu His Cys Gly Gly Val Leu Val Asn
            20                  25                  30

Glu Arg Trp Val Leu Thr Ala Ala His Cys Lys Met Asn Glu Tyr Thr
        35                  40                  45

Val His Leu Gly Ser Asp Thr Leu Gly Asp Arg Arg Ala Gln Arg Ile
    50                  55                  60

Lys Ala Ser Lys Ser Phe Arg His Pro Gly Tyr Ser Thr Gln Thr His
65                  70                  75                  80

Val Asn Asp Leu Met Leu Val Lys Leu Asn Ser Gln Ala Arg Leu Ser
                85                  90                  95

Ser Met Val Lys Lys Val Arg Leu Pro Ser Arg Cys Glu Pro Pro Gly
            100                 105                 110

Thr Thr Cys Thr Val Ser Gly Trp Gly Thr Thr Thr Ser Pro Asp Val
        115                 120                 125

Thr Phe Pro Ser Asp Leu Met Cys Val Asp Val Lys Leu Ile Ser Pro
    130                 135                 140

Gln Asp Cys Thr Lys Val Tyr Lys Asp Leu Leu Glu Asn Ser Met Leu
145                 150                 155                 160

Cys Ala Gly Ile Pro Asp Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Met Lys Lys His Arg
    210                 215                 220


<210> SEQ ID NO 148
<211> LENGTH: 232
<212> TYPE: PRT
<213> ORGANISM: Artificial Sequence
<220> FEATURE:
<223> OTHER INFORMATION: Cyno KLK7 pro-form

<400> SEQUENCE: 148

Gly Gln Glu Ala Gln Gly Asp Lys Ile Ile Asp Gly Ala Pro Cys Thr
1               5                   10                  15

Arg Gly Ser His Pro Trp Gln Val Ala Leu Leu Ser Gly Asn Gln Leu
            20                  25                  30

His Cys Gly Gly Val Leu Val Asn Glu Arg Trp Val Leu Thr Ala Ala
        35                  40                  45

His Cys Lys Met Asn Asp Tyr Ile Val His Leu Gly Ser Asp Thr Leu
    50                  55                  60

Gly Asp Arg Lys Ala Gln Arg Ile Lys Ala Ser Arg Ser Phe Arg His
65                  70                  75                  80

Pro Gly Tyr Ser Thr Gln Thr His Val Asn Asp Leu Met Leu Val Lys
                85                  90                  95

Leu Asn Ser Pro Ala Arg Leu Ser Ser Thr Val Lys Lys Val Arg Leu
            100                 105                 110

Pro Ser Arg Cys Glu Pro Pro Gly Thr Thr Cys Thr Val Ser Gly Trp
        115                 120                 125

Gly Thr Thr Thr Ser Pro Asp Val Thr Phe Pro Ser Asp Leu Met Cys
    130                 135                 140
```

```
Val Asp Val Lys Leu Ile Ser Ser Gln Asp Cys Thr Lys Val Tyr Lys
145                 150                 155                 160

Asp Met Leu Gly Asn Ser Met Leu Cys Ala Gly Ile Pro Asn Ser Lys
                165                 170                 175

Lys Asn Ala Cys Asn Gly Asp Ser Gly Gly Pro Leu Val Cys Arg Gly
            180                 185                 190

Thr Leu Gln Gly Leu Val Ser Trp Gly Thr Phe Pro Cys Gly Gln Pro
        195                 200                 205

Asn Asp Pro Gly Val Tyr Thr Gln Val Cys Lys Phe Thr Lys Trp Ile
    210                 215                 220

Asn Asp Thr Ile Lys Lys His Arg
225                 230


<210> SEQ ID NO 149
<211> LENGTH: 224
<212> TYPE: PRT
<213> ORGANISM: Artificial Sequence
<220> FEATURE:
<223> OTHER INFORMATION: Active Cyno KLK7

<400> SEQUENCE: 149

Ile Ile Asp Gly Ala Pro Cys Thr Arg Gly Ser His Pro Trp Gln Val
1               5                   10                  15

Ala Leu Leu Ser Gly Asn Gln Leu His Cys Gly Gly Val Leu Val Asn
            20                  25                  30

Glu Arg Trp Val Leu Thr Ala Ala His Cys Lys Met Asn Asp Tyr Ile
        35                  40                  45

Val His Leu Gly Ser Asp Thr Leu Gly Asp Arg Lys Ala Gln Arg Ile
    50                  55                  60

Lys Ala Ser Arg Ser Phe Arg His Pro Gly Tyr Ser Thr Gln Thr His
65                  70                  75                  80

Val Asn Asp Leu Met Leu Val Lys Leu Asn Ser Pro Ala Arg Leu Ser
                85                  90                  95

Ser Thr Val Lys Lys Val Arg Leu Pro Ser Arg Cys Glu Pro Pro Gly
            100                 105                 110

Thr Thr Cys Thr Val Ser Gly Trp Gly Thr Thr Thr Ser Pro Asp Val
        115                 120                 125

Thr Phe Pro Ser Asp Leu Met Cys Val Asp Val Lys Leu Ile Ser Ser
    130                 135                 140

Gln Asp Cys Thr Lys Val Tyr Lys Asp Met Leu Gly Asn Ser Met Leu
145                 150                 155                 160

Cys Ala Gly Ile Pro Asn Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Ile Lys Lys His Arg
    210                 215                 220


<210> SEQ ID NO 150
<211> LENGTH: 226
<212> TYPE: PRT
<213> ORGANISM: Artificial Sequence
<220> FEATURE:
<223> OTHER INFORMATION: Active mouse KLK5
```

<400> SEQUENCE: 150

Ile Val Asn Gly Ser Asp Cys Gln Lys Asp Ala Gln Pro Trp Gln Gly
1 5 10 15

Ala Leu Leu Leu Gly Pro Asn Lys Leu Tyr Cys Gly Ala Val Leu Ile
20 25 30

Ser Pro Gln Trp Leu Leu Thr Ala Ala His Cys Arg Lys Pro Val Phe
35 40 45

Arg Ile Arg Leu Gly His His Ser Met Ser Pro Val Tyr Glu Ser Gly
50 55 60

Gln Gln Met Phe Gln Gly Ile Lys Ser Ile Pro His Pro Gly Tyr Ser
65 70 75 80

His Pro Gly His Ser Asn Asp Leu Met Leu Ile Lys Met Asn Arg Lys
85 90 95

Ile Arg Asp Ser His Ser Val Lys Pro Val Glu Ile Ala Cys Asp Cys
100 105 110

Ala Thr Glu Gly Thr Arg Cys Met Val Ser Gly Trp Gly Thr Thr Ser
115 120 125

Ser Ser His Asn Asn Phe Pro Lys Val Leu Gln Cys Leu Asn Ile Thr
130 135 140

Val Leu Ser Glu Glu Arg Cys Lys Asn Ser Tyr Pro Gly Gln Ile Asp
145 150 155 160

Lys Thr Met Phe Cys Ala Gly Asp Glu Glu Gly Arg Asp Ser Cys Gln
165 170 175

Gly Asp Ser Gly Gly Pro Val Val Cys Asn Gly Lys Leu Gln Gly Leu
180 185 190

Val Ser Trp Gly Asp Phe Pro Cys Ala Gln Arg Asn Arg Pro Gly Val
195 200 205

Tyr Thr Asn Leu Cys Glu Phe Val Lys Trp Ile Lys Asp Thr Met Asn
210 215 220

Ser Asn
225

<210> SEQ ID NO 151
<211> LENGTH: 227
<212> TYPE: PRT
<213> ORGANISM: Artificial Sequence
<220> FEATURE:
<223> OTHER INFORMATION: active Cyno KLK5

<400> SEQUENCE: 151

Ile Ile Asn Gly Ser Asp Cys Asp Glu His Thr Gln Pro Trp Gln Ala
1 5 10 15

Ala Leu Leu Leu Gly Pro Asn Gln Leu Tyr Cys Gly Gly Val Leu Val
20 25 30

His Pro Gln Trp Leu Leu Thr Ala Ala His Cys Arg Lys Lys Val Phe
35 40 45

Arg Val Arg Leu Gly His Tyr Ser Leu Ser Pro Val Tyr Glu Ser Gly
50 55 60

Gln Gln Met Phe Gln Gly Ile Lys Ser Ile Pro His Pro Gly Tyr Ser
65 70 75 80

His Pro Gly His Ser Asn Asp Leu Met Leu Ile Lys Leu Asn Arg Arg
85 90 95

Ile His Ser Thr Lys Asp Val Arg Pro Ile Asn Val Ser Ser His Cys
100 105 110

Pro Ser Ala Gly Thr Lys Cys Leu Val Ser Gly Trp Gly Thr Thr Arg

```
        115                 120                 125

Ser Pro Gln Val His Phe Pro Lys Val Leu Gln Cys Leu Asn Ile Ser
    130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Glu Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Lys Pro Asn Arg Pro Gly Val
        195                 200                 205

Tyr Thr Asn Leu Cys Lys Phe Thr Lys Trp Ile Gln Glu Thr Ile Gln
    210                 215                 220

Ala Asn Ser
225


<210> SEQ ID NO 152
<211> LENGTH: 302
<212> TYPE: PRT
<213> ORGANISM: Artificial Sequence
<220> FEATURE:
<223> OTHER INFORMATION: Human LEKTI D8 Rabbit Fc

<400> SEQUENCE: 152

Glu Ala Ala Lys Glu Ile Cys Ser Glu Phe Arg Asp Gln Val Arg Asn
1               5                   10                  15

Gly Thr Leu Ile Cys Thr Arg Glu His Asn Pro Val Arg Gly Pro Asp
            20                  25                  30

Gly Lys Met His Gly Asn Lys Cys Ala Met Cys Ala Ser Val Phe Lys
        35                  40                  45

Leu Glu Glu Glu Glu Lys Lys Asn Asp Lys Glu Glu Lys Gly Lys Val
    50                  55                  60

Glu Ala Glu Lys Val Leu Glu Lys Thr Val Ala Pro Ser Thr Cys Ser
65                  70                  75                  80

Lys Pro Thr Cys Pro Pro Pro Glu Leu Leu Gly Gly Pro Ser Val Phe
                85                  90                  95

Ile Phe Pro Pro Lys Pro Lys Asp Thr Leu Met Ile Ser Arg Thr Pro
            100                 105                 110

Glu Val Thr Cys Val Val Val Asp Val Ser Gln Asp Asp Pro Glu Val
        115                 120                 125

Gln Phe Thr Trp Tyr Ile Asn Asn Glu Gln Val Arg Thr Ala Arg Pro
    130                 135                 140

Pro Leu Arg Glu Gln Gln Phe Asn Ser Thr Ile Arg Val Val Ser Thr
145                 150                 155                 160

Leu Pro Ile Ala His Gln Asp Trp Leu Arg Gly Lys Glu Phe Lys Cys
                165                 170                 175

Lys Val His Asn Lys Ala Leu Pro Ala Pro Ile Glu Lys Thr Ile Ser
            180                 185                 190

Lys Ala Arg Gly Gln Pro Leu Glu Pro Lys Val Tyr Thr Met Gly Pro
        195                 200                 205

Pro Arg Glu Glu Leu Ser Ser Arg Ser Val Ser Leu Thr Cys Met Ile
    210                 215                 220

Asn Gly Phe Tyr Pro Ser Asp Ile Ser Val Glu Trp Glu Lys Asn Gly
225                 230                 235                 240

Lys Ala Glu Asp Asn Tyr Lys Thr Thr Pro Ala Val Leu Asp Ser Asp
```

```
                245                 250                 255

Gly Ser Tyr Phe Leu Tyr Ser Lys Leu Ser Val Pro Thr Ser Glu Trp
            260                 265                 270

Gln Arg Gly Asp Val Phe Thr Cys Ser Val Met His Glu Ala Leu His
        275                 280                 285

Asn His Tyr Thr Gln Lys Ser Ile Ser Arg Ser Pro Gly Lys
    290                 295                 300


<210> SEQ ID NO 153
<211> LENGTH: 219
<212> TYPE: PRT
<213> ORGANISM: Artificial Sequence
<220> FEATURE:
<223> OTHER INFORMATION: Rabbit 10273 mIgG Light Chain

<400> SEQUENCE: 153

Ala Val Val Leu Thr Gln Thr Pro Ser Pro Met Ser Ala Ala Val Gly
1               5                   10                  15

Gly Thr Val Thr Ile Ser Cys Gln Ser Ser Gln Ser Val Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Asp
                85                  90                  95

Asp Val Asp Thr Tyr Thr Phe Gly Gly Gly Thr Glu Val Val Val Lys
            100                 105                 110

Arg Thr Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Cys
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 154
<211> LENGTH: 449
<212> TYPE: PRT
<213> ORGANISM: Artificial Sequence
<220> FEATURE:
<223> OTHER INFORMATION: Rabbit 10273 mIgG  Heavy Chain

<400> SEQUENCE: 154

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
            20                  25                  30
```

-continued

```
Met Ser Trp Val Arg Gln Ala Pro Gly Lys Gly Leu Glu Trp Ile Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Asp His
                85                  90                  95

Ile Tyr Arg Tyr Asp Asp Tyr Gly Asp Tyr Pro Thr Tyr Tyr Gly Met
            100                 105                 110

Asp Pro Trp Gly Pro Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys
```

<210> SEQ ID NO 155
<211> LENGTH: 657
<212> TYPE: DNA
<213> ORGANISM: Artificial Sequence
<220> FEATURE:
<223> OTHER INFORMATION: Rabbit 10273 mIgG Light Chain Nucl.

<400> SEQUENCE: 155
gcagtcgtgc tgactcagac accatcaccc atgtctgcag ctgtgggagg cacagtcacc 60
atcagttgcc agtccagtca gagtgtttat aataataacg acttagcctg gtatcagcag 120
aaaccagggc agcctcctaa gctcctgatc tacagggcat ccactctggc atctggggtc 180
ccgtcgcggt tcagcggcag tggatctggg acacagttca ctctcaccat cagcggcgtg 240
cagtgtgacg atgctgccac ttactactgt ctaggcggtt atgatgatga tgttgatacg 300
tatactttcg gcggagggac cgaggtggtg gtcaaacgta cggatgctgc accaactgta 360
tccatcttcc caccatccag tgagcagtta acatctggag gtgcctcagt cgtgtgcttc 420
ttgaacaact tctaccccaa agacatcaat gtcaagtgga agattgatgg cagtgaacga 480
caaaatggcg tcctgaacag ttggactgat caggacagca aagactgcac ctacagcatg 540
agcagcaccc tcacgttgac caaggacgag tatgaacgac ataacagcta tacctgtgag 600
gccactcaca agacatcaac ttcacccatt gtcaagagct tcaacaggaa tgagtgt 657

<210> SEQ ID NO 156
<211> LENGTH: 1347
<212> TYPE: DNA
<213> ORGANISM: Artificial Sequence
<220> FEATURE:
<223> OTHER INFORMATION: Rabbit 10273 mIgG Heavy Chain Nucl.

<400> SEQUENCE: 156
cagtcggtgg aggagtccgg gggtcgcctg gtcacgcctg ggacacccct gacactcacc 60
tgcacagtct ctggattctc cctcagtagc tatggaatga gctgggtccg ccaggctcca 120
gggaaggggc tggaatggat cggaattatt agtagtagtg gtagcacata ctacgcgagc 180
tgggcgaaag gccgattcac catctccaag acctcgacca cggtggatct gaaaatcgcc 240
agtccgacaa ccgaggacac ggccacctat ttctgtgcca gagatcacat ttataggtac 300
gatgactatg gtgattaccc tacctactac ggcatggacc cctggggccc aggcaccctg 360
gtcaccgtct cgagtgccaa aacgacaccc ccatctgtct atccactggc ccctggatct 420
gctgcccaaa ctaactccat ggtgaccctg ggatgcctgg tcaagggcta tttccctgag 480
ccagtgacag tgacctggaa ctctggatcc ctgtccagcg gtgtgcacac cttcccagct 540
gtcctgcagt ctgacctcta cactctgagc agctcagtga ctgtcccctc cagcacctgg 600
cccagcgaga ccgtcacctg caacgttgcc cacccggcca gcagcaccaa ggtggacaag 660
aaaattgtgc ccagggattg tggttgtaag ccttgcatat gtacagtccc agaagtatca 720
tctgtcttca tcttcccccc aaagcccaag gatgtgctca ccattactct gactcctaag 780
gtcacgtgtg ttgtggtaga catcagcaag gatgatcccg aggtccagtt cagctggttt 840
gtagatgatg tggaggtgca cacagctcag acgcaacccc gggaggagca gttcaacagc 900
actttccgct cagtcagtga acttcccatc atgcaccagg actggctcaa tggcaaggag 960
ttcaaatgca gggtcaacag tgcagctttc cctgccccca tcgagaaaac catctccaaa 1020
accaaaggca gaccgaaggc tccacaggtg tacaccattc cacctcccaa ggagcagatg 1080

```
gccaaggata aagtcagtct gacctgcatg ataacagact tcttccctga agacattact   1140

gtggagtggc agtggaatgg gcagccagcg gagaactaca agaacactca gcccatcatg   1200

gacacagatg gctcttactt cgtctacagc aagctcaatg tgcagaagag caactgggag   1260

gcaggaaata ctttcacctg ctctgtgtta catgagggcc tgcacaacca ccatactgag   1320

aagagcctct cccactctcc tggtaaa                                       1347


<210> SEQ ID NO 157
<211> LENGTH: 217
<212> TYPE: PRT
<213> ORGANISM: Artificial Sequence
<220> FEATURE:
<223> OTHER INFORMATION: Rabbit 10236 mIgG Light Chain

<400> SEQUENCE: 157

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys Arg Thr
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Cys Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215


<210> SEQ ID NO 158
<211> LENGTH: 438
<212> TYPE: PRT
<213> ORGANISM: Artificial Sequence
<220> FEATURE:
<223> OTHER INFORMATION: Rabbit 10236 mIgG Heavy Chain

<400> SEQUENCE: 158

Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
```

```
        35                  40                  45

Asp Ile Tyr Pro Ser Asp Ile Ile Asp Tyr Ala Ser Trp Ala Lys Gly
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95

Asn Asp Tyr Gly Leu Asp Ile Trp Gly Pro Gly Thr Leu Val Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220

Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Pro Lys Glu Gln Met Ala Lys Asp
            340                 345                 350

Lys Val Ser Leu Thr Cys Met Ile Thr Asp Phe Phe Pro Glu Asp Ile
        355                 360                 365

Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
        435

<210> SEQ ID NO 159
```

<211> LENGTH: 651
<212> TYPE: DNA
<213> ORGANISM: Artificial Sequence
<220> FEATURE:
<223> OTHER INFORMATION: Rabbit 10236 mIgG Light Chain Nucl.

<400> SEQUENCE: 159
gcctatgata tgacccagac tccagcctct gtggaggtag ctgtgggagg cacagtcacc 60
atcaagtgcc aggccagtca gagcattagc agttggttag cctggtatca gcagaaacca 120
ggtcagcctc ccaagctcct gatctatctg gcatccactc tggcatctgg ggtctcatcg 180
cggttcaaag gcagtggatc tgggacacag ttcactctca ccatcagcgg cgtggagtgt 240
gccgatgctg ccacttacta ctgtcaacag ggttatacta atagtaatat tattaatact 300
ttcggcggag ggaccgaggt ggtggtcaaa cgtacggatg ctgcaccaac tgtatccatc 360
ttcccaccat ccagtgagca gttaacatct ggaggtgcct cagtcgtgtg cttcttgaac 420
aacttctacc ccaaagacat caatgtcaag tggaagattg atggcagtga acgacaaaat 480
ggcgtcctga acagttggac tgatcaggac agcaaagact gcacctacag catgagcagc 540
accctcacgt tgaccaagga cgagtatgaa cgacataaca gctatacctg tgaggccact 600
cacaagacat caacttcacc cattgtcaag agcttcaaca ggaatgagtg t 651

<210> SEQ ID NO 160
<211> LENGTH: 1386
<212> TYPE: DNA
<213> ORGANISM: Artificial Sequence
<220> FEATURE:
<223> OTHER INFORMATION: Rabbit 10236 mIgG Heavy Chain Nucl.

<400> SEQUENCE: 160
cagtcggtgg aggagtccgg gggtcgcctg gtcacgcctg ggacacccct gacactcacc 60
tgcaccgtct ctgggttccc cctcagtaat tatgcaatga gctgggtccg ccaggctcca 120
gggaaggggc tggaatggat cggagacatt tatcctagtg atatcataga ctacgcgagc 180
tgggcgaaag gccgattcac catctcccaa acctcgacca cggtggagct gaaaatcacg 240
ggtccgacaa ccgaggacac ggccacctat ttctgtgcca gagacaacaa tgactatggt 300
ctggacatct ggggcccagg caccctggtc accgtctcga gtgccaaaac gacaccccca 360
tctgtctatc cactggcccc tggatctgct gcccaaacta actccatggt gaccctggga 420
tgcctggtca agggctattt ccctgagcca gtgacagtga cctggaactc tggatccctg 480
tccagcggtg tgcacacctt cccagctgtc ctgcagtctg acctctacac tctgagcagc 540
tcagtgactg tcccctccag cacctggccc agcgagaccg tcacctgcaa cgttgcccac 600
ccggccagca gcaccaaggt ggacaagaaa attgtgccca gggattgtgg ttgtaagcct 660
tgcatatgta cagtcccaga agtatcatct gtcttcatct tccccccaaa gcccaaggat 720
gtgctcacca ttactctgac tcctaaggtc acgtgtgttg tggtagacat cagcaaggat 780
gatcccgagg tccagttcag ctggtttgta gatgatgtgg aggtgcacac agctcagacg 840
caaccccggg aggagcagtt caacagcact ttccgctcag tcagtgaact tcccatcatg 900
caccaggact ggctcaatgg caaggagttc aaatgcaggg tcaacagtgc agctttccct 960
gcccccatcg agaaaaccat ctccaaaacc aaaggcagac cgaaggctcc acaggtgtac 1020
accattccac ctcccaagga gcagatggcc aaggataaag tcagtctgac ctgcatgata 1080
acagacttct tccctgaaga cattactgtg gagtggcagt ggaatgggca gccagcggag 1140
aactacaaga acactcagcc catcatggac acagatggct cttacttcgt ctacagcaag 1200
ctcaatgtgc agaagagcaa ctgggaggca ggaaatactt tcacctgctc tgtgttacat 1260
gagggcctgc acaaccacca tactgagaag agcctctccc actctcctgg taaatgatcc 1320
cagtgtcctt ggagccctct ggtcctacag gactctgaca cctacctcca cccctccctg 1380
tataaa 1386

<210> SEQ ID NO 161
<211> LENGTH: 214
<212> TYPE: PRT
<213> ORGANISM: Artificial Sequence
<220> FEATURE:
<223> OTHER INFORMATION: 10236 Light chain Fab

<400> SEQUENCE: 161

Ala Tyr Asp Met Thr Gln Thr Pro Ala Ser Val Glu Val Ala Val Gly
1 5 10 15

Gly Thr Val Thr Ile Lys Cys Gln Ala Ser Gln Ser Ile Ser Ser Trp
20 25 30

Leu Ala Trp Tyr Gln Gln Lys Pro Gly Gln Pro Pro Lys Leu Leu Ile
35 40 45

Tyr Leu Ala Ser Thr Leu Ala Ser Gly Val Ser Ser Arg Phe Lys Gly
50 55 60

Ser Gly Ser Gly Thr Gln Phe Thr Leu Thr Ile Ser Gly Val Glu Cys
65 70 75 80

Ala Asp Ala Ala Thr Tyr Tyr Cys Gln Gln Gly Tyr Thr Asn Ser Asn
85 90 95

Ile Ile Asn Thr Phe Gly Gly Gly Thr Glu Val Val Val Lys Arg Thr
100 105 110

Pro Val Ala Pro Thr Val Leu Ile Phe Pro Pro Ala Ala Asp Gln Val
115 120 125

Ala Thr Gly Thr Val Thr Ile Val Cys Val Ala Asn Lys Tyr Phe Pro
130 135 140

Asp Val Thr Val Thr Trp Glu Val Asp Gly Thr Thr Gln Thr Thr Gly
145 150 155 160

Ile Glu Asn Ser Lys Thr Pro Gln Asn Ser Ala Asp Cys Thr Tyr Asn
165 170 175

Leu Ser Ser Thr Leu Thr Leu Thr Ser Thr Gln Tyr Asn Ser His Lys
180 185 190

Glu Tyr Thr Cys Lys Val Thr Gln Gly Thr Thr Ser Val Val Gln Ser
195 200 205

Phe Asn Arg Gly Asp Cys
210

<210> SEQ ID NO 162
<211> LENGTH: 642
<212> TYPE: DNA
<213> ORGANISM: Artificial Sequence
<220> FEATURE:
<223> OTHER INFORMATION: 10236 Light Chain Fab Nucl.

<400> SEQUENCE: 162
gcctatgata tgacccagac tccagcctct gtggaggtag ctgtgggagg cacagtcacc 60
atcaagtgcc aggccagtca gagcattagc agttggttag cctggtatca gcagaaacca 120
ggtcagcctc ccaagctcct gatctatctg gcatccactc tggcatctgg ggtctcatcg 180
cggttcaaag gcagtggatc tgggacacag ttcactctca ccatcagcgg cgtggagtgt 240

```
gccgatgctg ccacttacta ctgtcaacag ggttatacta atagtaatat tattaatact    300

ttcggcggag ggaccgaggt ggtggtcaaa cgtacgccag ttgcacctac tgtcctcatc    360

ttcccaccag ctgctgatca ggtggcaact ggaacagtca ccatcgtgtg tgtggcgaat    420

aaatactttc ccgatgtcac cgtcacctgg gaggtggatg gcaccaccca aacaactggc    480

atcgagaaca gtaaaacacc gcagaattct gcagattgta cctacaacct cagcagcact    540

ctgacactga ccagcacaca gtacaacagc cacaaagagt acacctgcaa ggtgacccag    600

ggcacgacct cagtcgtcca gagcttcaat aggggtgact gt                      642
```

```
<210> SEQ ID NO 163
<211> LENGTH: 217
<212> TYPE: PRT
<213> ORGANISM: Artificial Sequence
<220> FEATURE:
<223> OTHER INFORMATION: 10236 heavy chain Fab

<400> SEQUENCE: 163

Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
        35                  40                  45

Asp Ile Tyr Pro Ser Asp Ile Ile Asp Tyr Ala Ser Trp Ala Lys Gly
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95

Asn Asp Tyr Gly Leu Asp Ile Trp Gly Pro Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Ser Gln Pro Val
            180                 185                 190

Thr Cys Asn Val Ala His Pro Ala Thr Asn Thr Lys Val Asp Lys Thr
        195                 200                 205

Val Ala Pro Ser Thr Cys Ser Lys Pro
    210                 215
```

```
<210> SEQ ID NO 164
<211> LENGTH: 651
<212> TYPE: DNA
<213> ORGANISM: Artificial Sequence
<220> FEATURE:
<223> OTHER INFORMATION: 10236 heavy chain Fab Nucl.

<400> SEQUENCE: 164

cagtcggtgg aggagtccgg gggtcgcctg gtcacgcctg ggacacccct gacactcacc     60

tgcaccgtct ctgggttccc cctcagtaat tatgcaatga gctgggtccg ccaggctcca    120
```

```
gggaaggggc tggaatggat cggagacatt tatcctagtg atatcataga ctacgcgagc    180

tgggcgaaag gccgattcac catctcccaa acctcgacca cggtggagct gaaaatcacg    240

ggtccgacaa ccgaggacac ggccacctat ttctgtgcca gagacaacaa tgactatggt    300

ctggacatct ggggcccagg caccctggtc accgtctcga gtgggcaacc taaggctcca    360

tcagtcttcc cactggcccc ctgctgcggg gacacaccca gctccacggt gaccctgggc    420

tgcctggtca aaggctacct cccggagcca gtgaccgtga cctggaactc gggcaccctc    480

accaatgggg tacgcacctt cccgtccgtc cggcagtcct caggcctcta ctcgctgagc    540

agcgtggtga gcgtgacctc aagcagccag cccgtcacct gcaacgtggc ccacccagcc    600

accaacacca aagtggacaa gaccgttgcg ccctcgacat gcagcaagcc c             651
```

```
<210> SEQ ID NO 165
<211> LENGTH: 216
<212> TYPE: PRT
<213> ORGANISM: Artificial Sequence
<220> FEATURE:
<223> OTHER INFORMATION: 10273 Light chain Fab

<400> SEQUENCE: 165

Ala Val Val Leu Thr Gln Thr Pro Ser Pro Met Ser Ala Ala Val Gly
1               5                   10                  15

Gly Thr Val Thr Ile Ser Cys Gln Ser Ser Gln Ser Val Tyr Asn Asn
            20                  25                  30

Asn Asp Leu Ala Trp Tyr Gln Gln Lys Pro Gly Gln Pro Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Asp
                85                  90                  95

Asp Val Asp Thr Tyr Thr Phe Gly Gly Gly Thr Glu Val Val Val Lys
            100                 105                 110

Arg Thr Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215


<210> SEQ ID NO 166
<211> LENGTH: 648
<212> TYPE: DNA
<213> ORGANISM: Artificial Sequence
<220> FEATURE:
<223> OTHER INFORMATION: 10273  Light Chain Fab Nucl.
```

<400> SEQUENCE: 166
gcagtcgtgc tgactcagac accatcaccc atgtctgcag ctgtgggagg cacagtcacc 60
atcagttgcc agtccagtca gagtgtttat aataataacg acttagcctg gtatcagcag 120
aaaccagggc agcctcctaa gctcctgatc tacagggcat ccactctggc atctggggtc 180
ccgtcgcggt tcagcggcag tggatctggg acacagttca ctctcaccat cagcggcgtg 240
cagtgtgacg atgctgccac ttactactgt ctaggcggtt atgatgatga tgttgatacg 300
tatactttcg gcggagggac cgaggtggtg gtcaaacgta cgccagttgc acctactgtc 360
ctcatcttcc caccagctgc tgatcaggtg gcaactggaa cagtcaccat cgtgtgtgtg 420
gcgaataaat actttcccga tgtcaccgtc acctgggagg tggatggcac cacccaaaca 480
actggcatcg agaacagtaa aacaccgcag aattctgcag attgtaccta caacctcagc 540
agcactctga cactgaccag cacacagtac aacagccaca aagagtacac ctgcaaggtg 600
acccagggca cgacctcagt cgtccagagc ttcaataggg gtgactgt 648

<210> SEQ ID NO 167
<211> LENGTH: 228
<212> TYPE: PRT
<213> ORGANISM: Artificial Sequence
<220> FEATURE:
<223> OTHER INFORMATION: 10273 heavy chain Fab

<400> SEQUENCE: 167

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Gly
20 25 30

Met Ser Trp Val Arg Gln Ala Pro Gly Lys Gly Leu Glu Trp Ile Gly
35 40 45

Ile Ile Ser Ser Ser Gly Ser Thr Tyr Tyr Ala Ser Trp Ala Lys Gly
50 55 60

Arg Phe Thr Ile Ser Lys Thr Ser Thr Thr Val Asp Leu Lys Ile Ala
65 70 75 80

Ser Pro Thr Thr Glu Asp Thr Ala Thr Tyr Phe Cys Ala Arg Asp His
85 90 95

Ile Tyr Arg Tyr Asp Asp Tyr Gly Asp Tyr Pro Thr Tyr Tyr Gly Met
100 105 110

Asp Pro Trp Gly Pro Gly Thr Leu Val Thr Val Ser Ser Gly Gln Pro
115 120 125

Lys Ala Pro Ser Val Phe Pro Leu Ala Pro Cys Cys Gly Asp Thr Pro
130 135 140

Ser Ser Thr Val Thr Leu Gly Cys Leu Val Lys Gly Tyr Leu Pro Glu
145 150 155 160

Pro Val Thr Val Thr Trp Asn Ser Gly Thr Leu Thr Asn Gly Val Arg
165 170 175

Thr Phe Pro Ser Val Arg Gln Ser Ser Gly Leu Tyr Ser Leu Ser Ser
180 185 190

Val Val Ser Val Thr Ser Ser Ser Gln Pro Val Thr Cys Asn Val Ala
195 200 205

His Pro Ala Thr Asn Thr Lys Val Asp Lys Thr Val Ala Pro Ser Thr
210 215 220

Cys Ser Lys Pro
225

<210> SEQ ID NO 168
<211> LENGTH: 684
<212> TYPE: DNA
<213> ORGANISM: Artificial Sequence
<220> FEATURE:
<223> OTHER INFORMATION: 10273 heavy chain Fab Nucl.

<400> SEQUENCE: 168

```
cagtcggtgg aggagtccgg gggtcgcctg gtcacgcctg ggacacccct gacactcacc     60

tgcacagtct ctggattctc cctcagtagc tatggaatga gctgggtccg ccaggctcca    120

gggaaggggc tggaatggat cggaattatt agtagtagtg gtagcacata ctacgcgagc    180

tgggcgaaag gccgattcac catctccaag acctcgacca cggtggatct gaaaatcgcc    240

agtccgacaa ccgaggacac ggccacctat ttctgtgcca gagatcacat ttataggtac    300

gatgactatg gtgattaccc tacctactac ggcatggacc cctggggccc aggcaccctg    360

gtcaccgtct cgagtgggca acctaaggct ccatcagtct tcccactggc cccctgctgc    420

ggggacacac ccagctccac ggtgaccctg ggctgcctgg tcaaaggcta cctcccggag    480

ccagtgaccg tgacctggaa ctcgggcacc ctcaccaatg ggtacgcac cttcccgtcc    540

gtccggcagt cctcaggcct ctactcgctg agcagcgtgg tgagcgtgac ctcaagcagc    600

cagcccgtca cctgcaacgt ggcccaccca gccaccaaca ccaaagtgga caagaccgtt    660

gcgccctcga catgcagcaa gccc                                           684
```

<210> SEQ ID NO 169
<211> LENGTH: 316
<212> TYPE: PRT
<213> ORGANISM: Artificial Sequence
<220> FEATURE:
<223> OTHER INFORMATION: Human LEKTI D5 Fab H chain

<400> SEQUENCE: 169

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Arg Glu Ile Val Lys Leu Cys Ser Gln Tyr Gln Asn
                85                  90                  95

Gln Ala Lys Asn Gly Ile Leu Phe Cys Thr Arg Glu Asn Asp Pro Ile
            100                 105                 110

Arg Gly Pro Asp Gly Lys Met His Gly Asn Leu Cys Ser Met Cys Gln
        115                 120                 125

Ala Tyr Phe Gln Ala Glu Asn Glu Glu Lys Lys Lys Ala Glu Ala Arg
    130                 135                 140

Ala Arg Ser Gly Gly Gly Gly Gly Gly Gly Gly Ser Lys Asn Thr Val
145                 150                 155                 160

Tyr Leu Gln Met Asn Ser Leu Arg Ala Glu Asp Thr Ala Val Tyr Tyr
                165                 170                 175

Cys Ala Arg Thr Val Pro Gly Tyr Ser Thr Ala Pro Tyr Phe Asp Leu
            180                 185                 190
```

Trp Gly Gln Gly Thr Leu Val Thr Val Ser Ser Ala Ser Thr Lys Gly
195 200 205

Pro Ser Val Phe Pro Leu Ala Pro Ser Ser Lys Ser Thr Ser Gly Gly
210 215 220

Thr Ala Ala Leu Gly Cys Leu Val Lys Asp Tyr Phe Pro Glu Pro Val
225 230 235 240

Thr Val Ser Trp Asn Ser Gly Ala Leu Thr Ser Gly Val His Thr Phe
245 250 255

Pro Ala Val Leu Gln Ser Ser Gly Leu Tyr Ser Leu Ser Ser Val Val
260 265 270

Thr Val Pro Ser Ser Ser Leu Gly Thr Gln Thr Tyr Ile Cys Asn Val
275 280 285

Asn His Lys Pro Ser Asn Thr Lys Val Asp Lys Lys Val Glu Pro Lys
290 295 300

Ser Cys His His His His His His His His His His
305 310 315

<210> SEQ ID NO 170
<211> LENGTH: 217
<212> TYPE: PRT
<213> ORGANISM: Artificial Sequence
<220> FEATURE:
<223> OTHER INFORMATION: Human LEKTI D5 Fab L chain

<400> SEQUENCE: 170

Asp Ile Gln Met Thr Gln Ser Pro Ser Ser Val Ser Ala Ser Val Gly
1 5 10 15

Asp Arg Val Thr Ile Thr Cys Gln Ser Ser Pro Ser Val Trp Ser Asn
20 25 30

Phe Leu Ser Trp Tyr Gln Gln Lys Pro Gly Lys Ala Pro Lys Leu Leu
35 40 45

Ile Tyr Glu Ala Ser Lys Leu Thr Ser Gly Val Pro Ser Arg Phe Ser
50 55 60

Gly Ser Gly Ser Gly Thr Asp Phe Thr Leu Thr Ile Ser Ser Leu Gln
65 70 75 80

Pro Glu Asp Phe Ala Thr Tyr Tyr Cys Gly Gly Gly Tyr Ser Ser Ile
85 90 95

Ser Asp Thr Thr Phe Gly Gly Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 171

-continued

```
<211> LENGTH: 217
<212> TYPE: PRT
<213> ORGANISM: Artificial Sequence
<220> FEATURE:
<223> OTHER INFORMATION: Rabbit/human chimeric light chain (hCK S171C)
      10236

<400> SEQUENCE: 171

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Cys Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 172
<211> LENGTH: 441
<212> TYPE: PRT
<213> ORGANISM: Artificial Sequence
<220> FEATURE:
<223> OTHER INFORMATION: Rabbit/human chimeric heavy chain 10236

<400> SEQUENCE: 172

Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
        35                  40                  45

Asp Ile Tyr Pro Ser Asp Ile Ile Asp Tyr Ala Ser Trp Ala Lys Gly
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95
```

Asn Asp Tyr Gly Leu Asp Ile Trp Gly Pro Gly Thr Leu Val Thr Val
100 105 110

Ser Ser Ala Ser Thr Lys Gly Pro Ser Val Phe Pro Leu Ala Pro Cys
115 120 125

Ser Arg Ser Thr Ser Glu Ser Thr Ala Ala Leu Gly Cys Leu Val Lys
130 135 140

Asp Tyr Phe Pro Glu Pro Val Thr Val Ser Trp Asn Ser Gly Ala Leu
145 150 155 160

Thr Ser Gly Val His Thr Phe Pro Ala Val Leu Gln Ser Ser Gly Leu
165 170 175

Tyr Ser Leu Ser Ser Val Val Thr Val Pro Ser Ser Ser Leu Gly Thr
180 185 190

Lys Thr Tyr Thr Cys Asn Val Asp His Lys Pro Ser Asn Thr Lys Val
195 200 205

Asp Lys Arg Val Glu Ser Lys Tyr Gly Pro Pro Cys Pro Pro Cys Pro
210 215 220

Ala Pro Glu Phe Leu Gly Gly Pro Ser Val Phe Leu Phe Pro Pro Lys
225 230 235 240

Pro Lys Asp Thr Leu Met Ile Ser Arg Thr Pro Glu Val Thr Cys Val
245 250 255

Val Val Asp Val Ser Gln Glu Asp Pro Glu Val Gln Phe Asn Trp Tyr
260 265 270

Val Asp Gly Val Glu Val His Asn Ala Lys Thr Lys Pro Arg Glu Glu
275 280 285

Gln Phe Asn Ser Thr Tyr Arg Val Val Ser Val Leu Thr Val Leu His
290 295 300

Gln Asp Trp Leu Asn Gly Lys Glu Tyr Lys Cys Lys Val Ser Asn Lys
305 310 315 320

Gly Leu Pro Ser Ser Ile Glu Lys Thr Ile Ser Lys Ala Lys Gly Gln
325 330 335

Pro Arg Glu Pro Gln Val Tyr Thr Leu Pro Pro Ser Gln Glu Glu Met
340 345 350

Thr Lys Asn Gln Val Ser Leu Thr Cys Leu Val Lys Gly Phe Tyr Pro
355 360 365

Ser Asp Ile Ala Val Glu Trp Glu Ser Asn Gly Gln Pro Glu Asn Asn
370 375 380

Tyr Lys Thr Thr Pro Pro Val Leu Asp Ser Asp Gly Ser Phe Phe Leu
385 390 395 400

Tyr Ser Arg Leu Thr Val Asp Lys Ser Arg Trp Gln Glu Gly Asn Val
405 410 415

Phe Ser Cys Ser Val Met His Glu Ala Leu His Asn His Tyr Thr Gln
420 425 430

Lys Ser Leu Ser Leu Ser Leu Gly Lys
435 440

<210> SEQ ID NO 173
<211> LENGTH: 308
<212> TYPE: PRT
<213> ORGANISM: Artificial Sequence
<220> FEATURE:
<223> OTHER INFORMATION: LEKTI-D5-Fc TEV

<400> SEQUENCE: 173

Glu Ile Val Lys Leu Cys Ser Gln Tyr Gln Asn Gln Ala Lys Asn Gly
1 5 10 15

-continued

```
Ile Leu Phe Cys Thr Arg Glu Asn Asp Pro Ile Arg Gly Pro Asp Gly
            20                  25                  30

Lys Met His Gly Asn Leu Cys Ser Met Cys Gln Ala Tyr Phe Gln Ala
        35                  40                  45

Glu Asn Glu Glu Lys Lys Lys Ala Glu Ala Arg Ala Arg Asn Leu Glu
    50                  55                  60

Glu Asn Leu Tyr Phe Gln Gly Val Asp Lys Lys Val Glu Pro Lys Ser
65                  70                  75                  80

Cys Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
            100                 105                 110

Met Ile Ser Arg Thr Pro Glu Val Thr Cys Val Val Val Asp Val Ser
        115                 120                 125

His Glu Asp Pro Glu Val Lys Phe Asn Trp Tyr Val Asp Gly Val Glu
    130                 135                 140

Val His Asn Ala Lys Thr Lys Pro Arg Glu Glu Gln Tyr Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Ala Leu Pro Ala Pro
            180                 185                 190

Ile Glu Lys Thr Ile Ser Lys Ala Lys Gly Gln Pro Arg Glu Pro Gln
        195                 200                 205

Val Tyr Thr Leu Pro Pro Ser Arg Asp Glu Leu Thr Lys Asn Gln Val
    210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Tyr Ser Lys Leu Thr
            260                 265                 270

Val Asp Lys Ser Arg Trp Gln Gln Gly Asn Val Phe Ser Cys Ser Val
        275                 280                 285

Met His Glu Ala Leu His Asn His Tyr Thr Gln Lys Ser Leu Ser Leu
    290                 295                 300

Ser Pro Gly Lys
305


<210> SEQ ID NO 174
<211> LENGTH: 315
<212> TYPE: PRT
<213> ORGANISM: Artificial Sequence
<220> FEATURE:
<223> OTHER INFORMATION: LEKTI-D8-Fc TEV

<400> SEQUENCE: 174

Glu Ala Ala Lys Glu Ile Cys Ser Glu Phe Arg Asp Gln Val Arg Asn
1               5                   10                  15

Gly Thr Leu Ile Cys Thr Arg Glu His Asn Pro Val Arg Gly Pro Asp
            20                  25                  30

Gly Lys Met His Gly Asn Lys Cys Ala Met Cys Ala Ser Val Phe Lys
        35                  40                  45

Leu Glu Glu Glu Glu Lys Lys Asn Asp Lys Glu Glu Lys Gly Lys Val
    50                  55                  60
```

Glu Ala Glu Lys Val Leu Glu Glu Asn Leu Tyr Phe Gln Gly Val Asp
65 70 75 80

Lys Lys Val Glu Pro Lys Ser Cys Asp Lys Thr His Thr Cys Pro Pro
85 90 95

Cys Pro Ala Pro Glu Leu Leu Gly Gly Pro Ser Val Phe Leu Phe Pro
100 105 110

Pro Lys Pro Lys Asp Thr Leu Met Ile Ser Arg Thr Pro Glu Val Thr
115 120 125

Cys Val Val Val Asp Val Ser His Glu Asp Pro Glu Val Lys Phe Asn
130 135 140

Trp Tyr Val Asp Gly Val Glu Val His Asn Ala Lys Thr Lys Pro Arg
145 150 155 160

Glu Glu Gln Tyr Asn Ser Thr Tyr Arg Val Val Ser Val Leu Thr Val
165 170 175

Leu His Gln Asp Trp Leu Asn Gly Lys Glu Tyr Lys Cys Lys Val Ser
180 185 190

Asn Lys Ala Leu Pro Ala Pro Ile Glu Lys Thr Ile Ser Lys Ala Lys
195 200 205

Gly Gln Pro Arg Glu Pro Gln Val Tyr Thr Leu Pro Pro Ser Arg Asp
210 215 220

Glu Leu Thr Lys Asn Gln Val Ser Leu Thr Cys Leu Val Lys Gly Phe
225 230 235 240

Tyr Pro Ser Asp Ile Ala Val Glu Trp Glu Ser Asn Gly Gln Pro Glu
245 250 255

Asn Asn Tyr Lys Thr Thr Pro Pro Val Leu Asp Ser Asp Gly Ser Phe
260 265 270

Phe Leu Tyr Ser Lys Leu Thr Val Asp Lys Ser Arg Trp Gln Gln Gly
275 280 285

Asn Val Phe Ser Cys Ser Val Met His Glu Ala Leu His Asn His Tyr
290 295 300

Thr Gln Lys Ser Leu Ser Leu Ser Pro Gly Lys
305 310 315

<210> SEQ ID NO 175
<211> LENGTH: 11
<212> TYPE: PRT
<213> ORGANISM: Artificial Sequence
<220> FEATURE:
<223> OTHER INFORMATION: 10236 CDR-L1

<400> SEQUENCE: 175

Gln Ala Ser Gln Ser Ile Ser Ser Trp Leu Ala
1 5 10

<210> SEQ ID NO 176
<211> LENGTH: 7
<212> TYPE: PRT
<213> ORGANISM: Artificial Sequence
<220> FEATURE:
<223> OTHER INFORMATION: 10236 CDR-L2

<400> SEQUENCE: 176

Leu Ala Ser Thr Leu Ala Ser
1 5

<210> SEQ ID NO 177
<211> LENGTH: 12
<212> TYPE: PRT
<213> ORGANISM: Artificial Sequence

```
<220> FEATURE:
<223> OTHER INFORMATION: 10236 CDR-L3

<400> SEQUENCE: 177

Gln Gln Gly Tyr Thr Asn Ser Asn Ile Ile Asn Thr
1               5                   10


<210> SEQ ID NO 178
<211> LENGTH: 10
<212> TYPE: PRT
<213> ORGANISM: Artificial Sequence
<220> FEATURE:
<223> OTHER INFORMATION: 10236 CDR-H1

<400> SEQUENCE: 178

Gly Phe Pro Leu Ser Asn Tyr Ala Met Ser
1               5                   10


<210> SEQ ID NO 179
<211> LENGTH: 16
<212> TYPE: PRT
<213> ORGANISM: Artificial Sequence
<220> FEATURE:
<223> OTHER INFORMATION: 10236 CDR-H2

<400> SEQUENCE: 179

Asp Ile Tyr Pro Ser Asp Ile Ile Asp Tyr Ala Ser Trp Ala Lys Gly
1               5                   10                  15


<210> SEQ ID NO 180
<211> LENGTH: 9
<212> TYPE: PRT
<213> ORGANISM: Artificial Sequence
<220> FEATURE:
<223> OTHER INFORMATION: 10236 CDR-H3

<400> SEQUENCE: 180

Asp Asn Asn Asp Tyr Gly Leu Asp Ile
1               5


<210> SEQ ID NO 181
<211> LENGTH: 110
<212> TYPE: PRT
<213> ORGANISM: Artificial Sequence
<220> FEATURE:
<223> OTHER INFORMATION: 10236 Rabbit VL

<400> SEQUENCE: 181

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys
            100                 105                 110
```

<210> SEQ ID NO 182
<211> LENGTH: 336
<212> TYPE: DNA
<213> ORGANISM: Artificial Sequence
<220> FEATURE:
<223> OTHER INFORMATION: 10236 Rabbit VL nucl.

<400> SEQUENCE: 182
gcctatgata tgacccagac tccagcctct gtggaggtag ctgtgggagg cacagtcacc 60
atcaagtgcc aggccagtca gagcattagc agttggttag cctggtatca gcagaaacca 120
ggtcagcctc ccaagctcct gatctatctg gcatccactc tggcatctgg ggtctcatcg 180
cggttcaaag gcagtggatc tgggacacag ttcactctca ccatcagcgg cgtggagtgt 240
gccgatgctg ccacttacta ctgtcaacag ggttatacta atagtaatat tattaatact 300
ttcggcggag ggaccgaggt ggtggtcaaa cgtacg 336

<210> SEQ ID NO 183
<211> LENGTH: 114
<212> TYPE: PRT
<213> ORGANISM: Artificial Sequence
<220> FEATURE:
<223> OTHER INFORMATION: 10236 Rabbit VH

<400> SEQUENCE: 183

Gln Ser Val Glu Glu Ser Gly Gly Arg Leu Val Thr Pro Gly Thr Pro
1 5 10 15

Leu Thr Leu Thr Cys Thr Val Ser Gly Phe Pro Leu Ser Asn Tyr Ala
20 25 30

Met Ser Trp Val Arg Gln Ala Pro Gly Lys Gly Leu Glu Trp Ile Gly
35 40 45

Asp Ile Tyr Pro Ser Asp Ile Ile Asp Tyr Ala Ser Trp Ala Lys Gly
50 55 60

Arg Phe Thr Ile Ser Gln Thr Ser Thr Thr Val Glu Leu Lys Ile Thr
65 70 75 80

Gly Pro Thr Thr Glu Asp Thr Ala Thr Tyr Phe Cys Ala Arg Asp Asn
85 90 95

Asn Asp Tyr Gly Leu Asp Ile Trp Gly Pro Gly Thr Leu Val Thr Val
100 105 110

Ser Ser

<210> SEQ ID NO 184
<211> LENGTH: 342
<212> TYPE: DNA
<213> ORGANISM: Artificial Sequence
<220> FEATURE:
<223> OTHER INFORMATION: 10236 Rabbit VH nucl.

<400> SEQUENCE: 184
cagtcggtgg aggagtccgg gggtcgcctg gtcacgcctg ggacacccct gacactcacc 60
tgcaccgtct ctgggttccc cctcagtaat tatgcaatga gctgggtccg ccaggctcca 120
gggaaggggc tggaatggat cggagacatt tatcctagtg atatcataga ctacgcgagc 180
tgggcgaaag gccgattcac catctcccaa acctcgacca cggtggagct gaaaatcacg 240
ggtccgacaa ccgaggacac ggccacctat ttctgtgcca gagacaacaa tgactatggt 300
ctggacatct ggggcccagg caccctggtc accgtctcga gt 342

<210> SEQ ID NO 185
<211> LENGTH: 228

<212> TYPE: PRT
<213> ORGANISM: Artificial Sequence
<220> FEATURE:
<223> OTHER INFORMATION: Mouse KLK7 pro-form

<400> SEQUENCE: 185

```
Gln Gly Glu Arg Ile Ile Asp Gly Tyr Lys Cys Lys Glu Gly Ser His
1               5                   10                  15

Pro Trp Gln Val Ala Leu Leu Lys Gly Asn Gln Leu His Cys Gly Gly
            20                  25                  30

Val Leu Val Asp Lys Tyr Trp Val Leu Thr Ala Ala His Cys Lys Met
        35                  40                  45

Gly Gln Tyr Gln Val Gln Leu Gly Ser Asp Lys Ile Gly Asp Gln Ser
    50                  55                  60

Ala Gln Lys Ile Lys Ala Thr Lys Ser Phe Arg His Pro Gly Tyr Ser
65                  70                  75                  80

Thr Lys Thr His Val Asn Asp Ile Met Leu Val Arg Leu Asp Glu Pro
                85                  90                  95

Val Lys Met Ser Ser Lys Val Glu Ala Val Gln Leu Pro Glu His Cys
            100                 105                 110

Glu Pro Pro Gly Thr Ser Cys Thr Val Ser Gly Trp Gly Thr Thr Thr
        115                 120                 125

Ser Pro Asp Val Thr Phe Pro Ser Asp Leu Met Cys Ser Asp Val Lys
    130                 135                 140

Leu Ile Ser Ser Arg Glu Cys Lys Lys Val Tyr Lys Asp Leu Leu Gly
145                 150                 155                 160

Lys Thr Met Leu Cys Ala Gly Ile Pro Asp Ser Lys Thr Asn Thr Cys
                165                 170                 175

Asn Gly Asp Ser Gly Gly Pro Leu Val Cys Asn Asp Thr Leu Gln Gly
            180                 185                 190

Leu Val Ser Trp Gly Thr Tyr Pro Cys Gly Gln Pro Asn Asp Pro Gly
        195                 200                 205

Val Tyr Thr Gln Val Cys Lys Tyr Lys Arg Trp Val Met Glu Thr Met
    210                 215                 220

Lys Thr His Arg
225
```

<210> SEQ ID NO 186
<211> LENGTH: 224
<212> TYPE: PRT
<213> ORGANISM: Artificial Sequence
<220> FEATURE:
<223> OTHER INFORMATION: Active Mouse KLK7

<400> SEQUENCE: 186

```
Ile Ile Asp Gly Tyr Lys Cys Lys Glu Gly Ser His Pro Trp Gln Val
1               5                   10                  15

Ala Leu Leu Lys Gly Asn Gln Leu His Cys Gly Gly Val Leu Val Asp
            20                  25                  30

Lys Tyr Trp Val Leu Thr Ala Ala His Cys Lys Met Gly Gln Tyr Gln
        35                  40                  45

Val Gln Leu Gly Ser Asp Lys Ile Gly Asp Gln Ser Ala Gln Lys Ile
    50                  55                  60

Lys Ala Thr Lys Ser Phe Arg His Pro Gly Tyr Ser Thr Lys Thr His
65                  70                  75                  80

Val Asn Asp Ile Met Leu Val Arg Leu Asp Glu Pro Val Lys Met Ser
                85                  90                  95
```

-continued

```
Ser Lys Val Glu Ala Val Gln Leu Pro Glu His Cys Glu Pro Pro Gly
            100                 105                 110

Thr Ser Cys Thr Val Ser Gly Trp Gly Thr Thr Thr Ser Pro Asp Val
        115                 120                 125

Thr Phe Pro Ser Asp Leu Met Cys Ser Asp Val Lys Leu Ile Ser Ser
    130                 135                 140

Arg Glu Cys Lys Lys Val Tyr Lys Asp Leu Leu Gly Lys Thr Met Leu
145                 150                 155                 160

Cys Ala Gly Ile Pro Asp Ser Lys Thr Asn Thr Cys Asn Gly Asp Ser
                165                 170                 175

Gly Gly Pro Leu Val Cys Asn Asp Thr Leu Gln Gly Leu Val Ser Trp
            180                 185                 190

Gly Thr Tyr Pro Cys Gly Gln Pro Asn Asp Pro Gly Val Tyr Thr Gln
        195                 200                 205

Val Cys Lys Tyr Lys Arg Trp Val Met Glu Thr Met Lys Thr His Arg
    210                 215                 220
```

ANTIBODIES AGAINST KLK5

FIELD OF THE INVENTION

The present invention relates to antibodies which bind and inhibit KLK5 and methods of using the same to treat diseases caused by KLK5 dysregulation. In particular, the present invention relates to anti-KLK5 antibodies and their use in the treatment of Netherton disease, ichthyoses such as congenital ichthyosis, atopic dermatitis, and cancer.

BACKGROUND OF THE INVENTION

Kallikrein-related peptidases (known as KLKs) constitute a single family of 15 highly conserved trypsin or chymotrypsin-like serine proteases encoded by the largest uninterrupted cluster of protease-encoding-genes (chromosome 19q13.4) in the human genome (Sotiropoulou G. et al., 2009; JBC 284:48, 32989-94).

KLK proteins are synthesized as inactive pre-pro-forms that are proteolytically processed to secrete inactive pro-forms. Such pro-forms are subsequently activated to mature peptidases by specific proteolytic removal of their N-terminal pro-peptide either by other KLKs or endopeptidase or by autocatalytic cleavage such as for KLK5. KLK5 has trypsin-like activity. In its pre-pro-form, it comprises a 29 amino acid signal peptide, followed by a 37 amino acid activation peptide. The active mature form consists of 237 amino acids comprising the mature enzyme which includes the serine-protease domain responsible for protease activity (Michael I. P et al., 2005; JBC 280:15, 14628-35).

Whilst KLK5 is found in many tissues, it appears to be most abundantly expressed in skin. Along with KLK7, KLK5 is expressed in the upper spinous and granular levels of skin along with KLK7, where keratinocytes undergo terminal differentiation and are transformed in corneocytes that build the stratum corneum. The stratum corneum function as a barrier to the outside environment and is maintained through constant replacement of corneocytes shed by the process of desquamation. Because KLK5 is capable of activating pro-KLK7 and other kallikreins, its role in desquamation is essential.

Following activation, mature KLK5 is inactivated by the endogenous inhibitor Lymphoepithelial Kazal-type inhibitor (LEKTI) which is encoded by the SPINK5 gene (Chavans P et al., 2005; Nat Genet 37, 56-65). LEKTI contains 15-domain serine protease inhibitor domains forming a tight complex with KLK5. Variation in pH govern this tight interaction with acidic pH releasing active KLK5 from the complex (Deraison C et al. 2007; Mol Biol Cell 18 3607-19).

Loss-of-function mutations in SPINK5 gene causes Netherton syndrome, a rare autosomal recessive skin disease characterized by ichthyosis features with severe inflammation, skin scaling, elevated IgE levels and constant allergic manifestations (Hovnanian A. 2013; Cell Tissue Res 351 289-300). Secondary to epidermal protease hyperactivity, lack of LEKTI causes stratum corneum detachment caused by KLK5 activity on desmoglein and on desmosome which in turn favors high permeability to various allergens causing atopic dermatitis-like lesions. KLK5 activity on KLK7 also contributes to a defective skin barrier leading to allergen and microbe penetration and production of IL-1beta.

SPINK5 $^{-/-}$ mice recapitulate a phenotype highly reminiscent of Netherton syndrome replicating cutaneous and inflammatory aspects of the disease (Yant T et al.; 2004, Genes Dev 18 2354-58). SPINK5 $^{-/-}$ epidermis from Netherton's syndrome patients displays unopposed KLK5 and KLK7 protease activity which appears to sustain activation of pro-inflammatory and pro-signaling pathways including the KLK5-PAR2-TSLP (thymic stromal lymphopoietin) axis. In both SPINK5 $^{-/-}$ and KLK5 $^{-/-}$ mice, the KLK5 knock-out was sufficient to correct such cutaneous manifestation of LEKTI knock-out, illustrating the crucial role of KLK5 in skin homeostasis.

In recent years, several studies have reported a genetic association between Atopic Dermatitis (AD) and LEKTI polymorphism with abnormal variants of LEKTI being expressed (Hovnanian A. 2013; Cell Tissue Res 351 289-300).

To date, no KLK5 specific therapies exist although a KLK7 inhibitor is in clinical development. Other approaches aimed at replacing LEKTI have been pursued, including gene addition by means of SPINK5 lentiviral or adenoviral vector and autologous grafts of genetically corrected patient keratinocytes (Di W L. et al.; 2011, Mol Ther 19 408-16).

Therefore, there remains a need for anti-KLK5 therapies, such as passive-immune therapies aimed at inhibiting KLK5 that could exert therapeutic effects in diseases associated with or caused by the dysregulation of KLK5.

SUMMARY OF THE INVENTION

The present invention addresses the above-identified need by providing inhibitory anti-KLK5 antibodies according to the following embodiments.

Embodiment 1

A monoclonal antibody which binds to kallikrein 5 (KLK5), wherein the antibody comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29.

Embodiment 2

The antibody according to Embodiment 1, wherein a. the variable light chain comprises a CDR-L1 comprising SEQ ID NO: 7, a CDR-L2 comprising SEQ ID NO: 2 and a CDR-L3 comprising SEQ ID NO: 3; and b. the variable heavy chain comprises a CDR-H1 com comprising SEQ ID NO: 4, a CDR-H2 comprising SEQ ID NO: 5 and a CDR-H3 comprising SEQ ID NO: 10 or 14 or 23.

Embodiment 3

The antibody according to Embodiments 1 or 2, wherein a. the variable light chain comprises a CDR-L1 comprising SEQ ID NO: 7, a CDR-L2 comprising SEQ ID NO: 2 and a CDR-L3 comprising SEQ ID NO: 3; and b. the variable heavy chain comprises a CDR-H1 com comprising SEQ ID NO: 4, a CDR-H2 comprising SEQ ID NO: 5 and a CDR-H3 comprising SEQ ID NO: 23.

Embodiment 4

The antibody according to any one of the preceding Embodiments wherein the antibody is a chimeric or humanized antibody.

Embodiment 5

The antibody according to any one of the preceding embodiments, wherein the antibody is a full-length antibody.

Embodiment 6

The antibody according to Embodiment 5, wherein the full-length antibody is selected from an IgG1, IgG4 or IgG4P.

Embodiment 7

The antibody according to any one of Embodiments 1 to 4, wherein the antibody is selected from a Fab, a Fab', a $F(ab')_2$, a scFv, a dAb or a VHH.

Embodiment 8

The antibody according to any one of Embodiments 1 to 7, wherein the antibody comprises:

a. a variable light chain comprising SEQ ID NO: 30 or 34 or 38 or 42 or 46; and/or b. a variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134.

Embodiment 9

The antibody according to any one of Embodiments 1 to 8, wherein the antibody comprises:

a. a variable light chain comprising SEQ ID NO: 38; and/or b. a variable heavy chain comprising SEQ ID NO: 110.

Embodiment 10

The antibody according to any one of Embodiments 1 to 6 or 8 or 9, wherein the antibody comprises:

a. a light chain comprising SEQ ID NO: 36 or 40 or 44 or 48; and b. a heavy chain comprising SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

Embodiment 11

The antibody according to any one of Embodiments 1 to 8, wherein the antibody comprises:

a. a light chain comprising SEQ ID NO: 40; and b. a heavy chain comprising SEQ ID NO: 112.

Embodiments 12

The antibody according to any one of the preceding Embodiments wherein KLK5 is human KLK5 comprising SEQ ID NO: 142 or 143 or 144 or cyno KLK5 comprising SEQ ID NO: 151.

Embodiment 13

The antibody according to any one of the preceding Embodiments which binds to kallikrein 5 (KLK5), wherein the antibody binds to an epitope of human KLK5 comprising at least one, preferably at least two or more, amino acid residue from the group consisting of Leu212, Ser213, Gln214, Lys215, Arg216, Glu218, Asp219, Ala220, Pro222, Gly233, Pro269, Asn270 and Pro272 with reference to SEQ ID NO: 142.

Embodiment 14

The antibody according to Embodiment 13, wherein the epitope is characterized by X-ray crystallography.

Embodiment 15

The antibody according to any one of Embodiments 1 to 14, wherein the antibody a. inhibits or reduces the protease activity of KLK5; and/or b. binds to KLK5 when KLK5 is bound to LEKTI, or a fragment of LEKTI; and/or c. does not compete with LEKTI, or a fragment of LEKTI, for binding KLK5; and/or d. forms a complex with KLK5 bound to LEKTI, or a fragment of LEKTI.

Embodiment 16

The antibody according to Embodiment 15 wherein the fragment of LEKTI is human LEKTI domain 5 comprising amino acids 1 to 64 of SEQ ID NO: 145 or LEKTI domain 8 comprising amino acids 1 to 71 of SEQ ID NO: 152.

Embodiment 17

The antibody according to any one of the preceding Embodiments wherein the antibody binds human KLK5, preferably human KLK5 comprising SEQ ID NO: 144 and cynomolgus monkey (cyno) KLK5, preferably cyno KLK5 comprising SEQ ID NO: 151.

Embodiment 18

The antibody according to any one of the preceding Embodiments wherein the antibody does not bind human or cyno kallikrein 2 (KLK2); or human or cyno kallikrein 4 (KLK4); or human or cyno kallikrein 7 (KLK7).

Embodiment 19

An antibody which competes for binding KLK5 with the antibody according to any one of Embodiments 1 to 18; and a. cross-blocks or is cross-blocked by the antibody according to any one of embodiments 1 to 18 for binding KLK5; or b. binds KLK5 to the same epitope as the antibody according to any one of embodiments 1 to 18; and wherein the antibody comprises a heavy chain variable region having at least 90% identity or similarity to the sequence according to SEQ ID NO: 38; and/or comprises a light chain variable region having at least 90% identity or similarity to the sequence according to SEQ ID NO: 110.

Embodiment 20

An isolated polynucleotide encoding the antibody according to any one of Embodiments 1 to 18.

Embodiment 21

The isolated polynucleotide according to Embodiment 20, wherein the polynucleotide encodes:

a. a light chain variable region, wherein the polynucleotide:

i. is at least 90% identical to SEQ ID NO: 31 or 35 or 39 or 43 or 47; or ii. comprises SEQ ID NO: 31 or 35 or 39 or 43 or 47; or iii. consists essentially of SEQ ID NO: 31 or 35 or 39 or 43 or 47; or b. a heavy chain variable region, wherein the polynucleotide:

i. is at least 90% identical to SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135; or ii. comprises SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135; or iii. consists essentially of SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135; or c. a light chain, wherein the polynucleotide:

i. is at least 90% identical to SEQ ID NO: 37 or 41 or 45 or 49; or ii. comprises SEQ ID NO: 37 or 41 or 45 or 49; or iii. consists essentially of SEQ ID NO: 37 or 41 or 45 or 49; or d. a heavy chain, wherein the polynucleotide:

i. is at least 90% identical to SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137; or ii. comprises SEQ ID NO: 53 or 57 or 61 or 65 or 69 or 73 or 77 or 81 or 85 ii. or 89 or 93 or 97 or 101 or 105 or 109 or 113 or 117 or 121 or 125 or 129 or 133 or 137; or iii. consists essentially of SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137.

Embodiment 22

A cloning or expression vector comprising one or more polynucleotides according to any one of Embodiments 20 or 21.

Embodiment 23

A host cell comprising:

a. one or more polynucleotides according to any one of Embodiments 20 or 21 or b. one or more expression vectors according to Embodiment 22.

Embodiment 24

A process for the production of an antibody according to any one of Embodiments 1 to 18, comprising culturing the host cell according to Embodiment 23 under suitable conditions for producing the antibody and isolating the antibody produced by the host cell.

Embodiment 25

A pharmaceutical composition comprising the antibody according to any one of Embodiments 1 to 18 and one or more pharmaceutically acceptable carriers, excipients of diluents.

Embodiment 26

The antibody or antigen-binding fragment thereof according to any one of Embodiments 1 to 18 or the pharmaceutical composition according to Embodiment 25 for use in therapy.

Embodiment 27

The antibody according to any one of Embodiments 1 to 18 or the pharmaceutical composition according to Embodiment 25 for use in the treatment of a disease characterized by dysregulation of KLK5 or by dysregulation of inhibition of KLK5.

Embodiment 28

The antibody for use according to Embodiment 27 wherein the disease is selected from Netherton's Syndrome, Atopic Dermatitis, Ichthyoses, Rosacea, Asthma or Cancer, such as ovarian cancer or bladder cancer or a combination thereof.

Embodiment 29

The antibody for use according to Embodiment 28 wherein the disease is Netherton's Syndrome.

Embodiment 30

The antibody for use according to Embodiment 28 wherein the disease is Atopic Dermatitis.

Embodiment 31

A method of treating diseases characterized by dysregulation of KLK5 or by dysregulation of inhibition of KLK5 in a patient comprising administering to said patient a therapeutically effective amount of an antibody according to any one of Embodiments 1 to 18 or the pharmaceutical composition according to Embodiment 25.

Embodiment 32

The method according to Embodiment 31 wherein the disease is selected from Netherton's Syndrome, Atopic Dermatitis, Ichthyoses, Rosacea, Asthma or Cancer, such as ovarian cancer or bladder cancer.

Embodiment 33

The antibody for use according to Embodiment 32 wherein the disease is Netherton's Syndrome.

Embodiment 34

The antibody for use according to Embodiment 32 wherein the disease is Atopic Dermatitis.

DETAILED DESCRIPTION OF THE INVENTION

Figure 1:
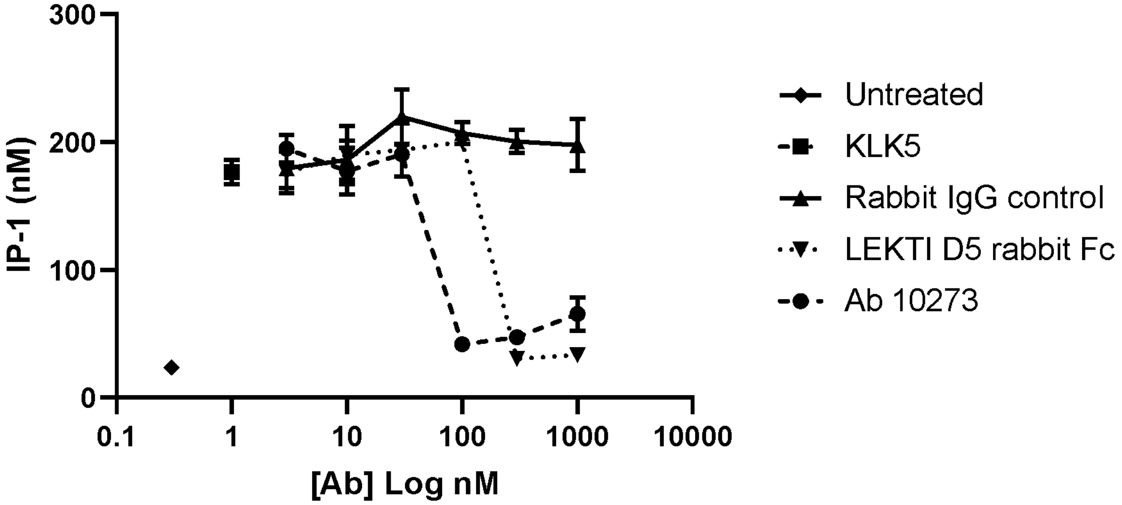
FIG. 1. Inhibition of IP-1 release from KLK5 stimulated keratinocytes with antibody 10273. The amount of IP-1 released into the culture medium following stimulation of keratinocytes with KLK5 in the presence or absence of rabbit antibody 10273 was determined. Antibody 10273 inhibited the release of IP-1 whereas the isotype control Ab showed no inhibitory effect.

The present disclosure will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of an anti-alpha synuclein antibody or antigen-binding fragment thereof that, when administered to a mammal or other subject for treating a disease, is sufficient to produce such treatment for the disease. The therapeutically effective amount will vary depending on the anti-alpha synuclein antibody or antigen-binding fragment thereof, the disease and its severity and the age, weight, etc., of the subject to be treated.

The term "isolated" means, throughout this specification, that the antibody, antigen-binding fragment or polynucleotide, as the case may be, exists in a physical milieu distinct from that in which it may occur in nature.

In a first aspect of the present invention, there is provided an antibody which binds to kallikrein 5 (KLK5), wherein the monoclonal antibody comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29.

Kallikrein 5 (KLK5, KLK-L2, SCTE or any other known synonym) has trypsin-like activity. It is expressed in pre-pro-form and comprises a 29 amino acid signal peptide according to the bioinformatics tool SignalP 5.0 (cbs.dtu.dk), followed by a 37 amino acid pro peptide sequence. Cleavage of the pro peptide produces the active mature enzyme consisting of 237 amino acids harboring an active site with a catalytic triad of residues typical of a serine-protease (Michael I. P et al., 2005; JBC 280:15, 14628-35).

Unless otherwise specified, the term KLK5 refers to any native pre- and pro-forms (i.e. unprocessed KLK5 comprising the signal sequence and activation peptide), alternative splicing or natural variants, mutants and KLK5 from other species (mouse, cynomolgus monkey, etc.) and active KLK5 (resulting from auto-cleavage or otherwise). When human KLK5 is specified, human KLK5 comprises the sequence given in SEQ ID NO: 144 (active human KLK5). Other KLK5 sequences referred herein comprises SEQ ID NO: 143 (human KLK5 pro-form lacking the signal sequence) or SEQ ID NO: 142 (full length human KLK5 with signal and pro-peptide sequences), the sequence corresponding to Uniprot Q9Y337 or natural variants comprising mutations at positions 55 and 153 (with reference to SEQ ID NO: 142). Examples of these mutations comprises human KLK5 comprising residues 23 to 293 according to SEQ ID NO: 142 having mutations Gly to Arg change at residue 55 (G55R) and/or Asp to Asn change at residue 153 (D153N).

The antibody according to the present invention is a monoclonal antibody. Monoclonal antibodies may be prepared by any method known in the art such as the hybridoma technique (Kohler & Milstein, 1975, Nature; 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96; Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93 (15): 7843-78481; WO92/02551; WO2004/051268 and WO2004/106377.

In one embodiment, the antibody which binds to kallikrein 5 (KLK5), comprises a variable light chain which comprises a CDR-L1 comprising SEQ ID NO: 7, a CDR-L2 comprising SEQ ID NO: 2 and a CDR-L3 comprising SEQ ID NO: 3; and a variable heavy chain which comprises a CDR-H1 com comprising SEQ ID NO: 4, a CDR-H2 comprising SEQ ID NO: 5 and a CDR-H3 comprising SEQ ID NO: 10 or 14 or 23.

In one preferred embodiment, the antibody which binds to kallikrein 5 (KLK5), comprises a variable light chain which comprises a CDR-L1 comprising SEQ ID NO: 7, a CDR-L2 comprising SEQ ID NO: 2 and a CDR-L3 comprising SEQ ID NO: 3; and a variable heavy chain comprises a CDR-H1 com comprising SEQ ID NO: 4, a CDR-H2 comprising SEQ ID NO: 5 and a CDR-H3 comprising SEQ ID NO: 23.

The antibody according to the present invention comprises complementarity determining regions (CDRs), three from a heavy chain and three from a light chain. Generally, the CDRs are in a framework and together form a variable region. By convention, the CDRs in the heavy chain variable region of an antibody or antigen-binding fragment thereof are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1991, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In addition to the CDR loops, a fourth loop exists between CDR-2 (CDR-L2 or CDR-H2) and CDR-3 (CDR-L3 or CDR-H3) which is formed by framework 3 (FR3). The Kabat numbering system defines framework 3 as positions 66-94 in a heavy chain and positions 57-88 in a light chain.

The term 'antibody' as used in the context of the present disclosure includes whole antibodies and functionally active fragments thereof i.e., molecules that contain an antigen binding domain that specifically binds an antigen, also termed antigen-binding fragments. Features described herein with respect to antibodies also apply to antigen-binding fragments unless context dictates otherwise. The antibody may be (or derived from) monoclonal, multivalent, multi-specific, bispecific, fully human, humanized or chimeric.

Whole antibodies, also known as "immunoglobulins (lg)" generally relate to intact or full-length antibodies i.e. comprising the elements of two heavy chains and two light chains, inter-connected by disulphide bonds, which assemble to define a characteristic Y-shaped three-dimensional structure. Classical natural whole antibodies are monospecific in that they bind one antigen type, and bivalent in that they have two independent antigen binding domains. The terms "intact antibody", "full-length antibody" and "whole antibody" are used interchangeably to refer to a monospecific bivalent antibody having a structure similar to a native antibody structure, including an Fc region as defined herein.

Each light chain is comprised of a light chain variable region (abbreviated herein as VL) and a light chain constant region (CL). Each heavy chain is comprised of a heavy chain variable region (abbreviated herein as VH) and a heavy chain constant region (CH) constituted of three constant domains CH1, CH2 and CH3, or four constant domains CH1, CH2, CH3 and CH4, depending on the Ig class. The "class" of an Ig or antibody refers to the type of constant region and includes IgA, IgD, IgE, IgG and IgM and several of them can be further divided into subclasses, e.g. IgG1, IgG2, IgG3, IgG4. The constant regions of the antibodies may mediate the binding of the immunoglobulin to host tissues or factors, including various cells of the immune system (e.g., effector cells) and the first component (Clq) of the classical complement system.

The term "constant region(s)" or "constant domain(s)", as used herein are used interchangeably to refer to the domain(s) of an antibody which is outside the variable regions. The constant domains are identical in all antibodies of the same isotype but are different from one isotype to another. Typically, the constant region of a heavy chain is formed, from N to C terminal, by CH1-hinge-CH2-CH3-optionally CH4, comprising three or four constant domains.

The constant region domains of the antibody molecule of the present invention, if present, may be selected having regard to the proposed function of the antibody, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody is intended for therapeutic uses and antibody effector functions are required. Alternatively, IgG2 and IgG4 isotypes may be used when the antibody is intended for therapeutic purposes and antibody effector functions are not required. It will be appreciated that sequence variants of these constant region domains may also be used. For example, IgG4 in which the serine at position 241 (numbered according to the Kabat numbering system) has been changed to proline as described in Angal et al. (Angal et al., 1993). A single amino acid substitution abolishes the heterogeneity of chimeric mouse/human (IgG4) antibody as observed during SDS-PAGE analysis (Mol Immunol 30, 105-108), may be used. This is termed herein IgG4P. This single amino acid substitution prevents the natural propensity for the heavy chains of IgG4 molecules to swap yielding chimeric molecules.

"Fc region", "Fc fragment" or simply "Fc", are used interchangeably to refer to the C-terminal region of an antibody comprising the constant region of an antibody excluding the first constant region immunoglobulin domain. Thus, Fc refers to the last two constant domains, CH2 and CH3, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index as in Kabat. In the context of human IgG1, the lower hinge refers to positions 226-236, the CH2 domain refers to positions 237-340 and the CH3 domain refers to positions 341-447 according to the EU index as in Kabat. The corresponding Fc region of other immunoglobulins can be identified by sequence alignments.

In the context of the present disclosure, when present, the constant region or Fc region may be natural, as defined above, or else may be modified in various ways, provided that it comprises a functional FcR binding domain, and preferably a functional FcRn binding domain. Preferably, the modified constant region or Fc region lead to improve functionalities and/or pharmacokinetics. The modifications may include deletion of certain portions of the Fc fragment. The modifications may further include various amino acid substitutions able to affect the biological properties of the antibody. Mutations for increasing FcRn binding and thus in vivo half-life may also be present. The modifications may further include modifications in the glycosylation profile of the antibody. The natural Fc fragment is glycosylated in the CH2 domain with the presence, on each of the two heavy chains, of an N-glycan bound to the asparagine residue at position 297 (Asn297). In the context of the present disclosure, the antibody may be glyco-modified, i-e engineered to have a particular glycosylation profile, which, for example, lead to improved properties, e.g. improved effector function, or improved serum half-life.

Antigen-binding fragments of antibodies include single chain antibodies (e.g. scFv and dsscFv), Fab, Fab', F(ab')2, Fv, single domain antibodies or nanobodies (e.g. VH or VL, or VHH or VNAR). Other antibody fragments for use in the present invention include the Fab and Fab' fragments described in International patent applications WO2011/117648, WO2005/003169, WO2005/003170 and WO2005/003171 (which are all incorporated herein by reference).

The methods for creating and manufacturing these antibody fragments are well known in the art (see for example Verma et al., 1998, Journal of Immunological Methods, 216, 165-181).

A typical "Fab' fragment" or "Fab" as used herein comprises a heavy and a light chain pair in which the heavy chain comprises a variable region VH, a constant domain CH1 and a natural or modified hinge region and the light chain comprises a variable region VL and a constant domain CL. Dimers of a Fab' according to the present disclosure create a F(ab')2 where, for example, dimerization may be through the hinge.

The term "single domain antibody" as used herein refers to an antibody fragment consisting of a single monomeric variable antibody domain. Examples of single domain antibodies include VH or VL or VHH or V-NAR.

The "Fv" refers to two variable domains, for example co-operative variable domains, such as a cognate pair or affinity matured variable domains, i.e. a VH and VL pair.

"Single chain variable fragment" or "scFv" as employed herein refers to a single chain variable fragment which is stabilized by a peptide linker between the VH and VL variable domains.

"Disulphide-stabilized single chain variable fragment" or "dsscFv" as employed herein refer to a single chain variable fragment which is stabilized by a peptide linker between the VH and VL variable domain and also includes an inter-domain disulphide bond between VH and VL. (see for example, Weatherill et al., Protein Engineering, Design & Selection, 25 (321-329), 2012, WO2007109254.

The disulfide bond between the variable domains VH and VL is between two of the residues listed below (unless the context indicates otherwise, Kabat numbering is employed in the list below) (Protein Science 6, 781-788 Zhu et al (1997); Weatherill et al., Protein Engineering, Design & Selection, 25 (321-329), 2012; J Biochem. 118, 825-831 Luo et al (1995); FEBS Letters 377 135-139 Young et al (1995); Proc. Natl. Acad. Sci. USA Vol. 90 pp. 7538-7542 Brinkmann et al (1993); Proteins 19, 35-47 Jung et al (1994) Biochemistry 29 1362-1367; Glockshuber et al (1990). Wherever reference is made to Kabat numbering, the relevant reference is Kabat et al., 1991 (5th edition, Bethesda, Md.), in Sequences of Proteins of Immunological Interest, US Department of Health and Human Services, NIH, USA.

VH37+VL95C;
VH44+VL100;
VH44+VL105;
VH45+VL87;
VH55+VL101;
VH100+VL50;
VH100b+VL4
VH98+VL 46;
VH101+VL46;
VH105+VL43,
VH106+VL57;

and a position or positions corresponding thereto in variable region pair located in the molecule:

The term "antibody" as used herein also encompasses monovalent, i.e. antibodies comprising only one antigen binding domain (e.g. one-armed antibodies comprising a full-length heavy chain and a full-length light chain interconnected, also termed "half-antibody").

The term "antibody" also encompasses multivalent antibodies comprising multiple specificities e.g. bispecific or trispecific or multispecific antibodies.

"Multispecific" or "multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen (also called multi-paratopic). Multi-specific antibodies are generally monovalent for each specificity (antigen). Multi-specific antibodies described herein encompass monovalent and multivalent, e.g. bivalent, trivalent, tetravalent multi-specific antibodies.

"Antigen-binding domain" as employed herein refers to a portion of the antibody, which comprises a part or the whole of one or more variable domains, for example a part or the whole of a pair of variable domains VH and VL, that interact specifically with the target antigen. A binding domain may comprise a single domain antibody. In one embodiment, each binding domain is monovalent. Preferably each binding domain comprises no more than one VH and one VL.

A variety of multi-specific antibody formats are known in the art. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Mol Immunol. 67 (2015): 95-106.

Techniques for making bispecific antibodies include, but are not limited to, CrossMab technology (Klein et al., Methods 154 (2019) 21-31), Knobs-in-holes engineering (e.g. WO1996027011, WO1998050431), DuoBody technology (e.g. WO2011131746), Azymetric technology (e.g. WO2012058768). Further technologies for making bispecific antibodies have been described for example in Godar et al., 2018, Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, κλ-body and orthogonal Fab.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. VH or VL), Fv, scFv, dsscFv, Fab, scFav. Appended IgG antibody formats include in particular DVD-IgG, IgG (H)-scFv, scFv-(H) IgG, IgG (L)-scFv, scFv-(L) IgG, IgG (L,H)-Fv, IgG (H)-V, V(H)-IgG, IgC (L)-V, V(L)-IgG, KIH IgG-scFab, 2scFv-IgG, IgG-2scFv, scFv4-Ig, Zybody and DVI-IgG (four-in-one), for example as described in Spiess et al., Alternative molecular formats and therapeutic applications for bispecific antibodies. Mol Immunol. 67 (2015): 95-106.

Multispecific antibody fragments include nanobody, nanobody-HAS, BITEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, F(ab')2, F(ab')2-scFv2, scFv-KIH, Fab-scFv-Fc, Tetravalent HCAb, scDiabody-Fc, Diabody-Fc, Tandem scFv-Fc; and intrabody, as described, for example, Spiess et al., for bispecific antibodies. Mol Immunol. 67 (2015): 95-106.

Multispecific fusion proteins include Dock and Lock, ImmTAC, HSAbody, scDiabody-HAS, and Tandem scFv-Toxin. Multispecific antibody conjugates include IgG-IgG; Cov-X-Body; and scFv1-PEG-scFv2.

Figure 2:
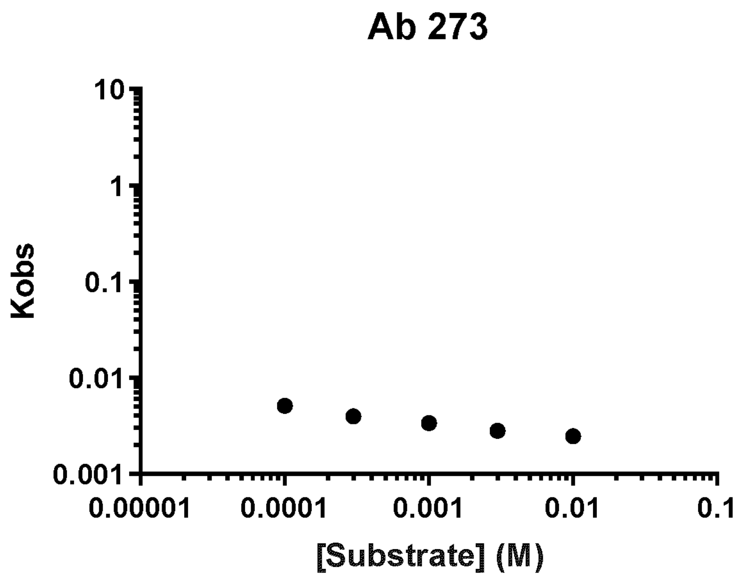
FIG. 2. $K_{obs}$ values were plotted against substrate concentration for antibody 10273 and the LEKTI-D5 Fc protein. Data shown is for 2 nM Ab 10273 and 2 nM LEKTI D5 Fc. The slopes show that antibody 10273 is a non-competitive inhibitor whilst the LEKTI protein is a competitive inhibitor.
Figure 2:
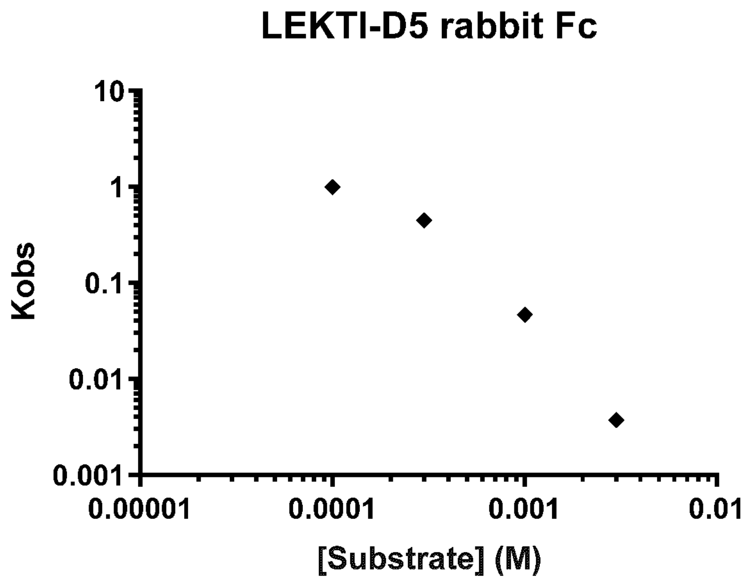

Additional multispecific antibody formats have been described for example in Brinkmann and Kontermann, mAbs, 9:2, 182-212 (2017), in particular in FIG. 2, for example tandem scFv, triplebody, Fab-VHH, taFv-Fc, scFv4-Ig, scFv2-Fcab, scFv4-IgG. Bibodies, tribodies and methods for producing the same are disclosed for example in WO99/37791.

Appended IgG and appended Fab comprise a whole IgG or a Fab fragment, respectively, which are engineered by appending at least one additional antigen-binding domain (e.g. two, three or four additional antigen-binding domains), for example a single domain antibody (such as VH or VL, or VHH), a scFv, a dsscFv, a dsFv to the N- and/or C-terminus of the heavy and/or light chain of said IgG or Fab, for example as described in WO2009/040562, WO2010035012, WO2011/030107; WO2011/061492, WO2011/061246 and WO2011/086091 which are all incorporated herein by reference. In particular, the Fab-Fv format was first disclosed in WO2009/040562 and the disulphide stabilized version thereof, the Fab-dsFv, first disclosed in WO2010/035012. A single linker Fab-dsFv, wherein the dsFv is connected to the Fab via a single linker between either the VL or VH domain of the Fv, and the C terminal of the LC or HC of the Fab, was first disclosed in WO2014/096390, incorporated herein by reference. An appended IgG comprising a full-length IgG1 engineered by appending a dsFv to the C-terminus of the heavy or light chain of the IgG, which was first disclosed in WO2015/197789, incorporated herein by reference.

Alternatively, another multispecific format comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in WO2015/197772, which is hereby incorporated by reference in its entirety. Another format comprises a Fab linked to only one scFv or dsscFv, as described for example in WO2013/068571 incorporated herein by reference, and Dave et al., Mabs, 8 (7) 1319-1335 (2016).

Other well-known formats of multispecific antibodies comprise:

Diabody as employed herein refers to two Fv pairs, a first VH/VL pair and a further VH/VL pair which have two inter-Fv linkers, such that the VH of a first Fv is linked to the VL of the second Fv and the VL of the first Fv is linked to the VH of the second Fv.

Triabody as employed herein refers to a format similar to the diabody comprising three Fvs and three inter-Fv linkers.

Tetrabody as employed herein refers to a format similar to the diabody comprising fours Fvs and four inter-Fv linkers.

Tandem scFv as employed herein refers to at least two scFvs linked via a single linker such that there is a single inter-Fv linker.

Tandem scFv-Fc as employed herein refers to at least two tandem scFvs, wherein each one is appended to the N-terminus of a CH2 domain, for example via a hinge, of constant region fragment —CH2CH3:

Fab-Fv as employed herein refers to a Fv fragment with a variable region appended to the C-terminal of each of the following, the CH1 of the heavy chain and CL of the light chain. The format may be provided as a PEGylated version thereof.

Fab'-Fv as employed herein is similar to FabFv, wherein the Fab portion is replaced by a Fab'. The format may be provided as a PEGylated version thereof.

Fab-dsFv as employed herein refers to a FabFv wherein an intra-Fv disulfide bond stabilizes the appended C-terminal variable regions. The format may be provided as a PEGylated version thereof.

Fab-scFv as employed herein is a Fab molecule with a scFv appended on the C-terminal of the light or heavy chain.

Fab'-scFv as employed herein is a Fab' molecule with a scFv appended on the C-terminal of the light or heavy chain.

DiFab as employed herein refers to two Fab molecules linked via their C-terminus of the heavy chains.

DiFab' as employed herein refers to two Fab' molecules linked via one or more disulfide bonds in the hinge region thereof.

As employed herein scdiabody is a diabody comprising an intra-Fv linker, such that the molecule comprises three linkers and forms a normal scFv whose VH and VL terminals are each linked to a one of the variable regions of a further Fv pair.

Scdiabody-Fc as employed herein is two scdiabodies, wherein each one is appended to the N-terminus of a CH2 domain, for example via a hinge, of constant region fragment —CH2CH3.

ScFv-Fc-scFv as employed herein refers to four scFvs, wherein one of each is appended to the N-terminus and the C-terminus of both the heavy and light chain of a —CH2CH3 fragment.

Scdiabody-CH3 as employed herein refers to two scdiabody molecules each linked, for example via a hinge to a CH3 domain.

IgG-scFv as employed herein is a full-length antibody with a scFv on the C-terminal of each of the heavy chains or each of the light chains.

scFv-IgG as employed herein is a full-length antibody with a scFv on the N-terminal of each of the heavy chains or each of the light chains.

V-IgG as employed herein is a full-length antibody with a variable domain on the N-terminal of each of the heavy chains or each of the light chains.

IgG-V as employed herein is a full-length antibody with a variable domain on the C-terminal of each of the heavy chains or each of the light chains DVD-Ig (also known as dual V domain IgG) is a full-length antibody with 4 additional variable domains, one on the N-terminus of each heavy and each light chain.

The monoclonal antibody according to the present invention is preferably a full-length antibody. More preferably, the full-length antibody is selected from an IgG1, IgG4 or IgG4P.

In another embodiment, the monoclonal antibody is selected from a Fab, a Fab', a F(ab')2, a scFv, a dAb or a VHH.

In one embodiment the antibody according to the present invention may comprise the framework regions of the animal in which the antibody was raised. For example, if the antibody was raised in rabbit, it will comprise the CDRs as defined above and the framework regions of the rabbit antibody such as an antibody comprising a light chain variable region according to SEQ ID NO: 30 (which nucleotide sequence is shown in SEQ ID NO: 31) and a heavy chain variable region according to SEQ ID NO: 32 (which nucleotide sequence is shown in SEQ ID NO: 33).

In one embodiment, the antibody may be a chimeric or humanized. Alternative the antibody may be human.

Chimeric antibodies are typically produced using recombinant DNA methods. The DNA may be modified by substituting the coding sequence for human L and H chains for the corresponding non-human (e.g. murine or rabbit) H and L constant regions (Morrison; PNAS 81, 6851 (1984)).

Human antibodies comprise heavy or light chain variable regions or full length heavy or light chains that are “the product of” or “derived from” a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is “the product of” or “derived from” a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is “the product of” or “derived from” a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertories (Winter G; (1994) Annu Rev Immunol 12:433-455, Green L L, (1999) J Immunol Methods 231:1 1-23).

In one preferred embodiment of the present invention, the antibody according to the present invention are humanized.

In one preferred embodiment, the monoclonal antibody which binds to kallikrein 5 (KLK5), comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

wherein the antibody is humanized; more preferably the variable light chain comprises a CDR-L1 comprising SEQ ID NO: 7 and the variable heavy chain comprises a CDR-H3 comprising SEQ ID NO: 23.

In a further preferred embodiment, the monoclonal antibody according to the present invention is preferably a full-length antibody which binds to kallikrein 5 (KLK5) and comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

wherein the antibody is humanized; more preferably the variable light chain comprises a CDR-L1 comprising SEQ ID NO: 7 and the variable heavy chain comprises a CDR-H3 comprising SEQ ID NO: 23. Even more preferably, the full-length antibody is selected from an IgG1, IgG4 or IgG4P.

As used herein, the term "humanized" antibody refers to an antibody wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). For a review, see Vaughan et al, Nature Biotechnology, 16, 535-539, 1998. In one embodiment, rather than the entire CDR being transferred, only one or more of the specificities determining residues from any one of the CDRs described herein above are transferred to the human antibody framework (see for example, Kashmiri et al., 2005, Methods, 36, 25-34). In one embodiment, only the specificity determining residues from one or more of the CDRs described herein above are transferred to the human antibody framework. In another embodiment, only the specificity determining residues from each of the CDRs described herein above are transferred to the human antibody framework.

When the CDRs are grafted, any appropriate acceptor variable region framework sequence may be used having regard to the class/type of the donor antibody from which the CDRs are derived, including mouse, primate and human framework regions.

Preferably, the humanized monoclonal antibody according to the present invention has a variable domain comprising human acceptor framework regions as well as one or more of the CDR's provided specifically herein. Thus, in one embodiment there is provided a humanized monoclonal antibody which binds KLK5, wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: imgt.org.

In a humanized antibody according to the present invention, the acceptor heavy and light chains do not necessarily need to be derived from the same antibody and may, if desired, comprise composite chains having framework regions derived from different chains.

A suitable framework region for the light chain of the humanized monoclonal antibody according to the present invention is derived from the human germline IGKV1D-13 JK4 comprising SEQ ID NO: 138 and which nucleotide sequence is shown in SEQ ID NO: 139.

A suitable framework region for the heavy chain of the humanized monoclonal antibody according to the present invention is derived from the human germline IGHV3-66 JH6 comprising the sequence as shown in SEQ ID NO: 140 and which nucleotide sequence is shown in SEQ ID NO: 141.

Accordingly, in one embodiment there is provided a humanized monoclonal antibody which binds to KLK5, wherein the antibody comprises a variable light chain and a variable heavy chain and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

more preferably the variable light chain comprises a CDR-L1 comprising SEQ ID NO: 7 and the variable heavy chain comprises a CDR-H3 comprising SEQ ID NO: 23; and wherein the light chain framework region is derived from the human germline IGKV1D-13 JK4 comprising SEQ ID NO: 138; and the heavy chain framework region is derived from the human germline IGHV3-66 JH6 comprising SEQ ID NO: 140.

In the humanized monoclonal antibody according to the present invention, the framework regions may not have the same exact sequences as those of the acceptor antibody. For instance, unusual residues may be changed to more frequently occurring residues for that acceptor chain class or type. Alternatively, selected residues in the acceptor framework regions may be changed so that they correspond to the residues found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967 (which is incorporated herein by reference).

Thus, in one embodiment 1, 2, 3, 4, 5, 6, 7 or 8 residues in the framework are replaced with an alternative amino acid residue.

Accordingly, in one embodiment, there is provided a humanized monoclonal antibody according to the present invention, wherein at least the residues at each of positions 24, 48, 49, 71, 73 and 78 (with reference to SEQ ID NO: 140) of the variable heavy chain are donor residues.

Preferably, residue at position 24 of the variable heavy chain is valine (instead of alanine) residue at position 48 is isoleucine (instead of valine), residue at position 49 is glycine (instead of serine), residue at position 71 is lysine (instead of arginine), residue at position 73 is serine (instead of asparagine) and residue at position 78 is valine (instead of leucine).

Accordingly, there is provided a humanized monoclonal antibody which binds to KLK5, wherein the antibody comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

more preferably the variable light chain comprises a CDR-L1 comprising SEQ ID NO: 7 and the variable heavy chain comprises a CDR-H3 comprising SEQ ID NO: 23; and wherein the light chain framework region is derived from the human germline IGKV1D-13 JK4 comprising SEQ ID NO: 138; and the heavy chain framework region is derived from the human germline IGHV3-66 JH6 comprising SEQ ID NO: 140 and wherein amino acid residues positions 24, 48, 49, 71, 73 and 78 (with reference to SEQ ID NO: 140) of the variable heavy chain are donor residues.

Accordingly, in one embodiment, the humanized monoclonal antibody which binds to KLK5, comprises:

a. a variable light chain comprising SEQ ID NO: 34 or 38 or 42 or 46; and
b. a variable heavy chain comprising SEQ ID NO: 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134.

Preferably, the humanized monoclonal antibody which binds to KLK5, comprises:

a. a variable light chain comprising SEQ ID NO: 38; and
b. a variable heavy chain comprising SEQ ID NO: 110.

In one embodiment, the invention provides an antibody comprising a sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment, the relevant sequence is SEQ ID NO: 38. In one embodiment the relevant sequence is SEQ ID NO: 110.

In one embodiment, the monoclonal antibody, which binds KLK5, comprises a light chain and a heavy chain, wherein the variable light chain comprises a sequence having at least 80%, 85%, 90%, 91%, 92%, 93%, 94%, 95% 96%, 97%, 98% or 99% identity or similarity to the sequence comprising in SEQ ID NO:38 and/or the variable heavy chain comprises a sequence having at least 80%, 85%, 90%, 91%, 92%, 93%, 94%, 95% 96%, 97%, 98% or 99% identity or similarity to the sequence comprising in SEQ ID NO: 110.

"Identity", "Identical" nor grammatical variations thereof, as used herein, indicate that at any particular position in the aligned sequences, the amino acid residue is identical between the sequences. "Similarity", "similar" or grammatical variations thereof as used herein, indicate that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);
lysine, arginine and histidine (amino acids having basic side chains);
aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In one embodiment, the antibody is a full-length antibody, preferably selected from an IgG1, and IgG4 or an IgG4P.

Therefore, the present invention provides for a full-length humanized monoclonal antibody which binds KLK5 and comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and
b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

more preferably the variable light chain comprises a CDR-L1 comprising SEQ ID NO: 7 and the variable heavy chain comprises a CDR-H3 comprising SEQ ID NO: 21; and wherein the antibody is an IgG4P isoform.

The present invention also provides for a full-length humanized monoclonal antibody which binds KLK5 and comprises:

a. a light chain comprising SEQ ID NO: 36 or 40 or 44 or 48; and b. a heavy chain comprising SEQ ID NO: 52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 32 or 50 or 54 or 58 or 62 or 66 or 70 or 74 or 78 or 82 or 86 or 90 or 94 or 98 or 106 or 110 or 114 or 118 or 126 or 134.

Preferably the full-length humanized monoclonal antibody, which binds KLK5 comprises:

a. a light chain comprising SEQ ID NO: 40; and b. a heavy chain comprising SEQ ID NO: 112.

In one embodiment, the monoclonal antibody, which binds KLK5, comprises a light chain which is at least 90%, 91%, 92%, 93%, 94%, 95% 96%, 97%, 98% or 99% similar or identical to the sequence given in SEQ ID NO: 40 but wherein the antibody has the sequence comprising in SEQ ID NO: 7 (or SEQ ID NO: 1 or 8 or 9) for CDR-L1, the sequence comprising in SEQ ID NO: 2 for CDR-L2 and the sequence comprising in SEQ ID NO: 3 for CDR-L3, and a heavy chain which is at least 90%, 91%, 92%, 93%, 94%, 95% 96%, 97%, 98% or 99% similar or identical to the sequence given in SEQ ID NO: 112 but wherein the antibody has the sequence comprising SEQ ID NO: 4 for CDR-H1, SEQ ID NO: 5 for CDR-H2 and SEQ ID NO: 6 or any one of SEQ ID NO: 10 to 29 for CDR-H3, preferably 10, 11, 13 to 16, 18, 20, 22 to 25, 27 or 29.

In yet another embodiment the monoclonal antibody, which binds KLK5, is a Fab' fragment comprising a light chain variable region comprising SEQ ID NO: 38 and a heavy chain variable region comprising SEQ ID NO: 110.

In another embodiment, the monoclonal antibody, which binds KLK5, is full-length IgG4 antibody comprising a light chain comprising to SEQ ID NO: 40 and a heavy chain comprising SEQ ID NO: 112.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment, a C-terminal amino acid from the antibody is cleaved during post-translation modifications.

In one embodiment, an N-terminal amino acid from the antibody is cleaved during post-translation modifications.

In another embodiment, the monoclonal antibody according the present invention binds human KLK5, preferably comprising SEQ ID NO: 144 or 143 or 142 and also binds cynomolgus monkey (cyno) KLK5, preferably cyno KLK5 comprising SEQ ID NO: 151.

In one embodiment, the monoclonal antibody binds to human and/or cyno kallikrein 5 (KLK5), wherein the antibody comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. the monoclonal antibody is a full-length antibody comprising a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In a preferred embodiment, the monoclonal antibody binds to human and/or cyno kallikrein 5 (KLK5), wherein the antibody comprises a variable light chain and a variable heavy chain, and wherein:

a. the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or b. the variable light chain comprises SEQ ID NO: 38; and the variable heavy chain comprising SEQ ID NO: 110; or c. the monoclonal antibody is a full-length antibody comprising a light chain and a heavy chain, wherein the light chain comprises SEQ ID NO: 40; and the heavy chain comprises SEQ ID NO: 112.

In another embodiment, the monoclonal antibody according to the present invention does not bind bind human or cyno kallikrein 2 (KLK2); or human or cyno kallikrein 4 (KLK4); or human or cyno . . . kallikrein 7 (KLK7). In other words, the antibody is specific for KLK5 and not for other kallikreins.

"Specific" as employed herein is intended to refer to an antibody that only recognizes the antigen to which it is specific or an antibody that has significantly higher binding affinity to the antigen to which it is specific (e.g. KLK5) compared to binding to antigens to which it is non-specific (gamma and beta synucleins), for example at least 5, 6, 7, 8, 9, 10 times higher binding affinity.

In one embodiment, the monoclonal antibody binds to human and/or cyno KLK5 and does not bind bind human or cyno KLK2; or human or cyno KLK4; or human or cyno KLK7, wherein the antibody comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO:

3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. the monoclonal antibody is a full-length antibody comprising a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In a preferred embodiment, the monoclonal antibody binds to human and/or cyno KLK5 and does not bind bind human or cyno KLK2; or human or cyno KLK4; or human or cyno KLK7, wherein the antibody comprises a variable light chain and a variable heavy chain, and wherein:

a. the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or b. the variable light chain comprises SEQ ID NO: 38; and the variable heavy chain comprising SEQ ID NO: 110; or c. the monoclonal antibody is a full-length antibody comprising a light chain and a heavy chain, wherein the light chain comprises SEQ ID NO: 40; and the heavy chain comprises SEQ ID NO: 112.

In one embodiment, according to the present invention, the binding of the antibody to KLK5 is characterized by a constant of dissociation ($K_D$) of about 7 nM or less, preferably 500 μM or less, preferably about 400 μM or less.

The term "$K_D$" as used herein refers to the constant of dissociation which is obtained from the ratio of $K_d$ to $K_a$ (i.e. $K_d/K_a$) and is expressed as a molar concentration (M). $K_d$ and $K_a$ refers to the dissociation rate and association rate, respectively, of a particular antigen-antibody (or antigen-binding fragment thereof) interaction. $K_D$ values for antibodies can be determined using methods well established in the art. A method for determining the $K_D$ of an antibody is by using surface plasmon resonance, such as BIACORE™ system for example as described in the Examples herein, using recombinant KLK5 or a suitable fusion protein/polypeptide thereof. In one example affinity is measured using recombinant KLK5 as described in the Examples herein. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In one embodiment, the antibody according to the present invention has a higher binding affinity (i.e. smaller $K_D$) for human KLK5 than for cyno or mouse KLK5. The term "affinity" refers to the strength of an interaction between the antibody and KLK5.

In one embodiment, the monoclonal antibody according to the present invention has an $IC_{50}$ of less than 800 μM for blocking KLK5 protease activity, preferably, the monoclonal antibody according to the present invention has an $IC_{50}$ of less than 18 μM for blocking KLK5 protease activity in the in-vitro assay as described herein.

The term $IC_{50}$ as used herein refers to the half maximal inhibitory concentration which is a measure of the effectiveness of a substance, such as an antibody, in inhibiting a specific biological or biochemical function, which in the present invention is the protease activity of KLK5. The $IC_{50}$ is a quantitative measure which indicates how much of a particular substance is needed to inhibit a given biological process or function or activity by half.

In another embodiment of the present invention, the monoclonal antibody which binds KLK5 wherein the antibody comprises a variable light chain and a variable heavy chain, and wherein:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and b. the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29;

wherein the antibody inhibits or reduces the protease activity of KLK5.

Within the present invention, the term "inhibit" (and grammatical variations thereof) indicates the effect the antibodies according to the present invention have with respect to KLK5 biological activity. Preferably, the biological activity of KLK5 is a protease activity, preferably serine protease activity. The effect results in a complete or partial hindering of the serine protease activity of KLK5.

Without wishing to be bound by theory it is believed that the monoclonal antibody according to the present invention binds to KLK5 and inhibits (for example completely or partially) or reduces the protease activity (preferably the serine protease activity) of KLK5; and/or i) binds to KLK5 when KLK5 is bound to LEKTI or a fragment of LEKTI and/or ii) does not compete with LEKTI, or a fragment of LEKTI, for binding KLK5 and/or iii) forms a complex with KLK5 bound to LEKTI or a fragment of LEKTI (i.e. forming a complex which comprise the antibody of the present invention, KLK5 and LEKTI, or a fragment of LEKTI).

The term "form a complex" (and any grammatical variation thereof) means that the antibody according to the present invention is capable of binding KLK5 when KLK5 is already bound to another protein such as LEKTI, or a fragment of LEKTI, or another antibody or an antibody fragment such as a Fab.

Preferably the antibody claimed herein inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI Within the present invention, the term "LEKTI" refers to the lympho-epithelial Kazal-type-related inhibitor consisting of 15 domains, and is cleaved into smaller, functional fragments by proprotein convertases such as protease furin, resulting in fragments of LEKTI comprised of one or more domains. These fragments are secreted into the extracellular space where they can form inhibitory complexes with proteases such as KLK5. LEKTI is also known as serine protease inhibitor Kazal-type 5 (SPINK5) and is a protein that in humans is encoded by the SPINK5 gene. In humans, three splice variants of LEKTI mRNA are generated leading to full-length, long and short isoforms of the protein that differ in their COOH-terminal regions only.

SPINK5 is a member of a gene family cluster located on chromosome 5q32 which encode inhibitors of serine proteases. This includes other epidermal proteins SPINK6 and LEKTI-2 (SPINK9) which are also included in the present invention within the term "LEKTI".

The advantage associated with an antibody capable of binding KLK5 and inhibiting KLK5 biological (i.e. protease) activity, yet not-competing with LEKTI or a fragment of LEKTI for binding KLK5, may enable inhibition of KLK5 activity in conditions where LEKTI dissociates from the KLK5: LEKTI complex, such as the progressively acidic environment from the stratum basale to the stratum corneum of the epidermis.

In these embodiments, the fragment of LEKTI is preferably human LEKTI domain 5 comprising amino acids 1 to 64 of SEQ ID NO: 145 or LEKTI domain 8 comprising amino acids 1 to 71 of SEQ ID NO: 152.

In one embodiment, the monoclonal antibody according to the invention binds to an epitope of human KLK5 comprising at least one, preferably at least two or more, amino acid residue from the group consisting of Leu212, Ser213, Gln214, Lys215, Arg216, Glu218, Asp219, Ala220, Pro222, Gly233, Pro269, Asn270 and Pro272 with reference to SEQ ID NO: 142. Preferably the epitope is characterized by X-ray crystallography. The numbers in parentheses correspond to the protease nomenclature.

Within the present invention, the term "epitope" is used interchangeably for both conformational and linear epitopes. A conformational epitope is composed of discontinued sections of the antigen's amino acid primary sequence and a linear epitope is formed by a sequence formed by continuous amino acids.

The epitope can be identified by any suitable epitope mapping method known in the art in combination with any one of the antibodies provided by the present invention. Examples of such methods include screening peptides of varying lengths derived from full length KLK5 for binding to the antibody or fragment thereof of the present invention and identifying the smallest fragment that can specifically bind to the antibody containing the sequence of the epitope recognized by the antibody. KLK5 peptides may be produced synthetically or by proteolytic digestion of the KLK5. Peptides that bind the antibody can be identified by, for example, mass spectrometric analysis. Methodologies such as NMR spectroscopy or X-ray crystallography can be used to identify the epitope bound by an antibody. Typically, when the epitope determination is performed by X-ray crystallography, amino acid residues of the antigen within 4 Å from CDRs are considered to be amino acid residues part of the epitope. Once identified, the epitope may serve for preparing fragments which bind an antibody of the present invention and, if required, used as an immunogen to obtain additional antibodies which bind the same epitope.

The epitope as indicated in the aspects and embodiments describing the present invention is preferably an epitope characterized by X-ray crystallography.

Furthermore, the present invention also provides for an antibody which competes for binding KLK5, preferably human KLK5, by cross-blocking or being cross-blocked by the antibody which binds to an epitope of human KLK5 comprising amino acid residues Leu212, Ser213, Gln214, Lys215, Arg216, Glu218, Asp219, Ala220, Pro222, Gly233, Pro269, Asn270 and Pro272 with reference to SEQ ID NO: 142 and which antibody comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or
2. a variable light chain comprising SEQ ID NO: 38; and a variable heavy chain comprising SEQ ID NO: 110.

In one embodiment, such competing antibody has a heavy chain variable region having at least 80% identity or similarity to the sequence comprising SEQ ID NO: 110; and/or has a light chain variable region having at least 80% identity or similarity to the sequence comprising SEQ ID NO: 38.

An antibody that "competes", "cross-blocks", "is cross-blocked" or "binds to the same epitope on human KLK5" (and any grammatical variation thereof) as the antibody of the present invention refers to an antibody that is not capable of forming a complex with KLK5 bound to the antibody of the present invention.

Competing antibodies can be identified using any suitable method in the art, for example by using competition ELISA or BIAcore assays where binding of KLK5 by the competing antibody by cross-blocking or by being cross-blocked prevents the binding of an antibody of the present invention or vice versa. Such competing assays may use isolated natural or recombinant KLK5 or a suitable fusion protein/polypeptide thereof. In one example competition is measured using recombinant human active KLK5 (such as for example comprising SEQ ID NO: 144).

The present invention also provides for the antibody as described and claimed herein to forms a complex with KLK5 wherein KLK, preferably human KLK5, is bound to (or may be bound by) another antibody, wherein the another antibody comprises:

1. a variable light chain comprising a CDR-L1 comprising SEQ ID NO: 175, a CDR-L2 comprising SEQ ID NO: 176 and a CDR-L3 comprising SEQ ID NO: 177; and a variable heavy chain comprising a CDR-H1 comprising SEQ ID NO: 178, a CDR-H2 comprising SEQ ID NO: 179 and a CDR-H3 comprising SEQ ID NO: 160; and/or
2. a variable light chain comprising SEQ ID NO: 161 and a variable heavy chain comprising SEQ ID NO: 163; and/or
3. a variable light chain encoded by a nucleotide comprising SEQ ID NO: 162 and a variable heavy chain encoded by a nucleotide comprising SEQ ID NO: 164.

In one embodiment, the antibody according to the present invention binds KLK5 and comprises:

1. a variable light chain and a variable heavy chain, and wherein the variable light chain comprises a CDR-L1 comprising SEQ ID NO: 1 or 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 10 to 29, preferably 10, 11, 13 to 16, 18, 20, 22 to 25, 27 or 29; or 2. a variable light chain comprising SEQ ID NO: 30 or 34 or 38 or 42 or 46; and a variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134;

wherein the antibody forms a complex with KLK5, preferably human KLK5, bound to another antibody, which another antibody comprises:

1. a variable light chain comprising a CDR-L1 comprising SEQ ID NO: 175, a CDR-L2 comprising SEQ ID NO: 176 and a CDR-L3 comprising SEQ ID NO: 177; and a variable heavy chain comprising a CDR-H1 comprising SEQ ID NO: 178, a CDR-H2 comprising SEQ ID NO: 179 and a CDR-H3 comprising. SEQ ID NO: 160; and/or
2. a variable light chain comprising SEQ ID NO: 161 and a variable heavy chain comprising SEQ ID NO: 163; and/or
3. a variable light chain encoded by a nucleotide comprising SEQ ID NO: 162 and a variable heavy chain encoded by a nucleotide comprising SEQ ID NO: 164.

Furthermore, the present invention also comprises a KLK5-antibody complex comprising:

a. KLK5, preferably human. KLK5; and
b. an antibody which binds KLK5 and comprises:
    1. a variable light chain and a variable heavy chain, and wherein the variable light chain comprises a CDR-L1 comprising SEQ ID NO: 1 or 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 10 to 29, preferably 10, 11, 13 to 16, 18, 20, 22 to 25, 27 or 29; or
    2. a variable light chain comprising SEQ ID NO: 30 or 34 or 38 or 42 or 46; and a variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; and
    c. another antibody which binds KLK5 and comprises:
        1. a variable light chain comprising a CDR-L1 comprising SEQ ID NO: 175, a CDR-L2 comprising SEQ ID NO: 176 and a CDR-L3 comprising SEQ ID NO: 177; and a variable heavy chain comprising a CDR-H1 comprising SEQ ID NO: 178, a CDR-H2 comprising SEQ ID NO: 179 and a CDR-H3 comprising SEQ ID NO: 160; wherein the antibody is optionally humanized; and/or
        2. a variable light chain comprising SEQ ID NO: 161 and a variable heavy chain comprising SEQ ID NO: 163; and/or
        3. a variable light chain encoded by a nucleotide comprising SEQ ID NO: 162 and a variable heavy chain encoded by a nucleotide comprising SEQ ID NO: 164.

It should be understood that the so called "another antibody" binds to KLK5, preferably human KLK5 to an epitope which is different from and not overlapping with the epitope described herein, as shown by the examples below. In this respect, such antibodies do not compete with one another.

Antibodies according to the present invention may be obtained using any suitable method known in the art. KLK5 including fusion proteins thereof, cells (recombinantly or naturally) expressing the KLK5 can be used to produce antibodies which specifically recognize KLK5. Various form of KLK5 as described herein may be used.

In one embodiment, the antigen used is active KLK5, preferably produced as described in the Examples below.

KLK5 or fragments thereof, for use to immunize a host, may be prepared by processes well known in the art from genetically engineered host cells comprising expression systems or they may be recovered from natural biological sources. KLK5 or a fragment thereof may in some instances be part of a larger protein such as a fusion protein for example fused to an affinity tag or similar.

Antibodies generated against KLK5 according to the present invention may be obtained, where immunization of an animal is necessary, by administering KLK5 to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Screening for antibodies can be performed using assays to measure binding to KLK5 and/or assays to measure the inhibition of KLK5 biological activity, preferably KLK5 protease activity.

Antibodies, including monoclonal antibodies contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the monoclonal antibody binding KLK5 according to the present invention may be engineered to have an appropriate isoelectric point. This may lead to antibodies with more robust properties, in particular suitable solubility and/or stability profiles and/or improved purification characteristics.

Thus, in one embodiment, the monoclonal antibody which binds KLK5, comprises:

a. a variable light chain comprising SEQ ID NO: SEQ ID NO: 30 or 34 or 38 or 42 or 46; and a variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
b. a light chain comprising SEQ ID NO: 36 or 40 or 44 or 48; and a heavy chain comprising SEQ ID NO: 52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136;

wherein the monoclonal antibody is engineered to have an isoelectric point different to that of the originally identified antibody.

The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value, acidic residues may be introduced to lower the pI, as required. It is important that when manipulating the pI care must be taken to retain the desirable activity of the antibody or fragment. Thus, in one embodiment the engineered antibody has the same or substantially the same activity as the "unmodified" antibody or fragment.

Programs such as **ExPASY® expasy.ch, and iut-arles.up.univ-mrs.fr, may be used to predict the isoelectric point of the antibody.

It will be appreciated that the affinity of antibodies provided by the present invention may be altered using any suitable method known in the art. The present invention therefore also relates to variants of the antibody which have an improved affinity for KLK5, in particular human KLK5. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998).

If desired the antibody according to the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain a fragment of the antibody linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111 In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 1251, 1311, 111 In and 99Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment, the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example, the antibody according to the present invention are attached to poly(ethyleneglycol) (PEG) moieties. In one particular embodiment, the antibody according to the present invention and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the antibody using recombinant DNA methods (see for example U.S. Pat. Nos. 5,219,996; 5,667,425; WO98/25971, WO2008/038024). In one example the antibody of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide; an imide, e.g. maleimide, a vinyl sulphone or a disulphide. Such starting materials may be obtained commercially (for example from Nektar, formerly Shearwater Polymers Inc., Huntsville, AL, USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 (see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington DC and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545).

In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

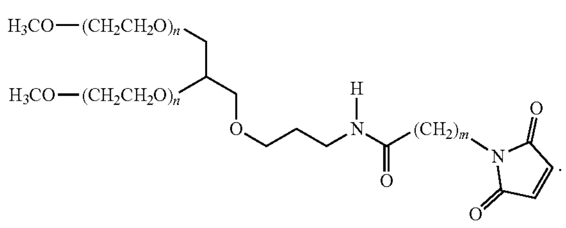

m is 2 or 5

Thus in one embodiment the PEG is 2,3-Bis(methylpolyoxyethylene-oxy)-1-{[3-(6-maleimido-1-oxohexyl) amino]propyloxy}hexane (the 2 arm branched PEG, —CH2) 3NHCO(CH2)5-MAL, Mw 40,000 known as SUNBRIGHT GL2-400MA3.

Further alternative PEG effector molecules of the following type:

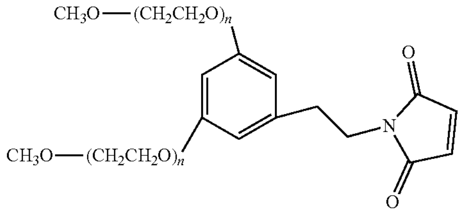

are available from Dr Reddy, NOF and Jenkem.

In one embodiment, the Fab or Fab' according to the present invention is conjugated to a PEG molecule.

In one embodiment, the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one embodiment, there is provided a Fab' conjugated to a polymer, such as a PEG molecule, a starch molecule or an albumin molecule. In one embodiment, there is provided a scFv conjugated to a polymer, such as a PEG molecule, a starch molecule or an albumin molecule. In one embodiment, the Fab or Fab' according to the present disclosure is conjugated to human serum albumin. In one embodiment, the antibody or fragment is conjugated to a starch molecule, for example to increase the half-life. Methods of conjugating starch to a protein as described in U.S. Pat. No. 8,017,739 incorporated herein by reference.

The present invention also provides for an isolated polynucleotide encoding the antibody according to the present invention. The isolated polynucleotide according to the present invention may comprise synthetic DNA, for instance produced by chemical processing, cDNA, genomic DNA or any combination thereof.

Standard techniques of molecular biology may be used to prepare DNA sequences coding for the antibody of the present invention. Desired DNA sequences may be synthesized completely or in part using oligonucleotide synthesis techniques. Site-directed mutagenesis and polymerase chain reaction (PCR) techniques may be used as appropriate.

In one embodiment, the isolated polynucleotide according to the invention encodes:

a. a light chain variable region, wherein the polynucleotide:
   i. is at least 90% identical to SEQ ID NO: 31 or 35 or 39 or 43 or 47; or
   ii. comprises SEQ ID NO: 31 or 35 or 39 or 43 or 47; or
   iii. consists essentially of SEQ ID NO: SEQ ID NO: 31 or 35 or 39 or 43 or 47;
b. a heavy chain variable region, wherein the polynucleotide:
   i. is at least 90% identical to SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135; or
   ii. comprises SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135; or
   iii. consists essentially SEQ ID NO: 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135;
c. a light chain, wherein the polynucleotide:
   i. is at least 90% identical to SEQ ID NO: 37 or 41 or 45 or 49; or
   ii. comprises SEQ ID NO: 37 or 41 or 45 or 49; or
   iii. consists essentially of SEQ ID NO: 37 or 41 or 45 or 49;
d. a heavy chain, wherein the polynucleotide:
   i. is at least 90% identical to SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137; or
   ii. comprises SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137; or
   iii. consists essentially of SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137.

In one embodiment, the present invention provides an isolated polynucleotide encoding the variable heavy chain of an antibody Fab' fragment or of an IgG1 or IgG4 antibody of the present invention which comprises the sequence given in 33 or 51 or 55 or 59 or 63 or 67 or 71 or 75 or 79 or 83 or 87 or 91 or 95 or 99 or 103 or 107 or 111 or 115 or 119 or 123 or 127 or 131 or 135. Also provided is an isolated polynucleotide encoding the variable light chain of an antibody Fab' fragment or of an IgG1 or IgG4 antibody of the present invention which comprises the sequence given in SEQ ID NO: 31 or 35 or 39 or 43 or 47.

In another embodiment, the present invention provides an isolated polynucleotide encoding the heavy chain and the light chain of an IgG4 (P) antibody of the present invention in which the polynucleotide encoding the heavy chain comprises the sequence given in SEQ ID NO: 53 or 57 or 61 or 65 or 69 or 73 or 77 or 81 or 85 or 89 or 93 or 97 or 101 or 105 or 109 or 113 or 117 or 121 or 125 or 129 or 133 or 137 and the polynucleotide encoding the light chain comprises the sequence given in SEQ ID NO: 37 or 41 or 45 or 49.

The present invention also provides for a cloning or expression vector comprising one or more polynucleotides described herein. In one example, the cloning or expression vector according to the present invention comprises one or more isolated polynucleotides comprising a sequence selected from SEQ ID NO: 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135 or 137.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody of the present invention. Bacterial, for example *E. coli*, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr-CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells. The host cell may be stably transformed or transfected with the isolated polynucleotide sequences or the expression vectors according to the present invention.

In one embodiment, the host cell according to the present invention is a CHO-DG44 cell stably transfected with an expression vectors comprising the isolated polynucleotide sequences of the present invention, preferably comprising the isolated polynucleotide sequences comprising SEQ ID NO: 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135 or 137.

The present invention also provides a process for the production of an antibody binding KLK5 according to the present invention comprising culturing a host cell according to the present invention under conditions suitable for producing the monoclonal antibody and isolating the so produced monoclonal antibody.

The antibody may comprise only a heavy or light chain, in which case only a heavy chain or light chain polynucleotide sequence needs to be used to transfect the host cells. For production of antibodies comprising both heavy and light chains, the cell line may be transfected with two vectors, a first vector encoding a light chain and a second vector encoding a heavy chain. Alternatively, a single vector may be used, the vector comprising polynucleotide sequences encoding the light chain and the heavy chain.

Thus, there is provided a process for culturing a host cell and expressing an antibody, isolating the latter and optionally purifying the same to provide an isolated antibody. Thus, in one embodiment there is provided an isolated monoclonal antibody binding KLK5, preferably human KLK5, such as a humanized monoclonal antibody, in particular an antibody according to the invention, in substantially purified from, in particular free or substantially free of endotoxin and/or host cell protein or DNA, wherein the monoclonal antibody binds to KLK, preferably, human KLK5 and comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 μg per mg of antibody product or less such as 100 μg per mg or less, in particular 20 μg per mg, as appropriate.

As the antibodies of the present invention are useful in the treatment, diagnosis and/or prophylaxis of a pathological condition, the present invention also provides for a pharmaceutical or diagnostic composition comprising the antibody according to the present invention in combination with one or more of a pharmaceutically acceptable carrier, excipient or diluents.

Preferably, the pharmaceutical or diagnostic composition comprises an antibody which binds KLK5, preferably human KLK5, and which comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In one embodiment, the antibody according to the present invention is the sole active ingredient. In another embodiment, the antibody according to the present invention is in combination with one or more additional active ingredients. Alternatively, the pharmaceutical compositions comprise the antibody according to the present invention which is the sole active ingredient and it may be administered individually to a patient in combination (e.g. simultaneously, sequentially or separately) with other therapeutic, diagnostic or palliative agents.

In another embodiment, the pharmaceutical composition comprises an antibody binding KLK5, preferably human KLK5, and comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 1.14 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. the monoclonal antibody is a full-length antibody comprising a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

and one or more pharmaceutically acceptable carriers, excipients of diluents.

Preferably, the pharmaceutical composition comprising an antibody which binds KLK5 wherein the antibody binds to KLK5, preferably, human KLK5 and which antibody comprises a light chain variable region of SEQ ID NO: 38 and a heavy chain variable region of SEQ ID NO: 110.

The pharmaceutical compositions according to the invention may be administered suitably to a patient to identify the therapeutically effective amount required. The term “therapeutically effective amount” as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody according to the invention may be in dry form, for reconstitution before use with an appropriate sterile liquid. Solid forms suitable for solution in, or suspension in, liquid vehicles prior to injection may also be prepared.

Once formulated, the compositions of the invention can be administered directly to the subject. Accordingly, provided herein is the use of an antibody according to the invention for the manufacture of a medicament.

Preferably, the pharmaceutical composition according to the present invention is adapted for administration to human subjects.

Hence, in another aspect the present invention provides for the monoclonal antibody which binds KLK5, preferably human KLK5, and comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In a preferred embodiment, the monoclonal antibody which binds KLK5, preferably human KLK5, and comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3;

and the variable heavy chain comprises a CDR-H1 com comprising SEQ ID NO: 4, a CDR-H2 comprising SEQ ID NO: 5 and a CDR-H3 comprising SEQ ID NO: 23; or 2. a variable light chain comprising SEQ ID NO: 38; and a variable heavy chain comprising SEQ ID NO: 110; or
3. a light chain comprising SEQ ID NO: 40 and a heavy chain comprising SEQ ID NO: 112.

In particular, the use in therapy comprises the use in the treatment of one or more diseases characterized by dysregulation of KLK5 or by dysregulation of inhibition of KLK5.

In yet another aspect, the present invention provides for method of treating one or more diseases characterized by dysregulation of KLK5 or by dysregulation of inhibition of KLK5 in a patient comprising administering to said patient a therapeutically effective amount of the monoclonal antibody which binds KLK5 wherein the antibody binds KLK5, preferably human KLK5, and comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In another aspect, the monoclonal antibody which binds KLK5, preferably human KLK5, or a pharmaceutical composition comprising the monoclonal antibody, wherein the monoclonal antibody or the composition is for use in the treatment of one or more diseases characterized by dysregulation of KLK5 or by dysregulation of inhibition of KLK5, wherein the antibody comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or
b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or
c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

In one preferred embodiment, the present invention provides for a method of treating one or more diseases characterized by dysregulation of KLK5 or by dysregulation of inhibition of KLK5 in a patient comprising administering to said patient a therapeutically effective amount of the antibody which binds KLK5, preferably human KLK5, and comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or
2. a variable light chain comprising SEQ ID NO: 38; and a variable heavy chain comprising-SEQ ID NO: 110; or
3. a light chain comprising SEQ ID NO: 40 and a heavy chain comprising SEQ ID NO: 112.

In another preferred embodiment, the monoclonal antibody which binds KLK5, preferably human KLK5, or a pharmaceutical composition comprising the monoclonal antibody, wherein the antibody or the pharmaceutical composition is for use in the treatment of one or more diseases characterized by dysregulation of KLK5 or by dysregulation of inhibition of KLK5, wherein the antibody comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or
2. a variable light chain comprising SEQ ID NO: 38; and a variable heavy chain comprising SEQ ID NO: 110; or
3. a light chain comprising SEQ ID NO: 40 and a heavy chain comprising SEQ ID NO: 112.

Preferably, the one or more diseases characterized by dysregulation of KLK5 or by dysregulation of inhibition of KLK5 are selected from Netherton's Syndrome, Atopic Dermatitis, Ichthyoses, Rosacea, Asthma or Cancer, such as ovarian cancer or bladder cancer or a combination thereof.

Therefore, the present invention provides for method of treating Netherton's Syndrome, Atopic. Dermatitis, Ichthyoses, Rosacea, Asthma or Cancer, such as ovarian cancer or bladder cancer or a combination thereof in a patient comprising administering to said patient a therapeutically effective amount of the monoclonal antibody which binds KLK5, preferably human KLK5, or a pharmaceutical composition comprising the monoclonal antibody, wherein the antibody or the pharmaceutical composition comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 1.14 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

More preferably, the method is for treating Netherton's Syndrome and/or Atopic Dermatitis.

In another aspect, there is provided a monoclonal antibody which binds KLK5, preferably human KLK5, or a pharmaceutical composition comprising the monoclonal antibody, wherein the antibody or the pharmaceutical composition is for use in the treatment of Netherton's Syndrome, Atopic Dermatitis, Ichthyoses, Rosacea, Asthma or Cancer, such as ovarian cancer or bladder cancer or a combination thereof, and wherein the monoclonal antibody or the pharmaceutical composition comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

More preferably, the antibody is for use in the treatment of Netherton's Syndrome and/or Atopic Dermatitis.

In another preferred embodiment, there is provided present invention provides for a method of treating Netherton's Syndrome, Atopic Dermatitis, Ichthyoses, Rosacea, Asthma or Cancer, such as ovarian cancer or bladder cancer or a combination thereof in a patient comprising administering to said patient a therapeutically effective amount of the antibody which binds KLK5, preferably human KLK5, or a pharmaceutical composition comprising the monoclonal antibody, wherein the antibody or the pharmaceutical composition, wherein the antibody or the pharmaceutical composition comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or
2. a variable light chain comprising SEQ ID NO: 38; and a variable heavy chain comprising SEQ ID NO: 110; or
3. a light chain comprising SEQ ID NO: 40 and a heavy chain comprising SEQ ID NO: 112.

More preferably, the method is for treating Netherton's Syndrome and/or Atopic Dermatitis.

In another preferred embodiment, the antibody which binds KLK5, preferably human KLK5, or a pharmaceutical composition comprising the monoclonal antibody, wherein the antibody or the pharmaceutical composition is for use in the treatment of Netherton's Syndrome, Atopic Dermatitis, Ichthyoses, Rosacea, Asthma or Cancer, such as ovarian cancer or bladder cancer, or a combination thereof, wherein the antibody or the pharmaceutical composition comprises:

1. a variable light chain and a variable heavy chain, and wherein the variable light chain comprises a CDR-L1 comprising SEQ ID NO: 7, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 23; or
2. a variable light chain comprising SEQ ID NO: 38; and a variable heavy chain comprising SEQ ID NO: 110; or
3. a light chain comprising SEQ ID NO: 40 and a heavy chain comprising SEQ ID NO: 112.

More preferably, the antibody is for use in the treatment of Netherton's Syndrome and/or Atopic Dermatitis.

Alternatively, the invention also provides for the use of the antibody which binds KLK5, preferably human KLK5, or a pharmaceutical composition comprising the monoclonal antibody, wherein the antibody or the pharmaceutical composition for the manufacture of a medicament for treating one or more diseases characterized by dysregulation of KLK5 or by dysregulation of inhibition of KLK5, wherein such dysregulation is preferably Netherton's Syndrome, Atopic Dermatitis, Ichthyoses, Rosacea, Asthma or Cancer, such as ovarian cancer or bladder cancer, or a combination thereof, more preferably Netherton's Syndrome and/or Atopic Dermatitis, wherein the antibody comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

Also provided by the present invention is the use of the antibody which binds KLK5 wherein the antibody binds to KLK5, preferably human KLK5, as diagnostically active agents or in diagnostic assays, for example for diagnosing Netherton's Syndrome, Atopic Dermatitis, Ichthyoses, Rosacea, Asthma or Cancer, such as ovarian cancer or bladder cancer.

More preferably the monoclonal antibody comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29; preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96 or 100 or 108 or 112 or 116 or 120 or 128 or 136.

The diagnosis may preferably be performed on biological samples. A "biological sample" encompasses a variety of sample types obtained from an individual and can be used in a diagnostic or monitoring assay. The definition encompasses blood such as plasma and serum, and other liquid samples of biological origin such as urine and saliva, cerebrospinal fluid, solid tissue samples such as a biopsy specimen, such as skin biopsies or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting KLK5 in a biological sample which has been obtained from an individual comprising the steps of i) contacting the biological sample with the antibody as described herein; and ii) detecting binding of the antibody to KLK5. By comparing the detected KLK5 level or the presence of a specific post-translationally modified form of KLK5 (including any pro-form) with a suitable control, one or more diseases characterized by dysregulation of KLK5 or by dysregulation of inhibition of KLK5 may be identified. Such a detection method can thus be used to determine whether a subject (including an embryo or a fetus) has, or is at risk of developing, diseases characterized by dysregulation of KLK5 or by dysregulation of inhibition of KLK5.

Therefore, the present invention provides for an antibody which binds KLK5 wherein the antibody binds to LK5, preferably human KLK5, wherein the antibody is for use in the diagnosis of one or more diseases characterized by dysregulation of KLK5 or by dysregulation of inhibition of KLK5, preferably in the diagnosis of Netherton's Syndrome, Atopic Dermatitis, Ichthyoses, Rosacea, Asthma or Cancer, such as ovarian cancer or bladder cancer, wherein the antibody comprises:

a. the variable light chain comprises a CDR-L1 comprising SEQ ID NO: 1 or 7 or 8 or 9, a CDR-L2 comprising SEQ ID NO: 2 and a CDR-L3 comprising SEQ ID NO: 3; and the variable heavy chain comprises a CDR-H1 com comprising SEQ ID NO: 4, a CDR-H2 comprising SEQ ID NO: 5 and a CDR-H3 comprising SEQ ID NO: 6 or any one of SEQ ID NO: 10 to 29, preferably 10, 11, 13 to 16, 18, 20, 22 to 25, 27 or 29; or b. the variable light chain comprises SEQ ID NO: 30 or 34 or 38 or 42 or 46; and the variable heavy chain comprising SEQ ID NO: 32 or 50 or 54 or 58 or 62 or 66 or 70 or 74 or 78 or 82 or 86 or 90 or 94 or 98 or 102 or 106 or 110 or 114 or 118 or 122 or 126 or 130 or 134, preferably 32 or 50 or 54 or 58 or 62 or 66 or 70 or 74 or 78 or 82 or 86 or 90 or 94 or 98 or 106 or 110 or 114 or 118 or 126 or 134; or c. a light chain and a heavy chain, wherein the light chain comprises SEQ ID NO: 36 or 40 or 44 or 48; and the heavy chain comprises SEQ ID NO:52 or 56 or 60 or 64 or 68 or 72 or 76 or 80 or 84 or 88 or 92 or 96 or 100 or 104 or 108 or 112 or 116 or 120 or 124 or 128 or 132 or 136, preferably 52 or 56 or 60 or 64 or 68 or 72 or 76 or 80 or 84 or 88 or 92 or 96, or 100 or 108 or 112 or 116 or 120 or 128 or 136.

The sequences included in the present invention are shown in Table 1:

TABLE 1

| Name | SEQ ID NO: | SEQUENCE |
|---|---|---|
| CDR-L1 | 1 | QSSQSVYNNNDLA |
| CDR-L2 | 2 | RASTLAS |
| CDR-L3 | 3 | LGGYDDDVDTYT |
| CDR-H1 | 4 | GFSLSSYGMS |
| CDR-H2 | 5 | IISSSGSTYYASWAKG |
| CDR-H3 | 6 | DHIYRYDDYGDYPTYYGMDP |

TABLE 1-continued

| Name | SEQ ID NO: | SEQUENCE |
|---|---|---|
| CDR-L1 Q1R | 7 | RSSQSVYNNNDLA |
| CDR-L1 Q1K | 8 | KSSQSVYNNNDLA |
| CDR-L1 Q1H | 9 | HSSQSVYNNNDLA |
| CDR-H3 D19N | 10 | DHIYRYDDYGDYPTYYGMNP |
| CDR-H3 D19E | 11 | DHIYRYDDYGDYPTYYGMEP |
| CDR-H3 Y4F | 12 | DHIFRYDDYGDYPTYYGMDP |
| CDR-H3 Y6F | 13 | DHIYRFDDYGDYPTYYGMDP |
| CDR-H3 Y9F | 14 | DHIYRYDDFGDYPTYYGMDP |
| CDR-H3 Y12F | 15 | DHIYRYDDYGDFPTYYGMDP |
| CDR-H3 Y15F | 16 | DHIYRYDDYGDYPTFYGMDP |
| CDR-H3 Y16F | 17 | DHIYRYDDYGDYPTYFGMDP |
| CDR-H3 T14N | 18 | DHIYRYDDYGDYPNYYGMDP |
| CDR-H3 T14V | 19 | DHIYRYDDYGDYPVYYGMDP |
| CDR-H3 T14S | 20 | DHIYRYDDYGDYPSYYGMDP |
| CDR-H3 Y4F/D19N | 21 | DHIFRYDDYGDYPTYYGMNP |
| CDR-H3 Y6F/D19N | 22 | DHIYRFDDYGDYPTYYGMNP |
| CDR-H3 Y9F/D19N | 23 | DHIYRYDDFGDYPTYYGMNP |
| CDR-H3 Y12F/D19N | 24 | DHIYRYDDYGDFPTYYGMNP |
| CDR-H3 Y15F/D19N | 25 | DHIYRYDDYGDYPTFYGMNP |
| CDR-H3 Y16F/D19N | 26 | DHIYRYDDYGDYPTYFGMNP |
| CDR-H3 T14N/D19N | 27 | DHIYRYDDYGDYPNYYGMNP |
| CDR-H3 T14V/D19N | 28 | DHIYRYDDYGDYPVYYGMNP |
| CDR-H3 T14S/D19N | 29 | DHIYRYDDYGDYPSYYGMNP |
| Rabbit VL | 30 | AVVLTQTPSPMSAAVGGTVTISCQSSQSVYNNNDLAWYQQKPGQPPKL LIYRASTLASGVPSRFSGSGSGTQFTLTISGVQCDDAATYYCLGGYDD DVDTYTFGGGTEVVVK |
| Rabbit VL nucleotide | 31 | gcagtcgtgctgactcagacaccatcacccatgtctgcagctgtggga ggcacagtcaccatcagttgccagtccagtcagagtgtttataataat |

TABLE 1-continued

| Name | SEQ ID NO: | SEQUENCE |
|---|---|---|
| | | aacgacttagcctggtatcagcagaaaccagggcagcctcctaagctc<br>ctgatctacagggcatccactctggcatctggggtcccgtcgcggttc<br>agcggcagtggatctgggacacagttcactctcaccatcagcggcgtg<br>cagtgtgacgatgctgccacttactactgtctaggcggttatgatgat<br>gatgttgatacgtatactttcggcggagggaccgaggtggtggtcaaa |
| Rabbit VH | 32 | QSVEESGGRLVTPGTPLTLTCTVSGFSLSSYGMSWVRQAPGKGLEWIG<br>IISSSGSTYYASWAKGRFTISKTSTTVDLKIASPTTEDTATYFCARDH<br>IYRYDDYGDYPTYYGMDPWGPGTLVTVSS |
| Rabbit VH nucleotide | 33 | cagtcggtggaggagtccgggggtcgcctggtcacgcctgggacaccc<br>ctgacactcacctgcacagtctctggattctccctcagtagctatgga<br>atgagctgggtccgccaggctccagggaaggggctggaatggatcgga<br>attattagtagtagtggtagcacatactacgcgagctgggcgaaaggc<br>cgattcaccatctccaagacctcgaccacggtggatctgaaaatcgcc<br>agtccgacaaccgaggacacggccacctatttctgtgccagagatcac<br>atttataggtacgatgactatggtgattaccctacctactacggcatg<br>gacccctggggcccaggcaccctggtcaccgtctcgagc |
| 10273 gL2 VL | 34 | AIQLTQSPSSLSASVGDRVTITCQSSQSVYNNNDLAWYQQKPGKAPKL<br>LIYRASTLASGVPSRFSGSGSGTDFTLTISSLQPEDFATYYCLGGYDD<br>DVDTYTFGGGTKVEIK |
| 10273 gL2 VL nucl. | 35 | gccattcaactgactcagtccccatcctccctgtccgcatccgtgggg<br>gatagagtcaccatcacctgtcagtcgagccagtcagtgtacaacaac<br>aacgacctggcctggtatcagcagaagccgggaaaggctcccaagttg<br>ctgatctaccgggcctcaacgctcgcgtcgggagtgcctagccgcttt<br>tccggttccggatctggcaccgacttcactctcaccatttcgagcctt<br>caaccggaggacttcgccacttactactgcctgggcggttacgatgac<br>gatgtggacacctacaccttcggcggagggaccaaagtggaaatcaag |
| 10273 gL2 Light chain | 36 | AIQLTQSPSSLSASVGDRVTITCQSSQSVYNNNDLAWYQQKPGKAPKL<br>LIYRASTLASGVPSRFSGSGSGTDFTLTISSLQPEDFATYYCLGGYDD<br>DVDTYTFGGGTKVEIKRTVAAPSVFIFPPSDEQLKSGTASVVCLLNNF<br>YPREAKVQWKVDNALQSGNSQESVTEQDSKDSTYSLSSTLTLSKADYE<br>KHKVYACEVTHQGLSSPVTKSFNRGEC |
| 10273 gL2 Light chain nucl. | 37 | gccattcaactgactcagtccccatcctccctgtccgcatccgtgggg<br>gatagagtcaccatcacctgtcagtcgagccagtcagtgtacaacaac<br>aacgacctggcctggtatcagcagaagccgggaaaggctcccaagttg<br>ctgatctaccgggcctcaacgctcgcgtcgggagtgcctagccgcttt<br>tccggttccggatctggcaccgacttcactctcaccatttcgagcctt<br>caaccggaggacttcgccacttactactgcctgggcggttacgatgac<br>gatgtggacacctacaccttcggcggagggaccaaagtggaaatcaag<br>cgtacggtggccgctccctccgtgttcatcttcccaccctccgacgag<br>cagctgaagtccggcaccgcctccgtcgtgtgcctgctgaacaacttc<br>taccccgcgaggccaaggtgcagtggaaggtggacaacgccctgcag<br>tccggcaactcccaggaatccgtcaccgagcaggactccaaggacagc<br>acctactccctgtcctccaccctgaccctgtccaaggccgactacgag<br>aagcacaaggtgtacgcctgcgaagtgacccaccagggcctgtccagc<br>cccgtgaccaagtccttcaaccggggcgagtgc |
| 10273 gL2 VL Q1R | 38 | AIQLTQSPSSLSASVGDRVTITCRSSQSVYNNNDLAWYQQKPGKAPKL<br>LIYRASTLASGVPSRFSGSGSGTDFTLTISSLQPEDFATYYCLGGYDD<br>DVDTYTFGGGTKVEIK |
| 10273 gL2 VL Q1R nucl. | 39 | gccattcaactgactcagtccccatcctccctgtccgcatccgtgggg<br>gatagagtcaccatcacctgtcggtcgagccagtcagtgtacaacaac<br>aacgacctggcctggtatcagcagaagccgggaaaggctcccaagttg<br>ctgatctaccgggcctcaacgctcgcgtcgggagtgcctagccgcttt<br>tccggttccggatctggcaccgacttcactctcaccatttcgagcctt<br>caaccggaggacttcgccacttactactgcctgggcggttacgatgac<br>gatgtggacacctacaccttcggcggagggaccaaagtggaaatcaag |
| 10273 gL2 Light chain Q1R | 40 | AIQLTQSPSSLSASVGDRVTITCRSSQSVYNNNDLAWYQQKPGKAPKL<br>LIYRASTLASGVPSRFSGSGSGTDFTLTISSLQPEDFATYYCLGGYDD<br>DVDTYTFGGGTKVEIKRTVAAPSVFIFPPSDEQLKSGTASVVCLLNNF<br>YPREAKVQWKVDNALQSGNSQESVTEQDSKDSTYSLSSTLTLSKADYE<br>KHKVYACEVTHQGLSSPVTKSFNRGEC |
| 10273 gL2 Light chain Q1R nucl. | 41 | gccattcaactgactcagtccccatcctccctgtccgcatccgtgggg<br>gatagagtcaccatcacctgtcggtcgagccagtcagtgtacaacaac<br>aacgacctggcctggtatcagcagaagccgggaaaggctcccaagttg<br>ctgatctaccgggcctcaacgctcgcgtcgggagtgcctagccgcttt<br>tccggttccggatctggcaccgacttcactctcaccatttcgagcctt<br>caaccggaggacttcgccacttactactgcctgggcggttacgatgac |

TABLE 1-continued

| Name | SEQ ID NO: | SEQUENCE |
|---|---|---|
| | | gatgtggacacctacaccttcggcggagggaccaaagtggaaatcaag cgtacggtggccgctccctccgtgttcatcttcccaccctccgacgag cagctgaagtccggcaccgcctccgtcgtgtgcctgctgaacaacttc taccccgcgaggccaaggtgcagtggaaggtggacaacgccctgcag tccggcaactcccaggaatccgtcaccgagcaggactccaaggacagc acctactccctgtcctccaccctgaccctgtccaaggccgactacgag aagcacaaggtgtacgcctgcgaagtgacccaccagggcctgtccagc cccgtgaccaagtccttcaaccggggcgagtgc |
| 10273 gL2 VL Q1K | 42 | AIQLTQSPSSLSASVGDRVTITCKSSQSVYNNNDLAWYQQKPGKAPKL LIYRASTLASGVPSRFSGSGSGTDFTLTISSLQPEDFATYYCLGGYDD DVDTYTFGGGTKVEIK |
| 10273 gL2 VL Q1K nucl. | 43 | gccattcaactgactcagtccccatcctccctgtccgcatccgtgggg gatagagtcaccatcacctgtaaatcgagccagtcagtgtacaacaac aacgacctggcctggtatcagcagaagccgggaaaggctcccaagttg ctgatctaccgggcctcaacgctcgcgtcgggagtgcctagccgcttt tccggttccggatctggcaccgacttcactctcaccatttcgagcctt caaccggaggacttcgccacttactactgcctgggcggttacgatgac gatgtggacacctacaccttcggcggagggaccaaagtggaaatcaag |
| 10273 gL2 Light chain Q1K | 44 | AIQLTQSPSSLSASVGDRVTITCKSSQSVYNNNDLAWYQQKPGKAPKL LIYRASTLASGVPSRFSGSGSGTDFTLTISSLQPEDFATYYCLGGYDD DVDTYTFGGGTKVEIKRTVAAPSVFIFPPSDEQLKSGTASVVCLLNNF YPREAKVQWKVDNALQSGNSQESVTEQDSKDSTYSLSSTLTLSKADYE KHKVYACEVTHQGLSSPVTKSFNRGEC |
| 10273 gL2 Light chain Q1K nucl. | 45 | gccattcaactgactcagtccccatcctccctgtccgcatccgtgggg gatagagtcaccatcacctgtaaatcgagccagtcagtgtacaacaac aacgacctggcctggtatcagcagaagccgggaaaggctcccaagttg ctgatctaccgggcctcaacgctcgcgtcgggagtgcctagccgcttt tccggttccggatctggcaccgacttcactctcaccatttcgagcctt caaccggaggacttcgccacttactactgcctgggcggttacgatgac gatgtggacacctacaccttcggcggagggaccaaagtggaaatcaag cgtacggtggccgctccctccgtgttcatcttcccaccctccgacgag cagctgaagtccggcaccgcctccgtcgtgtgcctgctgaacaacttc taccccgcgaggccaaggtgcagtggaaggtggacaacgccctgcag tccggcaactcccaggaatccgtcaccgagcaggactccaaggacagc acctactccctgtcctccaccctgaccctgtccaaggccgactacgag aagcacaaggtgtacgcctgcgaagtgacccaccagggcctgtccagc cccgtgaccaagtccttcaaccggggcgagtgc |
| 10273 gL2 VL Q1H | 46 | AIQLTQSPSSLSASVGDRVTITCHSSQSVYNNNDLAWYQQKPGKAPKL LIYRASTLASGVPSRFSGSGSGTDFTLTISSLQPEDFATYYCLGGYDD DVDTYTFGGGTKVEIK |
| 10273 gL2 VL Q1H nucl. | 47 | gccattcaactgactcagtccccatcctccctgtccgcatccgtgggg gatagagtcaccatcacctgtcactcgagccagtcagtgtacaacaac aacgacctggcctggtatcagcagaagccgggaaaggctcccaagttg ctgatctaccgggcctcaacgctcgcgtcgggagtgcctagccgcttt tccggttccggatctggcaccgacttcactctcaccatttcgagcctt caaccggaggacttcgccacttactactgcctgggcggttacgatgac gatgtggacacctacaccttcggcggagggaccaaagtggaaatcaag |
| 10273 gL2 Light chain Q1H | 48 | AIQLTQSPSSLSASVGDRVTITCHSSQSVYNNNDLAWYQQKPGKAPKL LIYRASTLASGVPSRFSGSGSGTDFTLTISSLQPEDFATYYCLGGYDD DVDTYTFGGGTKVEIKRTVAAPSVFIFPPSDEQLKSGTASVVCLLNNF YPREAKVQWKVDNALQSGNSQESVTEQDSKDSTYSLSSTLTLSKADYE KHKVYACEVTHQGLSSPVTKSFNRGEC |
| 10273 gL2 Light chain Q1H nucl. | 49 | gccattcaactgactcagtccccatcctccctgtccgcatccgtgggg gatagagtcaccatcacctgtcactcgagccagtcagtgtacaacaac aacgacctggcctggtatcagcagaagccgggaaaggctcccaagttg ctgatctaccgggcctcaacgctcgcgtcgggagtgcctagccgcttt tccggttccggatctggcaccgacttcactctcaccatttcgagcctt caaccggaggacttcgccacttactactgcctgggcggttacgatgac gatgtggacacctacaccttcggcggagggaccaaagtggaaatcaag cgtacggtggccgctccctccgtgttcatcttcccaccctccgacgag cagctgaagtccggcaccgcctccgtcgtgtgcctgctgaacaacttc taccccgcgaggccaaggtgcagtggaaggtggacaacgccctgcag tccggcaactcccaggaatccgtcaccgagcaggactccaaggacagc acctactccctgtcctccaccctgaccctgtccaaggccgactacgag aagcacaaggtgtacgcctgcgaagtgacccaccagggcctgtccagc cccgtgaccaagtccttcaaccggggcgagtgc |

TABLE 1-continued

| Name | SEQ ID NO: | SEQUENCE |
|---|---|---|
| 10273 gH1<br>VH | 50 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMDPWGQGTTVTVSS |
| 10273 gH1<br>VH nucl. | 51 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatggacccctggggtcaaggcaccactgtgactgtctcgagc |
| 10273 gH1<br>Heavy chain | 52 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMDPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1<br>Heavy chain<br>nucl. | 53 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatggacccctggggtcaaggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgcccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH1<br>VH D19N | 54 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMNPWGQGTTVTVSS |
| 10273 gH1<br>VH D19N<br>nucl. | 55 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatgaacccctggggtcaaggcaccactgtgactgtctcgagc |
| 10273 gH1<br>Heavy chain<br>D19N | 56 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL |

TABLE 1-continued

| Name | SEQ ID NO: | SEQUENCE |
|---|---|---|
| | | PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1 Heavy chain D19N nucl. | 57 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatgaacccctggggtcaaggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctaccccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH1 VH D19E | 58 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMEPWGQGTTVTVSS |
| 10273 gH1 VH D19E nucl. | 59 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatggagccctggggtcaaggcaccactgtgactgtctcgagc |
| 10273 gH1 Heavy chain D19E | 60 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMEPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1 Heavy chain D19E nucl. | 61 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatggagccctggggtcaaggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccccaaagcccaag<br>gacaccctgatgatctcccggacccccgaagtgacctgcgtggtggtg<br>gacgtgtcccaggaagatcccgaggtccagttcaattggtacgtggac |

TABLE 1-continued

| Name | SEQ ID NO: | SEQUENCE |
|---|---|---|
| | | ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH4 VH | 62 | EVQLVESGGGLVQPGGSLRLSCAASGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMDPWGQGTTVTVSS |
| 10273 gH4 VH nucl. | 63 | gaagtgcagctcgtcgaatccggtggcggactggtgcagcccggagga<br>tccctgaggctttcttgtgccgcctccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc |
| 10273 gH4 Heavy chain | 64 | EVQLVESGGGLVQPGGSLRLSCAASGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMDPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH4 Heavy chain nucl. | 65 | gaagtgcagctcgtcgaatccggtggcggactggtgcagcccggagga<br>tccctgaggctttcttgtgccgcctccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH4 VH D19N | 66 | EVQLVESGGGLVQPGGSLRLSCAASGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMNPWGQGTTVTVSS |
| 10273 gH4 VH D19N nucl. | 67 | gaagtgcagctcgtcgaatccggaggtggactggtgcagccaggcgga<br>agcctcaggttgtcctgcgcggcttcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc |

TABLE 1-continued

| Name | SEQ ID NO: | SEQUENCE |
|---|---|---|
| | | cgcgatcacatctaccgctatgacgactacggcgattacccgacttac<br>tacggaatgaacccctggggtcaaggcaccactgtgactgtctcgagc |
| 10273 gH4<br>Heavy chain<br>D19N | 68 | EVQLVESGGGLVQPGGSLRLSCAASGFSLSSYGMSWVRQAPGKGLEWI<br>GIISSSGSTYYASWAKGRFTISKDSSKNTVYLQMNSLRAEDTAVYYCA<br>RDHIYRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH4<br>Heavy chain<br>D19N nucl. | 69 | gaagtgcagctcgtcgaatccggaggtggactggtgcagccaggcgga<br>agcctcaggttgtcctgcgcggcttcagggttcagcctgtcgtcatac<br>ggaatgtcctgggtcagacaggcccctggcaaaggccttgagtggatt<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatgaacccctggggtcaaggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH5<br>VH | 70 | EVQLVESGGGLVQPGGSLRLSCAVSGFSLSSYGMSWVRQAPGKGLEWV<br>GIISSSGSTYYASWAKGRFTISKDSSKNTVYLQMNSLRAEDTAVYYCA<br>RDHIYRYDDYGDYPTYYGMDPWGQGTTVTVSS |
| 10273 gH5<br>VH nucl. | 71 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtgggtc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc |
| 10273 gH5<br>Heavy chain | 72 | EVQLVESGGGLVQPGGSLRLSCAVSGFSLSSYGMSWVRQAPGKGLEWV<br>GIISSSGSTYYASWAKGRFTISKDSSKNTVYLQMNSLRAEDTAVYYCA<br>RDHIYRYDDYGDYPTYYGMDPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH5<br>Heavy chain<br>nucl. | 73 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtgggtc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc |

TABLE 1-continued

| Name | SEQ ID NO: | SEQUENCE |
|---|---|---|
| | | gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgcccccctgccctgcccct<br>gaatttctgggcggaccttccgtgttcctgttcccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH5<br>VH D19N | 74 | EVQLVESGGGLVQPGGSLRLSCAVSGFSLSSYGMSWVRQAPGKGLEWV<br>GIISSSGSTYYASWAKGRFTISKDSSKNTVYLQMNSLRAEDTAVYYCA<br>RDHIYRYDDYGDYPTYYGMNPWGQGTTVTVSS |
| 10273 gH5<br>VH D19N<br>nucl. | 75 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtgggtc<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatgaacccctggggtcaaggcaccactgtgactgtctcgagc |
| 10273 gH5<br>Heavy chain<br>D19N | 76 | EVQLVESGGGLVQPGGSLRLSCAVSGFSLSSYGMSWVRQAPGKGLEWV<br>GIISSSGSTYYASWAKGRFTISKDSSKNTVYLQMNSLRAEDTAVYYCA<br>RDHIYRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH5<br>Heavy chain<br>D19N nucl. | 77 | gaagtgcagctcgtcgaatccggaggtggactggtgcagccaggcgga<br>agcctcaggttgtcctgcgcggtgtcagggttcagcctgtcgtcatac<br>ggaatgtcctgggtcagacaggcccctggcaaaggccttgagtgggtc<br>gggatcatctcctcctccgggtccacctactacgcctcttgggccaag<br>ggacggttcaccatttcgaaggacagctcgaagaacaccgtgtatctg<br>cagatgaacagcctgcgggcagaggacaccgctgtgtactactgtgcc<br>cgcgatcacatctaccgctatgacgactacggcgattacccgacttac<br>tacggaatgaacccctggggtcaaggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgcccccctgccctgcccct<br>gaatttctgggcggaccttccgtgttcctgttcccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |

TABLE 1-continued

| Name | SEQ ID NO: | SEQUENCE |
|---|---|---|
| 10273 gH8 VH | 78 | EVQLVESGGGLVQPGGSLRLSCAVSGFSLSSYGMSWVRQAPGKGLEWI GIISSSGSTYYASWAKGRFTISRDSSKNTVYLQMNSLRAEDTAVYYCA RDHIYRYDDYGDYPTYYGMDPWGQGTTVTVSS |
| 10273 gH8 VH nucl. | 79 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagccgggacagctccaagaacactgtgtacctc caaatgaactcgctgcgggctgaggacaccgccgtgtactactgcgcc cgcgatcacatctaccgctatgatgactacggggactacccgacctac tacggaatggacccttggggacagggcaccactgtgactgtctcgagc |
| 10273 gH8 Heavy chain | 80 | EVQLVESGGGLVQPGGSLRLSCAVSGFSLSSYGMSWVRQAPGKGLEWI GIISSSGSTYYASWAKGRFTISRDSSKNTVYLQMNSLRAEDTAVYYCA RDHIYRYDDYGDYPTYYGMDPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH8 Heavy chain nucl. | 81 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagccgggacagctccaagaacactgtgtacctc caaatgaactcgctgcgggctgaggacaccgccgtgtactactgcgcc cgcgatcacatctaccgctatgatgactacggggactacccgacctac tacggaatggacccttggggacagggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttcccccccaaagcccaag gacaccctgatgatctcccggacccccgaagtgacctgcgtggtggtg gacgtgtcccaggaagatcccgaggtccagttcaattggtacgtggac ggcgtggaagtgcacaatgccaagaccaagcccagagaggaacagttc aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgccccctagccaggaagagatgaccaag aaccaggtgtccctgacctgtctggtcaagggcttctaccccctccgac attgccgtggaatgggagtccaacggccagcccgagaacaactacaag accaccccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH8 VH D19N | 82 | EVQLVESGGGLVQPGGSLRLSCAVSGFSLSSYGMSWVRQAPGKGLEWI GIISSSGSTYYASWAKGRFTISRDSSKNTVYLQMNSLRAEDTAVYYCA RDHIYRYDDYGDYPTYYGMNPWGQGTTVTVSS |
| 10273 gH8 VH D19N nucl. | 83 | gaagtgcagctcgtcgaatccggaggtggactggtgcagccaggcgga agcctcaggttgtcctgcgcggtgtcagggttcagcctgtcgtcatac ggaatgtcctgggtcagacaggcccctggcaaaggccttgagtggatt gggatcatctcctcctccgggtccacctactacgcctcttgggccaag ggacggttcaccatttcgcgggacagctcgaagaacaccgtgtatctg cagatgaacagcctgcgggcagaggacaccgctgtgtactactgtgcc cgcgatcacatctaccgctatgacgactacggcgattacccgacttac tacggaatgaaccccctggggtcaaggcaccactgtgactgtctcgagc |
| 10273 gH8 Heavy chain D19N | 84 | EVQLVESGGGLVQPGGSLRLSCAVSGFSLSSYGMSWVRQAPGKGLEWI GIISSSGSTYYASWAKGRFTISRDSSKNTVYLQMNSLRAEDTAVYYCA RDHIYRYDDYGDYPTYYGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD |

TABLE 1-continued

| Name | SEQ ID NO: | SEQUENCE |
|---|---|---|
| | | GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH8 Heavy chain D19N nucl. | 85 | gaagtgcagctcgtcgaatccggaggtggactggtgcagccaggcgga agcctcaggttgtcctgcgcggtgtcagggttcagcctgtcgtcatac ggaatgtcctgggtcagacaggcccctggcaaaggccttgagtggatt gggatcatctcctcctccgggtccacctactacgcctcttgggccaag ggacggttcaccatttcgcgggacagctcgaagaacaccgtgtatctg cagatgaacagcctgcgggcagaggacaccgctgtgtactactgtgcc cgcgatcacatctaccgctatgacgactacggcgattacccgacttac tacggaatgaaccccctggggtcaaggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttcccccaaagcccaag gacaccctgatgatctcccggacccccgaagtgacctgcgtggtggtg gacgtgtcccaggaagatcccgaggtccagttcaattggtacgtggac ggcgtggaagtgcacaatgccaagaccaagcccagagaggaacagttc aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgccccctagccaggaagagatgaccaag aaccaggtgtccctgacctgtctggtcaagggcttctacccctccgac attgccgtggaatgggagtccaacggccagcccgagaacaactacaag accaccccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH10 VH | 86 | EVQLVESGGGLVQPGGSLRLSCAVSGFSLSSYGMSWVRQAPGKGLEWI GIISSSGSTYYASWAKGRFTISKDSSKNTLYLQMNSLRAEDTAVYYCA RDHIYRYDDYGDYPTYYGMDPWGQGTTVTVSS |
| 10273 gH10 VH nucl. | 87 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactttgtacctc caaatgaactcgctgcgggctgaggacaccgccgtgtactactgcgcc cgcgatcacatctaccgctatgatgactacggggactacccgacctac tacggaatggacccttggggacagggcaccactgtgactgtctcgagc |
| 10273 gH10 Heavy chain | 88 | EVQLVESGGGLVQPGGSLRLSCAVSGFSLSSYGMSWVRQAPGKGLEWI GIISSSGSTYYASWAKGRFTISKDSSKNTLYLQMNSLRAEDTAVYYCA RDHIYRYDDYGDYPTYYGMDPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH10 Heavy chain nucl. | 89 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactttgtacctc caaatgaactcgctgcgggctgaggacaccgccgtgtactactgcgcc cgcgatcacatctaccgctatgatgactacggggactacccgacctac tacggaatggacccttggggacagggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttcccccaaagcccaag gacaccctgatgatctcccggacccccgaagtgacctgcgtggtggtg |

TABLE 1-continued

| Name | SEQ ID NO: | SEQUENCE |
|---|---|---|
| | | gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH10 VH D19N | 90 | EVQLVESGGGLVQPGGSLRLSCAVSGFSLSSYGMSWVRQAPGKGLEWI<br>GIISSSGSTYYASWAKGRFTISKDSSKNTLYLQMNSLRAEDTAVYYCA<br>RDHIYRYDDYGDYPTYYGMNPWGQGTTVTVSS |
| 10273 gH10 VH D19N nucl. | 91 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactttgtacctc<br>caaatgaactcgctgcgggctgaggacaccgccgtgtactactgcgcc<br>cgcgatcacatctaccgctatgatgactacggggactacccgacctac<br>tacggaatgaacccttggggacagggcaccactgtgactgtctcgagc |
| 10273 gH10 Heavy chain D19N | 92 | EVQLVESGGGLVQPGGSLRLSCAVSGFSLSSYGMSWVRQAPGKGLEWI<br>GIISSSGSTYYASWAKGRFTISKDSSKNTLYLQMNSLRAEDTAVYYCA<br>RDHIYRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH10 Heavy chain D19N nucl. | 93 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactttgtacctc<br>caaatgaactcgctgcgggctgaggacaccgccgtgtactactgcgcc<br>cgcgatcacatctaccgctatgatgactacggggactacccgacctac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctacccctccgac<br>attgccgtggaatgggagtccaacggccagcccgagaacaactacaag<br>accacccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH11 VH | 94 | EVQLVESGGGLVQPGGSLRLSCAVSGFSLSSYGMSWVRQAPGKGLEWI<br>GIISSSGSTYYASWAKGRFTISRDNSKNTVYLQMNSLRAEDTAVYYCA<br>RDHIYRYDDYGDYPTYYGMDPWGQGTTVTVSS |
| 10273 gH11 VH nucl. | 95 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagccgggacaactccaagaacactgtgtacctc |

TABLE 1-continued

| Name | SEQ ID NO: | SEQUENCE |
|---|---|---|
| | | caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc |
| 10273 gH11<br>Heavy chain | 96 | EVQLVESGGGLVQPGGSLRLSCAVSGFSLSSYGMSWVRQAPGKGLEWI<br>GIISSSGSTYYASWAKGRFTISRDNSKNTVYLQMNSLRAEDTAVYYCA<br>RDHIYRYDDYGDYPTYYGMDPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH11<br>Heavy chain<br>nucl. | 97 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagccgggacaactccaagaacactgtgtacctc<br>caaatgaactcgctgcgggctgaggacaccgccgtgtactactgcgcc<br>cgcgatcacatctaccgctatgatgactacggggactacccgacctac<br>tacggaatggacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccctagccaggaagagatgaccaag<br>aaccaggtgtccctgacctgtctggtcaagggcttctaccccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH11<br>VH D19N | 98 | EVQLVESGGGLVQPGGSLRLSCAVSGFSLSSYGMSWVRQAPGKGLEWI<br>GIISSSGSTYYASWAKGRFTISRDNSKNTVYLQMNSLRAEDTAVYYCA<br>RDHIYRYDDYGDYPTYYGMNPWGQGTTVTVSS |
| 10273 gH11<br>VH D19N<br>nucl. | 99 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagccgggacaactccaagaacactgtgtacctc<br>caaatgaactcgctgcgggctgaggacaccgccgtgtactactgcgcc<br>cgcgatcacatctaccgctatgatgactacggggactacccgacctac<br>tacggaatgaacccttggggacagggcaccactgtgactgtctcgagc |
| 10273 gH11<br>Heavy chain<br>D19N | 100 | EVQLVESGGGLVQPGGSLRLSCAVSGFSLSSYGMSWVRQAPGKGLEWI<br>GIISSSGSTYYASWAKGRFTISRDNSKNTVYLQMNSLRAEDTAVYYCA<br>RDHIYRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH11<br>Heavy chain<br>D19N nucl. | 101 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagccgggacaactccaagaacactgtgtacctc<br>caaatgaactcgctgcgggctgaggacaccgccgtgtactactgcgcc<br>cgcgatcacatctaccgctatgatgactacggggactacccgacctac |

TABLE 1-continued

| Name | SEQ ID NO: | SEQUENCE |
|---|---|---|
| | | tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH1<br>VH<br>Y4F D19N | 102 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIFRYDDYGDYPTYYGMNPWGQGTTVTVSS |
| 10273 gH1<br>VH<br>Y4F D19N<br>nucl. | 103 | Gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatcttccgctatgatgactacggggactacccgacctac<br>tacggaatgaacccttggggacagggcaccactgtgactgtctcgagc |
| 10273 gH1<br>Heavy chain<br>Y4F D19N | 104 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIFRYDDYGDYPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1<br>Heavy chain<br>Y4F D19N<br>nucl. | 105 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatcttccgctatgatgactacggggactacccgacctac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |

TABLE 1-continued

| Name | SEQ ID NO: | SEQUENCE |
|---|---|---|
| 10273 gH1 VH Y6F D19N | 106 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRFDDYGDYPTYYGMNPWGQGTTVTVSS |
| 10273 gH1 VH Y6F D19N nucl. | 107 | Gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctttgatgactacggggactacccgacctac tacggaatgaacccttggggacagggcaccactgtgactgtctcgagc |
| 10273 gH1 Heavy chain Y6F D19N | 108 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRFDDYGDYPTYYGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH1 Heavy chain Y6F D19N nucl. | 109 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctttgatgactacggggactacccgacctac tacggaatgaacccttggggacagggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttcccccccaaagcccaag gacaccctgatgatctcccggacccccgaagtgacctgcgtggtggtg gacgtgtcccaggaagatcccgaggtccagttcaattggtacgtggac ggcgtggaagtgcacaatgccaagaccaagcccagagaggaacagttc aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgccccctagccaggaagagatgaccaag aaccaggtgtccctgacctgtctggtcaagggcttctaccccctccgac attgccgtggaatgggagtccaacggccagcccgagaacaactacaag accacccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH1 VH Y9F D19N | 110 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDFGDYPTYYGMNPWGQGTTVTVSS |
| 10273 gH1 VH Y9F D19N nucl. | 111 | Gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgacttcggggactacccgacctac tacggaatgaacccttggggacagggcaccactgtgactgtctcgagc |
| 10273 gH1 Heavy chain Y9F D19N | 112 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDFGDYPTYYGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD |

TABLE 1-continued

| Name | SEQ ID NO: | SEQUENCE |
|---|---|---|
| | | IAVEWESNGQPENNYKTTPPVLDSDGSFFLYSRLTVDKSRWQEGNVFS<br>CSVMHEALHNHYTQKSLSLSLGK |
| 10273 gH1<br>Heavy chain<br>Y9F D19N<br>nucl. | 113 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgacttcggggactacccgacctac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgcccccttagccaggaagagatgaccaag<br>aaccaggtgtccctgacctgtctggtcaagggcttctacccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH1<br>VH<br>Y12F D19N | 114 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDFPTYYGMNPWGQGTTVTVSS |
| 10273 gH1<br>VH<br>Y12F D19N<br>nucl. | 115 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggacttcccgacctac<br>tacggaatgaacccttggggacagggcaccactgtgactgtctcgagc |
| 10273 gH1<br>Heavy chain<br>Y12F D19N | 116 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDFPTYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1<br>Heavy chain<br>Y12F D19N<br>nucl. | 117 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggacttcccgacctac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttcccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc |

TABLE 1-continued

| Name | SEQ ID NO: | SEQUENCE |
|---|---|---|
| | | aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgcccccctagccaggaagagatgaccaag aaccaggtgtccctgacctgtctggtcaagggcttctacccctccgac attgccgtggaatgggagtccaacggccagcccgagaacaactacaag accacccccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH1 VH Y15F D19N | 118 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPTFYGMNPWGQGTTVTVSS |
| 10273 gH1 VH Y15F D19N nucl. | 119 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgactacggggactacccgaccttc tacggaatgaacccttggggacagggcaccactgtgactgtctcgagc |
| 10273 gH1 Heavy chain Y15F D19N | 120 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPTFYGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH1 Heavy chain Y15F D19N nucl. | 121 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgactacggggactacccgaccttc tacggaatgaacccttggggacagggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttcccccccaaagcccaag gacaccctgatgatctcccggacccccgaagtgacctgcgtggtggtg gacgtgtcccaggaagatcccgaggtccagttcaattggtacgtggac ggcgtggaagtgcacaatgccaagaccaagcccagagaggaacagttc aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgcccccctagccaggaagagatgaccaag aaccaggtgtccctgacctgtctggtcaagggcttctacccctccgac attgccgtggaatgggagtccaacggccagcccgagaacaactacaag accacccccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH1 VH Y16F D19N | 122 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPTYFGMNPWGQGTTVTVSS |
| 10273 gH1 VH Y16F D19N nucl. | 123 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc |

TABLE 1-continued

| Name | SEQ ID NO: | SEQUENCE |
|---|---|---|
| | | caaatgaactcgctgcgggctgaggacaccgccgtgtactactgcgcc cgcgatcacatctaccgctatgatgactacggggactacccgacctac ttcggaatgaaccccttggggacagggcaccactgtgactgtctcgagc |
| 10273 gH1 Heavy chain Y16F D19N | 124 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPTYFGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH1 Heavy chain Y16F D19N nucl. | 125 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgactacggggactacccgacctac ttcggaatgaaccccttggggacagggcaccactgtgactgtctcgagc gcttctacaaagggcccctccgtgttccctctggccccttgctcccgg tccacctccgagtctaccgccgctctgggctgcctggtcaaggactac ttccccgagcccgtgacagtgtcctggaactctggcgccctgacctcc ggcgtgcacaccttccctgccgtgctgcagtcctccggcctgtactcc ctgtcctccgtcgtgaccgtgccctcctccagcctgggcaccaagacc tacacctgtaacgtggaccacaagccctccaacaccaaggtggacaag cgggtggaatctaagtacggccctccctgccccccctgccctgcccct gaatttctgggcggaccttccgtgttcctgttccccccaaagcccaag gacaccctgatgatctcccggacccccgaagtgacctgcgtggtggtg gacgtgtcccaggaagatcccgaggtccagttcaattggtacgtggac ggcgtggaagtgcacaatgccaagaccaagcccagagaggaacagttc aactccacctaccgggtggtgtccgtgctgaccgtgctgcaccaggac tggctgaacggcaaagagtacaagtgcaaggtgtccaacaagggcctg ccctccagcatcgaaaagaccatctccaaggccaagggccagccccgc gagccccaggtgtacaccctgccccctagccaggaagagatgaccaag aaccaggtgtccctgacctgtctggtcaagggcttctaccccctccgac attgccgtggaatgggagtccaacggccagcccgagaacaactacaag accacccccccctgtgctggacagcgacggctccttcttcctgtactct cggctgaccgtggacaagtcccggtggcaggaaggcaacgtcttctcc tgctccgtgatgcacgaggccctgcacaaccactacacccagaagtcc ctgtccctgagcctgggcaag |
| 10273 gH1 VH T14N D19N | 126 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPNYYGMNPWGQGTTVTVSS |
| 10273 gH1 VH T14N D19N nucl. | 127 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgactacggggactacccgaactac tacggaatgaaccccttggggacagggcaccactgtgactgtctcgagc |
| 10273 gH1 Heavy chain T14N D19N | 128 | EVQLVESGGGLVQPGGSLRLSCAVSGFSLSSYGMSWVRQAPGKGLEWI GIISSSGSTYYASWAKGRFTISKDSSKNTVYLQMNSLRAEDTAVYYCA RDHIYRYDDYGDYPNYYGMNPWGQGTTVTVSSASTKGPSVFPLAPCSR STSESTAALGCLVKDYFPEPVTVSWNSGALTSGVHTFPAVLQSSGLYS LSSVVTVPSSSLGTKTYTCNVDHKPSNTKVDKRVESKYGPPCPPCPAP EFLGGPSVFLFPPKPKDTLMISRTPEVTCVVVDVSQEDPEVQFNWYVD GVEVHNAKTKPREEQFNSTYRVVSVLTVLHQDWLNGKEYKCKVSNKGL PSSIEKTISKAKGQPREPQVYTLPPSQEEMTKNQVSLTCLVKGFYPSD IAVEWESNGQPENNYKTTPPVLDSDGSFFLYSRLTVDKSRWQEGNVFS CSVMHEALHNHYTQKSLSLSLGK |
| 10273 gH1 Heavy chain T14N D19N nucl. | 129 | gaagtgcagctcgtcgaatccggtggcggactggtgcagcccggagga tccctgaggctttcttgtgccgtgtccgggttctccctgagctcctac gggatgtcgtgggtcagacaagcaccaggaaagggtctggagtggatc ggaattatctcctcctcgggctcaacctactacgcgtcatgggccaag ggccggttcaccattagcaaggacagctccaagaacactgtgtacctc caaatgaactcgctgcgggctgaggacaccgccgtgtactactgcgcc cgcgatcacatctaccgctatgatgactacggggactacccgaactac |

TABLE 1-continued

| Name | SEQ ID NO: | SEQUENCE |
|---|---|---|
| | | tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgcccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accacccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| 10273 gH1 VH T14V D19N | 130 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPVYYGMNPWGQGTTVTVSS |
| 10273 gH1 VH T14V D19N nucl. | 131 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccggtgtac<br>tacggaatgaacccttggggacagggcaccactgtgactgtctcgagc |
| 10273 gH1 Heavy chain T14V D19N | 132 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPVYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1 Heavy chain T14V D19N nucl. | 133 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccggtgtac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgcccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctacccctccgac<br>attgccgtggaatgggagtccaacggccagcccgagaacaactacaag<br>accacccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |

TABLE 1-continued

| Name | SEQ ID NO: | SEQUENCE |
|---|---|---|
| 10273 gH1 VH T14S D19N | 134 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPSYYGMNPWGQGTTVTVSS |
| 10273 gH1 VH T14S D19N nucl. | 135 | Gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgtcctac<br>tacggaatgaacccttggggacagggcaccactgtgactgtctcgagc |
| 10273 gH1 Heavy chain T14S D19N | 136 | EVQLVESGGGLVQPGGSLRLSCAVSGFSLSSYGMSWVRQAPGKGLEWI<br>GIISSSGSTYYASWAKGRFTISKDSSKNTVYLQMNSLRAEDTAVYYCA<br>RDHIYRYDDYGDYPSYYGMNPWGQGTTVTVSSASTKGPSVFPLAPCSR<br>STSESTAALGCLVKDYFPEPVTVSWNSGALTSGVHTFPAVLQSSGLYS<br>LSSVVTVPSSSLGTKTYTCNVDHKPSNTKVDKRVESKYGPPCPPCPAP<br>EFLGGPSVFLFPPKPKDTLMISRTPEVTCVVVDVSQEDPEVQFNWYVD<br>GVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSD<br>IAVEWESNGQPENNYKTTPPVLDSDGSFFLYSRLTVDKSRWQEGNVFS<br>CSVMHEALHNHYTQKSLSLSLGK |
| 10273 gH1 Heavy chain T14S D19N nucl. | 137 | gaagtgcagctcgtcgaatccggtggcggactggtgcagcccggagga<br>tccctgaggctttcttgtgccgtgtccgggttctccctgagctcctac<br>gggatgtcgtgggtcagacaagcaccaggaaagggtctggagtggatc<br>ggaattatctcctcctcgggctcaacctactacgcgtcatgggccaag<br>ggccggttcaccattagcaaggacagctccaagaacactgtgtacctc<br>caaatgaactcgctgcgggctgaggacaccgccgtgtactactgcgcc<br>cgcgatcacatctaccgctatgatgactacggggactacccgtcctac<br>tacggaatgaacccttggggacagggcaccactgtgactgtctcgagc<br>gcttctacaaagggcccctccgtgttccctctggccccttgctcccgg<br>tccacctccgagtctaccgccgctctgggctgcctggtcaaggactac<br>ttccccgagcccgtgacagtgtcctggaactctggcgccctgacctcc<br>ggcgtgcacaccttccctgccgtgctgcagtcctccggcctgtactcc<br>ctgtcctccgtcgtgaccgtgccctcctccagcctgggcaccaagacc<br>tacacctgtaacgtggaccacaagccctccaacaccaaggtggacaag<br>cgggtggaatctaagtacggccctccctgccccccctgccctgcccct<br>gaatttctgggcggaccttccgtgttcctgttccccccaaagcccaag<br>gacaccctgatgatctcccggacccccgaagtgacctgcgtggtggtg<br>gacgtgtcccaggaagatcccgaggtccagttcaattggtacgtggac<br>ggcgtggaagtgcacaatgccaagaccaagcccagagaggaacagttc<br>aactccacctaccgggtggtgtccgtgctgaccgtgctgcaccaggac<br>tggctgaacggcaaagagtacaagtgcaaggtgtccaacaagggcctg<br>ccctccagcatcgaaaagaccatctccaaggccaagggccagccccgc<br>gagccccaggtgtacaccctgccccctagccaggaagagatgaccaag<br>aaccaggtgtccctgacctgtctggtcaagggcttctaccctccgac<br>attgccgtggaatgggagtccaacggccagcccgagaacaactacaag<br>accaccccccctgtgctggacagcgacggctccttcttcctgtactct<br>cggctgaccgtggacaagtcccggtggcaggaaggcaacgtcttctcc<br>tgctccgtgatgcacgaggccctgcacaaccactacacccagaagtcc<br>ctgtccctgagcctgggcaag |
| Human IGKV1D-13 JK4 acceptor framework | 138 | AIQLTQSPSSLSASVGDRVTITCRASQGISSALAWYQQKPGKAPKLLIYDASS<br>LESGVPSRFSGSGSGTDFTLTISSLQPEDFATYYCQQFNSYPLTFGGGTKVEI<br>K |
| Human IGKV1D-13 JK4 acceptor framework nucl. | 139 | gccatccagttgacccagtctccatcctccctgtctgcatctgtaggagacag<br>agtcaccatcacttgccgggcaagtcagggcattagcagtgctttagcctggt<br>atcagcagaaaccagggaaagctcctaagctcctgatctatgatgcctccagt<br>ttggaaagtggggtcccatcaaggttcagcggcagtggatctgggacagattt<br>cactctcaccatcagcagcctgcagcctgaagattttgcaacttattactgtc<br>aacagtttaatagttaccctctcactttcggcggagggaccaaggtggagatc<br>aaa |
| Human IGHV3-66 JH6 acceptor framework | 140 | EVQLVESGGGLVQPGGSLRLSCAASGFTVSSNYMSWVRQAPGKGLEWVSVIYS<br>GGSTYYADSVKGRFTISRDNSKNTLYLQMNSLRAEDTAVYYCARYYYYYGMDV<br>WGQGTTVTVSS |

TABLE 1-continued

| Name | SEQ ID NO: | SEQUENCE |
|---|---|---|
| Human IGHV3-66 JH6 acceptor framework nucl. | 141 | gaggtgcagctggtggagtctgggggaggcttggtccagcctggggggtccct<br>gagactctcctgtgcagcctctggattcaccgtcagtagcaactacatgagct<br>gggtccgccaggctccagggaaggggctggagtgggtctcagttatttatagc<br>ggtggtagcacatactacgcagactccgtgaagggcagattcaccatctccag<br>agacaattccaagaacacgctgtatcttcaaatgaacagcctgagagccgagg<br>acacggctgtgtattactgtgcgagatactactactactacggtatggacgtc<br>tgggggcaagggaccacggtcaccgtctcctca |
| Human KLK5 (full length with signal sequence) | 142 | MATARPPWMWVLCALITALLLGVTEHVLANNDVSCDHPSNTVPSGSNQDLGAG<br>AGEDARSDDSSSRIINGSDCDMHTQPWQAALLLRPNQLYCGAVLVHPQWLLTA<br>AHCRKKVFRVRLGHYSLSPVYESGQQMFQGVKSIPHPGYSHPGHSNDLMLIKL<br>NRRIRPTKDVRPINVSSHCPSAGTKCLVSGWGTTKSPQVHFPKVLQCLNISVL<br>SQKRCEDAYPRQIDDTMFCAGDKAGRDSCQGDSGGPVVCNGSLQGLVSWGDYP<br>CARPNRPGVYTNLCKFTKWIQETIQANS |
| Human KLK5 pro-form | 143 | VTEHVLANNDVSCDHPSNTVPSGSNQDLGAGAGEDARSDDSSSRIINGSDCDM<br>HTQPWQAALLLRPNQLYCGAVLVHPQWLLTAAHCRKKVFRVRLGHYSLSPVYE<br>SGQQMFQGVKSIPHPGYSHPGHSNDLMLIKLNRRIRPTKDVRPINVSSHCPSA<br>GTKCLVSGWGTTKSPQVHFPKVLQCLNISVLSQKRCEDAYPRQIDDTMFCAGD<br>KAGRDSCQGDSGGPVVCNGSLQGLVSWGDYPCARPNRPGVYTNLCKFTKWIQE<br>TIQANS |
| Active human KLK5 | 144 | IINGSDCDMHTQPWQAALLLRPNQLYCGAVLVHPQWLLTAAHCRKKVF<br>RVRLGHYSLSPVYESGQQMFQGVKSIPHPGYSHPGHSNDLMLIKLNRR<br>IRPTKDVRPINVSSHCPSAGTKCLVSGWGTTKSPQVHFPKVLQCLNIS<br>VLSQKRCEDAYPRQIDDTMFCAGDKAGRDSCQGDSGGPVVCNGSLQGL<br>VSWGDYPCARPNRPGVYTNLCKFTKWIQETIQANS |
| Human LEKTI D5 Rabbit Fc | 145 | EIVKLCSQYQNQAKNGILFCTRENDPIRGPDGKMHGNLCSMCQAYFQA<br>ENEEKKKAEARARNLEKTVAPSTCSKPTCPPPELLGGPSVFIFPPKPK<br>DTLMISRTPEVTCVVVDVSQDDPEVQFTWYINNEQVRTARPPLREQQF<br>NSTIRVVSTLPIAHQDWLRGKEFKCKVHNKALPAPIEKTISKARGQPL<br>EPKVYTMGPPREELSSRSVSLTCMINGFYPSDISVEWEKNGKAEDNYK<br>TTPAVLDSDGSYFLYSKLSVPTSEWQRGDVFTCSVMHEALHNHYTQKS<br>ISRSPGK |
| Human KLK7 pro-form | 146 | EEAQGDKIIDGAPCARGSHPWQVALLSGNQLHCGGVLVNERWVLTAAH<br>CKMNEYTVHLGSDTLGDRRAQRIKASKSFRHPGYSTQTHVNDLMLVKL<br>NSQARLSSMVKKVRLPSRCEPPGTTCTVSGWGTTTSPDVTFPSDLMCV<br>DVKLISPQDCTKVYKDLLENSMLCAGIPDSKKNACNGDSGGPLVCRGT<br>LQGLVSWGTFPCGQPNDPGVYTQVCKFTKWINDTMKKHR |
| Active human KLK7 | 147 | IIDGAPCARGSHPWQVALLSGNQLHCGGVLVNERWVLTAAHCKMNEYT<br>VHLGSDTLGDRRAQRIKASKSFRHPGYSTQTHVNDLMLVKLNSQARLS<br>SMVKKVRLPSRCEPPGTTCTVSGWGTTTSPDVTFPSDLMCVDVKLISP<br>QDCTKVYKDLLENSMLCAGIPDSKKNACNGDSGGPLVCRGTLQGLVSW<br>GTFPCGQPNDPGVYTQVCKFTKWINDTMKKHR |
| Cyno KLK7 pro-form | 148 | GQEAQGDKIIDGAPCTRGSHPWQVALLSGNQLHCGGVLVNERWVLTAA<br>HCKMNDYIVHLGSDTLGDRKAQRIKASRSFRHPGYSTQTHVNDLMLVK<br>LNSPARLSSTVKKVRLPSRCEPPGTTCTVSGWGTTTSPDVTFPSDLMC<br>VDVKLISSQDCTKVYKDMLGNSMLCAGIPNSKKNACNGDSGGPLVCRG<br>TLQGLVSWGTFPCGQPNDPGVYTQVCKFTKWINDTIKKHR |
| Active Cyno KLK7 | 149 | IIDGAPCTRGSHPWQVALLSGNQLHCGGVLVNERWVLTAAHCKMNDYI<br>VHLGSDTLGDRKAQRIKASRSFRHPGYSTQTHVNDLMLVKLNSPARLS<br>STVKKVRLPSRCEPPGTTCTVSGWGTTTSPDVTFPSDLMCVDVKLISS<br>QDCTKVYKDMLGNSMLCAGIPNSKKNACNGDSGGPLVCRGTLQGLVSW<br>GTFPCGQPNDPGVYTQVCKFTKWINDTIKKHR |
| Active mouse KLK5 | 150 | IVNGSDCQKDAQPWQGALLLGPNKLYCGAVLISPQWLLTAAHCRKPVF<br>RIRLGHHSMSPVYESGQQMFQGIKSIPHPGYSHPGHSNDLMLIKMNRK<br>IRDSHSVKPVEIACDCATEGTRCMVSGWGTTSSSHNNFPKVLQCLNIT<br>VLSEERCKNSYPGQIDKTMFCAGDEEGRDSCQGDSGGPVVCNGKLQGL<br>VSWGDFPCAQRNRPGVYTNLCEFVKWIKDTMNSN |
| Active cyno KLK5 | 151 | IINGSDCDEHTQPWQAALLLGPNQLYCGGVLVHPQWLLTAAHCRKKVF<br>RVRLGHYSLSPVYESGQQMFQGIKSIPHPGYSHPGHSNDLMLIKLNRR<br>IHSTKDVRPINVSSHCPSAGTKCLVSGWGTTRSPQVHFPKVLQCLNIS<br>VLSQKRCEDAYPRQIDDTMFCAGDEAGRDSCQGDSGGPVVCNGSLQGL<br>VSWGDYPCAKPNRPGVYTNLCKFTKWIQETIQANS |
| Human LEKTI D8 Rabbit Fc | 152 | EAAKEICSEFRDQVRNGTLICTREHNPVRGPDGKMHGNKCAMCASVFK<br>LEEEEKKNDKEEKGKVEAEKVLEKTVAPSTCSKPTCPPPELLGGPSVF<br>IFPPKPKDTLMISRTPEVTCVVVDVSQDDPEVQFTWYINNEQVRTARP<br>PLREQQFNSTIRVVSTLPIAHQDWLRGKEFKCKVHNKALPAPIEKTIS |

TABLE 1-continued

| Name | SEQ ID NO: | SEQUENCE |
| --- | --- | --- |
| | | KARGQPLEPKVYTMGPPREELSSRSVSLTCMINGFYPSDISVEWEKNG KAEDNYKTTPAVLDSDGSYFLYSKLSVPTSEWQRGDVFTCSVMHEALH NHYTQKSISRSPGK |
| Rabbit 10273 mIgG Light Chain | 153 | AVVLTQTPSP MSAAVGGTVT ISCQSSQSVY NNNDLAWYQQ KPGQPPKLLI YRASTLASGV PSRFSGSGSG TQFTLTISGV QCDDAATYYC LGGYDDDVDT YTFGGGTEVV VKRTDAAPTV SIFPPSSEQL TSGGASVVCF LNNFYPKDIN VKWKIDGSER QNGVLNSWTD QDSKDCTYSM SSTLTLTKDE YERHNSYTCE ATHKTSTSPI VKSFNRNEC |
| Rabbit 10273 mIgG Heavy Chain | 154 | QSVEESGGRL VTPGTPLTLT CTVSGFSLSS YGMSWVRQAP GKGLEWIGII SSSGSTYYAS WAKGRFTISK TSTTVDLKIA SPTTEDTATY FCARDHIYRY DDYGDYPTYY GMDPWGPGTL VTVSSAKTTP PSVYPLAPGS AAQTNSMVTL GCLVKGYFPE PVTVTWNSGS LSSGVHTFPA VLQSDLYTLS SSVTVPSSTW PSETVTCNVA HPASSTKVDK KIVPRDCGCK PCICTVPEVS SVFIFPPKPK DVLTITLTPK VTCVVVDISK DDPEVQFSWF VDDVEVHTAQ TQPREEQFNS TFRSVSELPI MHQDWLNGKE FKCRVNSAAF PAPIEKTISK TKGRPKAPQV YTIPPPKEQM AKDKVSLTCM ITDFFPEDIT VEWQWNGQPA ENYKNTQPIM DTDGSYFVYS KLNVQKSNWE AGNTFTCSVL HEGLHNHHTE KSLSHSPGK |
| Rabbit 10273 mIgG Light Chain Nucl. | 155 | gcagtcgtgctgactcagacaccatcacccatgtctgcagctgtggga ggcacagtcaccatcagttgccagtccagtcagagtgtttataataat aacgacttagcctggtatcagcagaaaccagggcagcctcctaagctc ctgatctacagggcatccactctggcatctggggtcccgtcgcggttc agcggcagtggatctgggacacagttcactctcaccatcagcggcgtg cagtgtgacgatgctgccacttactactgtctaggcggttatgatgat gatgttgatacgtatactttcggcggagggaccgaggtggtggtcaaa cgtacggatgctgcaccaactgtatccatcttcccaccatccagtgag cagttaacatctggaggtgcctcagtcgtgtgcttcttgaacaacttc taccccaaagacatcaatgtcaagtggaagattgatggcagtgaacga caaaatggcgtcctgaacagttggactgatcaggacagcaaagactgc acctacagcatgagcagcaccctcacgttgaccaaggacgagtatgaa cgacataacagctatacctgtgaggccactcacaagacatcaacttca cccattgtcaagagcttcaacaggaatgagtgt |
| Rabbit 10273 mIgG Heavy Chain Nucl. | 156 | cagtcggtggaggagtccgggggtcgcctggtcacgcctgggacaccc ctgacactcacctgcacagtctctggattctccctcagtagctatgga atgagctgggtccgccaggctccagggaaggggctggaatggatcgga attattagtagtagtggtagcacatactacgcgagctgggcgaaaggc cgattcaccatctccaagacctcgaccacggtggatctgaaaatcgcc agtccgacaaccgaggacacggccacctatttctgtgccagagatcac atttataggtacgatgactatggtgattaccctacctactacggcatg gacccctggggcccaggcaccctggtcaccgtctcgagtgccaaaacg acacccccatctgtctatccactggcccctggatctgctgcccaaact aactccatggtgaccctgggatgcctggtcaagggctatttccctgag ccagtgacagtgacctggaactctggatccctgtccagcggtgtgcac accttcccagctgtcctgcagtctgacctctacactctgagcagctca gtgactgtcccctccagcacctggcccagcgagaccgtcacctgcaac gttgcccacccggccagcagcaccaaggtggacaagaaaattgtgccc agggattgtggttgtaagccttgcatatgtacagtcccagaagtatca tctgtcttcatcttccccccaaagcccaaggatgtgctcaccattact ctgactcctaaggtcacgtgtgttgtggtagacatcagcaaggatgat cccgaggtccagttcagctggtttgtagatgatgtggaggtgcacaca gctcagacgcaaccccgggaggagcagttcaacagcactttccgctca gtcagtgaacttcccatcatgcaccaggactggctcaatggcaaggag ttcaaatgcagggtcaacagtgcagctttccctgcccccatcgagaaa accatctccaaaaccaaaggcagaccgaaggctccacaggtgtacacc attccacctcccaaggagcagatggccaaggataaagtcagtctgacc tgcatgataacagacttcttccctgaagacattactgtggagtggcag tggaatgggcagccagcggagaactacaagaacactcagcccatcatg gacacagatggctcttacttcgtctacagcaagctcaatgtgcagaag agcaactgggaggcaggaaatactttcacctgctctgtgttacatgag ggcctgcacaaccaccatactgagaagagcctctcccactctcctggt aaa |
| Rabbit 10236 mIgG Light Chain | 157 | AYDMTQTPAS VEVAVGGTVT IKCQASQSIS SWLAWYQQKP GQPPKLLIYL ASTLASGVSS RFKGSGSGTQ FTLTISGVEC ADAATYYCQQ GYTNSNIINT FGGGTEVVVK RTDAAPTVSI FPPSSEQLTS GGASVVCFLN NFYPKDINVK WKIDGSERQN GVLNSWTDQD SKDCTYSMSS TLTLTKDEYE RHNSYTCEAT HKTSTSPIVK SFNRNEC |
| Rabbit 10236 mIgG Heavy Chain | 158 | QSVEESGGRL VTPGTPLTLT CTVSGFPLSN YAMSWVRQAP GKGLEWIGDI YPSDIIDYAS WAKGRFTISQ TSTTVELKIT GPTTEDTATY FCARDNNDYG LDIWGPGTLV TVSSAKTTPP SVYPLAPGSA AQTNSMVTLG CLVKGYFPEP VTVTWNSGSL SSGVHTFPAV LQSDLYTLSS SVTVPSSTWP SETVTCNVAH PASSTKVDKK IVPRDCGCKP CICTVPEVSS VFIFPPKPKD VLTITLTPKV |

TABLE 1-continued

| Name | SEQ ID NO: | SEQUENCE |
|---|---|---|
| | | TCVVVDISKD DPEVQFSWFV DDVEVHTAQT QPREEQFNST FRSVSELPIM HQDWLNGKEF KCRVNSAAFP APIEKTISKT KGRPKAPQVY TIPPPKEQMA KDKVSLTCMI TDFFPEDITV EWQWNGQPAE NYKNTQPIMD TDGSYFVYSK LNVQKSNWEA GNTFTCSVLH EGLHNHHTEK SLSHSPGK |
| Rabbit 10236 mIgG Light Chain Nucl. | 159 | gcctatgatatgacccagactccagcctctgtggaggtagctgtggga ggcacagtcaccatcaagtgccaggccagtcagagcattagcagttgg ttagcctggtatcagcagaaaccaggtcagcctcccaagctcctgatc tatctggcatccactctggcatctggggtctcatcgcggttcaaaggc agtggatctgggacacagttcactctcaccatcagcggcgtggagtgt gccgatgctgccacttactactgtcaacagggttatactaatagtaat attattaatactttcggcggagggaccgaggtggtggtcaaacgtacg gatgctgcaccaactgtatccatcttcccaccatccagtgagcagtta acatctggaggtgcctcagtcgtgtgcttcttgaacaacttctacccc aaagacatcaatgtcaagtggaagattgatggcagtgaacgacaaaat ggcgtcctgaacagttggactgatcaggacagcaaagactgcacctac agcatgagcagcaccctcacgttgaccaaggacgagtatgaacgacat aacagctatacctgtgaggccactcacaagacatcaacttcacccatt gtcaagagcttcaacaggaatgagtgt |
| Rabbit 10236 mIgG Heavy Chain Nucl. | 160 | cagtcggtggaggagtccgggggtcgcctggtcacgcctgggacaccc ctgacactcacctgcaccgtctctgggttcccccctcagtaattatgca atgagctgggtccgccaggctccagggaaggggctggaatggatcgga gacatttatcctagtgatatcatagactacgcgagctgggcgaaaggc cgattcaccatctcccaaacctcgaccacggtggagctgaaaatcacg ggtccgacaaccgaggacacggccacctatttctgtgccagagacaac aatgactatggtctggacatctggggcccaggcaccctggtcaccgtc tcgagtgccaaaacgacacccccatctgtctatccactggcccctgga tctgctgcccaaactaactccatggtgaccctgggatgcctggtcaag ggctatttccctgagccagtgacagtgacctggaactctggatccctg tccagcggtgtgcacaccttcccagctgtcctgcagtctgacctctac actctgagcagctcagtgactgtcccctccagcacctggcccagcgag accgtcacctgcaacgttgcccacccggccagcagcaccaaggtggac aagaaaattgtgcccagggattgtggttgtaagccttgcatatgtaca gtcccagaagtatcatctgtcttcatcttccccccaaagcccaaggat gtgctcaccattactctgactcctaaggtcacgtgtgttgtggtagac atcagcaaggatgatcccgaggtccagttcagctggtttgtagatgat gtggaggtgcacacagctcagacgcaaccccgggaggagcagttcaac agcactttccgctcagtcagtgaacttcccatcatgcaccaggactgg ctcaatggcaaggagttcaaatgcagggtcaacagtgcagctttccct gcccccatcgagaaaaccatctccaaaaccaaaggcagaccgaaggct ccacaggtgtacaccattccacctcccaaggagcagatggccaaggat aaagtcagtctgacctgcatgataacagacttcttccctgaagacatt actgtggagtggcagtggaatgggcagccagcggagaactacaagaac actcagcccatcatggacacagatggctcttacttcgtctacagcaag ctcaatgtgcagaagagcaactgggaggcaggaaatactttcacctgc tctgtgttacatgagggcctgcacaaccaccatactgagaagagcctc tcccactctcctggtaaatgatcccagtgtccttggagccctctggtc ctacaggactctgacacctacctccacccctccctgtataaa |
| 10236 Light chain Fab | 161 | AYDMTQTPASVEVAVGGTVTIKCQASQSISSWLAWYQQKPGQPPKLLI YLASTLASGVSSRFKGSGSGTQFTLTISGVECADAATYYCQQGYTNSN IINTFGGGTEVVVKRTPVAPTVLIFPPAADQVATGTVTIVCVANKYFP DVTVTWEVDGTTQTTGIENSKTPQNSADCTYNLSSTLTLTSTQYNSHK EYTCKVTQGTTSVVQSFNRGDC |
| 10236 Light Chain Fab Nucl. | 162 | gcctatgatatgacccagactccagcctctgtggaggtagctgtggga ggcacagtcaccatcaagtgccaggccagtcagagcattagcagttgg ttagcctggtatcagcagaaaccaggtcagcctcccaagctcctgatc tatctggcatccactctggcatctggggtctcatcgcggttcaaaggc agtggatctgggacacagttcactctcaccatcagcggcgtggagtgt gccgatgctgccacttactactgtcaacagggttatactaatagtaat attattaatactttcggcggagggaccgaggtggtggtcaaacgtacg ccagttgcacctactgtcctcatcttcccaccagctgctgatcaggtg gcaactggaacagtcaccatcgtgtgtgtggcgaataaatactttccc gatgtcaccgtcacctgggaggtggatggcaccacccaaacaactggc atcgagaacagtaaaacaccgcagaattctgcagattgtacctacaac ctcagcagcactctgacactgaccagcacacagtacaacagccacaaa gagtacacctgcaaggtgacccagggcacgacctcagtcgtccagagc ttcaataggggtgactgt |
| 10236 heavy chain Fab | 163 | QSVEESGGRLVTPGTPLTLTCTVSGFPLSNYAMSWVRQAPGKGLEWIG DIYPSDIIDYASWAKGRFTISQTSTTVELKITGPTTEDTATYFCARDN NDYGLDIWGPGTLVTVSSGQPKAPSVFPLAPCCGDTPSSTVTLGCLVK GYLPEPVTVTWNSGTLTNGVRTFPSVRQSSGLYSLSSVVSVTSSSQPV TCNVAHPATNTKVDKTVAPSTCSKP |

TABLE 1-continued

| Name | SEQ ID NO: | SEQUENCE |
|---|---|---|
| 10236 heavy chain Fab Nucl. | 164 | cagtcggtggaggagtccgggggtcgcctggtcacgcctgggacaccc ctgacactcacctgcaccgtctctgggttcccccctcagtaattatgca atgagctgggtccgccaggctccagggaaggggctggaatggatcgga gacatttatcctagtgatatcatagactacgcgagctgggcgaaaggc cgattcaccatctcccaaacctcgaccacggtggagctgaaaatcacg ggtccgacaaccgaggacacggccacctatttctgtgccagagacaac aatgactatggtctggacatctggggcccaggcaccctggtcaccgtc tcgagtgggcaacctaaggctccatcagtcttcccactggccccctgc tgcggggacacacccagctccacggtgaccctgggctgcctggtcaaa ggctacctcccggagccagtgaccgtgacctggaactcgggcaccctc accaatggggtacgcaccttcccgtccgtccggcagtcctcaggcctc tactcgctgagcagcgtggtgagcgtgacctcaagcagccagcccgtc acctgcaacgtggcccacccagccaccaacaccaaagtggacaagacc gttgcgccctcgacatgcagcaagccc |
| 10273 Light chain Fab | 165 | AVVLTQTPSPMSAAVGGTVTISCQSSQSVYNNNDLAWYQQKPGQPPKL LIYRASTLASGVPSRFSGSGSGTQFTLTISGVQCDDAATYYCLGGYDD DVDTYTFGGGTEVVVKRTPVAPTVLIFPPAADQVATGTVTIVCVANKY FPDVTVTWEVDGTTQTTGIENSKTPQNSADCTYNLSSTLTLTSTQYNS HKEYTCKVTQGTTSVVQSFNRGDC |
| 10273 Light Chain Fab Nucl. | 166 | gcagtcgtgctgactcagacaccatcacccatgtctgcagctgtggga ggcacagtcaccatcagttgccagtccagtcagagtgtttataataat aacgacttagcctggtatcagcagaaaccagggcagcctcctaagctc ctgatctacagggcatccactctggcatctggggtcccgtcgcggttc agcggcagtggatctgggacacagttcactctcaccatcagcggcgtg cagtgtgacgatgctgccacttactactgtctaggcggttatgatgat gatgttgatacgtatactttcggcggagggaccgaggtggtggtcaaa cgtacgccagttgcacctactgtcctcatcttcccaccagctgctgat caggtggcaactggaacagtcaccatcgtgtgtgtggcgaataaatac tttcccgatgtcaccgtcacctgggaggtggatggcaccacccaaaca actggcatcgagaacagtaaaacaccgcagaattctgcagattgtacc tacaacctcagcagcactctgacactgaccagcacacagtacaacagc cacaaagagtacacctgcaaggtgacccagggcacgacctcagtcgtc cagagcttcaataggggtgactgt |
| 10273 heavy chain Fab | 167 | QSVEESGGRLVTPGTPLTLTCTVSGFSLSSYGMSWVRQAPGKGLEWIG IISSSGSTYYASWAKGRFTISKTSTTVDLKIASPTTEDTATYFCARDH IYRYDDYGDYPTYYGMDPWGPGTLVTVSSGQPKAPSVFPLAPCCGDTP SSTVTLGCLVKGYLPEPVTVTWNSGTLTNGVRTFPSVRQSSGLYSLSS VVSVTSSSQPVTCNVAHPATNTKVDKTVAPSTCSKP |
| 10273 heavy chain Fab Nucl. | 168 | cagtcggtggaggagtccgggggtcgcctggtcacgcctgggacaccc ctgacactcacctgcacagtctctggattctccctcagtagctatgga atgagctgggtccgccaggctccagggaaggggctggaatggatcgga attattagtagtagtggtagcacatactacgcgagctgggcgaaaggc cgattcaccatctccaagacctcgaccacggtggatctgaaaatcgcc agtccgacaaccgaggacacggccacctatttctgtgccagagatcac atttataggtacgatgactatggtgattaccctacctactacggcatg gacccctggggcccaggcaccctggtcaccgtctcgagtgggcaacct aaggctccatcagtcttcccactggccccctgctgcggggacacaccc agctccacggtgaccctgggctgcctggtcaaaggctacctcccggag ccagtgaccgtgacctggaactcgggcaccctcaccaatggggtacgc accttcccgtccgtccggcagtcctcaggcctctactcgctgagcagc gtggtgagcgtgacctcaagcagccagcccgtcacctgcaacgtggcc cacccagccaccaacaccaaagtggacaagaccgttgcgccctcgaca tgcagcaagccc |
| Human LEKTI D5 Fab H chain | 169 | EVQLLESGGGLVQPGGSLRLSCAVSGIDLSNYAINWVRQAPGKGLEWI GIIWASGTTFYATWAKGRFTISRDNSGGGGSGGGGSREIVKLCSQYQN QAKNGILFCTRENDPIRGPDGKMHGNLCSMCQAYFQAENEEKKKAEAR ARSGGGGGGGGSKNTVYLQMNSLRAEDTAVYYCARTVPGYSTAPYFDL WGQGTLVTVSSASTKGPSVFPLAPSSKSTSGGTAALGCLVKDYFPEPV TVSWNSGALTSGVHTFPAVLQSSGLYSLSSVVTVPSSSLGTQTYICNV NHKPSNTKVDKKVEPKSCHHHHHHHHHH |
| Human LEKTI D5 Fab L chain | 170 | DIQMTQSPSSVSASVGDRVTITCQSSPSVWSNFLSWYQQKPGKAPKLL IYEASKLTSGVPSRFSGSGSGTDFTLTISSLQPEDFATYYCGGGYSSI SDTTFGGGTKVEIKRTVAAPSVFIFPPSDEQLKSGTASVVCLLNNFYP REAKVQWKVDNALQSGNSQESVTEQDSKDSTYSLSSTLTLSKADYEKH KVYACEVTHQGLSSPVTKSFNRGEC |
| Rabbit/human chimeric light chain | 171 | AYDMTQTPASVEVAVGGTVTIKCQASQSISSWLAWYQQKPGQPPKLLI YLASTLASGVSSRFKGSGSGTQFTLTISGVECADAATYYCQQGYTNSN IINTFGGGTEVVVKRTVAAPSVFIFPPSDEQLKSGTASVVCLLNNFYP |

TABLE 1-continued

| Name | SEQ ID NO: | SEQUENCE |
|---|---|---|
| (hCK S171C) 10236 | | REAKVQWKVDNALQSGNSQESVTEQDSKDCTYSLSSTLTLSKADYEKH KVYACEVTHQGLSSPVTKSFNRGEc |
| Rabbit/human chimeric heavy chain 10236 | 172 | QSVEESGGRLVTPGTPLTLTCTVSGFPLSNYAMSWVRQAPGKGLEWIG DIYPSDIIDYASWAKGRFTISQTSTTVELKITGPTTEDTATYFCARDN NDYGLDIWGPGTLVTVSSASTKGPSVFPLAPCSRSTSESTAALGCLVK DYFPEPVTVSWNSGALTSGVHTFPAVLQSSGLYSLSSVVTVPSSSLGT KTYTCNVDHKPSNTKVDKRVESKYGPPCPPCPAPEFLGGPSVFLFPPK PKDTLMISRTPEVTCVVVDVSQEDPEVQFNWYVDGVEVHNAKTKPREE QFNSTYRWSVLTVLHQDWLNGKEYKCKVSNKGLPSSIEKTISKAKGQ PREPQVYTLPPSQEEMTKNQVSLTCLVKGFYPSDIAVEWESNGQPENN YKTTPPVLDSDGSFFLYSRLTVDKSRWQEGNVFSCSVMHEALHNHYTQ KSLSLSLGK |
| LEKTI D5 Fc TEV | 173 | EIVKLCSQYQNQAKNGILFCTRENDPIRGPDGKMHGNLCSMCQAYFQA ENEEKKKAEARARNLEENLYFQGVDKKVEPKSCDKTHTCPPCPAPELL GGPSVFLFPPKPKDTLMISRTPEVTCVVVDVSHEDPEVKFNWYVDGVE VHNAKTKPREEQYNSTYRVVSVLTVLHQDWLNGKEYKCKVSNKALPAP IEKTISKAKGQPREPQVYTLPPSRDELTKNQVSLTCLVKGFYPSDIAV EWESNGQPENNYKTTPPVLDSDGSFFLYSKLTVDKSRWQQGNVFSCSV MHEALHNHYTQKSLSLSPGK |
| LEKTI D8 Fc TEV | 174 | EAAKEICSEFRDQVRNGTLICTREHNPVRGPDGKMHGNKCAMCASVFK LEEEEKKNDKEEKGKVEAEKVLEENLYFQGVDKKVEPKSCDKTHTCPP CPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVS NKALPAPIEKTISKAKGQPREPQVYTLPPSRDELTKNQVSLTCLVKGF YPSDIAVEWESNGQPENNYKTTPPVLDSDGSFFLYSKLTVDKSRWQQG NVFSCSVMHEALHNHYTQKSLSLSPGK |
| 10236 CDR-L1 | 175 | QASQSISSWLA |
| 10236 CDR-L2 | 176 | LASTLAS |
| 10236 CDR-L3 | 177 | QQGYTNSNIINT |
| 10236 CDR-H1 | 178 | GFPLSNYAMS |
| 10236 CDR-H2 | 179 | DIYPSDIIDYASWAKG |
| 10236 CDR-H3 | 180 | DNNDYGLDI |
| 10236 Rabbit VL | 181 | AYDMTQTPASVEVAVGGTVTIKCQASQSISSWLAWYQQKPGQPPKLLI YLASTLASGVSSRFKGSGSGTQFTLTISGVECADAATYYCQQGYTNSN IINTFGGGTEVVVK |
| 10236 Rabbit VL nucl. | 182 | gcctatgatatgacccagactccagcctctgtggaggtagctgtggga ggcacagtcaccatcaagtgccaggccagtcagagcattagcagttgg ttagcctggtatcagcagaaaccaggtcagcctcccaagctcctgatc tatctggcatccactctggcatctggggtctcatcgcggttcaaaggc agtggatctgggacacagttcactctcaccatcagcggcgtggagtgt gccgatgctgccacttactactgtcaacagggttatactaatagtaat attattaatactttcggcggagggaccgaggtggtggtcaaacgtacg |
| 10236 Rabbit VH | 183 | QSVEESGGRLVTPGTPLTLTCTVSGFPLSNYAMSWVRQAPGKGLEWIG DIYPSDIIDYASWAKGRFTISQTSTTVELKITGPTTEDTATYFCARDN NDYGLDIWGPGTLVTVSS |
| 10236 Rabbit VH nucl. | 184 | cagtcggtggaggagtccgggggtcgcctggtcacgcctgggacaccc ctgacactcacctgcaccgtctctgggttcccctcagtaattatgca atgagctgggtccgccaggctccagggaaggggctggaatggatcgga gacatttatcctagtgatatcatagactacgcgagctgggcgaaaggc cgattcaccatctcccaaacctcgaccacggtggagctgaaaatcacg ggtccgacaaccgaggacacggccacctatttctgtgccagagacaac aatgactatggtctggacatctggggcccaggcaccctggtcaccgtc tcgagt |
| Mouse KLK7 pro-form | 185 | QGERIIDGYKCKEGSHPWQVALLKGNQLHCGGVLVDKYWVLTAAHCKM GQYQVQLGSDKIGDQSAQKIKATKSFRHPGYSTKTHVNDIMLVRLDEP VKMSSKVEAVQLPEHCEPPGTSCTVSGWGTTTSPDVTFPSDLMCSDVK |

TABLE 1-continued

| Name | SEQ ID NO: | SEQUENCE |
|---|---|---|
| | | LISSRECKKVYKDLLGKTMLCAGIPDSKTNTCNGDSGGPLVCNDTLQG<br>LVSWGTYPCGQPNDPGVYTQVCKYKRWVMETMKTHR |
| Active Mouse KLK7 | 186 | IIDGYKCKEGSHPWQVALLKGNQLHCGGVLVDKYWVLTAAHCKMGQYQ<br>VQLGSDKIGDQSAQKIKATKSFRHPGYSTKTHVNDIMLVRLDEPVKMS<br>SKVEAVQLPEHCEPPGTSCTVSGWGTTTSPDVTFPSDLMCSDVKLISS<br>RECKKVYKDLLGKTMLCAGIPDSKTNTCNGDSGGPLVCNDTLQGLVSW<br>GTYPCGQPNDPGVYTQVCKYKRWVMETMKTHR |

The invention will now be further described by way of examples with references to embodiments illustrated in the accompanying drawings.

EXAMPLES

Example 1: Cloning, Expression and Purification of Kallikrein Proteins and LEKTI Domains An optimized nucleotide sequence encoding a protein according to SEQ ID NO: 142, was cloned into an in-house mammalian expression vector using HindIII/EcoRI sites, generating a vector encoding the human KLK5 protein with no tags.

The mouse and cynomolgus monkey (cyno) KLK5 sequences were similarly cloned to enable generation of the active forms of these proteins comprising SEQ ID NO: 150 and 151, respectively.

Domain 5 (D5) and Domain 8 (D8) of human LEKTI (Uniprot Q9NQ38) comprising residues 292-353 and 490-558 respectively (according to the numbering in Uniprot), were cloned and expressed for use as reference proteins in in vitro assays.

The human LEKTI Domain 5 and Domain 8 nucleotide sequences, both optimized for expression in mammalian cells, were separately cloned into an in-house mammalian expression vector encoding a rabbit Fc tag, using HindIII/XhoI sites, generating vectors encoding either the LEKTI domain 5 sequence with a C-terminal Rabbit Fc tag (SEQ ID NO: 145) or the LEKTI domain 8 sequence with a C-terminal rabbit Fc tag (SEQ ID NO: 152). The encoded proteins will be referred to as LEKTI D5 rabbit Fc and LEKTI D8 rabbit Fc, respectively The KLK5, LEKTI Domain 5 and LEKTI Domain 8 rabbit Fc fusion proteins were expressed by transient transfection using the Expi293™ Expression System (Life Technologies™) following the manufacturer's protocol. During expression, KLK5 auto-activates to yield active KLK5 (comprising SEQ ID NO: 144 or residues I67-S293 of SEQ ID NO: 142) in the supernatant. Cells were harvested 5 days post transfection and supernatants used immediately for purification. Supernatants comprising human (or mouse or cyno) active KLK5 were diluted 4-fold with Buffer A (50 mM Tris pH 7.0, 50 mM NaCl) and loaded onto a HiTrap SP HP cation exchange column. Bound proteins were eluted with a salt gradient generated over a total of 10 column volumes using Buffer A (50 mM Tris pH 7.0, 50 mM NaCl) and Buffer B (50 mM Tris pH 7.0, 1M NaCl). Fractions containing purified human (or mouse or cyno) active KLK5 were pooled, concentrated and purified further by size exclusion chromatography on an S200 26/60 column which had been equilibrated with 20 mM Tris, 150 mM NaCl, 5% glycerol at pH 7.2. SDS-PAGE analysis indicated that the proteins underwent glycosylation during expression. Analysis by mass spectrometry resulted in the expected molecular weight.

Supernatants comprising human LEKTI D5 rabbit Fc fusion protein (according to SEQ ID NO: 145) were first subject to Protein A affinity chromatography. The supernatants were loaded onto a 5 ml HITRAP™ Protein A column. Bound proteins were eluted with 1M citric acid buffer, pH 2.0 and fractions neutralized with 2M Tris-HCl pH 8.5. Fractions containing LEKTI D5 rabbit Fc fusion protein were pooled, concentrated and further purified by size exclusion chromatography using a S200 26/60 column that had been equilibrated with PBS. Fractions containing human LEKTI D5 rabbit Fc fusion protein were then pooled and concentrated. LEKTI D8 rabbit Fc fusion protein (according to SEQ ID NO: 152) was similarly purified from transfected cell culture supernatants.

A LEKTI D5 Fab fusion molecule (according to SEQ ID NO: 169 and 170) was expressed and purified by cation exchange chromatography. The LEKTI Domain 5 nucleotide sequence, flanked at the 5' and 3' termini by sequences encoding Gly4Ser linkers, was integrated into framework 3 of a heavy chain sequence of a Fab specific for albumin (as described in WO2020011868 which is incorporated herein by reference); a tag encoding a 10× His sequence was also placed at the 3' end of the Fab H chain. The LEKTI D5 Fab fusion heavy chain was optimized for expression in mammalian cells, cloned into an in-house expression vector and co-transfected with the appropriate light chain, also optimized for mammalian expression, in CHO SXE cells. Transfected-cells were cultured in a vented flask at 32° C. for 13 days. Supernatant was harvested, concentrated and buffer exchanged into 20 mM Tris, 50 mM NaCl, pH7.0 before being loaded onto a SP Sepharose HP column. Bound proteins were eluted with a salt gradient generated over a total of 10 column volumes using Buffer A (20 mM Tris pH 7.0, 50 mM NaCl) and Buffer B (20 mM Tris pH 7.0, 1M NaCl): Fractions containing LEKTI D5 Fab fusion were pooled and further purified by size exclusion chromatography using an S200 column equilibrated with PBS pH 7.4. Relevant fractions were pooled.

The human and cyno nucleotide sequences encoding full-length KLK7 were expressed in a similar manner to human KLK5, generating pro-KLK7 (comprising SEQ ID NO: 146 and 148, respectively). Unlike KLK5, KLK7 does not auto-activate during expression and so the active forms of human, mouse and cyno KLK7 (comprising SEQ ID NO: 147, 186 and 149, respectively) were generated by using thermolysin to cleave the pro-peptide sequence from the purified proteins. Human, mouse or cyno pro-KLK7 (comprising SEQ ID NO:146, 185 and 148, respectively) was diluted to 1 mg/ml in activation buffer (50 mM Tris pH 7.5, 10 mM CaCl2, 150 mM NaCl, 0.05% Brij 35). Thermolysin (25 mg) from SIGMA® was resuspended in 25 ml digestion buffer (50 mM Tris pH 8.0, 0.5 mM $CaCl_2$)), added at a ratio of 1:10 to the respective KLK7 proteins for 45 minutes at 37° C. before mixing with anion exchange DEAE resin (GE LIFE SCIENCES™) to bind and remove the thermolysin. The flow-through was collected as active (human, mouse or cyno) KLK7.

The active forms of human, mouse and cyno KLK7 were buffer exchanged into 50 mM Tris pH7.5, 150 mM NaCl, 5% glycerol, 1 mM EDTA and concentrated to circa 3.2 mg/ml.

Human KLK2 was sourced from R&D SYSTEMS™ (Catalog #4104-SE-010) as active protein.

Human KLK4 was sourced from R&D SYSTEMS™ (Catalog #1719-SE) as pro-form and activated as follows. Human pro-KLK4 was diluted to 200 μg/mL in 50 mM Tris, 10 mM $CaCl_2$), 150 mM NaCl, pH 7.5 and bacterial thermolysin sourced from R&D SYSTEMS™ (Catalog #3097-ZN) diluted in the same buffer to 2 μg/mL. Equal volumes of pro-human KLK4 and thermolysin were combined and incubated at room temperature for 10 minutes to allow activation. The reaction was stopped with EDTA to a final concentration of 10 mM.

Example 2: Generation of Antibodies by Immunization with KLK5

Female New Zealand White rabbits (>2 kg) received sub-cutaneous immunization with 100 μg of 0.4 mg/ml of human active KLK5 and human active KLK7 (expressed according to Example 1) mixed with an equal volume of complete Freund's adjuvant (Sigma®). Animals received boost injections at intervals of 21 days comprising of 100 μg of the same immunogen mixed in an equal volume of incomplete Freund's adjuvant (Sigma®). Termination occurred 14 days after the final boost when single cell suspensions of spleen, bone marrow, and peripheral blood mononuclear cells (PBMCs) were prepared and frozen in 10% dimethyl sulfoxide (DMSO) in fetal calf serum (FCS) at −80° C.

B cell cultures were prepared using a method similar to that described by Tickle et al., 2015 J Biomol Screen: 20 (4), 492-497. Briefly, lymph node cells, splenocytes, or peripheral blood mononuclear cells (PBMC) from immunized animals were cultured at a density of 2000 cells per well in barcoded 96-well tissue culture plates with 200 μl/well RPMI 1640 medium (GIBCO™) supplemented with 10% FCS (SIGMA-ALDRICH®), 2% HEPES solution (SIGMA-ALDRICH®), 2% L-Glutamine solution-(GIBCO™), 1% penicillin/streptomycin solution (GIBCO™), 0.2% Normocin (INVIVOGEN™), 0.1% β-mercaptoethanol (GIBCO™), and using a feeder cell expressing CD40L and IL-2 in the presence or absence of B-cell stimulating supernatant (BSS). BSS is generated by culturing PBMC in the presence of the mitogenic agents Phorbol-12-myristate-13-acetate (PMA) and Phytohemagglutinin-L (PHA-L) for 6 days before harvesting the supernatant. Plates were incubated six days at 37° C. and 5% $CO_2$. Cultures were set up using B cells from all immunized animals, and in total, approximately $1\times10^9$ B cells were screened.

After six days, supernatants were screened for binding to human KLK5 (produced as in example 1) by a multiplex homogeneous fluorescence-based binding assay using Sol-R2 streptavidin beads (TTP LABTECH™) coated with biotinylated human KLK5 as a source of target antigen and Sol-R4 streptavidin beads (TTP LABTECH™) coated with the related KLK7 for counter-screening. Lightning-Link Rapid Biotin Type B (EXPEDEON™) was used to biotinylate proteins using a 5-fold molar excess of protein compared to the provider's protocol to avoid complete modifications of all lysine residues. A total of 10 μL of supernatant from the barcoded 96-well tissue culture plates were transferred using an Agilent Bravo liquid handler into barcoded 384-well black-walled assay plates containing biotinylated KLK coated Sol-R beads as above and a FITC conjugated goat anti-rabbit Fc fragment specific (JACKSON IMMUNORESEARCH™). After 1 h incubation plates were read on a mirror-ball instrument (TTP-LABTECH™).

Following primary screening, supernatants positive for binding to KLK5 were consolidated on 96-well bar-coded master plates using a BECKMAN COULTER BIOMEKNXP™ hit-picking robot and B cells in cell culture plates were frozen at −80° C. First, consolidated supernatants were re-screened to confirm binding to human KLK5 by Fluorescence microvolume assay technology (FMAT). Briefly 10 μL of supernatant were transferred to barcoded black Greiner plates. 50 μL/plate of 10 μm superavidin (BANGS BEADS™) were coated with human biotinylated KLK5, mixed with ALEXA-647™ goat anti-rabbit IgG Fc fragment specific (JACKSON IMMUNORESEARCH™). The supernatant was then added and the plates read on an APPLIED BIOSYSTEMS™ Cellular Detection System 8200.

A number of antibodies were identified as binding to KLK5 and were subsequently investigated for their ability to specifically inhibit KLK5 and their specificity for KLK5 over other kallikreins.

Example 3: Identification of KLK5 Inhibitory Antibodies

To identify antibodies capable of inhibiting specifically KLK5 activity among the proteases and protease inhibitors present in the complex B cell supernatant, a screening assay was developed. Nunc Maxisorp black 384 (SIGMA-ALDRICH®) were coated with $F(ab')_2$ Fragment Goat Anti-Rabbit IgG Fc Fragment Specific (JACKSON IMMUNORESEARCH™) at 10 μg/mL in carbonate buffer and left overnight at 4° C. Plates were washed. 3 times on a BIOTEK™ plate washer with PBS/0.1% TWEEN®-20, and blocked with 20 μL/well PBS/1% BSA for 1 h at room temperature. B cell supernatants were then added to the plates, with 25 μL of 1 nM LEKTI D5 rabbit Fc fusion protein added to control wells as a positive control for inhibition and assay buffer A (50 mM Tris, 150 mM NaCl, 0.05% (v/v) TWEEN®-20, pH 7.6) added to a separate set of control wells as a negative control for inhibition. The plates were incubated overnight at room temperature and then washed three times on a BIOTEK™ plate washer with PBS/0.1% TWEEN®-20. 10 μL of 250 μM human KLK5 in assay buffer A were added to each well and the plates incubated overnight at room temperature to allow full association. Boc-VPR-AMC substrate (CAMBRIDGE RESEARCH BIOCHEMICALS™) in assay buffer A was added to the wells to a final concentration of 600 μM and the fluorescence ($\lambda_{ex}$380 nm $\lambda_{em}$430 nm) determined after 4 hours using a PHERASTAR® FSX (BMG LABTECH™) plate reader.

Data were analyzed to determine the percentage inhibition of KLK5 activity using the following equation:

$$\%\ \text{Inhibition} = 100 \cdot \left(1 - \frac{\text{Test} - \text{Positive}}{\text{Negative} - \text{Positive}}\right)$$

Where Test is the fluorescence value for a test antibody, Positive is the average of the fluorescence values of the positive control for inhibition wells and Negative is the average fluorescence values of the negative control for inhibition wells.

Supernatants that showed >40% inhibition were considered hits. This amounted to about 4% of all of the screened supernatants. These antibodies were selected for variable region recovery.

In order to identify the specific antibody secreting cells to allow recovery of antibody variable region genes from an heterogenous population of activated B cells, a deconvolution step had to be performed. The fluorescent foci method (Clargo et al., 2014) was used. Briefly, antibody secreting cells were statically incubated at 37° C. for 1 hour in the presence of streptavidin beads (NEW ENGLAND BIOLABS™) coated with biotinylated human KLK5 and a goat anti-rabbit Fc fragment-specific FITC conjugate (JACKSON IMMUNORESEARCH™). Antigen-specific antibody secreting cells were then identified from the fluorescent halo surrounding them. A number of these individual B cell clones, identified using an Olympus microscope, were then picked with an EPPENDORF® micromanipulator and deposited into a PCR tube. cDNA from the single cells was obtained by standard RT-PCR and subsequent PCR of the variable immunoglobulin sequences for the heavy and light chains were performed using immunoglobulin gene specific primers, followed by a nested PCR incorporating overlapping vector sites allowing for direct cloning of the variable region into a rabbit IgG (VH) or rabbit kappa (VL) mammalian expression vector. Heavy and light chain constructs were co-transfected into ExpiHEK-293 cells using EXPIFECTAMINE™ (LIFE TECHNOLOGIES™) and recombinant antibody expressed in 125 ml ERLENMEYER™ flask in a volume of 30 ml. After 5-7 days of culture, supernatants were harvested, and antibodies purified by Protein A affinity capture using the AKTA pure chromatography system. 1 ml Protein A HiTrap MabSelect SuRe column (GE HEALTHCARE®) was attached to the system and the column equilibrated in PBS pH 7.4 before applying cell culture supernatant to the column at a flow rate of 0.25 ml/min. The column was then washed with PBS pH 7.4, bound material eluted with sodium citrate pH 3.4 and neutralised with an appropriate volume of 2M Tris-HCL-pH-8.5. The eluted fractions were buffer exchanged into PBS (SIGMA®), pH7.4 and passed through a 0.22 μm filter. Final purified material was assayed by A280 scan, SE-UPLC (BEH200 method), and for endotoxin using the PTS Endosafe system.

From this analysis, rabbit antibodies 10236 and 10273 showed potent inhibition and were selected for further characterization.

Example 4: Identification of KLK5 Specific Inhibitory Antibodies

Purified rabbit antibodies 10236 and 10273 were then screened to confirm their inhibitory activity against KLK5 and determine specificity for KLK5 by using a panel of human sequence kallikrein family members including KLK2, KLK4 and KLK7 together with murine and cyno KLK5 and KLK7. A 10-point half log dilution series with a range of 600 nM to 20 μM was prepared for each antibody and 5 μL transferred to black 384 well assay plates (CORNING®, cat n.3575) using a BECKMAN COULTER FX™ and a Multidrop System. 15 μL of the active recombinant kallikrein protein were added to the relevant wells to achieve the following final assay concentrations: 60 μM Hu KLK5, 250 pM Hu KLK7, 500 pM Hu KLK2, 30 pM Hu KLK4, 30 pM cyno KLK5, 500 pM cyno KLK7 30 pM mouse KLK5 or 10 nM mouse KLK7, in assay buffer A (50 mM Tris, 150 mM NaCl, 200 μM EDTA, 0.05% (v/v) TWEEN®-20, pH 7.6). As controls, 20 μL assay buffer A was added to wells for 0% activity, as a positive control for inhibition, LEKTI D5 rabbit Fc was used at the same antibody concentration range and 15 μl of human KLK5 in 5 μL assay buffer A was used for 100% activity. Plates were incubated at room temperature overnight before addition of the following peptide substrates using a multidrop device: Boc-VPR-AMC (CAMBRIDGE RESEARCH BIOCHEMICALS™) for human KLK5 (300 μM), human KLK2 (30 μM), murine KLK5 (300 M) and cyno KLK5 (450 μM); KHLF-AMC (CAMBRIDGE RESEARCH BIOCHEMICALS™) for human and cyno KLK7 (90 UM and 150 UM, respectively), PFR-AMC (R&D SYSTEMS™) for human KLK4 (200 μM), and Mca-RPKPVE-Nval-WRK (Dnp)-NH2 (R&D SYSTEMS™) for murine KLK7 (150 μM). Samples were incubated for 4 hours and read on a PHERASTAR® FSX Plate Reader (BMG LABTECH™) at $\lambda_{ex}$380 nm and $\lambda_{em}$430 nm for Boc-VPR-AMC, PFR-AMC and KHLF-AMC; and at $\lambda_{ex}$320 nm and Aem400 nm for Mca-RPKPVE-Nval-WRK (Dnp)-NH2. Data were analysed to determine percentage inhibition as described in Example 3. Data were plotted against concentration of test antibody and a 4-parameter sigmoid fitted to determine $IC_{50}$ (GENEDATA SCREENER™).

In addition to rabbit antibody 10236, for this measurement, the polynucleotide sequences of rabbit variable regions of antibodies 10236 and 10273 were cloned on a modified version of the mouse C Kappa vector comprising the S171C mutation, to re-create the additional disulphide bond found in rabbit VK light chains not present in the mouse constant regions (SEQ ID NO: 155 and 156 for rabbit antibody 10273 mIgG and SEQ ID NO: 159 and 160 for rabbit antibody 10236 mIgG). This resulted in antibodies comprising SEQ ID NO: 157 and 158 for rabbit antibody 10236 mIgG and SEQ ID NO: 153 and 154 for rabbit antibody 10273 mIgG.

Rabbit antibodies 10236 and 10273 mIgGs showed potent inhibition of human KLK5 with no activity (i.e. below the 40% threshold as per selection criteria in example 2) against the other human family members tested (human KLK2, 4 and 7). Potent inhibition of cyno KLK5 but not cyno KLK7 was also demonstrated. No inhibitory activity was evident against either mouse KLK5 or KLK7. $IC_{50}$ results for rabbit antibody 10236, 10273 and LEKTI D5 rabbit Fc are shown in Table 2.

TABLE 2

| Antibody | Hu KLK5 | Hu KLK2 | Hu KLK4 | Hu KLK7 | Cy KLK5 | Cy KLK7 | Mu KLK5 | Mu KLK7 |
|---|---|---|---|---|---|---|---|---|
| | IC50 (M) | | | | | | | |
| 10236 mIgG | 2.40E−10 | NI | NI | NI | 3.30E−11 | NI | NI | NI |
| Rabbit 10236 IgG | 1.74E−10 | NI | NI | NI | 2.76E−11 | NI | NI | NI |

TABLE 2-continued

| Antibody | Hu KLK5 | Hu KLK2 | Hu KLK4 | Hu KLK7 | Cy KLK5 | Cy KLK7 | Mu KLK5 | Mu KLK7 |
|---|---|---|---|---|---|---|---|---|
| | IC50 (M) | | | | | | | |
| 10273 mIgG | 3.48E−11 | NI | NI | NI | 3.01E−10 | NI | NI | NI |
| LEKTI D5 Fc | 1.03E−10 | n/a | n/a | n/a | n/a | n/a | n/a | n/a |

NI = No Inhibition;
Hu = human;
Cy = cyno;
Mu = mouse;
n/a = not available

Example 5: Determination of Affinity of KLK5 Specific Abs

The kinetics of murine IgG molecules binding to human KLK5 were assessed by surface plasmon resonance (BIACORE™ T200) at 25° C.

A goat anti-mouse IgG Fc specific antibody (JACKSON IMMUNORESEARCH™) was immobilised on a CM5 Sensor Chip via amine coupling chemistry to a level of approximately 7000RU. Each analysis cycle consisted of capture of the anti-KLK5 IgG molecules to the anti Fc surface, injection of KLK5 analyte (prepared in house) for 300 s at 30 μl/min followed by 600 s dissociation. At the end of each cycle the surface was regenerated at a flowrate of 10 μL/min using a 60 s injection of 50 mM HCl followed by a 30 s injection of 5 mM NaOH and a final 60 s injection of 50 mM HCl. Human KLK5 was titrated from 20 nM to 0.25 nM (4×3-fold serial dilutions) in HBS-EP+ running buffer (GE HEALTHCARE®) supplemented with NaCl to a final concentration of 300 mM. Buffer blank injections were included to subtract instrument noise and drift.

Kinetic parameters were determined using a 1:1 binding model using BIACORE™ T200 Evaluation software.

The affinities of rabbit antibodies 10236 and 10273 are shown in Table 3.

TABLE 3

| Rabbit/mouse antibodies | ka (Ms^−1) | kd (s^−1) | KD (pM) |
|---|---|---|---|
| 10236 | 3.00E+06 | 5.17E−04 | 172.3 |
| 10273 | 1.14E+06 | 1.84E−04 | 160.0 |

Example 6: Characterization of Antibody 10273

KLK5-PAR2 Cellular Assay of Rabbit Antibody 10273

KLK5 has been shown to activate protease activated receptor-2 (PAR2) receptors at the surface of keratinocytes (K. Oikonomopoulou et al. Kallikrein-mediated cell signalling: targeting proteinase-activated receptors (PARs). Biol Chem, 387 (2006), pp. 817-824). This results in an NFkB-driven inflammatory cascade and the release of relevant cytokines such as TSLP.

As PAR2 is a Gq-coupled G-protein coupled receptor (GPCR), activation leads to phospholipase signaling and generation of inositol monophosphate (IP-1). Activation of endogenous PAR2 expressed on HaCat keratinocytes by exposure to recombinant KLK5, was monitored by detection of IP1 using an assay kit from Cisbio.

Confluent HaCat cells were harvested and plated in a 384 Fluoblock plate (CORNING®) at 10,000 cells/well and cultured in DMEM Medium+10% FBS+2 mM L-glutamine+Pen/Strep (LIFE TECHNOLOGIES™) at 37° C., 5% $CO_2$ overnight, after which they were treated according to the IP-One Gq Assay protocol (CISBIO™). Antibodies to be tested were serially diluted in 1× Stimulation Buffer B (IP-One Gq Assay kit, CISBIO™) from a top concentration of 2 μM and incubated for 1 h at 37° C. in the presence of 200 nM human recombinant KLK5. The antibody/KLK5 mix was added to HaCat cells and inositol 1 phosphate (IP1) was detected following the IP-One Gq assay protocol with fluorescence read at 665 nM and 620 nM on a Synergy Neo plate reader.

Antibody 10273 was able to almost completely inhibit IP1 release from KLK5 treated HaCat cells (FIG. 1), showing similar maximum inhibition of IP1 release but exhibiting greater potency compared to the LEKTI protein.

Mechanism of Action of Antibody 10273

Non-competitive enzyme inhibitors reduce the activity of an enzyme but are able to bind the enzyme equally well in the presence or absence of substrate. Inhibitor and substrate are both able to bind the enzyme concurrently, but cleaved product cannot be formed, resulting in the enzyme-substrate-inhibitor complex only being able to resolve into either enzyme-substrate or enzyme-inhibitor complexes. With non-competitive inhibitors, the rate of inhibition will be unaffected by increasing substrate concentration.

Antibody 10273 or LEKTI-D5 Fc protein were prepared in assay buffer (150 mM NaCl, 50 mM Tris, 200 UM EDTA, 0.05% (v/v) TWEEN®-20, pH 7.6) at either 300, 30 or 3 times the $IC_{50}$ for KLK5 (see above). 10 μL of the antibodies were added to a CORNING® low binding black low flange 384 well assay plate (CORNING®). 10 UL of a 5-point serial dilution of 30 mM-300 UM Boc-VPR-AMC (CAMBRIDGE RESEARCH BIOCHEMICALS™) was added to the plate. A PHERASTAR® FSX plate reader (BMG LABTECH™) was used to simultaneously start the reaction, via injection of 10 UL of either 1.8 nM KLK5 (Boc-VPR-AMC <1 mM) or 180 μM KLK5 (Boc-VPR-AMC >1 mM) and monitor fluorescence ($\lambda_{ex}$380 nm $\lambda_{em}$430 nm) every 30 seconds. The final reaction conditions contained antibody 10273 or LEKTI-D5 Fc protein at either 100, 10 or 1 times the $IC_{50}$ for KLK5 determined (as described above), a serial dilution of Boc-VPR-AMC between 10 mM and 100 UM and either 60 or 600 μM KLK5. Negative controls were prepared by replacing the antibody or KLK5 with assay buffer.

Data were analysed by subtracting the background fluorescence at each time point and plotting the fluorescence against time. Data were fit to the following equation (GraphPad-Prism®, GraphPad Software):

$$y = v_s \cdot x + \left(\frac{v_i - v_s}{k_{obs}} \cdot \left(1 - e^{-k_{obs} \cdot x}\right)\right)$$

This enabled $K_{obs}$ to be determined, the observed rate of time dependent inhibition, where vi is the initial reaction velocity and vs is the final velocity. Values for $K_{obs}$ were plotted against substrate concentration to determine the mechanism of inhibition (FIG. 2).

The rate of inhibition of KLK5 by antibody 10273 was unchanged with increasing substrate concentration demonstrating that antibody 10273 is a non-competitive inhibitor of KLK5 (FIG. 2A). The LEKTI-D5 Fc protein shows a decrease in the rate of inhibition with increasing substrate concentration demonstrating a competitive mechanism of action (FIG. 2B).

LEKTI Binding to KLK5 in the Presence of Antibody 10273

Surface plasmon resonance (SPR) experiments were carried out to determine whether antibody 10273 competed with the LEKTI D5 protein for binding to human KLK5. These assays enabled comparison of the affinity of LEKTI D5 Fab fusion for KLK5 protein alone to human KLK5 complexed with antibody 10273.

Kinetic measurements for the binding of LEKTI D5Fab fusion protein to human KLK5 were obtained using a BIACORE™ T200 (GE LIFE SCIENCES™). To prepare the surface, CM5 chips (GE LIFE SCIENCES™) were first activated with a 5-minute injection (30 μL min-1) of a mixture of EDC/NHS (GE LIFE SCIENCES™) followed by injection of 100 μg mL-1 LEKTI D5 Fab fusion (UCB) in acetate buffer, pH 5.0 (GE LIFE SCIENCES™) to achieve 80 RU immobilised LEKTI D5 Fab fusion on the chip surface. Finally, an injection of 1 M Ethanolamine hydrochloride-NaOH pH 8.5 was utilised to deactivate the surface. Increasing concentrations of human KLK5 from 0.32 to 32 nM in HBS-EP buffer (GE LIFE SCIENCES™) were then injected in the single cycle kinetics mode. Values resulting from buffer only injections were subtracted from those obtained for the KLK5 injections and kinetics determined by fitting to a 1:1 binding model in BIACORE™ evaluation software (GE LIFE SCIENCES™).

To determine whether human LEKTI was capable of binding human KLK5 when human KLK5 was bound by rabbit antibody 10273, antibody capture surfaces were prepared using a Goat anti-Rabbit Fc polyclonal and Ab 10273 captured as described in Example 4. 20 nM of human KLK5 was then injected until the surface reached saturation. LEKTI D5 Fab fusion protein (generated as described in example 1) was then injected at concentrations between 30 μM and 100 nM. Values from buffer only injections were first subtracted from those obtained with the analytes before fitting to a 1:1 binding kinetic model in BIACORE™ evaluation software (GE LIFE SCIENCES™).

As reference, LEKTI D5 Fab fusion protein was immobilised to the chip surface prior to monitoring the interaction with human KLK5. Human LEKTI D5 Fab fusion protein was able to bind to human KLK5 with an affinity of 19.7 nM when human KLK5 was already in complex with rabbit antibody 10273 (Table 4). Whilst the affinity of human LEKTI to human KLK5 in the absence of rabbit antibody 10273 is higher (40 μM), this analysis demonstrates that, by binding human KLK5 in the presence or absence of human LEKTI, rabbit antibody 10273 may provide additional inhibitory activity to human KLK5.

TABLE 4

| | ka (Ms^−1) | kd (s^−1) | KD (M) |
|---|---|---|---|
| Human KLK5 only | 5.70E+05 | 2.30E−05 | 4.00E−11 |
| 10273 + Human KLK5 | 2.87E+04 | 5.65E−04 | 1.34E−08* |

*average value n = 2

LEKTI-KLK5-Antibody 10273 Complex Formation

KLK5 was produced in HEK293 cells as a secreted protein with a N-terminal, TEV-cleavable 8×His-tag. The protein was first purified from conditioned media by $Ni^{2+}$ affinity chromatography. Fractions from the $Ni^{2+}$ column containing KLK5 were pooled and digested with TEV protease to remove the His tag then a second Ni affinity step was performed to remove the TEV protease, letting the cleaved KLK5 flow through the column. The flow through fraction from the second $Ni^{2+}$ column was concentrated and run on a size exclusion column in 50 mM Tris pH 7, 50 mM NaCl, 1 mM EDTA, 5% glycerol. KLK5 fractions from the SEC were pooled and concentrated to approximately 10 mg/ml and stored at −80° C.

LEKTI domain 5 (LEKTI D5 Fc TEV) according to SEQ ID NO: 173 and LEKTI domain 8 (LEKTI D8 Fc TEV) according to SEQ ID NO: 174 were produced in HEK293 cells as secreted proteins with a C-terminal, TEV-cleavable Fc tag. These proteins were purified by passing conditioned media over Protein A beads. Bound protein was eluted with 0.1M Citric acid, pH2.0 and fractions neutralized by the addition of 2M Tris-HCl, pH 8.5. Fractions from the Protein A column containing either LEKTI domain 5 or domain 8 were pooled and the Fc tag removed with TEV protease to give LEKTI D5 or LEKTI D8. The cleaved protein was concentrated to ~15 mg/ml for size exclusion chromatography. SEC was carried out in PBS, pH 7.2. LEKTI containing fractions were pooled and concentrated to ~10 mg/ml and stored frozen at −80° C.

Rabbit Fab antibody 10273 was expressed in HEK293 cells as a secreted protein. Expression constructs comprising SEQ ID NO: 166 and 168 were co-transfected at a 1:1 molar ratio. The secreted Fab (comprising SEQ ID NO: 165 and 167) was purified by passing conditioned media over Protein G beads and eluted with 0.1M glycine, pH 2.7. Fractions were neutralized by the addition of 2M Tris-HCl, pH8.5. The protein was dialyzed into PBS, pH 7.2 then concentrated to ~10 mg/ml and stored frozen at −80° C.

Figure 3:
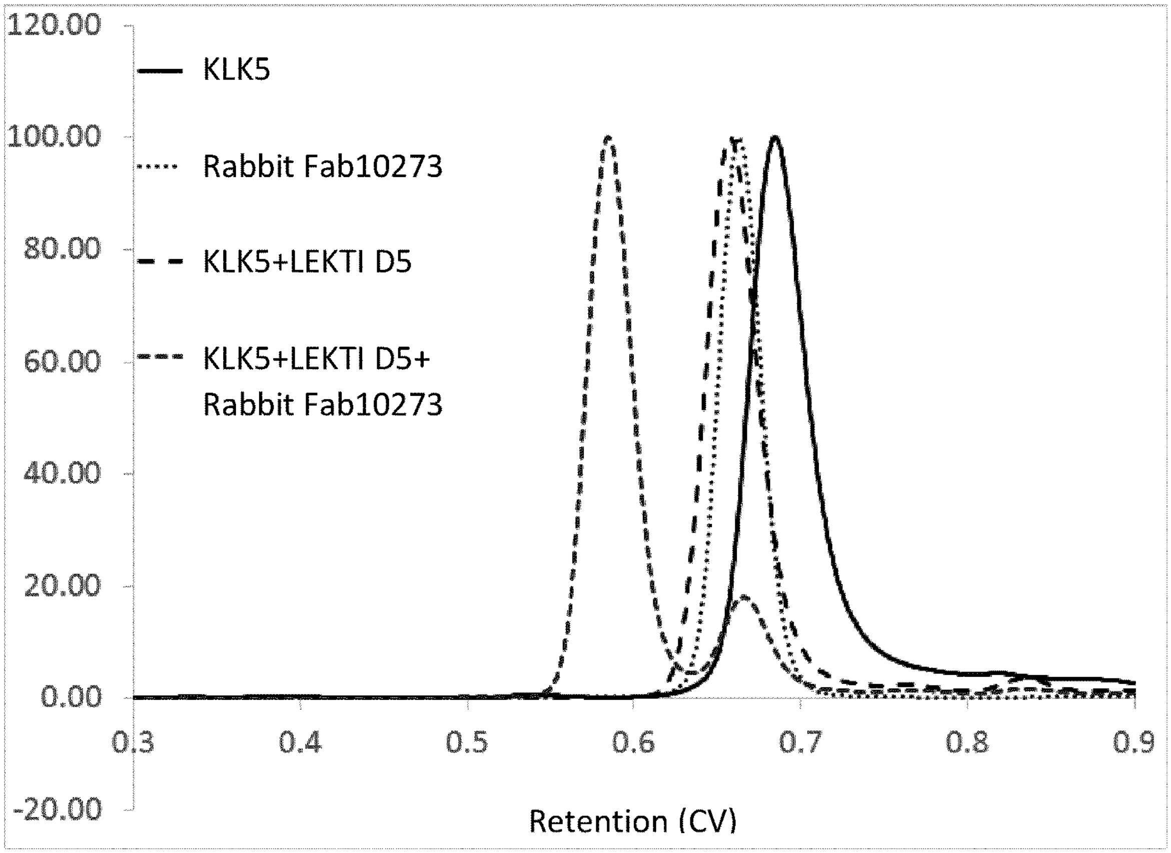
FIG. 3. Size exclusion chromatography panels A and B show the elution profiles of human KLK5 alone (solid trace), rabbit Fab antibody 10273 alone (dotted trace), human KLK5+LEKTI-D5 Fc (long dashed trace; panel A) or human KLK5+LEKTI D8 Fc (long dashed trace; panel B) and human KLK5+LEKTI D5 Fc+rabbit Fab antibody 10273 (short dashed trace, panel A) or human KLK5+LEKTI D8 Fc+rabbit Fab antibody 10273 (short dashed trace, panel B).
Figure 3:
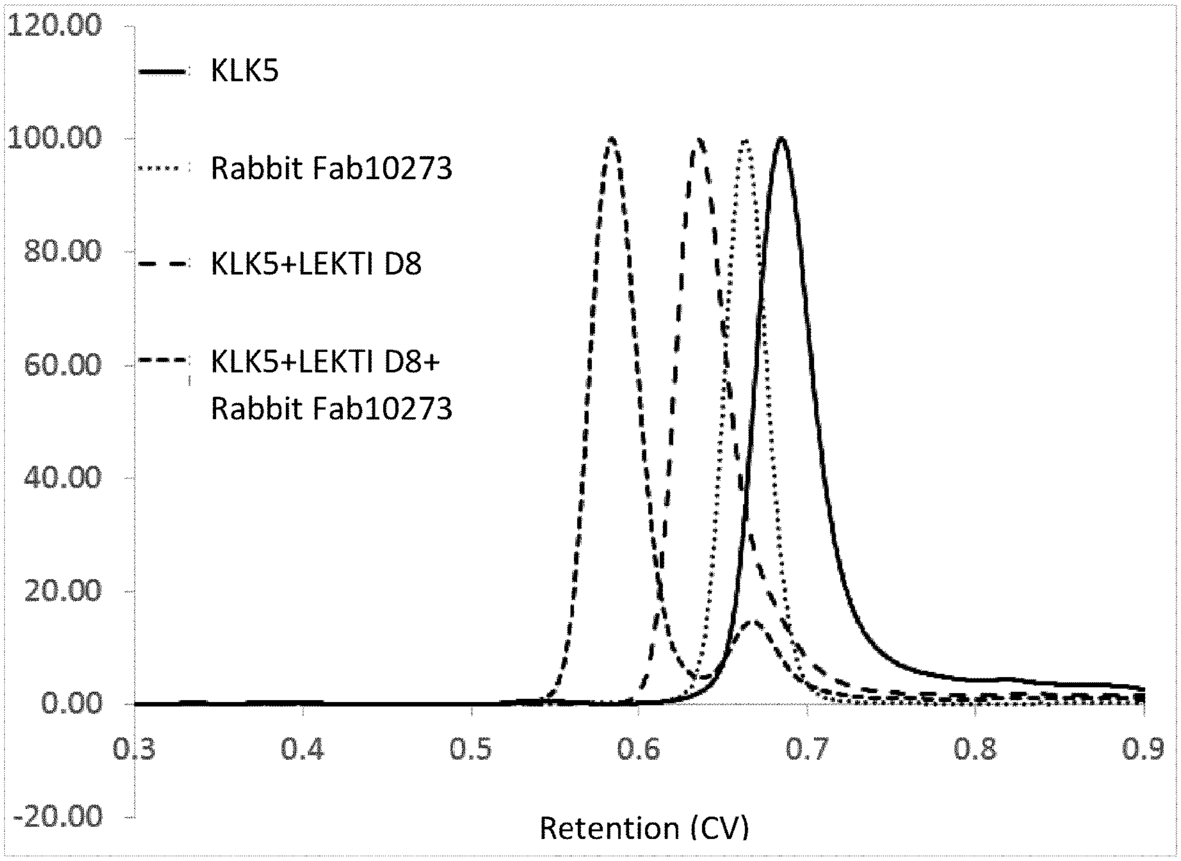

Complexes of KLK5, LEKTI D5 or LEKTI D8, and rabbit Fab antibody 10273 were formed by first incubating 25 UM KLK5 with 25 UM LEKTI D5 or LEKTI D8 for 60 minutes on ice then adding 25 UM rabbit Fab antibody 10273 and continuing the incubation for another 60 minutes on ice. The mixture was injected onto a Superdex 200 size exclusion column equilibrated with PBS, PH 7.2, which was connected in series to an HPLC. Peak fractions were collected for analysis by SDS-PAGE. FIGS. 3A and 3B shows the SEC chromatograms of human KLK5 alone (solid trace, far right), rabbit Fab antibody 10273 alone (dotted trace), the binary complex of human KLK+LEKTI D5 or D8 (FIG. 3A or 3B, respectively, long dash), and the ternary complex of KLK5+LEKTI D5 or D8+rabbit Fab antibody 10273 (FIG. 3A or 3B respectively, short dash, far left).

Figure 4:
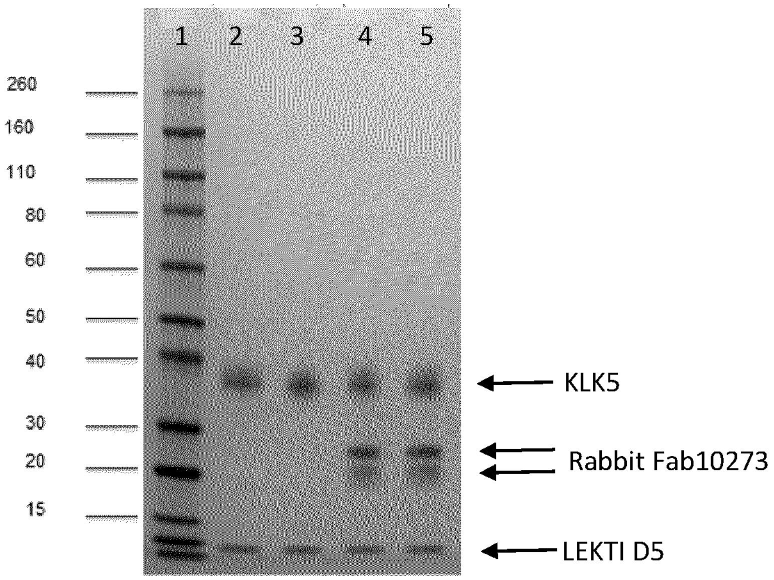
FIG. 4. A: SDS-PAGE of peak fractions from the SEC shown in FIG. 3A. Lane 1, MW markers, Lanes 2 and 3, fractions of the binary KLK5+LEKTI D5 complex, Lanes 4 and 5, peak fractions of the ternary KLK5+LEKTI D5+Rabbit Fab antibody 10273 complex. B: SDS-PAGE of peak fractions from the SEC shown in FIG. 3B. Lane 1, MW markers, Lanes 2 and 3, peak fractions of the binary KLK5+LEKTI D8 complex, Lanes 4 and 5, peak fractions of the ternary KLK5+LEKTI D8+Rabbit Fab antibody 10273 complex.
Figure 4:
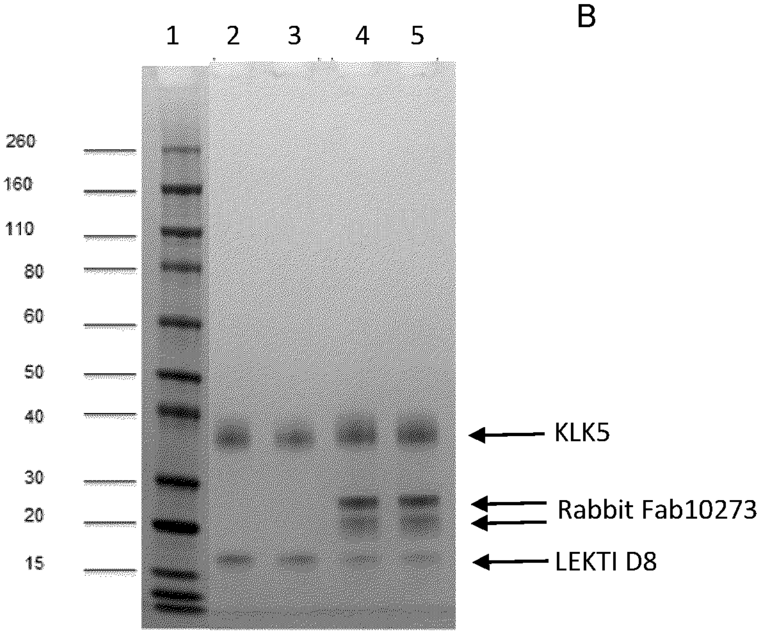

The molecular weight (MW) of the components of each peak was confirmed by SDS PAGE as shown in FIGS. 4A and 4B.

Complexes between KLK5, LEKTI D5 or LEKTI D8, and rabbit Fab antibody 10273 formed readily when mixed in a 1:1:1 ratio by mixing human KLK5 with each LEKTI fragment individually then incubating the binary complexes with rabbit Fab antibody 10273. Binary and ternary complexes were observed on SEC and by SDS-PAGE of peak fractions, indicating they were stable and suitable for isolation/purification from the other species.

Example 7: Crystallization of KLK5/Fab Antibody 10273/Fab Antibody 10236 Complex For the crystallography studies, human KLK5 was expressed by transient transfection using the EXPI293™ Expression System (LIFE TECHNOLOGIES™) following manufacturer's protocol, with the addition of kifunensine (SIGMAR) at a 5 mM final concentration. Kifunensine is a potent inhibitor of the mannosidase I enzyme and is primarily used in cell culture to make high mannose glycoproteins.

During expression of KLK5, the protein auto-activates to yield active KLK5 protein (residues I67-S293 (UniProt Q9Y337 numbering) of SEQ ID NO: 142 or SEQ ID NO: 144) in the supernatant. Cells were harvested 5 days post transfection and supernatants used immediately for purification. Supernatants comprising human KLK5 were diluted 4-fold with Buffer A (50 mM Tris pH 7.0, 50 mM NaCl) and loaded onto HiTrap SP HP cation exchange column. Bound proteins were eluted with Buffer B (50 mM Tris pH 7.0, 1M NaCl) gradient over 10 column volumes. Fractions containing purified human KLK5 were pooled and concentrated and purified further by size exclusion chromatography on S200 26/60 which had been equilibrated with 20 mM Tris, 150 mM NaCl at pH 7.2. KLK5 was characterized by SDS-PAGE and migrated to a position on the gel consistent with the expected molecular weight (MW) of the high mannose glycosylated protein ~35-38 kDa.

Figure 5:
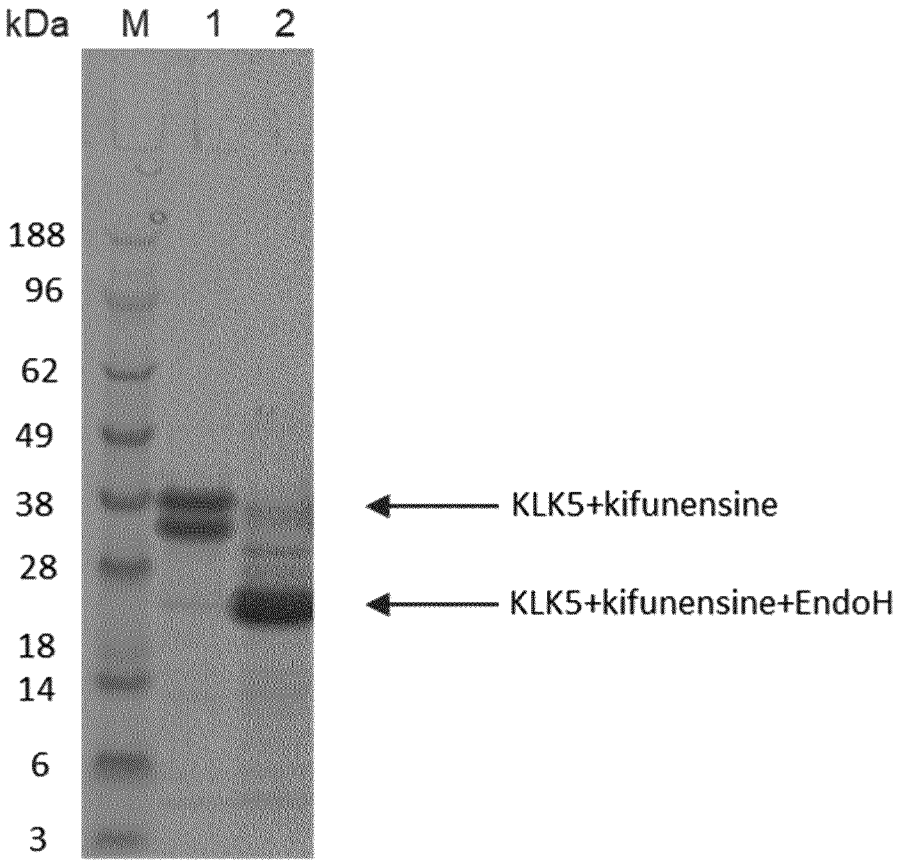
FIG. 5. SDS-PAGE of KLK5 produced for X-ray crystallography studies. Lane M, MW markers. Lane 1, human KLK5 purified from cultures grown in presence of kifunensine (kif). Lane 2, human KLK5 purified from kifunensine cultures and treated with Endoglycosidase H (Endo H).

Human KLK5 protein was then treated with Endoglycosidase H (Endo H) protein at ratio of 1:100 and incubated at 4° C. overnight to form a homogenous de-glycosylated KLK5 protein for structural studies. Endoglycosidase.H (Endo H) is a recombinant glycosidase cloned from *Streptomyces plicatus* and overexpressed in *E. coli*. Endo H cleaves the chitobiose core of high mannose and a limited number of hybrid oligosaccharides from N-linked glycoproteins. It does not cleave complex glycans. Enzymatic cleavage is between the two N-acetylglucosamine residues in the diacetylchitobiose core of the oligosaccharide, leaving one N-acetylglucosamine residue on the asparagine. This step was performed to ensure that a homogenous human KLK5 was available for crystallographic studies. KLK5 was characterized by SDS-PAGE (FIG. 5) and migrated to a position on the gel consistent with the expected molecular weight (MW) of the de-glycosylated protein ~25 kDa.

Rabbit Fab antibody 10273 was expressed as described in Example 6. Rabbit Fab antibody 10236 (comprising SEQ ID NO: 181 and 183) was expressed as described for rabbit Fab antibody 10273. In short, expression constructs comprising SEQ ID NO: 182 and 184 were co-transfected at a 1:1 molar ratio. Each of the secreted Fab proteins was purified by passing conditioned medium over Protein G beads and eluted with 0.1M glycine, pH 2.7. Fractions were neutralized by the addition of 2M Tris-HCl, pH8.5. The respective, individual proteins were dialyzed into PBS, pH 7.2, concentrated to ~10 mg/ml and stored frozen at −80° C.

A 1:1.5:1.5 human KLK5/rabbit Fab antibody 10273/rabbit Fab antibody 10236 complex was made, incubated at 4° C. overnight and purified by size exclusion chromatography (20 mM Tris, 150 mM NaCl, pH 7.2 elution buffer). A single peak containing the complex was concentrated to ~10.8 mg/ml prior to crystallization.

Crystallization conditions for the human KLK5/rabbit Fab antibody 10273/rabbit Fab antibody 10236 complex were identified using several commercially available crystallization screens. These were carried out in sitting drop format, using Swissci 96-well 2-drop MRC Crystallization plates (sourced from Molecular Dimensions, Cat No. MD11-00-100). First, the reservoirs were filled with 75 μL of each crystallization solution in the screens using a Microlab STAR liquid handling system (Hamilton). Then, 300 nL of the human KLK5/rabbit Fab antibody 10273/rabbit Fab antibody 10236 complex and 300 nL of the reservoir solutions were dispensed in the wells of the crystallization plates using a Mosquito liquid handler (TTP LABTECH™). A single crystal was obtained in condition 16 (well B4) of the MIDAS+HT-96 screen (Molecular Dimensions, Cat No. MD1-107). This condition contains 45% v/v Pentaerythritol Propoxylate (5/4), 0.2 M NaCl and 0.1 M MES monohydrate pH 6.0. The crystal was flash frozen in liquid nitrogen and diffraction data were collected at beamline 103 (Diamond Light Source, UK). The data was indexed and integrated using XDS (Kabsch, W. XDS. Acta Cryst. D66, 125-132 (2010)), followed by scaling using AIMLESS (2. Evans P R, Murshudov G N. How good are my data and what is the resolution? Acta Crystallogr D Biol Crystallogr. 2013; 69 (Pt 7): 1204-1214). The human KLK5/rabbit Fab antibody 10273/rabbit Fab antibody 10236 complex structure was solved by molecular replacement using Phaser (McCoy, A. J., Grosse-Kunstleve, R. W., Adams, P. D., Winn, M. D., Storoni, L. C., & Read, R. J. Phaser crystallographic software. J. Appl. Cryst. (2007). 40, 658-674) in the Phenix software suite (Adams P D, Afonine P V, Bunkóczi G, et al. The Phenix software for automated determination of macromolecular structures. Methods. 2011; 55 (1): 94-106). In this procedure, KLK5 structure 2PSX (Debela M, Goettig P, Magdolen V, Huber R, Schechter N M, Bode W. Structural basis of the zinc inhibition of human tissue kallikrein 5. J Mol Biol. 2007 Nov. 2; 373 (4): 1017-31) and a proprietary Fab model were used as molecular replacement templates. Coot (P. Emsley; B. Lohkamp; W. G. Scott; Cowtan (2010). "Features and Development of Coot". Acta Crystallographica. D66: 486-501) and phenix.refine (Towards automated crystallographic structure refinement with phenix.refine. P. V. Afonine, R. W. Grosse-Kunstleve, N. Echols, J. J. Headd, N. W. Moriarty, M. Mustyakimov, T. C. Terwilliger, A. Urzhumtsev, P. H. Zwart, and P. D. Adams. Acta Crystallogr D Biol Crystallogr 68, 352-67 (2012)) were used in the following cycles of manual model completion and refinement until acceptable Rwork, Rfree and Ramachandran statistics (as analysed by Molprobity (Williams et al. (2018) MolProbity: More and better reference data for improved all-atom structure validation. Protein Science 27:293-315)) were obtained.

The human KLK5/rabbit Fab antibody 10273/rabbit Fab antibody 10236 complex was observed in the crystal asymmetric unit. NCONT in the CCP4 software suite was used to determine the epitopes on KLK5, recognized by the Fab10273 and Fab10236 molecules. The KLK5 amino acid numbering is based on UnitProtKB entry Q9Y337 with standard protease numbering based on chymotrypsinogen in brackets. Table 5 shows the refinement statistics at the time the invention was first described.

TABLE 5

| | |
|---|---|
| Data collection | |
| Resolution (Å) | 87.77-2.45 (2.51-2.45) |
| Space group | I 1 2 1 |
| Cell parameters | |
| a, b, c (Å) | 76.97, 93.19, 261.27 |
| β (°) | 91.00 |
| $R_{merge}$ (%) | 4.10 (52.9) |
| $R_{meas}$ (%) | 5.70 (72.4) |
| $R_{pim}$ | 4.00 (49.2) |
| Average I/σ(I) | 13.3 (1.9) |
| Completeness | 99.3 (99.9) |
| No. of unique reflections | 67522 (4551) |
| Multiplicity | 3.5 (3.4) |
| Wilson B-factor (Å$^2$) | 62.535 |
| Refinement statistics | |
| Number of protein/solvent atoms | 7924/84 |
| Rwork/free (%) | 22.89/27.68 |
| Number of reflections in the 'free' set | 3302 |
| R.m.s. deviations from ideal values | |
| Bonds (Å) | 0.011 |
| Angles (°) | 1.158 |
| Average protein B factor (Å$^2$) | 69.33 |

Figure 6:
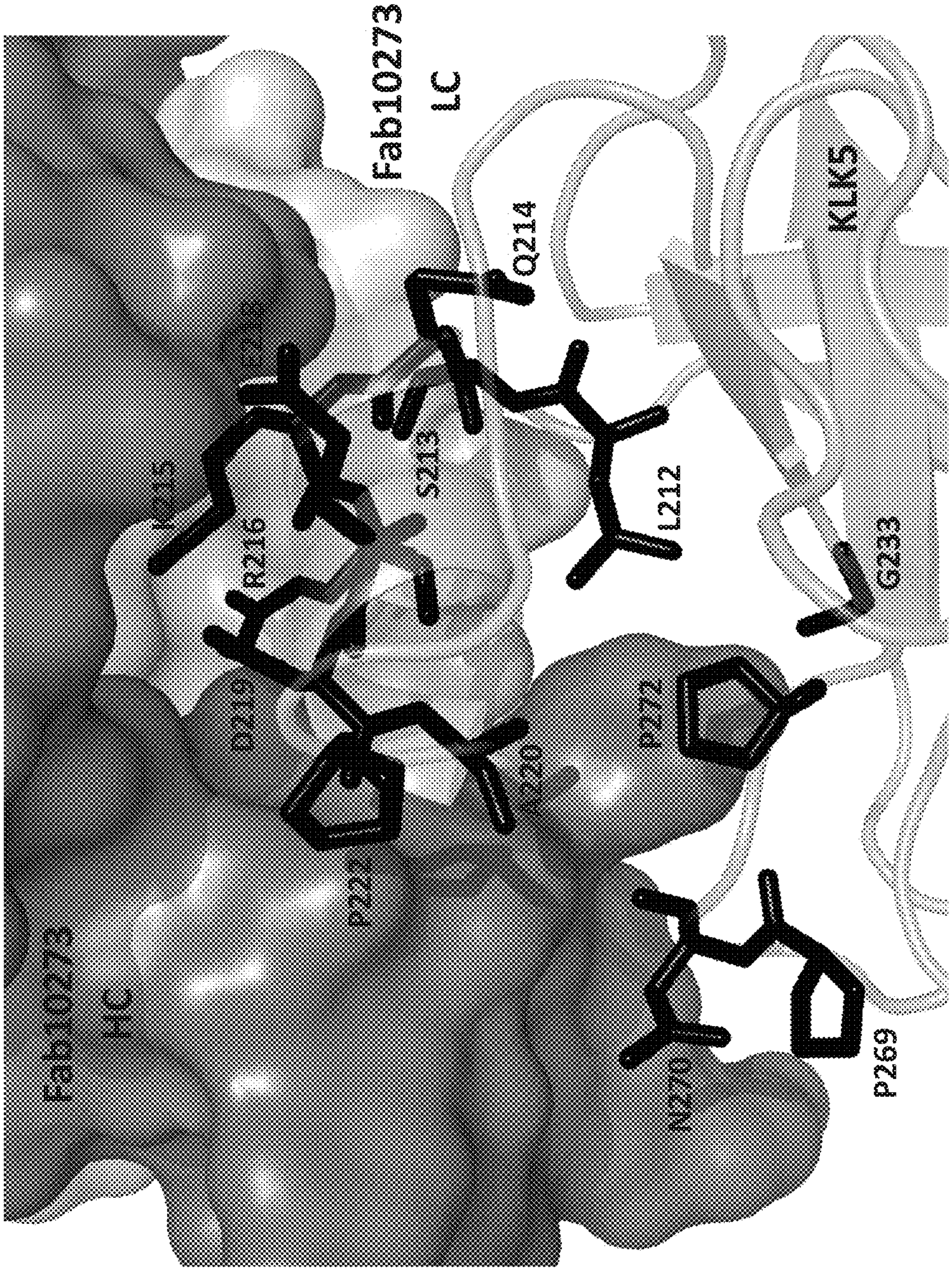
FIG. 6. Schematic representation of the human KLK5 epitope in complex with rabbit Fab antibody 10273. Fab heavy and light chains are shown in cartoon and dark and light surfaces, respectively transparent surface. Residues Leu212 (163), Ser213 (164), Gln214 (165), Lys215 (166), Arg216 (167), Glu218 (169), Asp219 (170), Ala220 (171), Pro222 (173), Gly233 (184), Pro269 (223), Asn270 (224) and Pro272 (226) which form the epitope on human KLK5 bound by antibody 10273 are depicted as black sticks.

The human KLK5 epitope bound by rabbit Fab antibody 10273 at 4 Å contact distance is composed of residues Leu212 (163), Ser213 (164), Gln214 (165), Lys215 (166), Arg216 (167), Glu218 (169), Asp219. (170), Ala220 (171), Pro222 (173), Gly233 (184), Pro269 (223), Asn270 (224) and Pro272 (226) with reference to SEQ ID NO: 142, whilst the numbers in parentheses correspond to the protease nomenclature. The binding site is shown in more details in FIG. 6.

Figure 7:
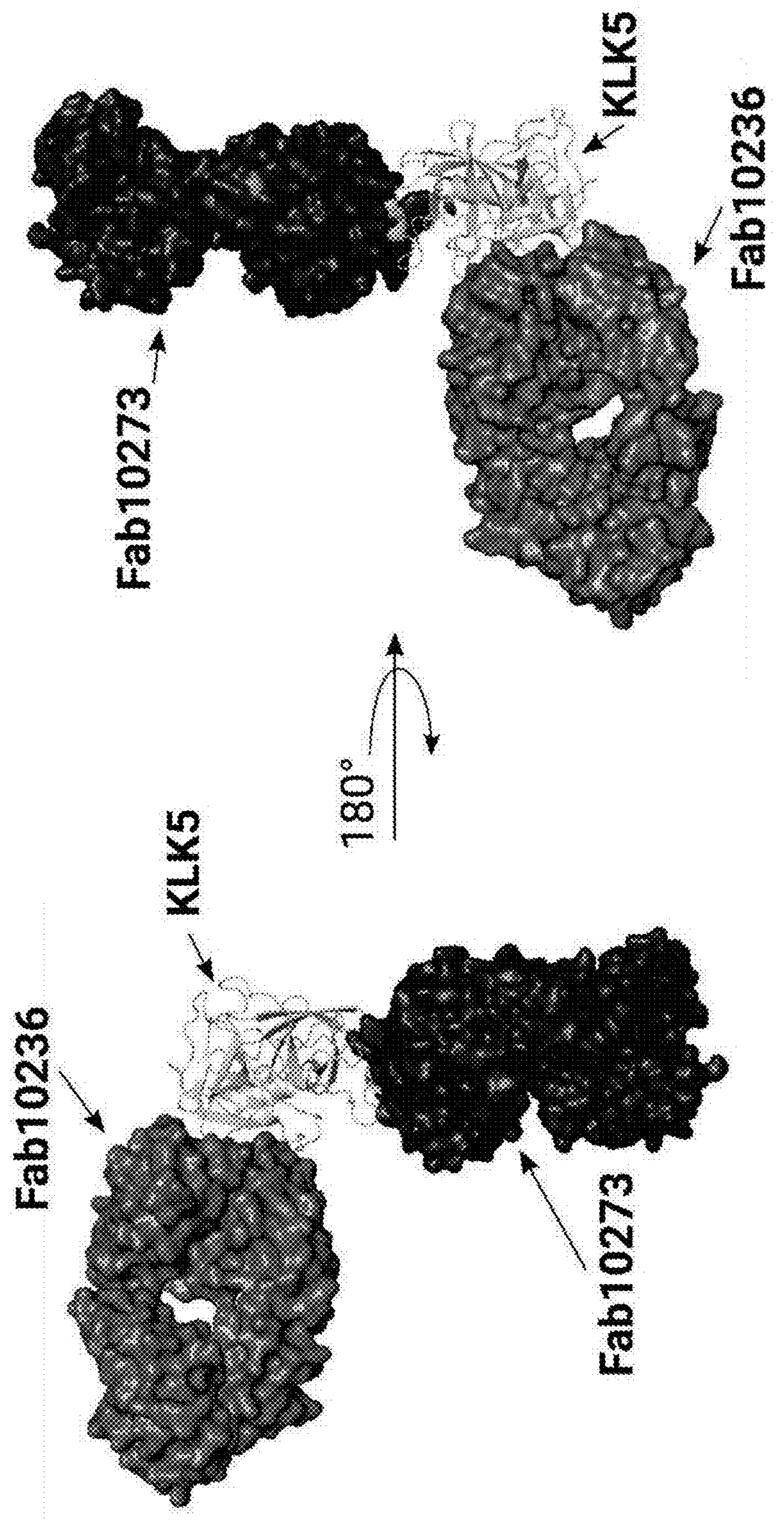
FIG. 7. Two orientations of the crystal structure of the human KLK5 in complex with rabbit Fab antibodies 10236 and 10273. Human KLK5 is shown as ribbon representation, rabbit Fab antibodies 10236 and 10273 are shown as solid surfaces.

Other amino acid residues in proximity of the epitope but at 5 Å contact distance between human KLK5 and rabbit Fab antibody 10273 comprised Ala181 (132), Val211 (162), Tyr221 (172), Asp234 (185) and Arg271 (225) with reference to SEQ ID NO: 142, whilst the numbers in parentheses correspond to the protease nomenclature. As shown in FIG. 7, antibodies 10236 and 10273 have very distinct, non-overlapping binding sites and binds different epitope on human KLK5.

Example 8: Antibody 10273 Humanization and Characterization

Humanization of Ab 10273

Figure 8:
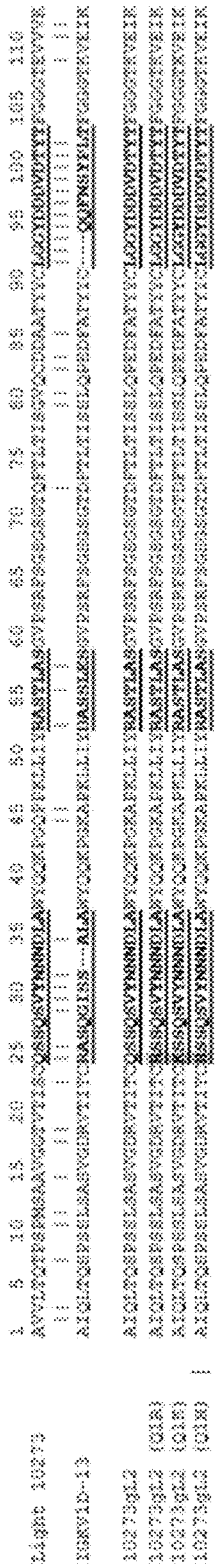
FIG. 8. Humanization of rabbit variable light chain sequence of antibody 10273. Grafts 10273 gL2, 10273 gL2 Q1R, 10273 gL2 Q1K and 10273 gL2 Q1H are humanized grafts of rabbit variable light chain of antibody 10273 using IGKV1D-13 human germline as the acceptor framework. The CDRs are shown in bold/underlined. Mutations in CDRL1 which lead to an increase of the overall pI are shown in bold/underlined and are highlighted: Q1R, Q1K or Q1H.
Figure 9:
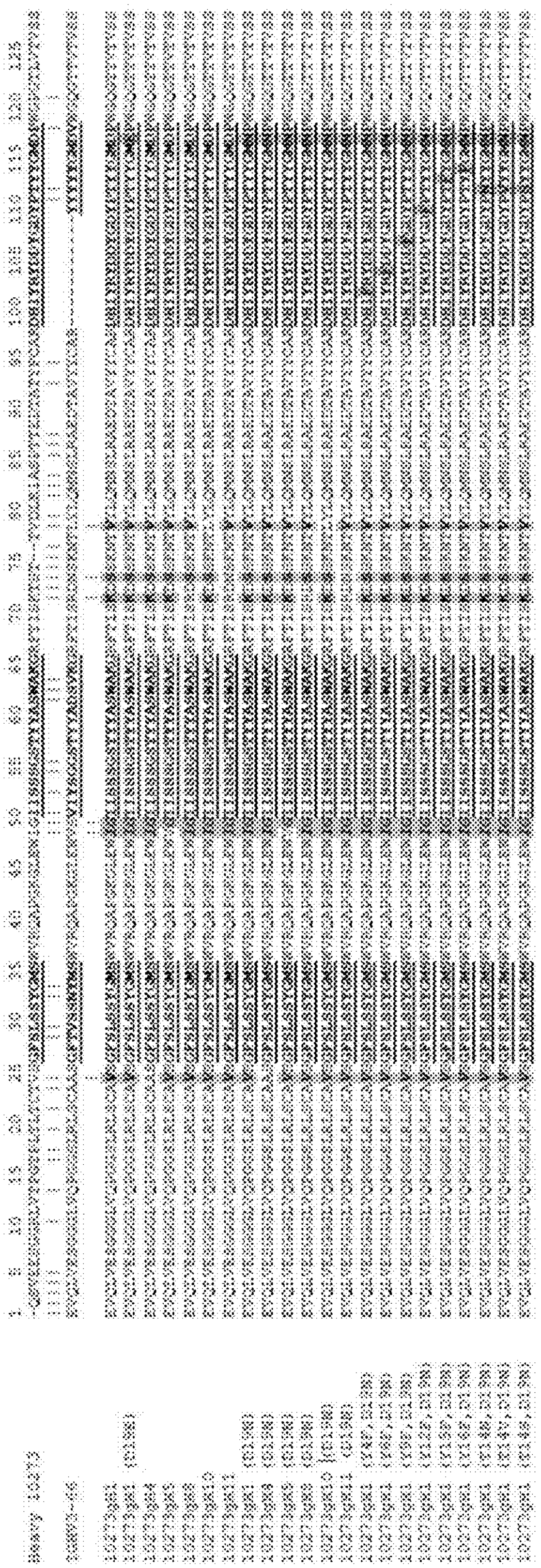
FIG. 9. Humanization of rabbit variable heavy chain sequence of antibody 10273. Grafts 10273gH1, gH4, gH5, gH8, gH10 and gH11 are humanized grafts of rabbit variable heavy chain of antibody 10273 using variable heavy chain using IGHV3-66 human germline as the acceptor framework. CDRs are shown in bold/underlined. Donor residues are shown in bold/italic and are grey shaded: V24, 148, G49, K71, S73 and V78. Mutations in CDR-H3 to remove a potential DP hydrolysis site (D116E) or to increase the pI (D116N) are shown in bold/underlined and are highlighted.

Rabbit antibody 10273 was humanized by grafting the CDRs from the rabbit V-regions onto human germline antibody V-region frameworks. In order to recover the activity of the antibodies, a number of framework residues from the rabbit V-regions were also retained in the humanized sequence. These residues were selected using the protocol outlined by Adair et al. (1991) (Humanized antibodies. WO91/09967). Alignments of the rabbit antibody (donor) V-region sequences with the human germline (acceptor) V-region sequences are shown in FIGS. 8 and 9, together with the designed humanized sequences. The CDRs grafted from the donor to the acceptor sequences are as defined by Kabat (Kabat et al., 1987), with the exception of CDR-H1 where the combined Chothia/Kabat definition is used (see Adair et al., 1991 Humanized antibodies. WO91/09967).

For antibody 10273, the human V-region IGKV1D-13 plus JK4 J-region (IMGT, imgt.org/) was chosen as the acceptor for the light chain CDRs. The framework residues in the humanized light chain graft gL2 are all from the human germline gene (FIG. 8).

Human V-region IGHV3-66 plus JH6 J-region (IMGT, imgt.org) was chosen as the acceptor for the heavy chain CDRs of antibody 10273. In common with many rabbit antibodies, the VH gene of antibody 10273 is shorter than the selected human acceptor. When aligned with the human acceptor sequence, framework 1 of the VH region of antibody 10273 lacks the N-terminal residue, which is retained in the humanized antibody (FIG. 9). Framework 3 of the 10273 rabbit VH region also lacks two residues (75 and 76) in the loop between beta sheet strands D and E: in the humanized grafts the gap is filled with the corresponding residues (Lysine 75, K75; Asparagine 76, N76) from the selected human acceptor sequence (FIG. 9). The framework residues in the humanized grafts of 10273 heavy chain are all from the human germline gene, with the exception of one or more residues from the group comprising residues 24, 48, 49, 71, 73 and 78, where the donor residues Valine (V24), Isoleucine (148), Glycine (G49), Lysine (K71), Serine (S73) or Valine (V78) were retained, respectively. Retention of residue G49 was essential for full potency of the humanized antibody. A potential hydrolysis site in CDRH3 was modified in graft gH3, by replacing the Aspartic acid residue at position 116 with glutamic acid (D116E).

The pI of the humanized 10273 antibodies is ~6.2. To facilitate the removal of impurities by ion-exchange chromatography during downstream processing, the pI was increased by mutation of residue 1 in CDRL1 with reference to SEQ ID NO: 1 of graft gL2 from a glutamine (Q) to either an Arginine (R), a Lysine (K) or a Histidine (H) residue. In addition, residue 19 in CDRH3 (with reference to SEQ ID NO: 6) was mutated from an Aspartic acid (D) to an Asparagine (N) residue to further increase the pI: unexpectedly, the mutation in CDRH3 (D19N) also conferred an increased affinity for KLK5.

In graft antibody 10273 gL2-Q24RgH1-D116N, the CDR-H3 contains 6 tyrosine residues. Mutants of this graft were prepared, substituting individual tyrosine residues with a phenylalanine residue to generate grafts 10273 gL2-Q1RgH1-D19N-Y4F, 10273 gL2-Q1RgH1-D19N-Y6F, 10273 gL2-Q1RgH1-D19N-Y9F; 10273 gL2-Q1RgH1-D19N-Y12F, 10273 gL2-Q1RgH1-D19N-Y15F, 10273 gL2-Q1RgH1-D19N-Y16F. Additional mutants were prepared by mutating the threonine occurring . . . before the double tyrosine at positions 15 and 16 with reference to SEQ ID NO: 6, leading to grafts, 10273 gL2-Q1RgH1-D19N-T14V and 10273 gL2-Q1RgH1-D19N-T14S.

The kinetics of these grafts for binding to human KLK5 were assessed by surface plasmon resonance (BIACORE™ T200) at 25° C.

A goat anti-human IgG Fc specific antibody (JACKSON IMMUNORESEARCH™) was immobilised on a CM5 Sensor Chip via amine coupling chemistry to a level of approximately 7000RU. Each analysis cycle consisted of capture of the anti-KLK5 IgG molecules to the anti Fc surface, injection of KLK5 analyte (prepared in house) for 180 s at 30 µl/min followed by 600 s dissociation. At the end of each cycle the surface was regenerated at a flowrate of 10 µL/min using a 60 s injection of 50 mM HCl followed by a 30 s injection of 5 mM NaOH and a final 60 s injection of 50 mM HCl. Human KLK5 was titrated from 20 nM to 0.74 nM (3×3-fold serial dilutions) in HBS-EP+ running buffer (GE HEALTHCARE®) supplemented with NaCl to a final concentration of 300 mM. Buffer blank injections were included to subtract instrument noise and drift.

Kinetic parameters were determined using a 1:1 binding model using BIACORE™ T200 Evaluation software.

Table 6 shows that not all mutations lead to antibody still capable of binding KLK5 with affinity similar or close to the parental antibody or the graft antibody they were derived from.

TABLE 6

| Descriptor | ka(1/Ms) | kd(1/s) | KD(pM) |
|---|---|---|---|
| 10273 gL2gH1 | 5.14E+05 | 8.45E−05 | 164.3 |
| 10273 gL2-Q1RgH1-D19N | 4.27E+05 | 1.75E−04 | 410.2* |
| 10273 gL2-Q1RgH1-D19N | 2.57E+05 | 1.33E−04 | 309.1* |
| 10273 gL2-Q1RgH1-D19N-Y6F | 2.98E+05 | 1.86E−04 | 625.4 |
| 10273 gL2-Q1RgH1-D19N-Y9F | 3.62E+05 | 2.00E−04 | 553.9 |
| 10273 gL2-Q1RgH1-D19N-Y12F | 4.32E+05 | 1.38E−04 | 318.5 |
| 10273 gL2-Q1RgH1-D19N-Y15F | 5.58E+05 | 1.39E−04 | 249.1 |
| 10273 gL2-Q1RgH1-D19N-T14S | 2.57E+05 | 1.65E−04 | 643.8 |
| 10273 gL2-Q1RgH1-D19N-Y4F | 4.51E+05 | 5.19E−04 | 1151.6 |
| 10273 gL2-Q1RgH1-D19N-Y16F | 2.77E+05 | 1.60E−03 | 5768.6 |
| 10273 gL2-Q1RgH1-D19N-T14V | 3.64E+05 | 2.51E−03 | 6898.4 |

*duplicate samples, same assay conditions, run at the beginning and at the end of experiment. The different values are within the expected experiment variability.

Profiling of Humanized Antibodies

KLK5 Selectivity

A series of investigations were performed to ensure the humanization of rabbit antibody 10273 did not alter the KLK5 selectivity over other kallikreins, did not reduce affinity or inhibition activity. Purified antibodies were then screened to confirm their inhibitory activity against KLK5 according to the methods described in example 4. Antibodies were tested on a 10-point half log dilution series with a range of 600 nM to 20 μM. Using a BECKMAN COULTER FX™ and a Multidrop System, 5 μL of each antibody was transferred to black 384 well assay plates (CORNING®, cat no. 3575) and 15 μL of selected active recombinant kallikrein enzymes in assay buffer A (150 mM NaCl, 50 mM Tris, 200 μM EDTA, 0.05% (v/v) TWEEN®-20, pH7.6 were added to achieve the following final assay concentrations: 60 μM human KLK5 (UCB), 250 μM KLK7 (UCB), 500 μM KLK2 (R&D SYSTEMS™), 30 μM KLK4 (UCB), as well as 30 μM cynomolgus monkey recombinant KLK5 (UCB), 500 μM cynomolgus monkey KLK7, 30 PM mouse KLK5 (UCB) and 5 nM mouse KLK7 (UCB). Enzymes prepared at UCB are indicated in brackets and prepared as described above in Example 1. The source of commercially available enzymes is indicated in brackets.

20 μL assay buffer A alone was added to wells for 0% activity. LEKTI D5 rabbit Fc (UCB prepared as described above) was used as a reference for inhibitory activity; 5 μl LEKTI D5 rabbit Fc at the same concentration range utilized for the 10236 Abs antibody was therefore added to 15 μl of the kallikrein enzymes. 15 μL of human KLK5 added to 5 μL assay buffer A was used as a 100% activity reference.

Antibodies and kallikreins were incubated at room temperature overnight. The following peptide substrates were added using a multidrop: Boc-VPR-AMC (CAMBRIDGE RESEARCH BIOCHEMICALS™) for human KLK5 (300M), human KLK2 (30 μM), murine KLK5 (300 M) and cyno KLK5 (450 μM); KHLF-AMC (CAMBRIDGE RESEARCH BIOCHEMICALS™) for human and cyno KLK7 (90 UM and 150 UM, respectively), PFR-AMC (R&D SYSTEMS™) for human KLK4 (200 μM), and Mca-RPKPVE-Nval-WRK (Dnp)-NH2 (R&D SYSTEMS™) for murine KLK7 (150 μM). Samples were incubated for 4 hours and read on a PHERASTAR® FSX Plate Reader (BMG LABTECH™) at $\lambda_{ex}$380 nm and $\lambda_{em}$430 nm for Boc-VPR-AMC, PFR-AMC and KHLF-AMC; and at $\lambda_{ex}$320 nm and $\lambda_{em}$400 nm for Mca-RPKPVE-Nval-WRK (Dnp)-NH2. Data were analysed to determine percentage inhibition as described in example 3. Data were plotted against concentration of test antibody and a 4-parameter sigmoid fitted to determine $IC_{50}$ (GENEDATA SCREENER™).

The humanised grafts of Ab 10273 retained specificity for KLK5 and showed little or no inhibition of the other KLK family members tested (data not shown).

Level of Inhibition of KLK5 by Humanized Grafts

A capture assay was developed to ascertain the level of inhibition of KLK5 activity mediated by the humanised Ab 273 graft variants.

Nunc Maxisorp black 384 well plates (SIGMA-ALDRICH®) were coated with $F(ab')_2$ Fragment Goat Anti-Human IgG Fcγ Fragment Specific (JACKSON IMMUNORESEARCH™) at 10 μg/mL in carbonate coating buffer and left overnight at 4° C. Plates were washed 3 times on a BIOTEK™ plate washer with PBS and 0.005% TWEEN®-20 and plates were blocked with 20 μL/well PBS with 1% BSA, for 1 hr at room temperature. Plates were washed as above and 10 μl of 5 nM antibody (diluted from stock using assay buffer: 150 mM NaCl, 50 mM Tris, 200 μM EDTA, 0.005% (v/v) TWEEN®-20, pH 7.6) added to the appropriate wells. The plates were sealed and incubated overnight at room temperature before washing. 10 μl of 250 μM KLK5 (diluted from stock in assay buffer) was then added to the relevant wells, incubated at room temperature for four hours before addition of 10 μl of 600 mM BVPR-AMC substrate. Antibody was omitted and was replaced by assay buffer for the "maximum activity" control wells whilst no substrate or no enzyme (replaced with assay buffer) was added to the "minimum activity" control wells. Fluorescence ($\lambda_{ex}$380 nm $\lambda_{em}$430 nm) was read every hour for four hours using a PHERASTAR® FSX plate reader.

Data were analysed to generate percentage inhibition of KLK5 values. Each Time 0 value was subtracted from its equivalent Time 4 hr value to give a normalized, baseline corrected set of data. The following formula was used to convert the normalized fluorescence values to % inhibition:

$$\%\ \text{Inhibition} = 100 \times \left(1 - \frac{\text{Test} - \text{Min}}{\text{Max} - \text{Min}}\right)$$

Min=minimum activity value; Max=maximum activity value

Figure 10:
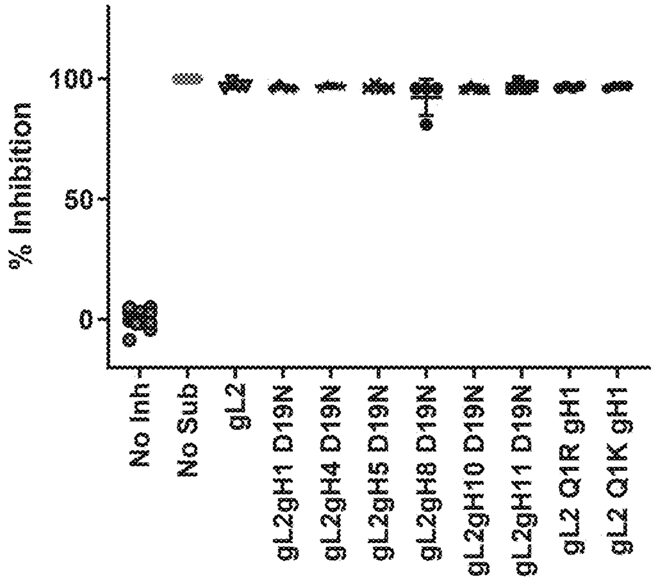
FIG. 10. Inhibition of human KLK5 by humanized grafts of antibody 10273. Humanized graft variants of Ab 10273 were assayed to determine the extent to which they inhibit KLK5 activity. The percent inhibition values were calculated and the data plotted as described in Example 8. No Inh=No inhibitor; No Sub=No substrate; No Enz=No enzyme.
Figure 10:
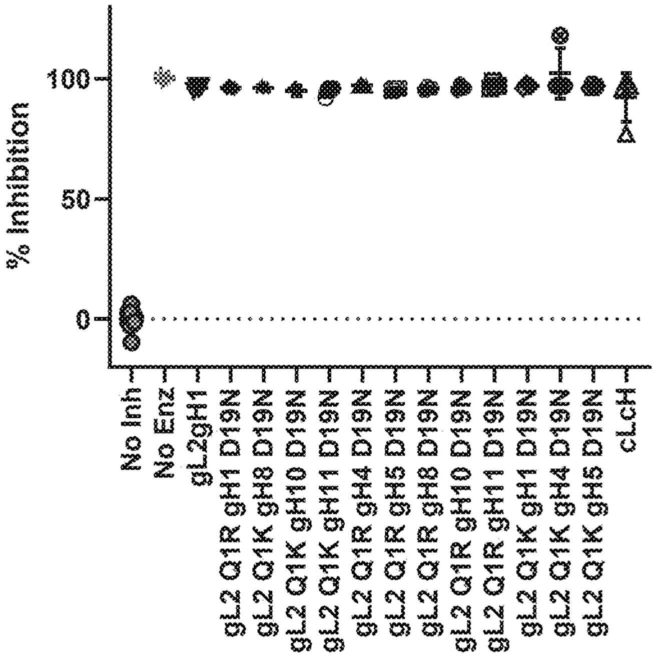

Data were plotted to generate the bar graphs shown FIG. 10. The percent inhibition values ranged from 95% to 97%, demonstrating that the antibodies 10273 grafts were able to almost completely inhibit KLK5 enzyme activity.

Example 9: Biophysical Characterization of Humanized Antibodies

Characterization of Antibodies by Mass Spectrometry

The identity of each antibody was confirmed by intact mass measurement of the heavy and light chains by LC-MS using a Waters ACQUITY UPLC System with a Xevo G2 Q-TOF mass spectrometer. Samples (~5 μg) were reduced with 5 mM tris(2-carboxyethyl)phosphine (TCEP) in 150 mM ammonium acetate at 37° C. for 40 minutes. The LC column was a Waters BioResolveT RP mAb Polyphenyl, 450 Å, 2.7 μm held at 80° C., equilibrated with 95% solvent A (water/0.02% trifluoroacetic acid (TFA)/0.08% formic acid) and 5% Solvent B (95% acetonitrile/5% water/0.02% TFA/0.08% formic acid) at a flow rate of 0.6 mL/minute. Proteins were eluted with a gradient from 5% to 50% solvent B over 8.8 minutes followed by a 95% solvent B wash and re-equilibration. UV data were acquired at 280 nm. MS conditions were as follows: Ion mode: ESI positive ion, resolution mode, mass range: 400-5000 m/z and external calibration with NaI. Data were analysed using Waters MassLynx and MaxEnt Software.

Intact mass (reduced chains) showed that the observed mass for the light chain was consistent with the expected mass. However, a +80Dalton difference was seen between the observed and expected heavy chain mass for all 10273 molecules except for 10273 gL2-Q1RgH1-D19N-Y9F (Table 7).

This was identified to be a post-translational modification of Tyr 9 in the heavy chain and was confirmed to be sulphation by Western blotting using an anti-sulpho-tyrosine antibody. Additionally, incubation of 10273 gL2-Q1RgH1-D19N with abalone sulphatase at 37° C. for 1 hr. reduced the proportion of the +80 Da modification by ~17% as judged by intact mass spectrometry.

TABLE 7

| Sample | description | Light Chain (Da) Exp | Obs | Δ | Heavy Chain (Da) Exp | Obs | Δ | % + 80 Da |
|---|---|---|---|---|---|---|---|---|
| hIgG4P | 10273 gL2gH1 | 23707.2 | 23709.0 | 1.8 | 51260.2 | 51343.6 | 83.4 | 95% |
| | 10273 gL2-Q1RgH1-D19N | 23735.2 | 23737.0 | 1.8 | 51259.2 | 51342.2 | 83.0 | 80% |
| | 10273 gL2-Q1RgH4-D19N gH13 | 23735.2 | 23734.8 | −0.4 | 51231.2 | 51316.0 | 84.8 | 100% |
| | 10273 gL2-Q1RgH1-D19N-Y4F | 23735.3 | 23737.8 | 2.5 | 51243.2 | 51327.8 | 84.6 | 85% |
| | 10273 gL2-Q1RgH1-D19N-Y6F | 23735.3 | 23737.8 | 2.5 | 51243.2 | 51327.8 | 84.6 | 75% |
| | 10273 gL2-Q1RgH1-D19N-Y9F | 23735.3 | 23737.8 | 2.5 | 51243.2 | 51247.8 | 4.6 | 0% |
| | 10273 gL2-Q1RgH1-D19N-Y12F | 23735.3 | 23737.8 | 2.5 | 51243.2 | 51327.8 | 84.6 | 75% |
| | 10273 gL2-Q1RgH1-D19N-Y15F | 23735.3 | 23737.8 | 2.5 | 51243.2 | 51328.0 | 84.8 | 85% |
| | 10273 gL2-Q1RgH1-D19N-Y16F | 23735.3 | 23737.8 | 2.5 | 51243.2 | 51327.6 | 84.4 | 75% |
| | 10273 gL2-Q1RgH1-D19N-T14V | 23735.3 | 23737.8 | 2.5 | 51257.2 | 51341.8 | 84.6 | 75% |
| | 10273 gL2-Q1RgH1-D19N-T14S | 23735.3 | 23737.8 | 2.5 | 51245.2 | 51329.4 | 84.2 | 65% |
| hIgG1 | 10273 gL2gH1 | 23707.2 | 23706.2 | −1.0 | 51417.4 | 51497.2 | 79.8 | 70% |

Exp. = Expected;
Obs = Observed;
Δ = Delta

Thermal Stability (Tm) Measurements

The melting temperature (Tm) or temperature at the midpoint of unfolding was determined using the Thermofluor assay.

For the Thermofluor assay, the fluorescent dye SYPRO® orange was used to monitor the protein unfolding process by binding to hydrophobic regions that become exposed as the temperature increases. The reaction mix contained 5 μL of 30×SYPRO® Orange Protein Gel Stain (THERMO FISHER SCIENTIFIC®, S6651), diluted from 5000× concentrate with test buffer. 45 UL of the 10273 Ab sample at 0.2 mg/mL, in PBS pH 7.4 was added to the dye and mixed. 10 μL of this solution was dispensed in quadruplicate into a 384 PCR optical well plate and was run on a QuantStudio 7 Real-Time PCR System (THERMO FISHER™). The PCR system heating device was set at 20° C. and increased to 99° C. at a rate of 1.1° C./min. A charge-coupled device monitored fluorescence changes in the wells. Fluorescence intensity increases were plotted, the inflection point of the slope (s) was used to generate apparent midpoint temperatures (Tm).

Two unfolding transitions were observed for all antibodies. The first can be attributed to the CH2 domain and the second can be attributed to an average of the Tm of the Fab unfolding domain and CH3 domain.

There was no difference in thermal stability between the 10273 IgG4P antibodies (Table 8). An increase in thermal stability was observed for the IgG1 format of antibody 10273 gL2gH1 compared with the corresponding IgG4P format as expected. (Heads et al "Relative stabilities of IgG1 and IgG4 Fab domains: influence of the light-heavy interchain disulfide bond architecture". Protein Sci 2012; 21:1315-22).

TABLE 8

| | Descriptor | Tm(°C) Fab domain | SD | CH2 domain | SD |
|---|---|---|---|---|---|
| hIgG4P | 10273 gL2gH1 | 75.1 | 0.1 | 66.3 | 0.2 |
| | 10273 gL2-Q1RgH1-D19N | 75.2 | 0.1 | 66.4 | 0.1 |
| | 10273 gL2-Q1RgH4-D19N | 75.1 | 0.2 | 66.5 | 0.2 |
| | 10273 gL2-Q1RgH1-D19N-Y4F | 75.7 | 0.1 | 66.6 | 0.2 |
| | 10273 gL2-Q1RgH1-D19N-Y6F | 75.8 | 0.2 | 66.4 | 0.2 |
| | 10273 gL2-Q1RgH1-D19N-Y9F | 75.6 | 0.1 | 66.6 | 0.1 |
| | 10273 gL2-Q1RgH1-D19N-Y12F | 75.5 | 0.1 | 66.7 | 0.2 |
| | 10273 gL2-Q1RgH1-D19N-Y15F | 75.5 | 0.1 | 66.5 | 0.2 |
| | 10273 gL2-Q1RgH1-D19N-Y16F | 75.4 | 0.2 | 66.4 | 0.2 |
| | 10273 gL2-Q1RgH1-D19N-T14V | 75.5 | 0.3 | 66.7 | 0.1 |
| | 10273 gL2-Q1RgH1-D19N-T14S | 75.3 | 0.2 | 66.3 | 0.3 |
| hIgG1 | 10273 gL2gH1 | 80.2 | 0.1 | 69.9 | 0.1 |

Further biophysical characterization was performed on three humanized IgG4P antibodies, antibodies 10273 gL2H1, gL2Q1R-gH1D19N and gL2Q1R-gH4D19N and one in the IgG1 format, antibody 10273 gL2gH1.

Experimental Isoelectric Point (PI) Measurement

An ICE3™ whole-capillary imaged capillary isoelectric focusing (cIEF) system (PROTEINSIMPLE®) was used to experimentally determine pI. The 10273 Ab samples were prepared by mixing the following: 30 UL sample (from a 1 mg/mL stock in HPLC grade water), 35 μL of 1% methylcellulose solution (PROTEINSIMPLE®, 101876), 4 UL pH 3-10 pharmalytes (PROTEINSIMPLE®, 042-848), 0.5 μL of 4.65, 0.5 μl 9.77 synthetic pI markers (PROTEINSIMPLE®, 102223 and 102219), and 12.5 μL of 8 M urea solution (SIGMA-ALDRICH®). HPLC grade water was used to make up the final volume to 100 μl. Samples were focused for 1 min at 1.5 kV, followed by 5 min at 3 kV, 280 nm images of the capillary were taken using the Protein Simple software. The resulting electropherograms were analysed using iCE3™ software and pI values were assigned (linear relationship between the pI markers).

A higher pI was observed as a consequence of mutations in the light chain Q1R and heavy chain D19N. A difference in isotype, that is IgG1 instead of IgG4P also resulted in an increased experimental pI. Both the mutations and a change in isotype could be exploited during manufacture for removal of host cell proteins in the first ion exchange step (AEX). An increased pI also allows for formulation in more common buffers (around pH 5 to 6).

TABLE 9

| | Descriptor | pI |
|---|---|---|
| IgG4P | 10273 gL2gH1 | 6.2 |
| | 10273 gL2-Q1RgH1-D19N | 6.6 |
| | 10273 gL2-Q1RgH4-D19N | 6.6 |
| IgG1 | 10273 gL2gH1 | 7.3 |

Hydrophobic Interaction Chromatography (HIC)

Hydrophobic Interaction chromatography (HIC) separates molecules in order of increasing hydrophobicity. Molecules bind to the hydrophobic stationary phase in the presence of high concentrations of polar salts and desorb into the mobile phase as the concentration of salt . . . decreases. A longer retention time equates to a greater apparent hydrophobicity.

The 10273 Ab samples at 2 mg/mL were diluted 1:2 with 1.6 M ammonium sulphate and PBS (pH 7.4). 10 μg (10 μL) of sample was injected onto a DIONEX PROPAC™ HIC-10 column (100 mm×4.6 mm) connected in series to an Agilent 1200 binary HPLC with a fluorescence detector. The separation was monitored by intrinsic fluorescence (excitation and emission wavelengths, 280 nm and 340 nm respectively). Using Buffer A (0.8 M ammonium sulphate 100 mM Phosphate pH7.4) and Buffer B (100 mM Phosphate pH7.4) the sample was analysed using gradient elution as follows, (i) 2 minute hold at 0% B, (ii) linear gradient from 0 to 100% B in 30 minutes (0.8 mL/minute) (iii) the column was washed with 100% B for 2 minutes and re-equilibrated in 0% B for 10 minutes prior to next sample injection. The column temperature was maintained at 20° C. The retention time (in minutes) is shown in Table 10.

TABLE 10

| | Descriptor | Main Peak retention time (min) |
|---|---|---|
| IgG4P | 10273 gL2gH1 | 16.3 |
| | 10273 gL2-Q1R gH1-D19N | 17.4 |
| | 10273 gL2-Q1R gH4-D19N | 19.8 |
| IgG1 | 10273 gL2gH1 | 15.1 |

Only small differences in retention time, that is, apparent hydrophobicity, were observed between the different 10273 antibodies and all were considered to exhibit greater than average measurements, hence potentially exhibiting a propensity to aggregate (Jain et al "Biophysical properties of the clinical-stage antibody landscape" Proc Natl Acad Sci USA. 2017 Jan. 31; 114 (5): 944-949. doi: 10.1073/pnas.1616408114. Epub 2017 Jan. 17). All molecules therefore showed a greater tendency to bind the HIC matrix. HIC matrix has been used as an alternative step to ion exchange in manufacture.

Solubility Measurement Using Polyethylene Glycol (PEG) Measurement

An understanding of colloidal stability (solubility) can be derived from examining the effect of polyethylene glycol (PEG) precipitation. PEG was used to reduce protein solubility in a quantitatively definable manner, by increasing the concentrations of PEG (w/v) and measuring the amount of protein remaining in solution. This assay serves to mimic the effect of high concentration solubility without using conventional concentration methods.

Stock 40% PEG 3350 (MERCK®, 202444) solutions (w/v) were prepared in PBS pH 7.4; 50 mM sodium acetate 125 mM sodium chloride pH 5.0 (common storage buffers) and 50 mM histidine, 250 mM proline pH 5.5 (common pre-formulation buffer). A serial titration was performed by an assist plus liquid handling robot (Integra, 4505), resulting in a range of 40% to 15.4% PEG 3350. To minimize non-equilibrium precipitation, sample preparation consisted of mixing the 10273 Ab samples and PEG solutions at a 1:1 volume ratio. 35 μL of the PEG 3350 stock solutions was added to a 96 well v bottom PCR plate (A1 to H1) by a liquid handling robot. 35 μL of a 2 mg/ml 10273 Ab solution was added to the PEG stock solutions resulting in a 1 mg/ml test concentration. This solution was mixed by automated slow repeat pipetting and incubated at 37° C. for 0.5 h to re-dissolve any non-equilibrium aggregates. Samples were then incubated at 20° C. for 24 h. The sample plate was subsequently centrifuged at 4000×g for 1 h at 20° C. 50 μL of supernatant was dispensed into a UV-Star®, half area, 96 well, μCLEAR®, microplate (Greiner, 675801). Protein concentrations were determined by UV spectrophotometry at 280 nm using a FLUOSTAR®Omega multi-detection microplate reader (BMG LABTECH™). The resulting values were plotted using GraphPad Prism version 7.04, PEG midpoint (PEG) score was derived from the midpoint of the sigmoidal dose-response (variable slope) fit.

The data is shown in Table 11 where a higher PEG midpoint (%) equates to a greater probability for high concentration stability/solubility.

At pH 7.4, 10273 gL2gH1 (IgG4P), shows the highest PEG midpoint (greatest predicted solubility), however shows the lowest solubility in acetate pH 5. This trend was different to the corresponding IgG1 molecule, where there was no difference in the predicted solubility between PBS pH 7.4 and acetate pH 5. Both 10273 gL2-Q1RgH1-D19N and 10273 gL2-Q1RgH4-D19N, showed a similar PEG mid-point in PBS pH 7.4 and the histidine pH 5.5 buffer, however there was a decrease in acetate pH 5.

TABLE 11

| | Descriptor | PEG mid-point pH 7.4 PBS | pH 5.0 acetate | pH 5.5 Histidine/Proline |
|---|---|---|---|---|
| IgG4P | 10273 gL2gH1 | 11.7 | 8.3 | 9.7 |
| | 10273 gL2-Q1RgH1-D19N | 10.5 | 9.1 | 10.1 |
| | 10273 gL2-Q1RgH4-D19N | 10.4 | 9.5 | 10.5 |
| IgG1 | 10273 gL2gH1 | 10.7 | 10.4 | not done |

Effect of Stress at Air-Liquid Interface (Aggregation Assay)

Proteins tend to unfold when exposed to an air-liquid interface, where hydrophobic surfaces are presented to the hydrophobic environment (air) and hydrophilic surfaces to the hydrophilic environment (water). Agitation of protein solutions achieves a large air-liquid interface that can drive aggregation. This assay serves to mimic stresses that the molecule would be subjected to during manufacture (for example ultra-filtration) and to provide stringent conditions in order to try to discriminate between different antibody molecules.

Samples in PBS pH 7.4 or 50 mM sodium acetate and 125 m sodium chloride, pH5 were stressed by vortexing using an EPPENDORF THERMOMIXER® Comfort. Prior to vortexing the concentration was adjusted to 1 mg/mL using the appropriate extinction coefficients (1.46 Abs 280 nm, 1 mg/mL, 1 cm path length) and the absorbance at 280 nm, 340 nm and 595 nm obtained using a VARIAN CARY® 50-Bio spectrophotometer to establish the time zero reading. Each sample was sub-aliquoted into 1.5 ml conical EPPENDORF®-style capped tubes (3×250 μL) and subjected to vortexing at 1400 rpm at 25° C. for 4 h. Aggregation (turbidity) was monitored by measurement of the samples at 595 nm using a VARIAN CARY® 50-Bio spectrophotometer.

Figure 11:
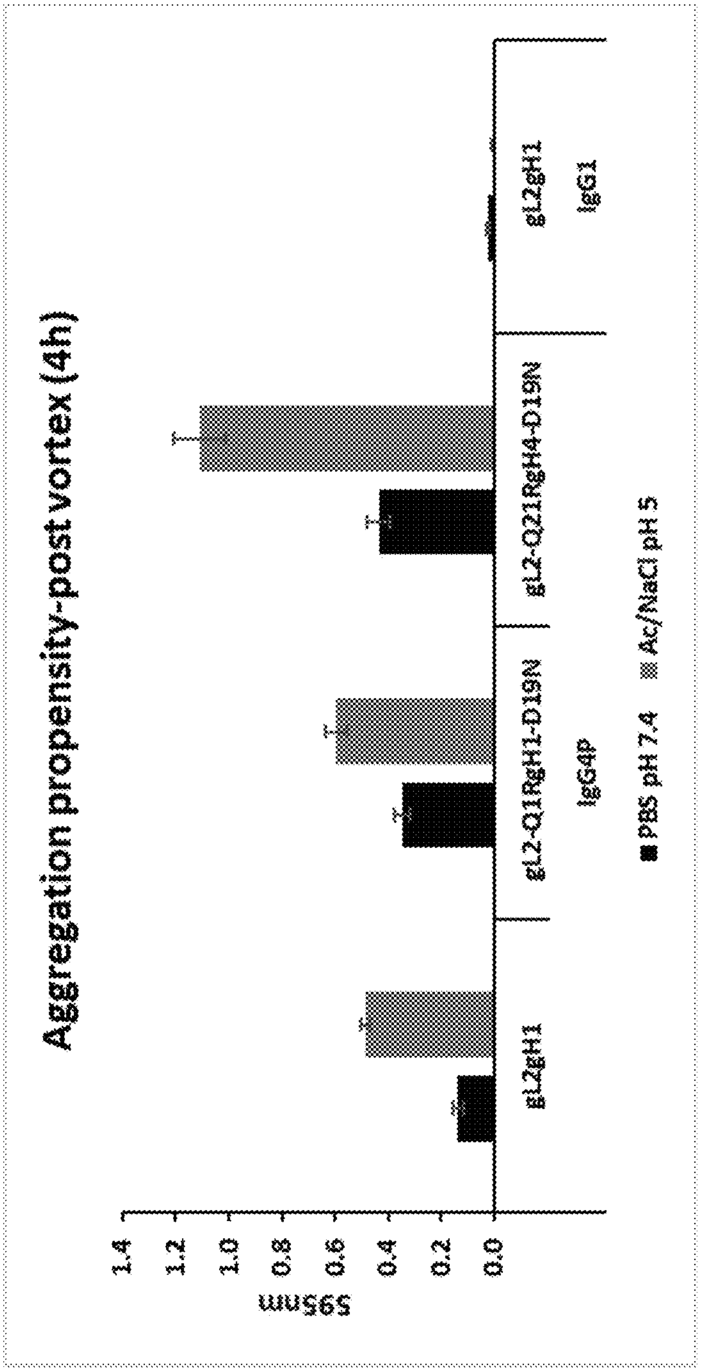
FIG. 11. Effect of vortexing on the aggregation stability of humanized grafts of antibody 10273 in two buffers of different composition and pH.

The aggregation propensity at 4 hours in two buffers for the different antibodies is shown in Table 12 and FIG. 11.

TABLE 12

| | | PBS pH 7.4 | | Ac/NaCl pH 5 | |
|---|---|---|---|---|---|
| | Descriptor | mean absorbance 595 nm/4 h | SD | mean absorbance 595 nm/4 h | SD |
| IgG4P | 10273 gL2gH1 | 0.14 | 0.02 | 0.49 | 0.02 |
| | 10273 gL2-Q1gH1-D19N | 0.35 | 0.03 | 0.60 | 0.04 |
| | 10273 gL2-Q1RgH4-D19N | 0.44 | 0.04 | 1.11 | 0.10 |
| IgG1 | 10273 gL2gH1 | 0.02 | 0.00 | 0.01 | 0.00 |

The IgG1 10273 gL2gH1 showed greatest aggregation stability in both buffers and generally all 10273 antibodies were more aggregation stable in PBS pH 7.4.

Chemical Denaturation (Unfolding) Using Guanidine Hydrochloride Unfolding by Circular Dichroism (CD)

The antibodies were subjected to unfolding using the chemical denaturant (guanidine hydrochloride) as test of robustness.

Guanidine HCl was titrated from 0-4 M, over 48 wells in a 96 well plate using the DRAGONFLY® (TTP LABTECH™, Cambridge, UK) and sample added at 7.5 μM (final) in 80 μL total volume before equilibration overnight at room temperature. 70 μL were transferred to a deep well plate for analysis by automated circular dichroism (CHIROSCAN™: ACD, Applied Photophysics, Leatherhead, UK). Circular dichroism measurement was acquired in the Far UV region 260-190 nm, using a 0.5 nm step size with 1 s/time-point, 1 nm bandwidth and a flow-cell cuvette of 0.2 mm pathlength. CD signal at 210 nm was fitted to a sigmodal, Bi-dose response curve in Origin 9b.

The 10273 antibodies tested appear to have similar denaturation profiles according to the chemical denaturation midpoints (Cm) (Table 13), with two apparent transitions, hence demonstrated similar robustness to chemical denaturant.

TABLE 13

| Descriptor | Cm1 | Cm2 |
|---|---|---|
| 10273 gL2gH1 | 1.38 | 2.69 |
| 10273 gL2-Q1R gH1-D19N | 1.36 | 2.7 |
| 10273 gL2-Q1R) gH4-D19N | 1.48 | 2.76 |

Assessment of Self-Interaction using AC-SINS (affinity capture self-interaction nanoparticle spectroscopy).

The set of 10273 antibodies were tested in the AC-SINS assay (Liu Y. MAbs, 2014 March-April; 6(2):483-92) to assess self-interaction propensity and hence inform on aggregation stability.

Goat anti human-Fcγ specific capture antibody (JACKSON IMMUNORESEARCH™) was buffer exchanged into 20 mM sodium acetate, pH 4.3, diluted to 0.4 mg/ml and 50 μL added to 450 μL citrate-stabilised 20 nm gold nanoparticles (TedPella, USA) and left overnight at room temp. The conjugated nanoparticles were blocked with 55 μL PEG-thiol for 1 hour, centrifuged at 21,000×g for 6 min, the supernatant removed and resuspended in 20 mM sodium acetate, pH4.3 to a final volume of 150 μL.

The 10273 antibodies were diluted to 22 μg/mL in PBS, pH7.4 (200 μL) and added to an equal volume non-specific whole IgG (JACKSON IMMUNORESEARCH™), vortexed briefly and 72 μL added to a 96-well plate. 8 μL of nanoparticles were added to each well (n=4). Absorbance were read on a BMG Labtech™ plate reader from 500-600 nm, fitted to Lorenzian curves (RShiny) and PBS only subtracted from the samples to give AAmax as detailed in Table 14. The greater AAmax, the greater the propensity for self-interaction. The tested 10273 antibodies showed a low Amax and Axmax (from PBS background) suggesting a low propensity of self-interaction.

TABLE 14

| Descriptor | λmax | Δλmax |
|---|---|---|
| 10273 gL2gH1 | 530.9 | 1.41 |
| 10273 gL2-Q1R gH1-D19N | 531.15 | 1.66 |
| 10273 gL2-Q1R gH4-D19N | 531.59 | 2.1 |

The invention claimed is:

1. A monoclonal antibody which binds to kallikrein 5 (KLK5), wherein the antibody comprises a variable light chain and a variable heavy chain, and wherein:

a) the variable light chain comprises a CDR-L1 comprising SEQ ID NO: 1, a CDR-L2 comprising SEQ ID NO: 2 and a CDR-L3 comprising SEQ ID NO: 3, and the variable heavy chain comprises a CDR-H1 comprising SEQ ID NO: 4, a CDR-H2 comprising SEQ ID NO: 5 and a CDR-H3 comprising SEQ ID NO: 6; or b) the variable light chain comprises a CDR-L1 comprising SEQ ID NO: 7, a CDR-L2 comprising SEQ ID NO: 2 and a CDR-L3 comprising SEQ ID NO: 3 and the variable heavy chain comprises a CDR-H1 comprising SEQ ID NO: 4, a CDR-H2 comprising SEQ ID NO: 5 and a CDR-H3 comprising any one of SEQ ID NO: 10, 21, 22, 23, 24, 25, 26, 27, or 28.

2. The antibody according to claim 1, wherein a) the variable light chain comprises a CDR-L1 comprising SEQ ID NO: 7, a CDR-L2 comprising SEQ ID NO: 2 and a CDR-L3 comprising SEQ ID NO: 3; and b) the variable heavy chain comprises a CDR-H1 comprising SEQ ID NO: 4, a CDR-H2 comprising SEQ ID NO: 5 and a CDR-H3 comprising SEQ ID NO: 10 or 23.

3. The antibody according to claim 1, wherein a) the variable light chain comprises a CDR-L1 comprising SEQ ID NO: 7, a CDR-L2 comprising SEQ ID NO: 2 and a CDR-L3 comprising SEQ ID NO: 3; and b) the variable heavy chain comprises a CDR-H1 comprising SEQ ID NO: 4, a CDR-H2 comprising SEQ ID NO: 5 and a CDR-H3 comprising SEQ ID NO: 23.

4. The antibody according to claim 1 wherein the antibody is a chimeric or humanized antibody.

5. The antibody according to claim 1, wherein the antibody is a full-length antibody.

6. The antibody according to claim 5, wherein the full-length antibody is selected from an IgG1, IgG4 or IgG4 in which the serine at position 241 according to the Kabat numbering system has been changed to a Proline.

7. The antibody according to claim 1, wherein the antibody is selected from a Fab, a Fab', a $F(ab')_2$, or a scFv.

8. The antibody according to claim 1, wherein the antibody comprises:

a) a variable light chain comprising SEQ ID NO: 34 and a variable heavy chain comprising SEQ ID NO 50; or b) a variable light chain comprising SEQ ID NO: 38 and a variable heavy chain comprising SEQ ID NO: 54 or 102 or 106 or 110 or 114 or 118 or 122 or 126 er-130 or 134.

9. The antibody according to claim 1, wherein the antibody comprises:

a) a variable light chain comprising SEQ ID NO: 38; and/or b) a variable heavy chain comprising SEQ ID NO: 110.

10. The antibody according to claim 1, wherein the antibody comprises:

a) a light chain comprising SEQ ID NO: 36 and a heavy chain comprising SEQ ID NO 52; or b) a light chain comprising SEQ ID NO: 40 and a heavy chain comprising any one of SEQ ID NO: 56 or 104 or 108 or 112 or 116 or 120 or 124 or 132 or 136.

11. The antibody according to claim 1, wherein the antibody comprises:

a) a light chain comprising SEQ ID NO: 40; and b) a heavy chain comprising SEQ ID NO: 112.

12. A pharmaceutical composition comprising the antibody according to claim 1 and one or more pharmaceutically acceptable carriers, excipients or diluents.

13. A method of treating diseases characterized by dysregulation of KLK5 or by dysregulation of inhibition of KLK5 in a patient comprising administering to said patient a therapeutically effective amount of an antibody according to claim 1 or a pharmaceutical composition comprising the antibody and one or more pharmaceutically acceptable carriers, excipients or diluents, wherein the disease is selected from Netherton's Syndrome, Atopic Dermatitis, Ichthyoses, Rosacea, Asthma or Cancer, wherein the method of treating diseases does not comprise preventing the diseases.

14. The method according to claim 13 wherein the disease is Netherton's Syndrome.

15. The method according to claim 13 wherein the disease is Atopic Dermatitis.

* * * * *